US009028819B2

(12) United States Patent
MacDonald et al.

(10) Patent No.: US 9,028,819 B2
(45) Date of Patent: *May 12, 2015

(54) METHODS OF ALLEVIATING ITCH BY ADMINISTERING HUMAN ANTIBODIES TO HUMAN PROTEASE-ACTIVATED RECEPTOR 2

(71) Applicant: Regeneron Pharmaceuticals, Inc., Tarrytown, NY (US)

(72) Inventors: Lynn MacDonald, White Plains, NY (US); Andrew J. Murphy, Croton-on-Hudson, NY (US); Nicholas J. Papadopoulos, LaGrangeville, NY (US); Marc R. Morra, Beacon Falls, CT (US); Robert R. Salzler, Durham, NC (US); Michael L. LaCroix-Fralish, Sleepy Hollow, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/850,644

(22) Filed: Mar. 26, 2013

(65) Prior Publication Data

US 2014/0179903 A1  Jun. 26, 2014

Related U.S. Application Data

(60) Continuation of application No. 13/325,098, filed on Dec. 14, 2011, now Pat. No. 8,425,907, which is a division of application No. 12/877,133, filed on Sep. 8, 2010, now Pat. No. 8,101,724.

(60) Provisional application No. 61/240,783, filed on Sep. 9, 2009, provisional application No. 61/242,821, filed on Sep. 16, 2009, provisional application No. 61/317,839, filed on Mar. 26, 2010.

(51) Int. Cl.
 A61K 39/395 (2006.01)
 C07K 16/28 (2006.01)
 A61K 45/06 (2006.01)
 A61K 39/00 (2006.01)

(52) U.S. Cl.
 CPC ....... *A61K 39/3955* (2013.01); *A61K 2039/505* (2013.01); *C07K 16/28* (2013.01); *C07K 2317/21* (2013.01); *C07K 2317/24* (2013.01); *C07K 2317/34* (2013.01); *A61K 45/06* (2013.01); *C07K 2317/76* (2013.01)

(58) Field of Classification Search
 CPC .......... C07K 2316/96; C07K 2317/21; C07K 2317/34; C07K 2317/56; C07K 2317/565; C07K 2317/76; A61K 39/3955; A61K 2039/505
 See application file for complete search history.

(56) References Cited

U.S. PATENT DOCUMENTS

| 5,874,400 | A  | 2/1999  | Sundelin et al. |
| 7,888,482 | B2 | 2/2011  | Virca et al. |
| 2007/0237759 | A1 | 10/2007 | Virca et al. |
| 2008/0213252 | A1 | 9/2008  | Lerner et al. |
| 2010/0119506 | A1 | 5/2010  | Litzenburger et al. |
| 2012/0172446 | A1 | 7/2012  | Dechelette et al. |

FOREIGN PATENT DOCUMENTS

| WO | 98/24893    | 6/1998  |
| WO | 2009005726  | 1/2009  |
| WO | 2009096695  | 8/2009  |
| WO | 2009117481  | 9/2009  |
| WO | 2010147440  | 12/2010 |
| WO | 2010147441  | 12/2010 |
| WO | 2011000930  | 1/2011  |

OTHER PUBLICATIONS

Akiyama, T., et al., "Enhanced scratching evoked by PAR-2 agonist and 5-HT but not histamine in a mouse model of chronic dry skin itch," Pain 151(2): 378-383 (2010, Epub: Aug. 14, 2010).
Akiyama, T., et al., "Scratching behavior and Fos expression in superficial dorsal horn elicited by protease-activated receptor agonists and other itch mediators in mice," J. Pharmacol. Exp. Ther. 329(3): 945-951 (2009, Epub: Mar. 17, 2009).
Akiyama, T. et al., "Differential itch- and pain-related behavioral responses and mu-opioid modulation in mice," Acta. Derm. Venereol. 90(6): 575-581 (2010).
Bueno, L., "Protease activated receptor 2: a new target for IBS treatment," Eur. Rev. Med. Pharmacol. Sci. 12 (Suppl. 1): 95-102 (2008).
Busso, N., et al., "Evaluation of protease-activated receptor 2 in murine models of arthritis," Arthritis Rheum. 56(1): 101-107 (2007).
Cenac, N., et al., "Role for protease activity in visceral pain in irritable bowel syndrome," J. Clin. Invest. 117(3): 636-647 (2007).
Costa, R., et al., "Evidence for the role of neurogenic inflammation components in trypsin-elicited scratching behaviour in mice," Br J. Pharmacol. 154(5): 1094-1103 (2008, Epub: May 5, 2008).
Coughlin, Sr., "Protease-activated receptors start a family," Proc. Natl. Acad. Sci. U.S.A. 91(20): 9200-9202 (1994).
Dai, Y., et al., "Sensitization of TRPA1 by PAR2 contributes to the sensation of inflammatory pain," J. Clin. Invest. 117 (7): 1979-1987 (2007).
Dulon, S., et al , "Proteinase-activated receptor-2 and human lung epithelial cells: disarming by neutrophil serine proteinases," Am. J. Respir. Cell. Mol. Biol. 28(3): 339-346 (2003).
Fiorucci, S., et al., "Role of PAR2 in pain and inflammation," Trends Pharmacol. Sci. 23(4): 153-155 (2002).

(Continued)

*Primary Examiner* — Robert Landsman
(74) *Attorney, Agent, or Firm* — Bozicevic Field & Francis LLP; Christopher Westberg

(57) ABSTRACT

The present invention provides antibodies that bind to protease-activated receptor-2 (PAR-2) and methods of using same. According to certain embodiments of the invention, the antibodies are fully human antibodies that bind to human PAR-2. The antibodies of the invention are useful, inter alia, for the treatment of diseases and disorders associated with one or more PAR-2 biological activities, including the treatment of pain conditions, inflammatory conditions and gastrointestinal conditions.

26 Claims, 5 Drawing Sheets

(56) References Cited

OTHER PUBLICATIONS

Frateschi, S., et al., "PAR2 absence completely rescues inflammation and ichthyosis caused by altered CAP1/Prss8 expression in mouse skin," Nat. Commun. 2:161 doi: 10.1038/ncomms1162 (2011).

Kelso, E.B., et al., "Therapeutic promise of proteinase-activated receptor-2 antagonism in joint inflammation," J. Pharmacol. Exp. Ther. 316(3): 1017-1024 (2006, Epub: Oct. 31, 2005).

Kelso, E.B., et al, "Expression and proinflammatory role of proteinase-activated receptor 2 in rheumatoid synovium: ex vivo studies using a novel proteinase-activated receptor 2 antagonist," Arthritis Rheum. 56(3): 765-771 (2007).

King, V., et al., "Amelioration of joint inflammation by a PAR-2-specific monoclonal antibody," Arthritis Res. Ther. 7 (Suppl. 1): P160 (2005).

MacFarlane, S.R., et al., "Proteinase-activated receptors," Pharmacol. Rev. 53(2): 245-282 (2001).

Molino, M., et al., "Interactions of mast cell tryptase with thrombin receptors and PAR-2," J. Biol. Chem. 272(7): 4043-4049 (1997).

Molino, M., et al., "Differential expression of functional protease-activated receptor-2 (PAR-2) in human vascular smooth muscle cells," Arterioscler Thromb. Vasc. Biol. 18(5): 825-832 (1998).

Napoli, C., et al. "Evidence that protease activated receptor 2 expression is enhanced in human coronary atherosclerotic lesions," J. Clin. Pathol. 57(5): 513-516 (2004).

Nickel, T.J., et al., "Constitutive expression of functionally active protease-activated receptors 1 and 2 in human conjunctival epithelial cells." Mediators Inflamm. 2006(article ID 61359): 1-8 (2006).

Nystedt, S., et al., "Molecular cloning of a potential proteinase activated receptor," Proc. Natl. Acad. Sci. U.S.A. 91 (20): 9208-9212 (1994).

Reddy et al., "Cowhage-Evoked Itch is Mediated by a Novel Cysteine Protease: A Ligand of Protease-Activated Receptors" J. Neurosci. 28(17):4331-4335 (Apr. 23, 2008).

Schmidlin: F., et al., "Protease-activated receptor 2 mediates eosinophil infiltration and hyperreactivity in allergic inflammation of the airway," J. Immunol. 169(9): 5315-5321 (2002).

Shimada, S.G., et al., "Scratching behavior in mice induced by the proteinase-activated receptor-2 agonist, SLIGRL-NH2," Eur. J Pharmacol. 530(3): 281-283 (2006, Epub: Dec. 13, 2005).

Smith-Swintosky, V.L., et al., "Protease-activated receptor-2 (PAR-2) is present in the rat hippocampus and is associated with nuerodegeneration," J. Neurochem. 69(5): 1890-1896(1997).

Soreide, K., "Proteinase-activated receptor 2 (PAR-2) in gastrointestinal and pancreatic pathophysiology, inflammation and neoplasia," Scand. J. Gastroenterol. 43(8): 902-909 (2008).

Steinhoff, M., et al., "Agonists of proteinase-activated receptor 2 induce inflammation by a neurogenic mechanism," Nat. Med. 6(2): 151-158 (2000).

Steinhoff, M., et al., "Proteinase-activated receptor-2 mediates itch: a novel pathway for pruritus in human skin," J. Neurosci. 23(15): 6176-6180 (2003).

Tsujii, K., et al., "Activation of proteinase-activated receptors induces itch-associated response through histamine-dependent and -independent pathways in mice," J. Pharmacol. Sci. 108(3): 385-388 (2008, Epub: Nov. 6, 2008).

Tsujii, K., et al., "Involvement of tryptase and proteinase-activated receptor-2 in spontaneous itch-associated response in mice with atopy-like dermatitis," J. Pharmacol. Sci. 109(3): 388-395 (2009, Epub: Mar. 7, 2009).

Ui, H., et al., "Potent pruritogenic action of tryptase mediated by PAR-2 receptor and its involvement in anti-pruritic effect of nafamostat mesilate in mice," Eur. J. Pharmacol. 530(1-2): 172-178 (2006, Epub: Dec. 15, 2006).

Vergnolle, N., "Protease-activated receptors as drug targets in inflammation and pain," Pharmacol. Ther. 123(3): 292-309 (2009, Epub: May 28, 2009.

Wang, J., et al., "Up-regulation and activation of proteinase-activated receptor 2 in early and delayed radiation injury in the rat intestine: influence of biological activators of proteinase-activated receptor 2," Radiat. Res. 160(5): 524-535 (2003).

Santa Cruz Biotechnology, PAR-2 Antibody (SAM11): sc-13504 [on-line] <http://www.scbt.jp/datasheet-13504/jt,;> [retrieved on Oct. 15, 2014].

Cheng et al., "Activated protein C blocks p53-mediated apoptosis in ischemic human brain endothelium and is neuroprotective" Nature Medicine 9(3):338-342 (2003).

```
H1H581P LCVR (SEQ ID NO:692)  DIVMTQTPLSSPVTLGQPASISCRSSQSLVHSDGNTYLSWLHQ
H2M588N LCVR (SEQ ID NO:106)  DIQMTQSPSSLSASVGDRVTITCRARQGISNN----LAWLQQ
H2M591N LCVR (SEQ ID NO:154)  DIQMTQYPSSLSASVGDRVTITCRARQGISNY----LAWLQQ
H2M618N LCVR (SEQ ID NO:346)  DIQMTQSPSSLSASVGDRVTITCRASQGISTY----LAWLQQ
                                                        |_____CDR1_____|

H1H581P LCVR (SEQ ID NO:692)  RPGQPPRLLIYKISNRFSGVPDRFSGSGSGAGTDFTLQISRVEAE
H2M588N LCVR (SEQ ID NO:106)  KPGKAPKSLIYAASSLQSGIPSKFSGSGSGTYFTLTISSLQPE
H2M591N LCVR (SEQ ID NO:154)  KPGKAPKSLIYAASSLQRGVPSKFSGSGSGTDFTLTISSLQPE
H2M618N LCVR (SEQ ID NO:346)  KPGKAPKSLIYATSSLQSGVPSKFSGSRSGTDFTLTISSLQPE
                                        |__CDR2__|

H1H581P LCVR (SEQ ID NO:692)  DVGIYYCMQATQFP-TFGGGTKVEIK
H2M588N LCVR (SEQ ID NO:106)  DFATYYCQQYKSSPLTFGGGTKVEIK
H2M591N LCVR (SEQ ID NO:154)  DSATYYCQQYKISPLTFGGGTKVEIK
H2M618N LCVR (SEQ ID NO:346)  DFATYYCQQYKSSPLTFGGGTKVEIK
                                     |____CDR3____|
```

| | C-terminal Biotin GTNRSSKGRSLIGKVDGT-B | N-terminal Biotin B-GTNRSSKGRSLIGKVDGT |
|---|---|---|
| No Cleavage | 2501 kDa | 2373 kDa |
| Cleavage @ ① | 2073 kDa | 988 kDa |
| Cleavage @ ❷ | 1558 kDa | N/A |

(B)

| Antibody | Time | 2501 kDa | 2073 kDa | 1558 kDa | 2373 kDa | 988 kDa |
|---|---|---|---|---|---|---|
| Neg Ctrl | 0 | X | | | X | |
| Neg Ctrl | 5 | | | X | | X |
| Neg Ctrl | 15 | | | X | | N/D |
| H4H581P | 0 | X | | | X | |
| H4H581P | 5 | | X | | | X |
| H4H581P | 15 | | X | | | N/D |
| H4H588N | 0 | X | | | X | |
| H4H588N | 5 | | | X | | X |
| H4H588N | 15 | | | X | | N/D |

Fig. 3

SEQUENCE LISTING

<160> NUMBER OF SEQ ID NOS: 887

<210> SEQ ID NO 1
<211> LENGTH: 348
<212> TYPE: DNA
<213> ORGANISM: Artificial Sequence
<220> FEATURE:
<223> OTHER INFORMATION: Synthetic

<400> SEQUENCE: 1

```
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctagagtg ggtctcaggt attacttgga atagtggtaa catggcctat     180
gcggactctg tgaagggccg attcaccatc tccagagaca cgccaagaa ctccctgtat      240 ctgcaaatga acagtctgag agctgaggac acggccttat attactgtgc aaaagaaaac     300 tgggccttg actactgggg ccagggaacc cgggtcatcg tctcctca                    348
```

<210> SEQ ID NO 2
<211> LENGTH: 116
<212> TYPE: PRT
<213> ORGANISM: Artificial Sequence
<220> FEATURE:
<223> OTHER INFORMATION: Synthetic

<400> SEQUENCE: 2

```
Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Gly Ile Thr Trp Asn Ser Gly Asn Met Ala Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Glu Asn Trp Ala Phe Asp Tyr Trp Gly Gln Gly Thr Arg Val
            100                 105                 110

Ile Val Ser Ser
        115
```

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3

```
ggattcacct ttgatgatta tgcc                                              24
```

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

```
Gly Phe Thr Phe Asp Asp Tyr Ala
  1               5
```

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
attacttgga atagtggtaa catg                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

```
Ile Thr Trp Asn Ser Gly Asn Met
  1               5
```

<210> SEQ ID NO 7
<211> LENGTH: 27
<212> TYPE: DNA
<213> ORGANISM: Artificial Sequence
<220> FEATURE:
<223> OTHER INFORMATION: Synthetic

<400> SEQUENCE: 7
gcaaaagaaa actgggcctt tgactac                                       27

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

```
Ala Lys Glu Asn Trp Ala Phe Asp Tyr
  1               5
```

<210> SEQ ID NO 9
<211> LENGTH: 336
<212> TYPE: DNA
<213> ORGANISM: Artificial Sequence
<220> FEATURE:
<223> OTHER INFORMATION: Synthetic

<400> SEQUENCE: 9
gatattgtga tgacccagac tccactctcc tcacctgtca cccttggaca gccggcctcc     60
atctcctgca ggtctagtca gagcctcgta cacagtgatg gaaacaccta cttgagttgg    120
cttcagcaga ggccaggcca gcctccaaga ctcctaattt ataagatttc taaccggttc    180
tctggggtcc cagacagatt cagtggcagt ggggcaggga cagatttcac actgaaaatc    240
agcagggtgg aagctgagga tgtcggggtt tatttctgca tgcaagctac acaatttccg    300 tacactttg gccaggggac caagctggag atcaaa                              336

<210> SEQ ID NO 10
<211> LENGTH: 112

```
<212> TYPE: PRT
<213> ORGANISM: Artificial Sequence
<220> FEATURE:
<223> OTHER INFORMATION: Synthetic

<400> SEQUENCE: 10

Asp Ile Val Met Thr Gln Thr Pro Leu Ser Ser Pro Val Thr Leu Gly
1               5                   10                  15

Gln Pro Ala Ser Ile Ser Cys Arg Ser Ser His Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Phe Cys Met Gln Ala
                85                  90                  95

Thr Gln Phe Pro Tyr Thr Phe Gly Gln Gly Thr Lys Leu Glu Ile Lys
            100                 105                 110

<210> SEQ ID NO 11
<211> LENGTH: 33
<212> TYPE: DNA
<213> ORGANISM: Artificial Sequence
<220> FEATURE:
<223> OTHER INFORMATION: Synthetic

<400> SEQUENCE: 11
cacagcctcg tacacagtga tggaaacacc tac                              33

<210> SEQ ID NO 12
<211> LENGTH: 11
<212> TYPE: PRT
<213> ORGANISM: Artificial Sequence
<220> FEATURE:
<223> OTHER INFORMATION: Synthetic

<400> SEQUENCE: 12

His Ser Leu Val His Ser Asp Gly Asn Thr Tyr
1               5                   10

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 aagatttct                                                         9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Lys Ile Ser
1
```

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15

```
atgcaagcta cacaatttcc gtacact                                          27
```

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Met Gln Ala Thr Gln Phe Pro Tyr Thr
 1               5

<210> SEQ ID NO 17
<211> LENGTH: 348
<212> TYPE: DNA
<213> ORGANISM: Artificial Sequence
<220> FEATURE:
<223> OTHER INFORMATION: Synthetic

<400> SEQUENCE: 17

```
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctagagtg ggtctcaggt attacttgga atagtggtaa catggcctat     180
gcggactctg tgaagggccg attcaccatc tccagagaca cgccaagaa ctccctgtat      240
ctgcaaatga acagtctgag agctgaggac acggcctat attactgtgc aaaagaaaac     300
tgggcctttg actactgggg ccagggaacc ctggtcaccg tctcctca                  348
```

<210> SEQ ID NO 18
<211> LENGTH: 116
<212> TYPE: PRT
<213> ORGANISM: Artificial Sequence
<220> FEATURE:
<223> OTHER INFORMATION: Synthetic

<400> SEQUENCE: 18

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Thr Trp Asn Ser Gly Asn Met Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Asn Trp Ala Phe Asp Tyr Trp Gly Gln Gly Thr Leu Val
            100                 105                 110

Thr Val Ser Ser
        115

<210> SEQ ID NO 19
<211> LENGTH: 336
<212> TYPE: DNA
<213> ORGANISM: Artificial Sequence
<220> FEATURE:
<223> OTHER INFORMATION: Synthetic

<400> SEQUENCE: 19

```
gatattgtga tgacccagac tccactctcc tcacctgtca cccttggaca gccggcctcc      60
atctcctgca ggtctagtca gcctcgtaca cacagtgatg gaaacaccta cttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tatttctgca tgcaagctac acaatttccg     300
tacacttttg gccaggggac caagctggag atcaaa                                336
```

<210> SEQ ID NO 20
<211> LENGTH: 112
<212> TYPE: PRT
<213> ORGANISM: Artificial Sequence
<220> FEATURE:
<223> OTHER INFORMATION: Synthetic

<400> SEQUENCE: 20

```
Asp Ile Val Met Thr Gln Thr Pro Leu Ser Ser Pro Val Thr Leu Gly
 1               5                  10                  15

Gln Pro Ala Ser Ile Ser Cys Arg Ser Ser His Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Phe Cys Met Gln Ala
                85                  90                  95

Thr Gln Phe Pro Tyr Thr Phe Gly Gln Gly Thr Lys Leu Glu Ile Lys
            100                 105                 110
```

<210> SEQ ID NO 21
<211> LENGTH: 348
<212> TYPE: DNA
<213> ORGANISM: Artificial Sequence
<220> FEATURE:
<223> OTHER INFORMATION: Synthetic

<400> SEQUENCE: 21

```
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg gtctcaggt attacttgga atagtggtaa catgggctat     180
gcggactctg tgaagggccg attcaccatc tccagagaca cgccaagaa ctccctgtat     240 ctgcaaatga acagtctgag agctgaggac acggccttgt attactgtgc aaaagaaaac     300 tgggccttg actactgggg ccagggaacc ctggtcaccg tctcctca                   348
```

<210> SEQ ID NO 22
<211> LENGTH: 116

<212> TYPE: PRT
<213> ORGANISM: Artificial Sequence
<220> FEATURE:
<223> OTHER INFORMATION: Synthetic

<400> SEQUENCE: 22

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Thr Trp Asn Ser Gly Asn Met Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Asn Trp Ala Phe Asp Tyr Trp Gly Gln Gly Thr Leu Val
            100                 105                 110

Thr Val Ser Ser
        115

<210> SEQ ID NO 23
<211> LENGTH: 337
<212> TYPE: DNA
<213> ORGANISM: Artificial Sequence
<220> FEATURE:
<223> OTHER INFORMATION: Synthetic

<400> SEQUENCE: 23
gatattgtga tgacccagac tccactctcc tcacctgtca cccttggaca gccggcctcc      60
atctcctgca ggtctagtca cagcctcgta cacagtgatg aaacacccta cttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tattactgca tgcaagctac acaatttccg     300
tacacttttg gccaggggac caagctggag atcaaac                              337

<210> SEQ ID NO 24
<211> LENGTH: 112
<212> TYPE: PRT
<213> ORGANISM: Artificial Sequence
<220> FEATURE:
<223> OTHER INFORMATION: Synthetic

<400> SEQUENCE: 24

Asp Ile Val Met Thr Gln Thr Pro Leu Ser Ser Pro Val Thr Leu Gly
1               5                   10                  15

Gln Pro Ala Ser Ile Ser Cys Arg Ser Ser His Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala 85                  90                  95
Thr Gln Phe Pro Tyr Thr Phe Gly Gln Gly Thr Lys Leu Glu Ile Lys
             100                 105                 110

<210> SEQ ID NO 25
<211> LENGTH: 348
<212> TYPE: DNA
<213> ORGANISM: Artificial Sequence
<220> FEATURE:
<223> OTHER INFORMATION: Synthetic

<400> SEQUENCE: 25
gaagtgcagc tggtggagtc tgggggaggc gtggtccagc ctggcaggtc cctgagactc    60
tcctgtgcag cctctggatt cacctttgat gattatacca tgcactgggt ccggcaagtt   120
ccagggaagg acctgaagtg gtctcaggt attacttgga atggtggtag aaaagcctat   180
gcggactctg tgaagggccg attcaccatc tccagagaca acgccaagaa ctccctcttt   240
ctgcaaatga acagtctgag agctgaggac acggccttct attactgtgc aaaagaagat   300
gaggcttttg actactgggg ccagggaacc ctggtcaccg tctcctca                348

<210> SEQ ID NO 26
<211> LENGTH: 116
<212> TYPE: PRT
<213> ORGANISM: Artificial Sequence
<220> FEATURE:
<223> OTHER INFORMATION: Synthetic

<400> SEQUENCE: 26

Glu Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Asp Asp Tyr
             20                  25                  30

Thr Met His Trp Val Arg Gln Val Pro Gly Lys Asp Leu Lys Trp Val
         35                  40                  45

Ser Gly Ile Thr Trp Asn Gly Gly Arg Lys Ala Tyr Ala Asp Ser Val
     50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Phe Tyr Tyr Cys
                 85                  90                  95

Ala Lys Glu Asp Glu Ala Phe Asp Tyr Trp Gly Gln Gly Thr Leu Val
            100                 105                 110

Thr Val Ser Ser
        115

<210> SEQ ID NO 27
<211> LENGTH: 24
<212> TYPE: DNA
<213> ORGANISM: Artificial Sequence
<220> FEATURE:
<223> OTHER INFORMATION: Synthetic

<400> SEQUENCE: 27
ggattcacct ttgatgatta tacc                                           24

<210> SEQ ID NO 28
<211> LENGTH: 8
<212> TYPE: PRT
<213> ORGANISM: Artificial Sequence
<220> FEATURE:

<223> OTHER INFORMATION: Synthetic

<400> SEQUENCE: 28

Gly Phe Thr Phe Asp Asp Tyr Thr
 1               5

<210> SEQ ID NO 29
<211> LENGTH: 24
<212> TYPE: DNA
<213> ORGANISM: Artificial Sequence
<220> FEATURE:
<223> OTHER INFORMATION: Synthetic

<400> SEQUENCE: 29
attacttgga atggtggtag aaaa                                          24

<210> SEQ ID NO 30
<211> LENGTH: 8
<212> TYPE: PRT
<213> ORGANISM: Artificial Sequence
<220> FEATURE:
<223> OTHER INFORMATION: Synthetic

<400> SEQUENCE: 30

Ile Thr Trp Asn Gly Gly Arg Lys
 1               5

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
gcaaaagaag atgaggcttt tgactac                                       27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Ala Lys Glu Asp Glu Ala Phe Asp Tyr
 1               5

<210> SEQ ID NO 33
<211> LENGTH: 336
<212> TYPE: DNA
<213> ORGANISM: Artificial Sequence
<220> FEATURE:
<223> OTHER INFORMATION: Synthetic

<400> SEQUENCE: 33
gatattgtga tgacccagac tccactctcc tcacctgtca cccttggaca gccggcctcc      60
atctcctgca ggtctagtca aagcctcgta cacagtgatg caacaccta cttgagttgg     120 cttcagcaga ggccaggcca gcctccaaga ctcctaattt ataagatttc taaccggttt    180
tttggggtcc cagacagatt cagtggcagt ggggcaggga cagatttcac actgaaaatc    240
agcagggtgg aggctgagga tgtcggcgtt tattactgca tgcaagcaac acaatttccg    300
tacacttttg gccaggggac caagctggag atcaaa                             336

<210> SEQ ID NO 34
<211> LENGTH: 112
<212> TYPE: PRT
<213> ORGANISM: Artificial Sequence
<220> FEATURE:
<223> OTHER INFORMATION: Synthetic

<400> SEQUENCE: 34

```
Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
             20                  25                  30

Asp Gly Asn Thr Tyr Leu Ser Trp Leu Gln Gln Arg Pro Gly Gln Pro
         35                  40                  45

Pro Arg Leu Leu Ile Tyr Lys Ile Ser Asn Arg Phe Phe Gly Val Pro
     50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Thr Gln Phe Pro Tyr Thr Phe Gly Gln Gly Thr Lys Leu Glu Ile Lys
            100                 105                 110
```

<210> SEQ ID NO 35
<211> LENGTH: 33
<212> TYPE: DNA
<213> ORGANISM: Artificial Sequence
<220> FEATURE:
<223> OTHER INFORMATION: Synthetic

<400> SEQUENCE: 35
caaagcctcg tacacagtga tggcaacacc tac                                    33

<210> SEQ ID NO 36
<211> LENGTH: 11
<212> TYPE: PRT
<213> ORGANISM: Artificial Sequence
<220> FEATURE:
<223> OTHER INFORMATION: Synthetic

<400> SEQUENCE: 36

```
Gln Ser Leu Val His Ser Asp Gly Asn Thr Tyr
 1               5                  10
```

<210> SEQ ID NO 37
<211> LENGTH: 9
<212> TYPE: DNA
<213> ORGANISM: Artificial Sequence
<220> FEATURE:
<223> OTHER INFORMATION: Synthetic

<400> SEQUENCE: 37 aagatttct                                                                9

<210> SEQ ID NO 38
<211> LENGTH: 3
<212> TYPE: PRT
<213> ORGANISM: Artificial Sequence
<220> FEATURE:
<223> OTHER INFORMATION: Synthetic

<400> SEQUENCE: 38

Lys Ile Ser

<210> SEQ ID NO 39
<211> LENGTH: 27
<212> TYPE: DNA
<213> ORGANISM: Artificial Sequence
<220> FEATURE:
<223> OTHER INFORMATION: Synthetic

<400> SEQUENCE: 39
atgcaagcaa cacaatttcc gtacact                                        27

<210> SEQ ID NO 40
<211> LENGTH: 9
<212> TYPE: PRT
<213> ORGANISM: Artificial Sequence
<220> FEATURE:
<223> OTHER INFORMATION: Synthetic

<400> SEQUENCE: 40

Met Gln Ala Thr Gln Phe Pro Tyr Thr
 1               5

<210> SEQ ID NO 41
<211> LENGTH: 348
<212> TYPE: DNA
<213> ORGANISM: Artificial Sequence
<220> FEATURE:
<223> OTHER INFORMATION: Synthetic

<400> SEQUENCE: 41
gaagtgcagc tggtggagtc tgggggaggc gtggtccagc ctggcaggtc cctgagactc      60
tcctgtgcag cctctggatt cacctttgat gattatacca tgcactgggt ccggcaagtt     120
ccagggaagg acctgaagtg ggtctcaggt attacttgga atggtggtag aaaagcctat     180
gcggactctg tgaagggccg attcaccatc tccagagaca acgccaagaa ctccctcttt     240
ctgcaaatga acagtctgag agctgaggac acggccttct attactgtgc aaaagaagat     300
gaggcttttg actactgggg ccagggaacc ctggtcaccg tctcctca                 348

<210> SEQ ID NO 42
<211> LENGTH: 116
<212> TYPE: PRT
<213> ORGANISM: Artificial Sequence
<220> FEATURE:
<223> OTHER INFORMATION: Synthetic

<400> SEQUENCE: 42

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Asp Asp Tyr
             20                  25                  30

Thr Met His Trp Val Arg Gln Val Pro Gly Lys Asp Leu Lys Trp Val
         35                  40                  45

Ser Gly Ile Thr Trp Asn Gly Gly Arg Lys Ala Tyr Ala Asp Ser Val
     50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Phe Tyr Tyr Cys
                 85                  90                  95

Ala Lys Glu Asp Glu Ala Phe Asp Tyr Trp Gly Gln Gly Thr Leu Val
            100                 105                 110

Thr Val Ser Ser
        115

<210> SEQ ID NO 43
<211> LENGTH: 336
<212> TYPE: DNA
<213> ORGANISM: Artificial Sequence
<220> FEATURE:
<223> OTHER INFORMATION: Synthetic

<400> SEQUENCE: 43

```
gatattgtga tgacccagac tccactctcc tcacctgtca cccttggaca gccggcctcc    60
atctcctgca ggtctagtca aagcctcgta cacagtgatg gcaacaccta cttgagttgg   120
cttcagcaga ggccaggcca gcctccaaga ctcctaattt ataagatttc taaccggttt   180
tttggggtcc cagacagatt cagtggcagt ggggcaggga cagatttcac actgaaaatc   240
agcagggtgg aggctgagga tgtcggcgtt tattactgca tgcaagcaac acaatttccg   300
tacacttttg gccaggggac caagctggag atcaaa                             336
```

<210> SEQ ID NO 44
<211> LENGTH: 112
<212> TYPE: PRT
<213> ORGANISM: Artificial Sequence
<220> FEATURE:
<223> OTHER INFORMATION: Synthetic

<400> SEQUENCE: 44

Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Phe Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Tyr Thr Phe Gly Gln Gly Thr Lys Leu Glu Ile Lys
            100                 105                 110

<210> SEQ ID NO 45
<211> LENGTH: 348
<212> TYPE: DNA
<213> ORGANISM: Artificial Sequence
<220> FEATURE:
<223> OTHER INFORMATION: Synthetic

<400> SEQUENCE: 45

```
gaagtgcagc tggtggagtc tgggggaggc ttggtacagc ctggcaggtc cctgagactc    60
tcctgtgcag cctctggatt cacctttgat gattatacca tgcactgggt ccggcaagct   120
ccagggaagg gcctggagtg ggtctcaggt attacttgga tggtggtag aaaaggctat   180 gcggactctg tgaagggccg attcaccatc tccagagaca acgccaagaa ctccctgtat   240
ctgcaaatga acagtctgag agctgaggac acggccttgt attactgtgc aaaagaagat   300
gaggcttttg actactgggg ccaggggaacc ctggtcaccg tctcctca               348
```

<210> SEQ ID NO 46
<211> LENGTH: 116
<212> TYPE: PRT
<213> ORGANISM: Artificial Sequence
<220> FEATURE:
<223> OTHER INFORMATION: Synthetic

<400> SEQUENCE: 46

```
Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Gly Ile Thr Trp Asn Gly Gly Arg Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Asp Glu Ala Phe Asp Tyr Trp Gly Gln Gly Thr Leu Val
            100                 105                 110

Thr Val Ser Ser
        115
```

<210> SEQ ID NO 47
<211> LENGTH: 337
<212> TYPE: DNA
<213> ORGANISM: Artificial Sequence
<220> FEATURE:
<223> OTHER INFORMATION: Synthetic

<400> SEQUENCE: 47

```
gatattgtga tgacccagac tccactctcc tcacctgtca cccttggaca gccggcctcc      60
atctcctgca ggtctagtca aagcctcgta cacagtgatg caacaccta cttgagttgg     120 cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tattactgca tgcaagcaac acaatttccg     300 tacactttg gccaggggac caagctggag atcaaac                               337
```

<210> SEQ ID NO 48
<211> LENGTH: 112
<212> TYPE: PRT
<213> ORGANISM: Artificial Sequence
<220> FEATURE:
<223> OTHER INFORMATION: Synthetic

<400> SEQUENCE: 48

```
Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
```

```
                65                  70                  75                  80
Ser Arg Val Glu Ala Glu Asp Val Gly Val Tyr Tyr Cys Met Gln Ala
                    85                  90                  95

Thr Gln Phe Pro Tyr Thr Phe Gly Gln Gly Thr Lys Leu Glu Ile Lys
                100                 105                 110
```

<210> SEQ ID NO 49
<211> LENGTH: 348
<212> TYPE: DNA
<213> ORGANISM: Artificial Sequence
<220> FEATURE:
<223> OTHER INFORMATION: Synthetic

<400> SEQUENCE: 49

```
gaagtgcagt tggtggagtc tgggggaggc ttggcacagc ctggcaggtc cctgagagtc      60
tcctgttcag cctctggatt caattttgat gattatgcca tgcactgggt ccggcaagct     120
ccggggaagg gcctggagtg ggtctcaggt attagttgga atagtggtag cagaggctat     180
gcggactctg tgaagggccg cttcaccatc tccagagaca acgccaagaa ctccctgtat     240
ctgcaaatga acagtctgag agctgaggac acggccttgt attactgtgt aaaagagaac     300
tgggcctttg aatactgggg ccagggaacc ctggtcaccg tctcctca                  348
```

<210> SEQ ID NO 50
<211> LENGTH: 116
<212> TYPE: PRT
<213> ORGANISM: Artificial Sequence
<220> FEATURE:
<223> OTHER INFORMATION: Synthetic

<400> SEQUENCE: 50

```
Glu Val Gln Leu Val Glu Ser Gly Gly Gly Leu Ala Gln Pro Gly Arg
  1               5                  10                  15

Ser Leu Arg Val Ser Cys Ser Ala Ser Gly Phe Asn Phe Asp Asp Tyr
                 20                  25                  30

Ala Met His Trp Val Arg Gln Ala Pro Gly Lys Gly Leu Glu Trp Val
             35                  40                  45

Ser Gly Ile Ser Trp Asn Ser Gly Ser Arg Gly Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Val Lys Glu Asn Trp Ala Phe Glu Tyr Trp Gly Gln Gly Thr Leu Val
                100                 105                 110

Thr Val Ser Ser
            115
```

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51

```
ggattcaatt ttgatgatta tgcc                                              24
```

<210> SEQ ID NO 52
<211> LENGTH: 8

<212> TYPE: PRT
<213> ORGANISM: Artificial Sequence
<220> FEATURE:
<223> OTHER INFORMATION: Synthetic

<400> SEQUENCE: 52

Gly Phe Asn Phe Asp Asp Tyr Ala
 1               5

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
attagttgga atagtggtag caga                                           24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Ser Trp Asn Ser Gly Ser Arg
 1               5

<210> SEQ ID NO 55
<211> LENGTH: 27
<212> TYPE: DNA
<213> ORGANISM: Artificial Sequence
<220> FEATURE:
<223> OTHER INFORMATION: Synthetic

<400> SEQUENCE: 55
gtaaaagaga actgggcctt tgaatac                                        27

<210> SEQ ID NO 56
<211> LENGTH: 9
<212> TYPE: PRT
<213> ORGANISM: Artificial Sequence
<220> FEATURE:
<223> OTHER INFORMATION: Synthetic

<400> SEQUENCE: 56

Val Lys Glu Asn Trp Ala Phe Glu Tyr
 1               5

<210> SEQ ID NO 57
<211> LENGTH: 336
<212> TYPE: DNA
<213> ORGANISM: Artificial Sequence
<220> FEATURE:
<223> OTHER INFORMATION: Synthetic

<400> SEQUENCE: 57
gatattgtga tgacccagac tccactctcc tcacctgtca cccttggaca gccggcctcc    60
atctcctgca ggtctagtca tagcctcgta cacagtgatg gaagcaccta cttgagttgg   120
cttcagcaga ggccaggcca gcctccaaga ctcctaattt ataaatttc taaccgattc    180 tctggggtcc cagacagatt cagtggcagt ggggcaggga cagatttcac actgaaaatc   240
agcagggtgg aagctgagga tgtcgggctt tattactgca tgcaggctac acaatttccg   300 tacactttg gccaggggac caagctggag atcaaa          336

<210> SEQ ID NO 58
<211> LENGTH: 112
<212> TYPE: PRT
<213> ORGANISM: Artificial Sequence
<220> FEATURE:
<223> OTHER INFORMATION: Synthetic

<400> SEQUENCE: 58

Asp Ile Val Met Thr Gln Thr Pro Leu Ser Ser Pro Val Thr Leu Gly
1               5                   10                  15

Gln Pro Ala Ser Ile Ser Cys Arg Ser Ser His Ser Leu Val His Ser
            20                  25                  30

Asp Gly Ser Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Leu Tyr Tyr Cys Met Gln Ala
                85                  90                  95

Thr Gln Phe Pro Tyr Thr Phe Gly Gln Gly Thr Lys Leu Glu Ile Lys
            100                 105                 110

<210> SEQ ID NO 59
<211> LENGTH: 33
<212> TYPE: DNA
<213> ORGANISM: Artificial Sequence
<220> FEATURE:
<223> OTHER INFORMATION: Synthetic

<400> SEQUENCE: 59
catagcctcg tacacagtga tggaagcacc tac          33

<210> SEQ ID NO 60
<211> LENGTH: 11
<212> TYPE: PRT
<213> ORGANISM: Artificial Sequence
<220> FEATURE:
<223> OTHER INFORMATION: Synthetic

<400> SEQUENCE: 60

His Ser Leu Val His Ser Asp Gly Ser Thr Tyr
1               5                   10

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 aaaatttct          9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Lys Ile Ser
 1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
atgcaggcta cacaatttcc gtacact                                      27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Met Gln Ala Thr Gln Phe Pro Tyr Thr
 1               5

<210> SEQ ID NO 65
<211> LENGTH: 348
<212> TYPE: DNA
<213> ORGANISM: Artificial Sequence
<220> FEATURE:
<223> OTHER INFORMATION: Synthetic

<400> SEQUENCE: 65
gaagtgcagc tggtggagtc tgggggaggc ttggcacagc ctggcaggtc cctgagagtc    60
tcctgttcag cctctggatt caattttgat gattatgcca tgcactgggt ccggcaagct   120
ccggggaagg gcctggagtg gctctcaggt attagttgga atagtggtag cagaggctat   180
gcggactctg tgaagggccg cttcaccatc tccagagaca acgccaagaa ctccctgtat   240
ctgcaaatga acagtctgag agctgaggac acggccttgt attactgtgt aaaagagaac   300
tgggcctttg aatactgggg ccagggaacc ctggtcaccg tctcctca                348

<210> SEQ ID NO 66
<211> LENGTH: 116
<212> TYPE: PRT
<213> ORGANISM: Artificial Sequence
<220> FEATURE:
<223> OTHER INFORMATION: Synthetic

<400> SEQUENCE: 66

Glu Val Gln Leu Val Glu Ser Gly Gly Gly Leu Ala Gln Pro Gly Arg
 1               5                  10                  15

Ser Leu Arg Val Ser Cys Ser Ala Ser Gly Phe Asn Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Arg Gly Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Val Lys Glu Asn Trp Ala Phe Glu Tyr Trp Gly Gln Gly Thr Leu Val
            100                 105                 110
Thr Val Ser Ser
        115

<210> SEQ ID NO 67
<211> LENGTH: 336
<212> TYPE: DNA
<213> ORGANISM: Artificial Sequence
<220> FEATURE:
<223> OTHER INFORMATION: Synthetic

<400> SEQUENCE: 67
gatattgtga tgacccagac tccactctcc tcacctgtca cccttggaca gccggcctcc     60
atctcctgca ggtctagtca tagcctcgta cacagtgatg gaagcaccta cttgagttgg    120
cttcagcaga ggccaggcca gcctccaaga ctcctaattt ataaaatttc taaccgattc    180
tctggggtcc cagacagatt cagtggcagt ggggcaggga cagatttcac actgaaaatc    240
agcagggtgg aagctgagga tgtcgggctt tattactgca tgcaggctac acaatttccg    300 tacactttg gccaggggac caagctggag atcaaa                              336

<210> SEQ ID NO 68
<211> LENGTH: 112
<212> TYPE: PRT
<213> ORGANISM: Artificial Sequence
<220> FEATURE:
<223> OTHER INFORMATION: Synthetic

<400> SEQUENCE: 68

Asp Ile Val Met Thr Gln Thr Pro Leu Ser Ser Pro Val Thr Leu Gly
1               5                   10                  15

Gln Pro Ala Ser Ile Ser Cys Arg Ser Ser His Ser Leu Val His Ser
            20                  25                  30

Asp Gly Ser Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Leu Tyr Tyr Cys Met Gln Ala
                85                  90                  95

Thr Gln Phe Pro Tyr Thr Phe Gly Gln Gly Thr Lys Leu Glu Ile Lys
            100                 105                 110

<210> SEQ ID NO 69
<211> LENGTH: 348
<212> TYPE: DNA
<213> ORGANISM: Artificial Sequence
<220> FEATURE:
<223> OTHER INFORMATION: Synthetic

<400> SEQUENCE: 69
gaagtgcagc tggtggagtc tgggggaggc ttggtacagc ctggcaggtc cctgagactc     60
tcctgtgcag cctctggatt caattttgat gattatgcca tgcactgggt ccggcaagct    120
ccagggaagg gcctggagtg ggtctcaggt attagttgga atagtggtag cagaggctat    180
gcggactctg tgaagggccg attcaccatc tccagagaca cgccaagaa ctccctgtat    240 ctgcaaatga acagtctgag agctgaggac acggccttgt attactgtgt aaaagagaac    300

```
tgggcctttg aatactgggg ccagggaacc ctggtcaccg tctcctca        348
```

<210> SEQ ID NO 70
<211> LENGTH: 116
<212> TYPE: PRT
<213> ORGANISM: Artificial Sequence
<220> FEATURE:
<223> OTHER INFORMATION: Synthetic

<400> SEQUENCE: 70

```
Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Asn Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Arg Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Glu Asn Trp Ala Phe Glu Tyr Trp Gly Gln Gly Thr Leu Val
            100                 105                 110

Thr Val Ser Ser
        115
```

<210> SEQ ID NO 71
<211> LENGTH: 337
<212> TYPE: DNA
<213> ORGANISM: Artificial Sequence
<220> FEATURE:
<223> OTHER INFORMATION: Synthetic

<400> SEQUENCE: 71

```
gatattgtga tgacccagac tccactctcc tcacctgtca cccttggaca gccggcctcc    60
atctcctgca ggtctagtca tagcctcgta cacagtgatg gaagcaccta cttgagttgg   120
cttcagcaga ggccaggcca gcctccaaga ctcctaattt ataaatttc taaccggttc    180 tctgggtcc cagacagatt cagtggcagt ggggcaggga cagatttcac actgaaaatc    240
agcagggtgg aagctgagga tgtcggggtt tattactgca tgcaggctac acaatttccg    300 tacactttg gccaggggac caagctggag atcaaac                              337
```

<210> SEQ ID NO 72
<211> LENGTH: 112
<212> TYPE: PRT
<213> ORGANISM: Artificial Sequence
<220> FEATURE:
<223> OTHER INFORMATION: Synthetic

<400> SEQUENCE: 72

```
Asp Ile Val Met Thr Gln Thr Pro Leu Ser Ser Pro Val Thr Leu Gly
 1               5                  10                  15

Gln Pro Ala Ser Ile Ser Cys Arg Ser Ser His Ser Leu Val His Ser
            20                  25                  30

Asp Gly Ser Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
```

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Tyr Thr Phe Gly Gln Gly Thr Lys Leu Glu Ile Lys
            100                 105                 110

<210> SEQ ID NO 73
<211> LENGTH: 348
<212> TYPE: DNA
<213> ORGANISM: Artificial Sequence
<220> FEATURE:
<223> OTHER INFORMATION: Synthetic

<400> SEQUENCE: 73
gaagtgcagc tggtggagtc tgggggaggc ttggtacagg ctggcaggtc cctgcgactc      60
tcctgtgcag cctctggatt cacctttgat gattatgcca tgcactgggt ccggcaagct     120
ccagggaagg gcctggagtg ggtctcaggt attagttgga atagtggtag cagaggctat     180
gcggactctg tgaagggccg attcaccatc tccagagaca acgccaaaaa ctccctgcat     240
ctgcaaatgt acagtctgag agctgaggac acggccttgt attactgtgc aaaagagaac     300
tggtcctttg actactgggg ccagggaacc ctggtcaccg tctcctca                  348

<210> SEQ ID NO 74
<211> LENGTH: 116
<212> TYPE: PRT
<213> ORGANISM: Artificial Sequence
<220> FEATURE:
<223> OTHER INFORMATION: Synthetic

<400> SEQUENCE: 74

Glu Val Gln Leu Val Glu Ser Gly Gly Gly Leu Val Gln Ala Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Arg Gly Tyr Ala Asp Ser Val
        50                  55                  60

Lys Gly Arg Phe Thr Ile Ser Arg Asp Asn Ala Lys Asn Ser Leu His
65                  70                  75                  80

Leu Gln Met Tyr Ser Leu Arg Ala Glu Asp Thr Ala Leu Tyr Tyr Cys
                85                  90                  95

Ala Lys Glu Asn Trp Ser Phe Asp Tyr Trp Gly Gln Gly Thr Leu Val
            100                 105                 110

Thr Val Ser Ser
        115

<210> SEQ ID NO 75
<211> LENGTH: 24
<212> TYPE: DNA
<213> ORGANISM: Artificial Sequence
<220> FEATURE:
<223> OTHER INFORMATION: Synthetic

<400> SEQUENCE: 75
ggattcacct ttgatgatta tgcc                                             24

<210> SEQ ID NO 76
<211> LENGTH: 8
<212> TYPE: PRT
<213> ORGANISM: Artificial Sequence
<220> FEATURE:
<223> OTHER INFORMATION: Synthetic

<400> SEQUENCE: 76

Gly Phe Thr Phe Asp Asp Tyr Ala
 1               5

<210> SEQ ID NO 77
<211> LENGTH: 24
<212> TYPE: DNA
<213> ORGANISM: Artificial Sequence
<220> FEATURE:
<223> OTHER INFORMATION: Synthetic

<400> SEQUENCE: 77
attagttgga atagtggtag caga                                              24

<210> SEQ ID NO 78
<211> LENGTH: 8
<212> TYPE: PRT
<213> ORGANISM: Artificial Sequence
<220> FEATURE:
<223> OTHER INFORMATION: Synthetic

<400> SEQUENCE: 78

Ile Ser Trp Asn Ser Gly Ser Arg
 1               5

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
gcaaaagaga actggtcctt tgactac                                           27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Ala Lys Glu Asn Trp Ser Phe Asp Tyr
 1               5

<210> SEQ ID NO 81
<211> LENGTH: 336
<212> TYPE: DNA
<213> ORGANISM: Artificial Sequence
<220> FEATURE:
<223> OTHER INFORMATION: Synthetic

<400> SEQUENCE: 81
gatattgtga tgacccagac tccactctcc tcacctgtca cccttggaca gccggcctcc      60
atctcctgca ggtctagtca aagcctcgta cacagtgatg aaacacccta cttgagttgg     120
cttcagcaga ggccaggcca gcctccaaga ctcctaattt ataagatttc ttaccggttc     180
tctggggtcc cagacagatt cagtggcagt ggggcaggga cagatttcac actgaaaatc        240
agcagggtgg caactgagga tgtcggggtt tattactgca tgcaagctac acaattgccg        300 tacactttg gccaggggac caagctggag atcaaa        336

```
<210> SEQ ID NO 82
<211> LENGTH: 112
<212> TYPE: PRT
<213> ORGANISM: Artificial Sequence
<220> FEATURE:
<223> OTHER INFORMATION: Synthetic

<400> SEQUENCE: 82

Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Tyr Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Ala Thr Glu Asp Val Gly Val Tyr Tyr Cys Met Gln Ala
                85                  90                  95

Thr Gln Leu Pro Tyr Thr Phe Gly Gln Gly Thr Lys Leu Glu Ile Lys
            100                 105                 110

<210> SEQ ID NO 83
<211> LENGTH: 33
<212> TYPE: DNA
<213> ORGANISM: Artificial Sequence
<220> FEATURE:
<223> OTHER INFORMATION: Synthetic

<400> SEQUENCE: 83
caaagcctcg tacacagtga tggaaacacc tac        33

<210> SEQ ID NO 84
<211> LENGTH: 11
<212> TYPE: PRT
<213> ORGANISM: Artificial Sequence
<220> FEATURE:
<223> OTHER INFORMATION: Synthetic

<400> SEQUENCE: 84

Gln Ser Leu Val His Ser Asp Gly Asn Thr Tyr
 1               5                  10

<210> SEQ ID NO 85
<211> LENGTH: 9
<212> TYPE: DNA
<213> ORGANISM: Artificial Sequence
<220> FEATURE:
<223> OTHER INFORMATION: Synthetic

<400> SEQUENCE: 85 aagatttct        9

<210> SEQ ID NO 86
<211> LENGTH: 3
<212> TYPE: PRT
<213> ORGANISM: Artificial Sequence
```

```
<220> FEATURE:
<223> OTHER INFORMATION: Synthetic

<400> SEQUENCE: 86

Lys Ile Ser
 1

<210> SEQ ID NO 87
<211> LENGTH: 27
<212> TYPE: DNA
<213> ORGANISM: Artificial Sequence
<220> FEATURE:
<223> OTHER INFORMATION: Synthetic

<400> SEQUENCE: 87
atgcaagcta cacaattgcc gtacact                                            27

<210> SEQ ID NO 88
<211> LENGTH: 9
<212> TYPE: PRT
<213> ORGANISM: Artificial Sequence
<220> FEATURE:
<223> OTHER INFORMATION: Synthetic

<400> SEQUENCE: 88

Met Gln Ala Thr Gln Leu Pro Tyr Thr
 1               5

<210> SEQ ID NO 89
<211> LENGTH: 348
<212> TYPE: DNA
<213> ORGANISM: Artificial Sequence
<220> FEATURE:
<223> OTHER INFORMATION: Synthetic

<400> SEQUENCE: 89
gaagtgcagc tggtggagtc tgggggaggc ttggtacagg ctggcaggtc cctgcgactc        60
tcctgtgcag cctctggatt caccttggat gattatgcca tgcactgggt ccggcaagct       120
ccagggaagg gcctggagtg ggtctcaggt attagttgga atagtggtag cagaggctat       180
gcggactctg tgaagggccg attcaccatc tccagagaca acgccaaaaa ctccctgcat       240
ctgcaaatgt acagtctgag agctgaggac acggccttgt attactgtgc aaaagagaac       300
tggtcctttg actactgggg ccagggaacc ctggtcaccg tctcctca                    348

<210> SEQ ID NO 90
<211> LENGTH: 116
<212> TYPE: PRT
<213> ORGANISM: Artificial Sequence
<220> FEATURE:
<223> OTHER INFORMATION: Synthetic

<400> SEQUENCE: 90

Glu Val Gln Leu Val Glu Ser Gly Gly Gly Leu Val Gln Ala Gly Arg
 1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Gly Ile Ser Trp Asn Ser Gly Ser Arg Gly Tyr Ala Asp Ser Val
     50                  55                  60

Lys Gly Arg Phe Thr Ile Ser Arg Asp Asn Ala Lys Asn Ser Leu His
 65                  70                  75                  80
```

```
Leu Gln Met Tyr Ser Leu Arg Ala Glu Asp Thr Ala Leu Tyr Tyr Cys
                85                  90                  95

Ala Lys Glu Asn Trp Ser Phe Asp Tyr Trp Gly Gln Gly Thr Leu Val
            100                 105                 110

Thr Val Ser Ser
        115

<210> SEQ ID NO 91
<211> LENGTH: 336
<212> TYPE: DNA
<213> ORGANISM: Artificial Sequence
<220> FEATURE:
<223> OTHER INFORMATION: Synthetic

<400> SEQUENCE: 91
gatattgtga tgacccagac tccactctcc tcacctgtca cccttggaca gccggcctcc      60
atctcctgca ggtctagtca aagcctcgta cacagtgatg gaaacaccta cttgagttgg     120
cttcagcaga ggccaggcca gcctccaaga ctcctaattt ataagatttc ttaccggttc     180
tctggggtcc cagacagatt cagtggcagt ggggcaggga cagatttcac actgaaaatc     240
agcagggtgg aactgagga tgtcgggggtt tattactgca tgcaagctac acaattgccg     300 tacactttg gccaggggac caagctggag atcaaa                                336

<210> SEQ ID NO 92
<211> LENGTH: 112
<212> TYPE: PRT
<213> ORGANISM: Artificial Sequence
<220> FEATURE:
<223> OTHER INFORMATION: Synthetic

<400> SEQUENCE: 92

Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Tyr Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Ala Thr Glu Asp Val Gly Val Tyr Tyr Cys Met Gln Ala
                85                  90                  95

Thr Gln Leu Pro Tyr Thr Phe Gly Gln Gly Thr Lys Leu Glu Ile Lys
            100                 105                 110

<210> SEQ ID NO 93
<211> LENGTH: 348
<212> TYPE: DNA
<213> ORGANISM: Artificial Sequence
<220> FEATURE:
<223> OTHER INFORMATION: Synthetic

<400> SEQUENCE: 93
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg gtctcaggt attagttgga atagtggtag cagaggctat     180
```

```
gcggactctg tgaagggccg attcaccatc tccagagaca acgccaagaa ctccctgtat    240
ctgcaaatga acagtctgag agctgaggac acggccttgt attactgtgc aaaagagaac    300
tggtcctttg actactgggg ccagggaacc ctggtcaccg tctcctca                 348
```

<210> SEQ ID NO 94
<211> LENGTH: 116
<212> TYPE: PRT
<213> ORGANISM: Artificial Sequence
<220> FEATURE:
<223> OTHER INFORMATION: Synthetic

<400> SEQUENCE: 94

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Arg Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Asn Trp Ser Phe Asp Tyr Trp Gly Gln Gly Thr Leu Val
            100                 105                 110

Thr Val Ser Ser
        115
```

<210> SEQ ID NO 95
<211> LENGTH: 337
<212> TYPE: DNA
<213> ORGANISM: Artificial Sequence
<220> FEATURE:
<223> OTHER INFORMATION: Synthetic

<400> SEQUENCE: 95

```
gatattgtga tgacccagac tccactctcc tcacctgtca cccttggaca gccggcctcc    60
atctcctgca ggtctagtca aagcctcgta cacagtgatg gaaacaccta cttgagttgg    120
cttcagcaga ggccaggcca gcctccaaga ctcctaattt ataagatttc taaccggttc    180
tctggggtcc cagacagatt cagtggcagt ggggcaggga cagatttcac actgaaaatc    240
agcagggtgg aagctgagga tgtcggggtt tattactgca tgcaagctac acaattgccg    300
tacacttttg gccaggggac caagctggag atcaaac                             337
```

<210> SEQ ID NO 96
<211> LENGTH: 112
<212> TYPE: PRT
<213> ORGANISM: Artificial Sequence
<220> FEATURE:
<223> OTHER INFORMATION: Synthetic

<400> SEQUENCE: 96

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
```

```
                35                  40                  45
Pro Arg Leu Leu Ile Tyr Lys Ile Ser Asn Arg Phe Ser Gly Val Pro
         50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Thr Gln Leu Pro Tyr Thr Phe Gly Gln Gly Thr Lys Leu Glu Ile Lys
            100                 105                 110
```

<210> SEQ ID NO 97
<211> LENGTH: 357
<212> TYPE: DNA
<213> ORGANISM: Artificial Sequence
<220> FEATURE:
<223> OTHER INFORMATION: Synthetic

<400> SEQUENCE: 97

```
gaggtgcagc tgttggagtc tgggggaggc ttggtacagc cggggggtc cctgagactc      60 tcctgtgcag cctctggatt caccttagc agctatgcca tgacctgggt ccgccaggct    120
ccggggaagg ggctgtattg gtctcagct attagtggtg gtcgtggtag cgcatactac    180
gcagactccg tgaagggccg gttcaccatc tccagagaca attccaagaa cacgctgtat    240
ctgcaaatga acagcctgcg agccgaggac acggccgtat attactgtgc gaaagagggg    300
gatagtggct acgatttggc ctactggggc cggggaaccc tggtcaccgt ctcgtca       357
```

<210> SEQ ID NO 98
<211> LENGTH: 119
<212> TYPE: PRT
<213> ORGANISM: Artificial Sequence
<220> FEATURE:
<223> OTHER INFORMATION: Synthetic

<400> SEQUENCE: 98

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Thr Trp Val Arg Gln Ala Pro Gly Lys Gly Leu Tyr Trp Val
         35                  40                  45

Ser Ala Ile Ser Gly Gly Arg Gly Ser Ala Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Gly Asp Ser Gly Tyr Asp Leu Ala Tyr Trp Gly Arg Gly
            100                 105                 110

Thr Leu Val Thr Val Ser Ser
        115
```

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99

```
ggattcacct ttagcagcta tgcc                                              24
```

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

```
Gly Phe Thr Phe Ser Ser Tyr Ala
  1               5
```

<210> SEQ ID NO 101
<211> LENGTH: 24
<212> TYPE: DNA
<213> ORGANISM: Artificial Sequence
<220> FEATURE:
<223> OTHER INFORMATION: Synthetic

<400> SEQUENCE: 101

```
attagtggtg gtcgtggtag cgca                                              24
```

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

```
Ile Ser Gly Gly Arg Gly Ser Ala
  1               5
```

<210> SEQ ID NO 103
<211> LENGTH: 36
<212> TYPE: DNA
<213> ORGANISM: Artificial Sequence
<220> FEATURE:
<223> OTHER INFORMATION: Synthetic

<400> SEQUENCE: 103

```
gcgaaagagg gggatagtgg ctacgatttg gcctac                                 36
```

<210> SEQ ID NO 104
<211> LENGTH: 12
<212> TYPE: PRT
<213> ORGANISM: Artificial Sequence
<220> FEATURE:
<223> OTHER INFORMATION: Synthetic

<400> SEQUENCE: 104

```
Ala Lys Glu Gly Asp Ser Gly Tyr Asp Leu Ala Tyr
  1               5                  10
```

<210> SEQ ID NO 105
<211> LENGTH: 321
<212> TYPE: DNA
<213> ORGANISM: Artificial Sequence
<220> FEATURE:
<223> OTHER INFORMATION: Synthetic

<400> SEQUENCE: 105

```
gacatccaga tgacccagtc tccatcctca ctgtccgcat ctgtaggaga cagagtcacc       60
atcacttgtc gggcgaggca gggcattagt aataatttag cctggcttca gcagaaacca      120
```

-continued

```
gggaaagccc ctaagtccct gatctatgct gcatccagtt tgcaaagtgg gatcccatca    180
aagttcagcg gcagtggatc tgggacatat ttcactctca ccatcagcag cctgcagcct    240
gaagattttg cgacttatta ctgccaacaa tataaaagtt ccccgctcac tttcggcgga    300
gggaccaagg tggagatcaa a                                              321
```

```
<210> SEQ ID NO 106
<211> LENGTH: 107
<212> TYPE: PRT
<213> ORGANISM: Artificial Sequence
<220> FEATURE:
<223> OTHER INFORMATION: Synthetic

<400> SEQUENCE: 106
```

Asp Ile Gln Met Thr Gln Ser Pro Ser Ser Leu Ser Ala Ser Val Gly
1               5                   10                  15

Asp Arg Val Thr Ile Thr Cys Arg Ala Arg Gln Gly Ile Ser Asn Asn
            20                  25                  30

Leu Ala Trp Leu Gln Gln Lys Pro Gly Lys Ala Pro Lys Ser Leu Ile
        35                  40                  45

Tyr Ala Ala Ser Ser Leu Gln Ser Gly Ile Pro Ser Lys Phe Ser Gly
    50                  55                  60

Ser Gly Ser Gly Thr Tyr Phe Thr Leu Thr Ile Ser Ser Leu Gln Pro
65                  70                  75                  80

Glu Asp Phe Ala Thr Tyr Tyr Cys Gln Gln Tyr Lys Ser Ser Pro Leu
                85                  90                  95

Thr Phe Gly Gly Gly Thr Lys Val Glu Ile Lys
            100                 105

```
<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
cagggcatta gtaataat                                                   18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108
```

Gln Gly Ile Ser Asn Asn
1               5

```
<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gctgcatcc                                                              9

<210> SEQ ID NO 110
```

```
<211> LENGTH: 3
<212> TYPE: PRT
<213> ORGANISM: Artificial Sequence
<220> FEATURE:
<223> OTHER INFORMATION: Synthetic

<400> SEQUENCE: 110

Ala Ala Ser
 1

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
caacaatata aaagttcccc gctcact                                        27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Gln Gln Tyr Lys Ser Ser Pro Leu Thr
 1               5

<210> SEQ ID NO 113
<211> LENGTH: 357
<212> TYPE: DNA
<213> ORGANISM: Artificial Sequence
<220> FEATURE:
<223> OTHER INFORMATION: Synthetic

<400> SEQUENCE: 113
gaggtgcagc tgttggagtc tgggggaggc ttggtacagc cggggggggtc cctgagactc     60 tcctgtgcag cctctggatt cacctttagc agctatgcca tgacctgggt ccgccaggct    120
ccggggaagg ggctgtattg ggtctcagct attagtggtg gtcgtggtag cgcatactac    180
gcagactccg tgaagggccg gttcaccatc tccagagaca attccaagaa cacgctgtat    240
ctgcaaatga acagcctgcg agccgaggac acggccgtat attactgtgc gaaagagggg    300
gatagtggct acgatttggc ctactggggc cggggaaccc tggtcaccgt ctcctca       357

<210> SEQ ID NO 114
<211> LENGTH: 119
<212> TYPE: PRT
<213> ORGANISM: Artificial Sequence
<220> FEATURE:
<223> OTHER INFORMATION: Synthetic

<400> SEQUENCE: 114

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Thr Trp Val Arg Gln Ala Pro Gly Lys Gly Leu Tyr Trp Val
         35                  40                  45

Ser Ala Ile Ser Gly Gly Arg Gly Ser Ala Tyr Tyr Ala Asp Ser Val
     50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Gly Asp Ser Gly Tyr Asp Leu Ala Tyr Trp Gly Arg Gly
            100                 105                 110

Thr Leu Val Thr Val Ser Ser
        115

<210> SEQ ID NO 115
<211> LENGTH: 321
<212> TYPE: DNA
<213> ORGANISM: Artificial Sequence
<220> FEATURE:
<223> OTHER INFORMATION: Synthetic

<400> SEQUENCE: 115
gacatccaga tgacccagtc tccatcctca ctgtccgcat ctgtaggaga cagagtcacc    60
atcacttgtc gggcgaggca gggcattagt aataatttag cctggcttca gcagaaacca   120
gggaaagccc ctaagtccct gatctatgct gcatccagtt tgcaaagtgg gatcccatca   180
aagttcagcg gcagtggatc tgggacatat ttcactctca ccatcagcag cctgcagcct   240
gaagattttg cgacttatta ctgccaacaa tataaaagtt ccccgctcac tttcggcgga   300
gggaccaagg tggagatcaa a                                             321

<210> SEQ ID NO 116
<211> LENGTH: 107
<212> TYPE: PRT
<213> ORGANISM: Artificial Sequence
<220> FEATURE:
<223> OTHER INFORMATION: Synthetic

<400> SEQUENCE: 116

Asp Ile Gln Met Thr Gln Ser Pro Ser Ser Leu Ser Ala Ser Val Gly
  1               5                  10                  15

Asp Arg Val Thr Ile Thr Cys Arg Ala Arg Gln Gly Ile Ser Asn Asn
             20                  25                  30

Leu Ala Trp Leu Gln Gln Lys Pro Gly Lys Ala Pro Lys Ser Leu Ile
         35                  40                  45

Tyr Ala Ala Ser Ser Leu Gln Ser Gly Ile Pro Ser Lys Phe Ser Gly
     50                  55                  60

Ser Gly Ser Gly Thr Tyr Phe Thr Leu Thr Ile Ser Ser Leu Gln Pro
 65                  70                  75                  80

Glu Asp Phe Ala Thr Tyr Tyr Cys Gln Gln Tyr Lys Ser Ser Pro Leu
                 85                  90                  95

Thr Phe Gly Gly Gly Thr Lys Val Glu Ile Lys
            100                 105

<210> SEQ ID NO 117
<211> LENGTH: 357
<212> TYPE: DNA
<213> ORGANISM: Artificial Sequence
<220> FEATURE:
<223> OTHER INFORMATION: Synthetic

<400> SEQUENCE: 117
gaggtgcagc tgttggagtc tgggggaggc ttggtacagc ctggggggtc cctgagactc    60
tcctgtgcag cctctggatt cacctttagc agctatgcca tgagctgggt ccgccaggct   120
```

-continued

```
ccagggaagg ggctggagtg ggtctcagct attagtggtg gtcgtggtag cgcatactac    180
gcagactccg tgaagggccg gttcaccatc tccagagaca attccaagaa cacgctgtat    240
ctgcaaatga acagcctgag agccgaggac acggccgtat attactgtgc gaaagagggg    300
gatagtggct acgatttggc ctactggggc cagggaaccc tggtcaccgt ctcctca       357
```

<210> SEQ ID NO 118
<211> LENGTH: 119
<212> TYPE: PRT
<213> ORGANISM: Artificial Sequence
<220> FEATURE:
<223> OTHER INFORMATION: Synthetic

<400> SEQUENCE: 118

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Gly Arg Gly Ser Ala Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Gly Asp Ser Gly Tyr Asp Leu Ala Tyr Trp Gly Gln Gly
            100                 105                 110

Thr Leu Val Thr Val Ser Ser
        115
```

<210> SEQ ID NO 119
<211> LENGTH: 322
<212> TYPE: DNA
<213> ORGANISM: Artificial Sequence
<220> FEATURE:
<223> OTHER INFORMATION: Synthetic

<400> SEQUENCE: 119

```
gacatccaga tgacccagtc tccatcctca ctgtctgcat ctgtaggaga cagagtcacc    60
atcacttgtc gggcgagtca gggcattagt aataatttag cctggtttca gcagaaacca    120
gggaaagccc ctaagtccct gatctatgct gcatccagtt tgcaaagtgg ggtcccatca    180
aggttcagcg gcagtggatc tgggacagat ttcactctca ccatcagcag cctgcagcct    240
gaagattttg caacttatta ctgccaacaa tataaaagtt ccccgctcac tttcggcgga    300
gggaccaagg tggagatcaa ac                                             322
```

<210> SEQ ID NO 120
<211> LENGTH: 107
<212> TYPE: PRT
<213> ORGANISM: Artificial Sequence
<220> FEATURE:
<223> OTHER INFORMATION: Synthetic

<400> SEQUENCE: 120

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Asn
```

```
                    20                  25                  30

Leu Ala Trp Phe Gln Gln Lys Pro Gly Lys Ala Pro Lys Ser Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Ser Ser Pro Leu
                85                  90                  95

Thr Phe Gly Gly Gly Thr Lys Val Glu Ile Lys
            100                 105

<210> SEQ ID NO 121
<211> LENGTH: 357
<212> TYPE: DNA
<213> ORGANISM: Artificial Sequence
<220> FEATURE:
<223> OTHER INFORMATION: Synthetic

<400> SEQUENCE: 121
gaggtgcagc tgttggagtc gggggggaggc ttggtacagc ctgggggtc cctgagactc    60 tcctgtgcaa cctctggatt cacctttagc agatatacca tgacctgggt ccgccaggct   120
ccagggaagg gctgttttg gtctcaggt attggtggta gtggtggtcg cgatactac     180 gcagactccg tgaagggccg gttcaccctc tccagagaca attccaagaa cacgctgtat   240
ctgcaaatga acagcctgag agccgaggac acggccgtat attactgtgc gaaagagggg   300
gatagtggct acgatttgga ctactggggc cggggaaccc tggtcaccgt ctcgtca     357

<210> SEQ ID NO 122
<211> LENGTH: 119
<212> TYPE: PRT
<213> ORGANISM: Artificial Sequence
<220> FEATURE:
<223> OTHER INFORMATION: Synthetic

<400> SEQUENCE: 122

Glu Val Gln Leu Leu Glu Ser Gly Gly Gly Leu Val Gln Pro Gly Gly
1               5                   10                  15

Ser Leu Arg Leu Ser Cys Ala Thr Ser Gly Phe Thr Phe Ser Arg Tyr
            20                  25                  30

Thr Met Thr Trp Val Arg Gln Ala Pro Gly Lys Gly Leu Phe Trp Val
        35                  40                  45

Ser Gly Ile Gly Gly Ser Gly Arg Ala Tyr Tyr Ala Asp Ser Val
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Asp Ser Gly Tyr Asp Leu Asp Tyr Trp Gly Arg Gly
            100                 105                 110

Thr Leu Val Thr Val Ser Ser
        115

<210> SEQ ID NO 123
<211> LENGTH: 24
<212> TYPE: DNA
<213> ORGANISM: Artificial Sequence
<220> FEATURE:
```

<223> OTHER INFORMATION: Synthetic

<400> SEQUENCE: 123
ggattcacct ttagcagata tacc                                          24

<210> SEQ ID NO 124
<211> LENGTH: 8
<212> TYPE: PRT
<213> ORGANISM: Artificial Sequence
<220> FEATURE:
<223> OTHER INFORMATION: Synthetic

<400> SEQUENCE: 124

Gly Phe Thr Phe Ser Arg Tyr Thr
1               5

<210> SEQ ID NO 125
<211> LENGTH: 24
<212> TYPE: DNA
<213> ORGANISM: Artificial Sequence
<220> FEATURE:
<223> OTHER INFORMATION: Synthetic

<400> SEQUENCE: 125
attggtggta gtggtggtcg cgca                                          24

<210> SEQ ID NO 126
<211> LENGTH: 8
<212> TYPE: PRT
<213> ORGANISM: Artificial Sequence
<220> FEATURE:
<223> OTHER INFORMATION: Synthetic

<400> SEQUENCE: 126

Ile Gly Gly Ser Gly Gly Arg Ala
1               5

<210> SEQ ID NO 127
<211> LENGTH: 36
<212> TYPE: DNA
<213> ORGANISM: Artificial Sequence
<220> FEATURE:
<223> OTHER INFORMATION: Synthetic

<400> SEQUENCE: 127
gcgaaagagg gggatagtgg ctacgatttg gactac                             36

<210> SEQ ID NO 128
<211> LENGTH: 12
<212> TYPE: PRT
<213> ORGANISM: Artificial Sequence
<220> FEATURE:
<223> OTHER INFORMATION: Synthetic

<400> SEQUENCE: 128

Ala Lys Glu Gly Asp Ser Gly Tyr Asp Leu Asp Tyr
1               5                   10

<210> SEQ ID NO 129
<211> LENGTH: 321
<212> TYPE: DNA
<213> ORGANISM: Artificial Sequence
<220> FEATURE:
<223> OTHER INFORMATION: Synthetic

<400> SEQUENCE: 129

```
gacatccaga tgacccagta tccatcctca ctgtctgcat ctgtaggaga cagagtcacc    60
atcacttgtc gggcgaggca gggcataagt aattatttag cctggcttca gcagaaacca   120
gggaaagccc ctaagtccct gatctatgct gcatccagtt tgcaaagggg ggtcccatca   180
aagttcagcg gcagtggatc tgggacagat ttcactctca ccatcagcag cctgcagcct   240
gaagattctg caacttatta ctgccaacaa tataaaattt ccccgctcac tttcggcgga   300
gggaccaagg tggagatcaa g                                             321
```

<210> SEQ ID NO 130
<211> LENGTH: 107
<212> TYPE: PRT
<213> ORGANISM: Artificial Sequence
<220> FEATURE:
<223> OTHER INFORMATION: Synthetic

<400> SEQUENCE: 130

```
Asp Ile Gln Met Thr Gln Tyr Pro Ser Ser Leu Ser Ala Ser Val Gly
  1               5                  10                  15

Asp Arg Val Thr Ile Thr Cys Arg Ala Arg Gln Gly Ile Ser Asn Tyr
             20                  25                  30

Leu Ala Trp Leu Gln Gln Lys Pro Gly Lys Ala Pro Lys Ser Leu Ile
         35                  40                  45

Tyr Ala Ala Ser Ser Leu Gln Arg Gly Val Pro Ser Lys Phe Ser Gly
     50                  55                  60

Ser Gly Ser Gly Thr Asp Phe Thr Leu Thr Ile Ser Ser Leu Gln Pro
 65                  70                  75                  80

Glu Asp Ser Ala Thr Tyr Tyr Cys Gln Gln Tyr Lys Ile Ser Pro Leu
                 85                  90                  95

Thr Phe Gly Gly Gly Thr Lys Val Glu Ile Lys
            100                 105
```

<210> SEQ ID NO 131
<211> LENGTH: 18
<212> TYPE: DNA
<213> ORGANISM: Artificial Sequence
<220> FEATURE:
<223> OTHER INFORMATION: Synthetic

<400> SEQUENCE: 131

```
cagggcataa gtaattat                                                  18
```

<210> SEQ ID NO 132
<211> LENGTH: 6
<212> TYPE: PRT
<213> ORGANISM: Artificial Sequence
<220> FEATURE:
<223> OTHER INFORMATION: Synthetic

<400> SEQUENCE: 132

```
Gln Gly Ile Ser Asn Tyr
  1               5
```

<210> SEQ ID NO 133
<211> LENGTH: 9
<212> TYPE: DNA
<213> ORGANISM: Artificial Sequence
<220> FEATURE:
<223> OTHER INFORMATION: Synthetic

<400> SEQUENCE: 133

```
gctgcatcc                                                             9
```

<210> SEQ ID NO 134
<211> LENGTH: 3
<212> TYPE: PRT
<213> ORGANISM: Artificial Sequence
<220> FEATURE:
<223> OTHER INFORMATION: Synthetic

<400> SEQUENCE: 134

Ala Ala Ser
 1

<210> SEQ ID NO 135
<211> LENGTH: 27
<212> TYPE: DNA
<213> ORGANISM: Artificial Sequence
<220> FEATURE:
<223> OTHER INFORMATION: Synthetic

<400> SEQUENCE: 135
caacaatata aaatttcccc gctcact                                          27

<210> SEQ ID NO 136
<211> LENGTH: 9
<212> TYPE: PRT
<213> ORGANISM: Artificial Sequence
<220> FEATURE:
<223> OTHER INFORMATION: Synthetic

<400> SEQUENCE: 136

Gln Gln Tyr Lys Ile Ser Pro Leu Thr
 1               5

<210> SEQ ID NO 137
<211> LENGTH: 357
<212> TYPE: DNA
<213> ORGANISM: Artificial Sequence
<220> FEATURE:
<223> OTHER INFORMATION: Synthetic

<400> SEQUENCE: 137
gaggtgcagc tgttggagtc tgggggaggc ttggtacagc ctggggggtc cctgagactc      60
tcctgtgcaa cctctggatt cacctttagc agatatacca tgacctgggt ccgccaggct     120
ccagggaagg ggctgttttg ggtctcaggt attggtggta gtggtggtcg cgcatactac     180
gcagactccg tgaagggccg gttcaccctc tccagagaca attccaagaa cacgctgtat     240
ctgcaaatga acagcctgag agccgaggac acggccgtat attactgtgc gaaagagggg     300
gatagtggct acgatttgga ctactggggc cggggaaccc tggtcaccgt ctcctca       357

<210> SEQ ID NO 138
<211> LENGTH: 119
<212> TYPE: PRT
<213> ORGANISM: Artificial Sequence
<220> FEATURE:
<223> OTHER INFORMATION: Synthetic

<400> SEQUENCE: 138

Glu Val Gln Leu Leu Glu Ser Gly Gly Gly Leu Val Gln Pro Gly Gly
 1               5                  10                  15

Ser Leu Arg Leu Ser Cys Ala Thr Ser Gly Phe Thr Phe Ser Arg Tyr
             20                  25                  30

Thr Met Thr Trp Val Arg Gln Ala Pro Gly Lys Gly Leu Phe Trp Val
         35                  40                  45

```
Ser Gly Ile Gly Gly Ser Gly Gly Arg Ala Tyr Tyr Ala Asp Ser Val
    50                  55                  60

Lys Gly Arg Phe Thr Leu Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Gly Asp Ser Gly Tyr Asp Leu Asp Tyr Trp Gly Arg Gly
            100                 105                 110

Thr Leu Val Thr Val Ser Ser
            115
```

<210> SEQ ID NO 139
<211> LENGTH: 321
<212> TYPE: DNA
<213> ORGANISM: Artificial Sequence
<220> FEATURE:
<223> OTHER INFORMATION: Synthetic

<400> SEQUENCE: 139

```
gacatccaga tgacccagtc tccatcctca ctgtctgcat ctgtaggaga cagagtcacc    60
atcacttgtc gggcgaggca gggcataagt aattatttag cctggcttca gcagaaacca   120
gggaaagccc ctaagtccct gatctatgct gcatccagtt tgcaaagggg ggtcccatca   180
aagttcagcg gcagtggatc tgggacagat ttcactctca ccatcagcag cctgcagcct   240
gaagattctg caacttatta ctgccaacaa tataaaattt ccccgctcac tttcggcgga   300
gggaccaagg tggagatcaa a                                             321
```

<210> SEQ ID NO 140
<211> LENGTH: 107
<212> TYPE: PRT
<213> ORGANISM: Artificial Sequence
<220> FEATURE:
<223> OTHER INFORMATION: Synthetic

<400> SEQUENCE: 140

```
Asp Ile Gln Met Thr Gln Ser Pro Ser Ser Leu Ser Ala Ser Val Gly
  1               5                  10                  15

Asp Arg Val Thr Ile Thr Cys Arg Ala Arg Gln Gly Ile Ser Asn Tyr
             20                  25                  30

Leu Ala Trp Leu Gln Gln Lys Pro Gly Lys Ala Pro Lys Ser Leu Ile
         35                  40                  45

Tyr Ala Ala Ser Ser Leu Gln Arg Gly Val Pro Ser Lys Phe Ser Gly
 50                  55                  60

Ser Gly Ser Gly Thr Asp Phe Thr Leu Thr Ile Ser Ser Leu Gln Pro
 65                  70                  75                  80

Glu Asp Ser Ala Thr Tyr Tyr Cys Gln Gln Tyr Lys Ile Ser Pro Leu
                 85                  90                  95

Thr Phe Gly Gly Gly Thr Lys Val Glu Ile Lys
            100                 105
```

<210> SEQ ID NO 141
<211> LENGTH: 357
<212> TYPE: DNA
<213> ORGANISM: Artificial Sequence
<220> FEATURE:
<223> OTHER INFORMATION: Synthetic

<400> SEQUENCE: 141

```
gaggtgcagc tgttggagtc tgggggaggc ttggtacagc ctggggggtc cctgagactc    60
tcctgtgcag cctctggatt cacctttagc agatatacca tgagctgggt ccgccaggct   120
ccagggaagg ggctggagtg ggtctcagct attggtggta gtggtggtcg cgcatactac   180
gcagactccg tgaagggccg gttcaccatc tccagagaca attccaagaa cacgctgtat   240
ctgcaaatga acagcctgag agccgaggac acggccgtat attactgtgc gaaagagggg   300
gatagtggct acgatttgga ctactggggc cagggaaccc tggtcaccgt ctcctca     357
```

<210> SEQ ID NO 142
<211> LENGTH: 119
<212> TYPE: PRT
<213> ORGANISM: Artificial Sequence
<220> FEATURE:
<223> OTHER INFORMATION: Synthetic

<400> SEQUENCE: 142

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ser Ala Ile Gly Gly Ser Gly Gly Arg Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Asp Ser Gly Tyr Asp Leu Asp Tyr Trp Gly Gln Gly
            100                 105                 110

Thr Leu Val Thr Val Ser Ser
        115
```

<210> SEQ ID NO 143
<211> LENGTH: 322
<212> TYPE: DNA
<213> ORGANISM: Artificial Sequence
<220> FEATURE:
<223> OTHER INFORMATION: Synthetic

<400> SEQUENCE: 143

```
gacatccaga tgacccagtc tccatcctca ctgtctgcat ctgtaggaga cagagtcacc    60
atcacttgtc gggcgagtca gggcataagt aattatttag cctggtttca gcagaaacca   120
gggaaagccc ctaagtccct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgccaacaa tataaaattt ccccgctcac tttcggcgga   300
gggaccaagg tggagatcaa ac                                            322
```

<210> SEQ ID NO 144
<211> LENGTH: 107
<212> TYPE: PRT
<213> ORGANISM: Artificial Sequence
<220> FEATURE:
<223> OTHER INFORMATION: Synthetic

<400> SEQUENCE: 144

```
Asp Ile Gln Met Thr Gln Ser Pro Ser Ser Leu Ser Ala Ser Val Gly
```

```
            1               5                  10                 15
Asp Arg Val Thr Ile Thr Cys Arg Ala Ser Gln Gly Ile Ser Asn Tyr
                20                  25                  30

Leu Ala Trp Phe Gln Gln Lys Pro Gly Lys Ala Pro Lys Ser Leu Ile
                35                  40                  45

Tyr Ala Ala Ser Ser Leu Gln Ser Gly Val Pro Ser Arg Phe Ser Gly
                50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Gln Gln Tyr Lys Ile Ser Pro Leu
                85                  90                  95

Thr Phe Gly Gly Gly Thr Lys Val Glu Ile Lys
                100                 105
```

<210> SEQ ID NO 145
<211> LENGTH: 357
<212> TYPE: DNA
<213> ORGANISM: Artificial Sequence
<220> FEATURE:
<223> OTHER INFORMATION: Synthetic

<400> SEQUENCE: 145

```
gaggtgcagc tgttggagtc ggggggaggc ttggtacagc ctggggggtc cctgagactc    60
tcctgtgcaa cctctggatt cacctttagc agatatacca tgacctgggt ccgccaggct   120
ccagggaagg ggctgttttg ggtctcaggt attggtggta gtggtggtcg cgcatactac   180
gcagactccg tgaagggccg gttcaccctc tccagagaca attccaagaa cacgctgtat   240
ctgcaaatga acagcctgag agccgaggac acggccgtat attactgtgc gaaagagggg   300
gatagtggct acgatttgga ctactggggc cggggaaccc tggtcaccgt ctcgtca      357
```

<210> SEQ ID NO 146
<211> LENGTH: 119
<212> TYPE: PRT
<213> ORGANISM: Artificial Sequence
<220> FEATURE:
<223> OTHER INFORMATION: Synthetic

<400> SEQUENCE: 146

```
Glu Val Gln Leu Leu Glu Ser Gly Gly Gly Leu Val Gln Pro Gly Gly
 1               5                  10                  15

Ser Leu Arg Leu Ser Cys Ala Thr Ser Gly Phe Thr Phe Ser Arg Tyr
                20                  25                  30

Thr Met Thr Trp Val Arg Gln Ala Pro Gly Lys Gly Leu Phe Trp Val
                35                  40                  45

Ser Gly Ile Gly Gly Ser Gly Gly Arg Ala Tyr Tyr Ala Asp Ser Val
 50                 55                  60

Lys Gly Arg Phe Thr Leu Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Lys Glu Gly Asp Ser Gly Tyr Asp Leu Asp Tyr Trp Gly Arg Gly
                100                 105                 110

Thr Leu Val Thr Val Ser Ser
                115
```

<210> SEQ ID NO 147
<211> LENGTH: 24

```
<212> TYPE: DNA
<213> ORGANISM: Artificial Sequence
<220> FEATURE:
<223> OTHER INFORMATION: Synthetic

<400> SEQUENCE: 147
ggattcacct ttagcagata tacc                                              24

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

Gly Phe Thr Phe Ser Arg Tyr Thr
 1               5

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
attggtggta gtggtggtcg cgca                                              24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Gly Gly Ser Gly Gly Arg Ala
 1               5

<210> SEQ ID NO 151
<211> LENGTH: 36
<212> TYPE: DNA
<213> ORGANISM: Artificial Sequence
<220> FEATURE:
<223> OTHER INFORMATION: Synthetic

<400> SEQUENCE: 151
gcgaaagagg gggatagtgg ctacgatttg gactac                                 36

<210> SEQ ID NO 152
<211> LENGTH: 12
<212> TYPE: PRT
<213> ORGANISM: Artificial Sequence
<220> FEATURE:
<223> OTHER INFORMATION: Synthetic

<400> SEQUENCE: 152

Ala Lys Glu Gly Asp Ser Gly Tyr Asp Leu Asp Tyr
 1               5                   10

<210> SEQ ID NO 153
<211> LENGTH: 321
<212> TYPE: DNA
<213> ORGANISM: Artificial Sequence
<220> FEATURE:
<223> OTHER INFORMATION: Synthetic
```

<400> SEQUENCE: 153

```
gacatccaga tgacccagta tccatcctca ctgtctgcat ctgtaggaga cagagtcacc    60
atcacttgtc gggcgaggca gggcataagt aattatttag cctggcttca gcagaaacca   120
gggaaagccc ctaagtccct gatctatgct gcatccagtt tgcaaagggg ggtcccatca   180
aagttcagcg gcagtggatc tgggacagat ttcactctca ccatcagcag cctgcagcct   240
gaagattctg caacttatta ctgccaacaa tataaaattt ccccgctcac tttcggcgga   300
gggaccaagg tggagatcaa g                                              321
```

<210> SEQ ID NO 154
<211> LENGTH: 107
<212> TYPE: PRT
<213> ORGANISM: Artificial Sequence
<220> FEATURE:
<223> OTHER INFORMATION: Synthetic

<400> SEQUENCE: 154

Asp Ile Gln Met Thr Gln Tyr Pro Ser Ser Leu Ser Ala Ser Val Gly
1               5                   10                  15
Asp Arg Val Thr Ile Thr Cys Arg Ala Arg Gln Gly Ile Ser Asn Tyr
            20                  25                  30
Leu Ala Trp Leu Gln Gln Lys Pro Gly Lys Ala Pro Lys Ser Leu Ile
        35                  40                  45
Tyr Ala Ala Ser Ser Leu Gln Arg Gly Val Pro Ser Lys Phe Ser Gly
    50                  55                  60
Ser Gly Ser Gly Thr Asp Phe Thr Leu Thr Ile Ser Ser Leu Gln Pro
65                  70                  75                  80
Glu Asp Ser Ala Thr Tyr Tyr Cys Gln Gln Tyr Lys Ile Ser Pro Leu
                85                  90                  95
Thr Phe Gly Gly Gly Thr Lys Val Glu Ile Lys
            100                 105

<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155

```
cagggcataa gtaattat                                                  18
```

<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

Gln Gly Ile Ser Asn Tyr
1               5

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 gctgcatcc                                                                                  9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Ala Ala Ser
 1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
caacaatata aaatttcccc gctcact                                                             27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Gln Gln Tyr Lys Ile Ser Pro Leu Thr
 1               5

<210> SEQ ID NO 161
<211> LENGTH: 357
<212> TYPE: DNA
<213> ORGANISM: Artificial Sequence
<220> FEATURE:
<223> OTHER INFORMATION: Synthetic

<400> SEQUENCE: 161
gaggtgcagc tgttggagtc tgggggaggc ttggtacagc ctgggggttc cctgagactc        60
tcctgtgcaa cctctggatt cacctttagc agatatacca tgacctgggt ccgccaggct       120
ccagggaagg gctgttttg gtctcaggt attggtggta gtggtggtcg cgcatactac        180
gcagactccg tgaagggccg gttcaccctc tccagagaca attccaagaa cacgctgtat       240
ctgcaaatga acagcctgag agccgaggac acggccgtat attactgtgc gaaagagggg       300
gatagtggct acgatttgga ctactggggc cggggaaccc tggtcaccgt ctcctca          357

<210> SEQ ID NO 162
<211> LENGTH: 119
<212> TYPE: PRT
<213> ORGANISM: Artificial Sequence
<220> FEATURE:
<223> OTHER INFORMATION: Synthetic

<400> SEQUENCE: 162

Glu Val Gln Leu Leu Glu Ser Gly Gly Gly Leu Val Gln Pro Gly Gly
 1               5                  10                  15

Ser Leu Arg Leu Ser Cys Ala Thr Ser Gly Phe Thr Phe Ser Arg Tyr
            20                  25                  30

Thr Met Thr Trp Val Arg Gln Ala Pro Gly Lys Gly Leu Phe Trp Val
            35                  40                  45

Ser Gly Ile Gly Gly Ser Gly Gly Arg Ala Tyr Tyr Ala Asp Ser Val
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Asp Ser Gly Tyr Asp Leu Asp Tyr Trp Gly Arg Gly
            100                 105                 110

Thr Leu Val Thr Val Ser Ser
            115

<210> SEQ ID NO 163
<211> LENGTH: 321
<212> TYPE: DNA
<213> ORGANISM: Artificial Sequence
<220> FEATURE:
<223> OTHER INFORMATION: Synthetic

<400> SEQUENCE: 163
gacatccaga tgacccagtc tccatcctca ctgtctgcat ctgtaggaga cagagtcacc    60
atcacttgtc gggcgaggca gggcataagt aattatttag cctggcttca gcagaaacca   120
gggaaagccc ctaagtccct gatctatgct gcatccagtt tgcaaagggg ggtcccatca   180
aagttcagcg gcagtggatc tgggacagat ttcactctca ccatcagcag cctgcagcct   240
gaagattctg caacttatta ctgccaacaa tataaaattt ccccgctcac tttcggcgga   300
gggaccaagg tggagatcaa a                                             321

<210> SEQ ID NO 164
<211> LENGTH: 107
<212> TYPE: PRT
<213> ORGANISM: Artificial Sequence
<220> FEATURE:
<223> OTHER INFORMATION: Synthetic

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys Arg Ala Arg Gln Gly Ile Ser Asn Tyr
            20                  25                  30

Leu Ala Trp Leu Gln Gln Lys Pro Gly Lys Ala Pro Lys Ser Leu Ile
        35                  40                  45

Tyr Ala Ala Ser Ser Leu Gln Arg Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Tyr Lys Ile Ser Pro Leu
                85                  90                  95

Thr Phe Gly Gly Gly Thr Lys Val Glu Ile Lys
            100                 105

<210> SEQ ID NO 165
<211> LENGTH: 357
<212> TYPE: DNA
<213> ORGANISM: Artificial Sequence
<220> FEATURE:
<223> OTHER INFORMATION: Synthetic

<400> SEQUENCE: 165

```
gaggtgcagc tgttggagtc tgggggaggc ttggtacagc ctgggggggtc cctgagactc    60
tcctgtgcag cctctggatt cacctttagc agatatacca tgagctgggt ccgccaggct   120
ccagggaagg ggctggagtg ggtctcagct attggtggta gtggtggtcg cgcatactac   180
gcagactccg tgaagggccg gttcaccatc tccagagaca attccaagaa cacgctgtat   240
ctgcaaatga acagcctgag agccgaggac acggccgtat attactgtgc gaaagagggg   300
gatagtggct acgatttgga ctactggggc cagggaaccc tggtcaccgt ctcctca      357
```

<210> SEQ ID NO 166
<211> LENGTH: 119
<212> TYPE: PRT
<213> ORGANISM: Artificial Sequence
<220> FEATURE:
<223> OTHER INFORMATION: Synthetic

<400> SEQUENCE: 166

```
Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Ser Arg Tyr
             20                  25                  30
Thr Met Ser Trp Val Arg Gln Ala Pro Gly Lys Gly Leu Glu Trp Val
         35                  40                  45
Ser Ala Ile Gly Gly Ser Gly Gly Arg Ala Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Glu Gly Asp Ser Gly Tyr Asp Leu Asp Tyr Trp Gly Gln Gly
                100                 105                 110
Thr Leu Val Thr Val Ser Ser
            115
```

<210> SEQ ID NO 167
<211> LENGTH: 322
<212> TYPE: DNA
<213> ORGANISM: Artificial Sequence
<220> FEATURE:
<223> OTHER INFORMATION: Synthetic

<400> SEQUENCE: 167

```
gacatccaga tgacccagtc tccatcctca ctgtctgcat ctgtaggaga cagagtcacc    60
atcacttgtc gggcgagtca gggcataagt aattatttag cctggtttca gcagaaacca   120
gggaaagccc ctaagtccct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgccaacaa tataaaattt ccccgctcac tttcggcgga   300
gggaccaagg tggagatcaa ac                                            322
```

<210> SEQ ID NO 168
<211> LENGTH: 107
<212> TYPE: PRT
<213> ORGANISM: Artificial Sequence
<220> FEATURE:
<223> OTHER INFORMATION: Synthetic

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Ile Ser Pro Leu
                85                  90                  95

Thr Phe Gly Gly Gly Thr Lys Val Glu Ile Lys
            100                 105

<210> SEQ ID NO 169
<211> LENGTH: 348
<212> TYPE: DNA
<213> ORGANISM: Artificial Sequence
<220> FEATURE:
<223> OTHER INFORMATION: Synthetic

<400> SEQUENCE: 169

```
gaagtgcagt tggtggagtc tgggggaggc ttagtacagc ctggcaggtc cctgagactc      60
tcctgtgcag cctctggatt cacctttgat gattatgcca tgcactgggt ccggcaagct     120
ccagggaagg gcctggaatg ggtctcaggt attagttgga atagcggtag caaaggcttt     180
gcggactctg tgaagggccg gttcaccatc tccagagaca acgccaagaa ctccctctat     240
ctgcaaatga acagtctgag agttgaagac acggccttgt attactgtgc aaaagagaac     300
tggtcctttg actactgggg ccagggaacc ctggtcaccg tctcctca                  348
```

<210> SEQ ID NO 170
<211> LENGTH: 116
<212> TYPE: PRT
<213> ORGANISM: Artificial Sequence
<220> FEATURE:
<223> OTHER INFORMATION: Synthetic

<400> SEQUENCE: 170

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Lys Gly Phe Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Leu Tyr Tyr Cys
                85                  90                  95

Ala Lys Glu Asn Trp Ser Phe Asp Tyr Trp Gly Gln Gly Thr Leu Val
            100                 105                 110

Thr Val Ser Ser
        115

<210> SEQ ID NO 171
<211> LENGTH: 24
<212> TYPE: DNA
<213> ORGANISM: Artificial Sequence
<220> FEATURE:
<223> OTHER INFORMATION: Synthetic

<400> SEQUENCE: 171
ggattcacct ttgatgatta tgcc                                           24

<210> SEQ ID NO 172
<211> LENGTH: 8
<212> TYPE: PRT
<213> ORGANISM: Artificial Sequence
<220> FEATURE:
<223> OTHER INFORMATION: Synthetic

<400> SEQUENCE: 172

Gly Phe Thr Phe Asp Asp Tyr Ala
 1               5

<210> SEQ ID NO 173
<211> LENGTH: 24
<212> TYPE: DNA
<213> ORGANISM: Artificial Sequence
<220> FEATURE:
<223> OTHER INFORMATION: Synthetic

<400> SEQUENCE: 173
attagttgga atagcggtag caaa                                           24

<210> SEQ ID NO 174
<211> LENGTH: 8
<212> TYPE: PRT
<213> ORGANISM: Artificial Sequence
<220> FEATURE:
<223> OTHER INFORMATION: Synthetic

<400> SEQUENCE: 174

Ile Ser Trp Asn Ser Gly Ser Lys
 1               5

<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175
gcaaaagaga actggtcctt tgactac                                        27

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Ala Lys Glu Asn Trp Ser Phe Asp Tyr
 1               5

<210> SEQ ID NO 177
<211> LENGTH: 336
<212> TYPE: DNA

<213> ORGANISM: Artificial Sequence
<220> FEATURE:
<223> OTHER INFORMATION: Synthetic

<400> SEQUENCE: 177

```
gatattgtga tgacccagac tccactctcc tcgcctgtca cccttggaca gccggcctcc    60
atctcctgca ggtctagtca aagcctcgta cacagtgatg gaaatatcta cttgagttgg   120
cttcagcaga ggccaggcca gcctccaaga ctcctaattt ataagatttc taaccggttc   180
tctggggtcc cagacagatt cagtggcagt ggggcaggga cagatttcac actgaaaatc   240
agcagggtgg aagctgaaga tgtcggaatt tattattgca tgcaagcttc gcattttccg   300
tacactttg gccaggggac caagctggag atcaaa                              336
```

<210> SEQ ID NO 178
<211> LENGTH: 112
<212> TYPE: PRT
<213> ORGANISM: Artificial Sequence
<220> FEATURE:
<223> OTHER INFORMATION: Synthetic

<400> SEQUENCE: 178

```
Asp Ile Val Met Thr Gln Thr Pro Leu Ser Ser Pro Val Thr Leu Gly
  1               5                  10                  15
Gln Pro Ala Ser Ile Ser Cys Arg Ser Ser Gln Ser Leu Val His Ser
             20                  25                  30
Asp Gly Asn Ile Tyr Leu Ser Trp Leu Gln Gln Arg Pro Gly Gln Pro
         35                  40                  45
Pro Arg Leu Leu Ile Tyr Lys Ile Ser Asn Arg Phe Ser Gly Val Pro
     50                  55                  60
Asp Arg Phe Ser Gly Ser Gly Ala Gly Thr Asp Phe Thr Leu Lys Ile
 65                  70                  75                  80
Ser Arg Val Glu Ala Glu Asp Val Gly Ile Tyr Tyr Cys Met Gln Ala
                 85                  90                  95
Ser His Phe Pro Tyr Thr Phe Gly Gln Gly Thr Lys Leu Glu Ile Lys
                100                 105                 110
```

<210> SEQ ID NO 179
<211> LENGTH: 33
<212> TYPE: DNA
<213> ORGANISM: Artificial Sequence
<220> FEATURE:
<223> OTHER INFORMATION: Synthetic

<400> SEQUENCE: 179

```
caaagcctcg tacacagtga tggaaatatc tac                                 33
```

<210> SEQ ID NO 180
<211> LENGTH: 11
<212> TYPE: PRT
<213> ORGANISM: Artificial Sequence
<220> FEATURE:
<223> OTHER INFORMATION: Synthetic

<400> SEQUENCE: 180

```
Gln Ser Leu Val His Ser Asp Gly Asn Ile Tyr
  1               5                  10
```

<210> SEQ ID NO 181
<211> LENGTH: 9
<212> TYPE: DNA
<213> ORGANISM: Artificial Sequence
<220> FEATURE:
<223> OTHER INFORMATION: Synthetic

<400> SEQUENCE: 181 aagatttct                                                                                      9

<210> SEQ ID NO 182
<211> LENGTH: 3
<212> TYPE: PRT
<213> ORGANISM: Artificial Sequence
<220> FEATURE:
<223> OTHER INFORMATION: Synthetic

<400> SEQUENCE: 182

Lys Ile Ser
 1

<210> SEQ ID NO 183
<211> LENGTH: 27
<212> TYPE: DNA
<213> ORGANISM: Artificial Sequence
<220> FEATURE:
<223> OTHER INFORMATION: Synthetic

<400> SEQUENCE: 183
atgcaagctt cgcattttcc gtacact                                                                  27

<210> SEQ ID NO 184
<211> LENGTH: 9
<212> TYPE: PRT
<213> ORGANISM: Artificial Sequence
<220> FEATURE:
<223> OTHER INFORMATION: Synthetic

<400> SEQUENCE: 184

Met Gln Ala Ser His Phe Pro Tyr Thr
 1               5

<210> SEQ ID NO 185
<211> LENGTH: 348
<212> TYPE: DNA
<213> ORGANISM: Artificial Sequence
<220> FEATURE:
<223> OTHER INFORMATION: Synthetic

<400> SEQUENCE: 185
gaagtgcagc tggtggagtc tgggggaggc ttagtacagc ctggcaggtc cctgagactc      60
tcctgtgcag cctctggatt cacctttgat gattatgcca tgcactgggt ccggcaagct     120
ccagggaagg gcctggaatg ggtctcaggt attagttgga atagcggtag caaaggcttt     180
gcggactctg tgaagggccg gttcaccatc tccagagaca cgccaagaa ctccctctat      240 ctgcaaatga acagtctgag agttgaagac acggccttgt attactgtgc aaaagagaac     300
tggtcctttg actactgggg ccagggaacc ctggtcaccg tctcctca                  348

<210> SEQ ID NO 186
<211> LENGTH: 116
<212> TYPE: PRT
<213> ORGANISM: Artificial Sequence
<220> FEATURE:
<223> OTHER INFORMATION: Synthetic

<400> SEQUENCE: 186

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Lys Gly Phe Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Leu Tyr Tyr Cys
                85                  90                  95

Ala Lys Glu Asn Trp Ser Phe Asp Tyr Trp Gly Gln Gly Thr Leu Val
            100                 105                 110

Thr Val Ser Ser
        115

<210> SEQ ID NO 187
<211> LENGTH: 336
<212> TYPE: DNA
<213> ORGANISM: Artificial Sequence
<220> FEATURE:
<223> OTHER INFORMATION: Synthetic

<400> SEQUENCE: 187
gatattgtga tgacccagac tccactctcc tcgcctgtca cccttggaca gccggcctcc     60
atctcctgca ggtctagtca agcctcgta cacagtgatg gaaatatcta cttgagttgg    120
cttcagcaga ggccaggcca gcctccaaga ctcctaattt ataagatttc taaccggttc    180
tctggggtcc cagacagatt cagtggcagt ggggcaggga cagatttcac actgaaaatc    240
agcagggtgg aagctgaaga tgtcggaatt tattattgca tgcaagcttc gcattttccg    300
tacacttttg gccaggggac caagctggag atcaaa                              336

<210> SEQ ID NO 188
<211> LENGTH: 112
<212> TYPE: PRT
<213> ORGANISM: Artificial Sequence
<220> FEATURE:
<223> OTHER INFORMATION: Synthetic

<400> SEQUENCE: 188

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Ile Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Ser His Phe Pro Tyr Thr Phe Gly Gln Gly Thr Lys Leu Glu Ile Lys
            100                 105                 110

<210> SEQ ID NO 189
<211> LENGTH: 348
<212> TYPE: DNA

```
<213> ORGANISM: Artificial Sequence
<220> FEATURE:
<223> OTHER INFORMATION: Synthetic

<400> SEQUENCE: 189
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagcggtag caaaggctat     180
gcggactctg tgaagggccg attcaccatc tccagagaca acgccaagaa ctccctgtat     240
ctgcaaatga acagtctgag agctgaggac acggccttgt attactgtgc aaaagagaac     300
tggtcctttg actactgggg ccagggaacc ctggtcaccg tctcctca                  348

<210> SEQ ID NO 190
<211> LENGTH: 116
<212> TYPE: PRT
<213> ORGANISM: Artificial Sequence
<220> FEATURE:
<223> OTHER INFORMATION: Synthetic

<400> SEQUENCE: 190

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Asn Trp Ser Phe Asp Tyr Trp Gly Gln Gly Thr Leu Val
            100                 105                 110

Thr Val Ser Ser
        115

<210> SEQ ID NO 191
<211> LENGTH: 337
<212> TYPE: DNA
<213> ORGANISM: Artificial Sequence
<220> FEATURE:
<223> OTHER INFORMATION: Synthetic

<400> SEQUENCE: 191
gatattgtga tgacccagac tccactctcc tcacctgtca cccttggaca gccggcctcc      60
atctcctgca ggtctagtca aagcctcgta cacagtgatg aaatatctta cttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcgggggtt tattactgca tgcaagcttc gcatttccg     300 tacactttg gccaggggac caagctggag atcaaac                               337

<210> SEQ ID NO 192
<211> LENGTH: 112
<212> TYPE: PRT
<213> ORGANISM: Artificial Sequence
```

<220> FEATURE:
<223> OTHER INFORMATION: Synthetic

<400> SEQUENCE: 192

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Ile Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser His Phe Pro Tyr Thr Phe Gly Gln Gly Thr Lys Leu Glu Ile Lys
            100                 105                 110

<210> SEQ ID NO 193
<211> LENGTH: 348
<212> TYPE: DNA
<213> ORGANISM: Artificial Sequence
<220> FEATURE:
<223> OTHER INFORMATION: Synthetic

<400> SEQUENCE: 193
gaagtgcaat tggtggagtc tgggggaaac ttggtacagc ctggcaggtc cctgagactc     60
tcctgtgcag cctctggatt cacctttgat gattatgcca tgcactgggt ccggcaagct    120
ccagggaagg gctggagtg gtctcaggt atcagttgga atagtggtag tagaggctat      180
gcggactctg tgaagggccg attcaccatt tccagagaca acgccaaaaa ctccctgtat    240
ctgcaaatga acagtctgag aactgaggac acggcctttt attattgtac aaaagaagac    300 gaggctttg actactgggg ccagggaacc ctggtcaccg tctcctca                  348

<210> SEQ ID NO 194
<211> LENGTH: 116
<212> TYPE: PRT
<213> ORGANISM: Artificial Sequence
<220> FEATURE:
<223> OTHER INFORMATION: Synthetic

<400> SEQUENCE: 194

Glu Val Gln Leu Val Glu Ser Gly Gly Asn Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Arg Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Thr Glu Asp Thr Ala Phe Tyr Tyr Cys
                85                  90                  95

Thr Lys Glu Asp Glu Ala Phe Asp Tyr Trp Gly Gln Gly Thr Leu Val
            100                 105                 110

Thr Val Ser Ser
        115

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195
ggattcacct ttgatgatta tgcc                                          24

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

Gly Phe Thr Phe Asp Asp Tyr Ala
1               5

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197
atcagttgga atagtggtag taga                                          24

<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198

Ile Ser Trp Asn Ser Gly Ser Arg
1               5

<210> SEQ ID NO 199
<211> LENGTH: 27
<212> TYPE: DNA
<213> ORGANISM: Artificial Sequence
<220> FEATURE:
<223> OTHER INFORMATION: Synthetic

<400> SEQUENCE: 199
acaaaagaag acgaggcttt tgactac                                       27

<210> SEQ ID NO 200
<211> LENGTH: 9
<212> TYPE: PRT
<213> ORGANISM: Artificial Sequence
<220> FEATURE:
<223> OTHER INFORMATION: Synthetic

<400> SEQUENCE: 200

Thr Lys Glu Asp Glu Ala Phe Asp Tyr
1               5

<210> SEQ ID NO 201
<211> LENGTH: 336
<212> TYPE: DNA
<213> ORGANISM: Artificial Sequence
<220> FEATURE:
<223> OTHER INFORMATION: Synthetic

<400> SEQUENCE: 201

```
gatattgtga tgacccagac tccactctcc tcacctgtca cccttggaca gccggcctcc      60
atctcctgca ggtctagtca aagcctcgta cacagtgatc gaaacaccta cttgagttgg     120
cttcagcaga ggccaggcca gcctccaaga ctccttattt ataagatttc taaccggttc     180
tctggggtcc cagacagatt cagtggcagt ggggcaggga cagatttcac actgaaaatc     240
agcagggtgg aagctgagga tgtcgggttt tattactgca tgcaggccac acaatttccg     300
tacacttttg gccagggac caaactgcag atcaat                                336
```

<210> SEQ ID NO 202
<211> LENGTH: 112
<212> TYPE: PRT
<213> ORGANISM: Artificial Sequence
<220> FEATURE:
<223> OTHER INFORMATION: Synthetic

<400> SEQUENCE: 202

```
Asp Ile Val Met Thr Gln Thr Pro Leu Ser Ser Pro Val Thr Leu Gly
1               5                   10                  15
Gln Pro Ala Ser Ile Ser Cys Arg Ser Ser Gln Ser Leu Val His Ser
            20                  25                  30
Asp Arg Asn Thr Tyr Leu Ser Trp Leu Gln Gln Arg Pro Gly Gln Pro
        35                  40                  45
Pro Arg Leu Leu Ile Tyr Lys Ile Ser Asn Arg Phe Ser Gly Val Pro
    50                  55                  60
Asp Arg Phe Ser Gly Ser Gly Ala Gly Thr Asp Phe Thr Leu Lys Ile
65                  70                  75                  80
Ser Arg Val Glu Ala Glu Asp Val Gly Phe Tyr Tyr Cys Met Gln Ala
                85                  90                  95
Thr Gln Phe Pro Tyr Thr Phe Gly Gln Gly Thr Lys Leu Gln Ile Asn
            100                 105                 110
```

<210> SEQ ID NO 203
<211> LENGTH: 33
<212> TYPE: DNA
<213> ORGANISM: Artificial Sequence
<220> FEATURE:
<223> OTHER INFORMATION: Synthetic

<400> SEQUENCE: 203

```
caaagcctcg tacacagtga tcgaaacacc tac                                   33
```

<210> SEQ ID NO 204
<211> LENGTH: 11
<212> TYPE: PRT
<213> ORGANISM: Artificial Sequence
<220> FEATURE:
<223> OTHER INFORMATION: Synthetic

<400> SEQUENCE: 204

```
Gln Ser Leu Val His Ser Asp Arg Asn Thr Tyr
1               5                   10
```

<210> SEQ ID NO 205

<211> LENGTH: 9
<212> TYPE: DNA
<213> ORGANISM: Artificial Sequence
<220> FEATURE:
<223> OTHER INFORMATION: Synthetic

<400> SEQUENCE: 205 aagatttct                                                                 9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Lys Ile Ser
 1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
atgcaggcca cacaatttcc gtacact                                             27

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Met Gln Ala Thr Gln Phe Pro Tyr Thr
 1               5

<210> SEQ ID NO 209
<211> LENGTH: 348
<212> TYPE: DNA
<213> ORGANISM: Artificial Sequence
<220> FEATURE:
<223> OTHER INFORMATION: Synthetic

<400> SEQUENCE: 209
gaagtgcagc tggtggagtc tgggggaaac ttggtacagc ctggcaggtc cctgagactc        60
tcctgtgcag cctctggatt cacctttgat gattatgcca tgcactgggt ccggcaagct       120
ccagggaagg gcctggagtg ggtctcaggt atcagttgga atagtggtag tagaggctat       180
gcggactctg tgaagggccg attcaccatt tccagagaca cgccaaaaa ctccctgtat        240 ctgcaaatga acagtctgag aactgaggac acggcctttt attattgtac aaaagaagac       300
gaggcttttg actactgggg ccagggaacc ctggtcaccg tctcctca                    348

<210> SEQ ID NO 210
<211> LENGTH: 116
<212> TYPE: PRT
<213> ORGANISM: Artificial Sequence
<220> FEATURE:
<223> OTHER INFORMATION: Synthetic

<400> SEQUENCE: 210

Glu Val Gln Leu Val Glu Ser Gly Gly Asn Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Arg Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Thr Glu Asp Thr Ala Phe Tyr Tyr Cys
                85                  90                  95

Thr Lys Glu Asp Glu Ala Phe Asp Tyr Trp Gly Gln Gly Thr Leu Val
            100                 105                 110

Thr Val Ser Ser
        115

<210> SEQ ID NO 211
<211> LENGTH: 336
<212> TYPE: DNA
<213> ORGANISM: Artificial Sequence
<220> FEATURE:
<223> OTHER INFORMATION: Synthetic

<400> SEQUENCE: 211
gatattgtga tgacccagac tccactctcc tcacctgtca cccttggaca gccggcctcc      60
atctcctgca ggtctagtca aagcctcgta cacagtgatc gaaacaccta cttgagttgg     120
cttcagcaga ggccaggcca gcctccaaga ctccttattt ataagatttc taaccggttc     180
tctggggtcc cagacagatt cagtggcagt ggggcaggga cagatttcac actgaaaatc     240
agcagggtgg aagctgagga tgtcgggttt tattactgca tgcaggccac acaatttccg     300
tacacttttg gccaggggac caagctggag atcaaa                               336

<210> SEQ ID NO 212
<211> LENGTH: 112
<212> TYPE: PRT
<213> ORGANISM: Artificial Sequence
<220> FEATURE:
<223> OTHER INFORMATION: Synthetic

<400> SEQUENCE: 212

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Arg Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Thr Gln Phe Pro Tyr Thr Phe Gly Gln Gly Thr Lys Leu Glu Ile Lys
            100                 105                 110

<210> SEQ ID NO 213
<211> LENGTH: 348
<212> TYPE: DNA
<213> ORGANISM: Artificial Sequence
<220> FEATURE:
<223> OTHER INFORMATION: Synthetic

<400> SEQUENCE: 213

```
gaagtgcagc tggtggagtc tgggggaggc ttggtacagc ctggcaggtc cctgagactc    60
tcctgtgcag cctctggatt cacctttgat gattatgcca tgcactgggt ccggcaagct   120
ccagggaagg gcctggagtg ggtctcaggt atcagttgga atagtggtag tagaggctat   180
gcggactctg tgaagggccg attcaccatc tccagagaca cgccaagaa ctccctgtat    240
ctgcaaatga acagtctgag agctgaggac acggccttgt attactgtac aaaagaagac   300
gaggcttttg actactgggg ccagggaacc ctggtcaccg tctcctca               348
```

<210> SEQ ID NO 214
<211> LENGTH: 116
<212> TYPE: PRT
<213> ORGANISM: Artificial Sequence
<220> FEATURE:
<223> OTHER INFORMATION: Synthetic

<400> SEQUENCE: 214

```
Glu Val Gln Leu Val Glu Ser Gly Gly Gly Leu Val Gln Pro Gly Arg
 1               5                  10                  15
Ser Leu Arg Leu Ser Cys Ala Ala Ser Gly Phe Thr Phe Asp Asp Tyr
             20                  25                  30
Ala Met His Trp Val Arg Gln Ala Pro Gly Lys Gly Leu Glu Trp Val
         35                  40                  45
Ser Gly Ile Ser Trp Asn Ser Gly Ser Arg Gly Tyr Ala Asp Ser Val
     50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Leu Tyr Tyr Cys
                 85                  90                  95
Thr Lys Glu Asp Glu Ala Phe Asp Tyr Trp Gly Gln Gly Thr Leu Val
            100                 105                 110
Thr Val Ser Ser
        115
```

<210> SEQ ID NO 215
<211> LENGTH: 337
<212> TYPE: DNA
<213> ORGANISM: Artificial Sequence
<220> FEATURE:
<223> OTHER INFORMATION: Synthetic

<400> SEQUENCE: 215

```
gatattgtga tgacccagac tccactctcc tcacctgtca cccttggaca gccggcctcc    60
atctcctgca ggtctagtca agcctcgta cacagtgatc gaaacaccta cttgagttgg   120
cttcagcaga ggccaggcca gcctccaaga ctcctaattt ataagatttc taaccggttc   180
tctggggtcc cagacagatt cagtggcagt ggggcaggga cagatttcac actgaaaatc   240
agcagggtgg aagctgagga tgtcggggtt tattactgca tgcaggccac acaatttccg   300
tacacttttg gccaggggac caagctggag atcaaac                           337
```

<210> SEQ ID NO 216

<211> LENGTH: 112
<212> TYPE: PRT
<213> ORGANISM: Artificial Sequence
<220> FEATURE:
<223> OTHER INFORMATION: Synthetic

<400> SEQUENCE: 216

Asp Ile Val Met Thr Gln Thr Pro Leu Ser Ser Val Thr Leu Gly
1               5                   10                  15

Gln Pro Ala Ser Ile Ser Cys Arg Ser Ser Gln Ser Leu Val His Ser
            20                  25                  30

Asp Arg Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Tyr Thr Phe Gly Gln Gly Thr Lys Leu Glu Ile Lys
            100                 105                 110

<210> SEQ ID NO 217
<211> LENGTH: 348
<212> TYPE: DNA
<213> ORGANISM: Artificial Sequence
<220> FEATURE:
<223> OTHER INFORMATION: Synthetic

<400> SEQUENCE: 217
gaagtgcagc tggtggagtc tgggggaggc ttggtacagc ctggcaggtc cctgagactc      60
tcctgtgcag cctctggctt cacctttgat gattatgcca tgcactgggt ccggcaagct     120
ccggggaagg gcctagagtg ggtctcaggt attacttgga atagtggtac catgycctat     180
gcggactctg tgaagggccg attcaccatc tccagagaca acgccaagaa ctccctgtat     240
ctgcaaatga acagtctgag agctgaggac acggccttat attactgtgc aaaagaaaac     300
tgggcctttg actactgggg ccagggaacc ctggtcaccg tctcctca                  348

<210> SEQ ID NO 218
<211> LENGTH: 116
<212> TYPE: PRT
<213> ORGANISM: Artificial Sequence
<220> FEATURE:
<223> OTHER INFORMATION: Synthetic

<400> SEQUENCE: 218

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Thr Trp Asn Ser Gly Thr Met Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Asn Trp Ala Phe Asp Tyr Trp Gly Gln Gly Thr Leu Val
                100                 105                 110
Thr Val Ser Ser
        115

<210> SEQ ID NO 219
<211> LENGTH: 24
<212> TYPE: DNA
<213> ORGANISM: Artificial Sequence
<220> FEATURE:
<223> OTHER INFORMATION: Synthetic

<400> SEQUENCE: 219
ggcttcacct ttgatgatta tgcc                                          24

<210> SEQ ID NO 220
<211> LENGTH: 8
<212> TYPE: PRT
<213> ORGANISM: Artificial Sequence
<220> FEATURE:
<223> OTHER INFORMATION: Synthetic

<400> SEQUENCE: 220

Gly Phe Thr Phe Asp Asp Tyr Ala
1               5

<210> SEQ ID NO 221
<211> LENGTH: 24
<212> TYPE: DNA
<213> ORGANISM: Artificial Sequence
<220> FEATURE:
<223> OTHER INFORMATION: Synthetic

<400> SEQUENCE: 221
attacttgga atagtggtac catg                                          24

<210> SEQ ID NO 222
<211> LENGTH: 8
<212> TYPE: PRT
<213> ORGANISM: Artificial Sequence
<220> FEATURE:
<223> OTHER INFORMATION: Synthetic

<400> SEQUENCE: 222

Ile Thr Trp Asn Ser Gly Thr Met
1               5

<210> SEQ ID NO 223
<211> LENGTH: 27
<212> TYPE: DNA
<213> ORGANISM: Artificial Sequence
<220> FEATURE:
<223> OTHER INFORMATION: Synthetic

<400> SEQUENCE: 223
gcaaaagaaa actgggcctt tgactac                                       27

<210> SEQ ID NO 224
<211> LENGTH: 9
<212> TYPE: PRT
<213> ORGANISM: Artificial Sequence
<220> FEATURE:
<223> OTHER INFORMATION: Synthetic

<400> SEQUENCE: 224

Ala Lys Glu Asn Trp Ala Phe Asp Tyr

<210> SEQ ID NO 225
<211> LENGTH: 336
<212> TYPE: DNA
<213> ORGANISM: Artificial Sequence
<220> FEATURE:
<223> OTHER INFORMATION: Synthetic

<400> SEQUENCE: 225

```
gatattgtga tgacccagac tccactctcc tcacctgtca cccttggaca gccggcctcc      60
atctcctgca ggtctagtca cagcctcgta cacagtgatg gaaacaccta cttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcgggggtt tatttctgca tgcaagctac acaatttccg     300
tacacttttg gccaggggac caagctggag atcaaa                              336
```

<210> SEQ ID NO 226
<211> LENGTH: 112
<212> TYPE: PRT
<213> ORGANISM: Artificial Sequence
<220> FEATURE:
<223> OTHER INFORMATION: Synthetic

<400> SEQUENCE: 226

Asp Ile Val Met Thr Gln Thr Pro Leu Ser Ser Pro Val Thr Leu Gly
1               5                   10                  15
Gln Pro Ala Ser Ile Ser Cys Arg Ser Ser His Ser Leu Val His Ser
            20                  25                  30
Asp Gly Asn Thr Tyr Leu Ser Trp Leu Gln Gln Arg Pro Gly Gln Pro
        35                  40                  45
Pro Arg Leu Leu Ile Tyr Lys Ile Ser Asn Arg Phe Ser Gly Val Pro
    50                  55                  60
Asp Arg Phe Ser Gly Ser Gly Ala Gly Thr Asp Phe Thr Leu Lys Ile
65                  70                  75                  80
Ser Arg Val Glu Ala Glu Asp Val Gly Val Tyr Phe Cys Met Gln Ala
                85                  90                  95
Thr Gln Phe Pro Tyr Thr Phe Gly Gln Gly Thr Lys Leu Glu Ile Lys
            100                 105                 110

<210> SEQ ID NO 227
<211> LENGTH: 33
<212> TYPE: DNA
<213> ORGANISM: Artificial Sequence
<220> FEATURE:
<223> OTHER INFORMATION: Synthetic

<400> SEQUENCE: 227

```
cacagcctcg tacacagtga tggaaacacc tac                                  33
```

<210> SEQ ID NO 228
<211> LENGTH: 11
<212> TYPE: PRT
<213> ORGANISM: Artificial Sequence
<220> FEATURE:
<223> OTHER INFORMATION: Synthetic

<400> SEQUENCE: 228

His Ser Leu Val His Ser Asp Gly Asn Thr Tyr
1               5                   10

<210> SEQ ID NO 229
<211> LENGTH: 9
<212> TYPE: DNA
<213> ORGANISM: Artificial Sequence
<220> FEATURE:
<223> OTHER INFORMATION: Synthetic

<400> SEQUENCE: 229 aagatttct                                                                  9

<210> SEQ ID NO 230
<211> LENGTH: 3
<212> TYPE: PRT
<213> ORGANISM: Artificial Sequence
<220> FEATURE:
<223> OTHER INFORMATION: Synthetic

<400> SEQUENCE: 230

Lys Ile Ser
 1

<210> SEQ ID NO 231
<211> LENGTH: 27
<212> TYPE: DNA
<213> ORGANISM: Artificial Sequence
<220> FEATURE:
<223> OTHER INFORMATION: Synthetic

<400> SEQUENCE: 231
atgcaagcta cacaatttcc gtacact                                             27

<210> SEQ ID NO 232
<211> LENGTH: 9
<212> TYPE: PRT
<213> ORGANISM: Artificial Sequence
<220> FEATURE:
<223> OTHER INFORMATION: Synthetic

<400> SEQUENCE: 232

Met Gln Ala Thr Gln Phe Pro Tyr Thr
 1               5

<210> SEQ ID NO 233
<211> LENGTH: 348
<212> TYPE: DNA
<213> ORGANISM: Artificial Sequence
<220> FEATURE:
<223> OTHER INFORMATION: Synthetic

<400> SEQUENCE: 233
gaagtgcagc tggtggagtc tgggggaggc ttggtacagc ctggcaggtc cctgagactc        60
tcctgtgcag cctctggctt cacctttgat gattatgcca tgcactgggt ccggcaagct       120
ccggggaagg gcctagagtg ggtctcaggt attacttgga atagtggtac catggcctat       180
gcggactctg tgaagggccg attcaccatc tccagagaca cgccaagaa ctccctgtat        240 ctgcaaatga acagtctgag agctgaggac acggccttat attactgtgc aaaagaaaac      300
tgggcctttg actactgggg ccagggaacc ctggtcaccg tctcctca                   348

<210> SEQ ID NO 234
<211> LENGTH: 116
<212> TYPE: PRT
<213> ORGANISM: Artificial Sequence
<220> FEATURE:

<223> OTHER INFORMATION: Synthetic

<400> SEQUENCE: 234

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Thr Trp Asn Ser Gly Thr Met Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Asn Trp Ala Phe Asp Tyr Trp Gly Gln Gly Thr Leu Val
            100                 105                 110

Thr Val Ser Ser
            115

<210> SEQ ID NO 235
<211> LENGTH: 336
<212> TYPE: DNA
<213> ORGANISM: Artificial Sequence
<220> FEATURE:
<223> OTHER INFORMATION: Synthetic

<400> SEQUENCE: 235
gatattgtga tgacccagac tccactctcc tcacctgtca cccttggaca gccggcctcc      60
atctcctgca ggtctagtca gagcctcgta cacagtgatg gaaacaccta cttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tatttctgca tgcaagctac acaatttccg     300
tacactttg gccaggggac caagctggag atcaaa                                336

<210> SEQ ID NO 236
<211> LENGTH: 112
<212> TYPE: PRT
<213> ORGANISM: Artificial Sequence
<220> FEATURE:
<223> OTHER INFORMATION: Synthetic

<400> SEQUENCE: 236

Asp Ile Val Met Thr Gln Thr Pro Leu Ser Ser Pro Val Thr Leu Gly
1               5                   10                  15

Gln Pro Ala Ser Ile Ser Cys Arg Ser Ser His Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Phe Cys Met Gln Ala
                85                  90                  95

Thr Gln Phe Pro Tyr Thr Phe Gly Gln Gly Thr Lys Leu Glu Ile Lys

<210> SEQ ID NO 237
<211> LENGTH: 348
<212> TYPE: DNA
<213> ORGANISM: Artificial Sequence
<220> FEATURE:
<223> OTHER INFORMATION: Synthetic

<400> SEQUENCE: 237

```
gaagtgcagc tggtggagtc tgggggaggc ttggtacagc ctggcaggtc cctgagactc    60
tcctgtgcag cctctggctt cacctttgat gattatgcca tgcactgggt ccggcaagct   120
ccagggaagg gcctggagtg gtctcaggt attacttgga atagtggtac catgggctat   180
gcggactctg tgaagggccg attcaccatc tccagagaca cgccaagaa ctccctgtat   240
ctgcaaatga acagtctgag agctgaggac acggccttgt attactgtgc aaaagaaaac   300
tgggcctttg actactgggg ccagggaacc ctggtcaccg tctcctca                348
```

<210> SEQ ID NO 238
<211> LENGTH: 116
<212> TYPE: PRT
<213> ORGANISM: Artificial Sequence
<220> FEATURE:
<223> OTHER INFORMATION: Synthetic

<400> SEQUENCE: 238

```
Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Thr Trp Asn Ser Gly Thr Met Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Asn Trp Ala Phe Asp Tyr Trp Gly Gln Gly Thr Leu Val
            100                 105                 110

Thr Val Ser Ser
        115
```

<210> SEQ ID NO 239
<211> LENGTH: 337
<212> TYPE: DNA
<213> ORGANISM: Artificial Sequence
<220> FEATURE:
<223> OTHER INFORMATION: Synthetic

<400> SEQUENCE: 239

```
gatattgtga tgacccagac tccactctcc tcacctgtca cccttggaca gccggcctcc    60
atctcctgca ggtctagtca gagcctcgta cacagtgatg aaacacccta cttgagttgg   120
cttcagcaga ggccaggcca gcctccaaga ctcctaattt ataagatttc taaccggttc   180
tctggggtcc cagacagatt cagtggcagt ggggcaggga cagatttcac actgaaaatc   240
agcagggtga agctgaggat gtcgggggtt attactgca tgcaagctac acaatttccg   300
tacacttttg gccaggggac caagctggag atcaaac                            337
```

<210> SEQ ID NO 240
<211> LENGTH: 112
<212> TYPE: PRT
<213> ORGANISM: Artificial Sequence
<220> FEATURE:
<223> OTHER INFORMATION: Synthetic

<400> SEQUENCE: 240

Asp Ile Val Met Thr Gln Thr Pro Leu Ser Ser Pro Val Thr Leu Gly
1               5                   10                  15

Gln Pro Ala Ser Ile Ser Cys Arg Ser Ser His Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Tyr Thr Phe Gly Gln Gly Thr Lys Leu Glu Ile Lys
            100                 105                 110

<210> SEQ ID NO 241
<211> LENGTH: 384
<212> TYPE: DNA
<213> ORGANISM: Artificial Sequence
<220> FEATURE:
<223> OTHER INFORMATION: Synthetic

<400> SEQUENCE: 241
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagtggtag cataggctat     180
gcggactctg tgaagggccg attcaccatc tccagagaca acgccaagaa ctccctgtat     240
ctgcaaatga acagtctgag agctgaggac acggccttgt attactgtgc aaaagataga     300
ttccctccgt ataagtataa cagtggtggt ttttctgatg cttttgaaat ctggggccaa     360
gggacaatgg tcaccgtctc ttca                                            384

<210> SEQ ID NO 242
<211> LENGTH: 128
<212> TYPE: PRT
<213> ORGANISM: Artificial Sequence
<220> FEATURE:
<223> OTHER INFORMATION: Synthetic

<400> SEQUENCE: 242

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr

```
                65                  70                  75                  80
Leu Gln Met Asn Ser Leu Arg Ala Glu Asp Thr Ala Leu Tyr Tyr Cys
                        85                  90                  95

Ala Lys Asp Arg Phe Pro Pro Tyr Lys Tyr Asn Ser Gly Gly Phe Ser
                100                 105                 110

Asp Ala Phe Glu Ile Trp Gly Gln Gly Thr Met Val Thr Val Ser Ser
                115                 120                 125
```

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
ggattcacct ttgatgatta tgcc         24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

```
Gly Phe Thr Phe Asp Asp Tyr Ala
  1               5
```

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
attagttgga atagtggtag cata         24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

```
Ile Ser Trp Asn Ser Gly Ser Ile
  1               5
```

<210> SEQ ID NO 247
<211> LENGTH: 63
<212> TYPE: DNA
<213> ORGANISM: Artificial Sequence
<220> FEATURE:
<223> OTHER INFORMATION: Synthetic

<400> SEQUENCE: 247
gcaaaagata gattccctcc gtataagtat aacagtggtg gttttttctga tgcttttgaa    60 atc                                                                   63

<210> SEQ ID NO 248
<211> LENGTH: 21
<212> TYPE: PRT

<213> ORGANISM: Artificial Sequence
<220> FEATURE:
<223> OTHER INFORMATION: Synthetic

<400> SEQUENCE: 248

Ala Lys Asp Arg Phe Pro Pro Tyr Lys Tyr Asn Ser Gly Gly Phe Ser
1               5                   10                  15

Asp Ala Phe Glu Ile
            20

<210> SEQ ID NO 249
<211> LENGTH: 324
<212> TYPE: DNA
<213> ORGANISM: Artificial Sequence
<220> FEATURE:
<223> OTHER INFORMATION: Synthetic

<400> SEQUENCE: 249

```
gaaattgtgt tgacgcagtc tccaggcacc ctgtctttgt ctccagggga aagagccacc      60
ctctcctgca gggccagtca gagttttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gttcaccgat caccttcggc     300
caagggacac gactggagat tgaa                                             324
```

<210> SEQ ID NO 250
<211> LENGTH: 108
<212> TYPE: PRT
<213> ORGANISM: Artificial Sequence
<220> FEATURE:
<223> OTHER INFORMATION: Synthetic

<400> SEQUENCE: 250

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Phe Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Glu
            100                 105

<210> SEQ ID NO 251
<211> LENGTH: 21
<212> TYPE: DNA
<213> ORGANISM: Artificial Sequence
<220> FEATURE:
<223> OTHER INFORMATION: Synthetic

<400> SEQUENCE: 251
cagagtttta gcagcagcta c                                                21

<210> SEQ ID NO 252

```
<211> LENGTH: 7
<212> TYPE: PRT
<213> ORGANISM: Artificial Sequence
<220> FEATURE:
<223> OTHER INFORMATION: Synthetic

<400> SEQUENCE: 252

Gln Ser Phe Ser Ser Ser Tyr
 1               5

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 ggtgcatcc                                                                  9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Gly Ala Ser
 1

<210> SEQ ID NO 255
<211> LENGTH: 27
<212> TYPE: DNA
<213> ORGANISM: Artificial Sequence
<220> FEATURE:
<223> OTHER INFORMATION: Synthetic

<400> SEQUENCE: 255
cagcagtatg gtagttcacc gatcacc                                             27

<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256

Gln Gln Tyr Gly Ser Ser Pro Ile Thr
 1               5

<210> SEQ ID NO 257
<211> LENGTH: 384
<212> TYPE: DNA
<213> ORGANISM: Artificial Sequence
<220> FEATURE:
<223> OTHER INFORMATION: Synthetic

<400> SEQUENCE: 257
gaagtgcagc tggtggagtc tgggggaggc ttggtacagc ctggcaggtc cctgagactc         60
tcctgtgcag cctctggatt cacctttgat gattatgcca tgcactgggt ccggcaagct        120
ccagggaagg gcctggagtg ggtctcaggt attagttgga atagtggtag cataggctat        180
gcggactctg tgaagggccg attcaccatc tccagagaca cgccaagaa ctccctgtat        240
```

```
ctgcaaatga acagtctgag agctgaggac acggccttgt attactgtgc aaaagataga    300
ttccctccgt ataagtataa cagtggtggt ttttctgatg cttttgaaat ctggggccaa    360
gggacaatgg tcaccgtctc ttca                                           384
```

<210> SEQ ID NO 258
<211> LENGTH: 128
<212> TYPE: PRT
<213> ORGANISM: Artificial Sequence
<220> FEATURE:
<223> OTHER INFORMATION: Synthetic

<400> SEQUENCE: 258

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Arg Phe Pro Pro Tyr Lys Tyr Asn Ser Gly Gly Phe Ser
            100                 105                 110

Asp Ala Phe Glu Ile Trp Gly Gln Gly Thr Met Val Thr Val Ser Ser
        115                 120                 125
```

<210> SEQ ID NO 259
<211> LENGTH: 324
<212> TYPE: DNA
<213> ORGANISM: Artificial Sequence
<220> FEATURE:
<223> OTHER INFORMATION: Synthetic

<400> SEQUENCE: 259

```
gaaattgtgt tgacgcagtc tccaggcacc ctgtctttgt ctccagggga aagagccacc    60
ctctcctgca gggccagtca gagttttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gttcaccgat caccttcggc   300
caagggacac gactggagat taaa                                           324
```

<210> SEQ ID NO 260
<211> LENGTH: 108
<212> TYPE: PRT
<213> ORGANISM: Artificial Sequence
<220> FEATURE:
<223> OTHER INFORMATION: Synthetic

<400> SEQUENCE: 260

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Phe Ser Ser Ser
            20                  25                  30

Tyr Leu Ala Trp Tyr Gln Gln Lys Pro Gly Gln Ala Pro Arg Leu Leu
```

```
                35                  40                  45
Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Ile Thr Phe Gly Gln Gly Thr Arg Leu Glu Ile Lys
            100                 105
```

<210> SEQ ID NO 261
<211> LENGTH: 384
<212> TYPE: DNA
<213> ORGANISM: Artificial Sequence
<220> FEATURE:
<223> OTHER INFORMATION: Synthetic

<400> SEQUENCE: 261

```
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg gtctcaggt attagttgga atagtggtag cataggctat      180
gcggactctg tgaagggccg attcaccatc tccagagaca acgccaagaa ctccctgtat     240
ctgcaaatga acagtctgag agctgaggac acggccttgt attactgtgc aaaagataga     300
ttccctccgt ataagtataa cagtggtggt ttttctgatg cttttgaaat ctggggccaa     360
gggacaatgg tcaccgtctc ttca                                            384
```

<210> SEQ ID NO 262
<211> LENGTH: 128
<212> TYPE: PRT
<213> ORGANISM: Artificial Sequence
<220> FEATURE:
<223> OTHER INFORMATION: Synthetic

<400> SEQUENCE: 262

```
Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Gly Ile Ser Trp Asn Ser Gly Ser Ile Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
             85                  90                  95

Ala Lys Asp Arg Phe Pro Pro Tyr Lys Tyr Asn Ser Gly Gly Phe Ser
            100                 105                 110

Asp Ala Phe Glu Ile Trp Gly Gln Gly Thr Met Val Thr Val Ser Ser
        115                 120                 125
```

<210> SEQ ID NO 263
<211> LENGTH: 325
<212> TYPE: DNA
<213> ORGANISM: Artificial Sequence
<220> FEATURE:
<223> OTHER INFORMATION: Synthetic

<400> SEQUENCE: 263

```
gaaattgtgt tgacgcagtc tccaggcacc ctgtctttgt ctccagggga aagagccacc    60
ctctcctgca gggccagtca gagttttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gttcaccgat caccttcggc   300
caagggacac gactggagat taaac                                         325
```

<210> SEQ ID NO 264
<211> LENGTH: 108
<212> TYPE: PRT
<213> ORGANISM: Artificial Sequence
<220> FEATURE:
<223> OTHER INFORMATION: Synthetic

<400> SEQUENCE: 264

```
Glu Ile Val Leu Thr Gln Ser Pro Gly Thr Leu Ser Leu Ser Pro Gly
 1               5                  10                  15
Glu Arg Ala Thr Leu Ser Cys Arg Ala Ser Gln Ser Phe Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Ile Thr Phe Gly Gln Gly Thr Arg Leu Glu Ile Lys
            100                 105
```

<210> SEQ ID NO 265
<211> LENGTH: 366
<212> TYPE: DNA
<213> ORGANISM: Artificial Sequence
<220> FEATURE:
<223> OTHER INFORMATION: Synthetic

<400> SEQUENCE: 265

```
gaggtgcagc tggtggagtc tgggggaggc ttggtacagc ctggggggtc cctgagactc    60
tcctgtgcag cctctggatt caccttcagt agctacgaca tgcactgggt ccgccaagtt   120
acaggaaaag gtctggaatg gtctcagtc attggtactg ttggtgacac atactatcca   180
ggctccctga agggccgatt caccatctcc agagaaaatg ccaagaactc cttgtatctt   240
caaatgaaca ccctgagagc cggggacacg gctgtttatt actgtgcaag aactggagca   300
gcagcccact cgtactacta cggtatggac gtctggggcc aagggaccat ggtcaccgtc   360
tcctca                                                              366
```

<210> SEQ ID NO 266
<211> LENGTH: 122
<212> TYPE: PRT
<213> ORGANISM: Artificial Sequence
<220> FEATURE:
<223> OTHER INFORMATION: Synthetic

<400> SEQUENCE: 266

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Asp Met His Trp Val Arg Gln Val Thr Gly Lys Gly Leu Glu Trp Val
             35                  40                  45

Ser Val Ile Gly Thr Val Gly Asp Thr Tyr Tyr Pro Gly Ser Leu Lys
 50                  55                  60

Gly Arg Phe Thr Ile Ser Arg Glu Asn Ala Lys Asn Ser Leu Tyr Leu
 65                  70                  75                  80

Gln Met Asn Thr Leu Arg Ala Gly Asp Thr Ala Val Tyr Tyr Cys Ala
             85                  90                  95

Arg Thr Gly Ala Ala Ala His Ser Tyr Tyr Tyr Gly Met Asp Val Trp
            100                 105                 110

Gly Gln Gly Thr Met Val Thr Val Ser Ser
            115                 120

<210> SEQ ID NO 267
<211> LENGTH: 24
<212> TYPE: DNA
<213> ORGANISM: Artificial Sequence
<220> FEATURE:
<223> OTHER INFORMATION: Synthetic

<400> SEQUENCE: 267
ggattcacct tcagtagcta cgac                                        24

<210> SEQ ID NO 268
<211> LENGTH: 8
<212> TYPE: PRT
<213> ORGANISM: Artificial Sequence
<220> FEATURE:
<223> OTHER INFORMATION: Synthetic

<400> SEQUENCE: 268

Gly Phe Thr Phe Ser Ser Tyr Asp
 1               5

<210> SEQ ID NO 269
<211> LENGTH: 21
<212> TYPE: DNA
<213> ORGANISM: Artificial Sequence
<220> FEATURE:
<223> OTHER INFORMATION: Synthetic

<400> SEQUENCE: 269
attggtactg ttggtgacac a                                           21

<210> SEQ ID NO 270
<211> LENGTH: 7
<212> TYPE: PRT
<213> ORGANISM: Artificial Sequence
<220> FEATURE:
<223> OTHER INFORMATION: Synthetic

<400> SEQUENCE: 270

Ile Gly Thr Val Gly Asp Thr
 1               5

<210> SEQ ID NO 271
<211> LENGTH: 48
<212> TYPE: DNA
```

<213> ORGANISM: Artificial Sequence
<220> FEATURE:
<223> OTHER INFORMATION: Synthetic

<400> SEQUENCE: 271

```
gcaagaactg agcagcagc ccactcgtac tactacggta tggacgtc          48
```

<210> SEQ ID NO 272
<211> LENGTH: 16
<212> TYPE: PRT
<213> ORGANISM: Artificial Sequence
<220> FEATURE:
<223> OTHER INFORMATION: Synthetic

<400> SEQUENCE: 272

Ala Arg Thr Gly Ala Ala Ala His Ser Tyr Tyr Tyr Gly Met Asp Val
 1               5                  10                  15

<210> SEQ ID NO 273
<211> LENGTH: 336
<212> TYPE: DNA
<213> ORGANISM: Artificial Sequence
<220> FEATURE:
<223> OTHER INFORMATION: Synthetic

<400> SEQUENCE: 273

```
gatattgtga tgactcagtc tccactctcc ctgcccgtca cccctggaga gccggcctcc    60
atctcctgca ggtctagtca gagcctcctg tatagtaatg gatacaacta tttggattgg   120
tacctacaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggaatt tattactgca tgcaagctct acaaactccg   300
tggacgttcg gccaagggac caaggtggaa atcaaa                              336
```

<210> SEQ ID NO 274
<211> LENGTH: 112
<212> TYPE: PRT
<213> ORGANISM: Artificial Sequence
<220> FEATURE:
<223> OTHER INFORMATION: Synthetic

<400> SEQUENCE: 274

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu Tyr Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 275
<211> LENGTH: 33
<212> TYPE: DNA
<213> ORGANISM: Artificial Sequence
<220> FEATURE:
<223> OTHER INFORMATION: Synthetic

<400> SEQUENCE: 275
cagagcctcc tgtatagtaa tggatacaac tat    33

<210> SEQ ID NO 276
<211> LENGTH: 11
<212> TYPE: PRT
<213> ORGANISM: Artificial Sequence
<220> FEATURE:
<223> OTHER INFORMATION: Synthetic

<400> SEQUENCE: 276

Gln Ser Leu Leu Tyr Ser Asn Gly Tyr Asn Tyr
 1               5                  10

<210> SEQ ID NO 277
<211> LENGTH: 9
<212> TYPE: DNA
<213> ORGANISM: Artificial Sequence
<220> FEATURE:
<223> OTHER INFORMATION: Synthetic

<400> SEQUENCE: 277 ttgggttct    9

<210> SEQ ID NO 278
<211> LENGTH: 3
<212> TYPE: PRT
<213> ORGANISM: Artificial Sequence
<220> FEATURE:
<223> OTHER INFORMATION: Synthetic

<400> SEQUENCE: 278

Leu Gly Ser
 1

<210> SEQ ID NO 279
<211> LENGTH: 27
<212> TYPE: DNA
<213> ORGANISM: Artificial Sequence
<220> FEATURE:
<223> OTHER INFORMATION: Synthetic

<400> SEQUENCE: 279
atgcaagctc tacaaactcc gtggacg    27

<210> SEQ ID NO 280
<211> LENGTH: 9
<212> TYPE: PRT
<213> ORGANISM: Artificial Sequence
<220> FEATURE:
<223> OTHER INFORMATION: Synthetic

<400> SEQUENCE: 280

Met Gln Ala Leu Gln Thr Pro Trp Thr
 1               5

<210> SEQ ID NO 281
<211> LENGTH: 363
<212> TYPE: DNA
<213> ORGANISM: Artificial Sequence
<220> FEATURE:
<223> OTHER INFORMATION: Synthetic

<400> SEQUENCE: 281

```
gaggtgcagc tggtggagtc tgggggaggc ttggtacagc ctggggggtc cctgagactc    60
tcctgtgcag cctctggatt caccttcagt agctacgaca tgcactgggt ccgccaagtt   120
acaggaaaag gtctggaatg ggtctcagtc attggtactg ttggtgacac atactatcca   180
ggctccctga agggccgatt caccatctcc agagaaaatg ccaagaactc cttgtatctt   240
caaatgaaca ccctgagagc cggggacacg gctgtttatt actgtgcaag aactggagca   300 gcagccccact cgtactacta cggtatggac gtctggggcc aagggaccac ggtcaccgtc   360
tcc                                                                 363
```

<210> SEQ ID NO 282
<211> LENGTH: 121
<212> TYPE: PRT
<213> ORGANISM: Artificial Sequence
<220> FEATURE:
<223> OTHER INFORMATION: Synthetic

<400> SEQUENCE: 282

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met His Trp Val Arg Gln Val Thr Gly Lys Gly Leu Glu Trp Val
        35                  40                  45

Ser Val Ile Gly Thr Val Gly Asp Thr Tyr Tyr Pro Gly Ser Leu Lys
    50                  55                  60

Gly Arg Phe Thr Ile Ser Arg Glu Asn Ala Lys Asn Ser Leu Tyr Leu
65                  70                  75                  80

Gln Met Asn Thr Leu Arg Ala Gly Asp Thr Ala Val Tyr Tyr Cys Ala
                85                  90                  95

Arg Thr Gly Ala Ala Ala His Ser Tyr Tyr Tyr Gly Met Asp Val Trp
            100                 105                 110

Gly Gln Gly Thr Thr Val Thr Val Ser
        115                 120
```

<210> SEQ ID NO 283
<211> LENGTH: 336
<212> TYPE: DNA
<213> ORGANISM: Artificial Sequence
<220> FEATURE:
<223> OTHER INFORMATION: Synthetic

<400> SEQUENCE: 283

```
gatattgtga tgactcagtc tccactctcc ctgcccgtca cccctggaga gccggcctcc    60
atctcctgca ggtctagtca gagcctcctg tatagtaatg gatacaacta tttggattgg   120
tacctacaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggaatt tattactgca tgcaagctct acaaactccg   300
tggacgttcg gccaagggac caaggtggaa atcaaa                             336
```

<210> SEQ ID NO 284
<211> LENGTH: 112
<212> TYPE: PRT
<213> ORGANISM: Artificial Sequence
<220> FEATURE:
<223> OTHER INFORMATION: Synthetic

<400> SEQUENCE: 284

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 285
<211> LENGTH: 364
<212> TYPE: DNA
<213> ORGANISM: Artificial Sequence
<220> FEATURE:
<223> OTHER INFORMATION: Synthetic

<400> SEQUENCE: 285
gaggtgcagc tggtggagtc tgggggaggc ttggtacagc ctggggggtc cctgagactc    60
tcctgtgcag cctctggatt caccttcagt agctacgaca tgcactgggt ccgccaagct   120
acaggaaaag gtctggagtg ggtctcagct attggtactg ttggtgacac atactatcca   180
ggctccgtga agggccgatt caccatctcc agagaaaatg ccaagaactc cttgtatctt   240
caaatgaaca gcctgagagc cggggacacg gctgtgtatt actgtgcaag aactggagca   300 gcagccccact cgtactacta cggtatggac gtctggggcc aagggaccac ggtcaccgtc   360
tcct                                                                364

<210> SEQ ID NO 286
<211> LENGTH: 121
<212> TYPE: PRT
<213> ORGANISM: Artificial Sequence
<220> FEATURE:
<223> OTHER INFORMATION: Synthetic

<400> SEQUENCE: 286

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Val Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Thr Gly Ala Ala Ala His Ser Tyr Tyr Tyr Gly Met Asp Val Trp
            100                 105                 110

Gly Gln Gly Thr Thr Val Thr Val Ser

```
                 115                 120

<210> SEQ ID NO 287
<211> LENGTH: 337
<212> TYPE: DNA
<213> ORGANISM: Artificial Sequence
<220> FEATURE:
<223> OTHER INFORMATION: Synthetic

<400> SEQUENCE: 287
gatattgtga tgactcagtc tccactctcc ctgcccgtca cccctggaga gccggcctcc      60
atctcctgca ggtctagtca gagcctcctg tatagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactccg    300
tggacgttcg gccaagggac caaggtggaa atcaaac                             337

<210> SEQ ID NO 288
<211> LENGTH: 112
<212> TYPE: PRT
<213> ORGANISM: Artificial Sequence
<220> FEATURE:
<223> OTHER INFORMATION: Synthetic

<400> SEQUENCE: 288

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 289
<211> LENGTH: 357
<212> TYPE: DNA
<213> ORGANISM: Artificial Sequence
<220> FEATURE:
<223> OTHER INFORMATION: Synthetic

<400> SEQUENCE: 289
gaggtgcagc tgttggagtc tgggggaggc ttggtacagc ctggggggtc cctgagactc      60
tcctgtgcag cctctggatt cacctttagc agctatgcca tgacctgggt ccgccaggct    120
ccagggaagg ggctgtattg ggtctcagct attagtggta gtggtggtag cgcatactac    180
gcagactccg tgaagggccg gttcaccatc tccagagaca attccaagaa cacgctgtat    240
ctgcaaatga acagcctgag agccgaggac acggccgtat attactgtgc gaaagagggg    300
gatagtggct acgatttgga ctactggggc cggggaaccc tggtcaccgt ctcgtca      357

<210> SEQ ID NO 290
```

<211> LENGTH: 119
<212> TYPE: PRT
<213> ORGANISM: Artificial Sequence
<220> FEATURE:
<223> OTHER INFORMATION: Synthetic

<400> SEQUENCE: 290

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Thr Trp Val Arg Gln Ala Pro Gly Lys Gly Leu Tyr Trp Val
        35                  40                  45
Ser Ala Ile Ser Gly Ser Gly Gly Ser Ala Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Glu Gly Asp Ser Gly Tyr Asp Leu Asp Tyr Trp Gly Arg Gly
            100                 105                 110
Thr Leu Val Thr Val Ser Ser
        115

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
ggattcacct ttagcagcta tgcc                                          24

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

Gly Phe Thr Phe Ser Ser Tyr Ala
1               5

<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
attagtggta gtggtggtag cgca                                          24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

```
Ile Ser Gly Ser Gly Gly Ser Ala
  1               5
```

<210> SEQ ID NO 295
<211> LENGTH: 36
<212> TYPE: DNA
<213> ORGANISM: Artificial Sequence
<220> FEATURE:
<223> OTHER INFORMATION: Synthetic

<400> SEQUENCE: 295

| | |
|---|---:|
| gcgaaagagg gggatagtgg ctacgatttg gactac | 36 |

<210> SEQ ID NO 296
<211> LENGTH: 12
<212> TYPE: PRT
<213> ORGANISM: Artificial Sequence
<220> FEATURE:
<223> OTHER INFORMATION: Synthetic

<400> SEQUENCE: 296

```
Ala Lys Glu Gly Asp Ser Gly Tyr Asp Leu Asp Tyr
  1               5                  10
```

<210> SEQ ID NO 297
<211> LENGTH: 321
<212> TYPE: DNA
<213> ORGANISM: Artificial Sequence
<220> FEATURE:
<223> OTHER INFORMATION: Synthetic

<400> SEQUENCE: 297

| | |
|---|---:|
| gacatccaga tgacccagtc tccatcctca ctgtctgcat ctgtaggaga cagagtcacc | 60 |
| atcacttgtc gggcgaggca gggcattagt aattatttag cctggcttca gcagaaacca | 120 |
| gggaaagccc ctaagtccct gatctatgct gcatccagtt tgcaaagtgg ggtcccatca | 180 |
| aagttcagcg gcagtggatc tgggacagat ttcactctca ccatcagcag cctgcagcct | 240 |
| gaagattttg caacttatta ctgccaacaa tataaaagtt ccccgctcac tttcggcgga | 300 |
| gggaccaagg tggagatcaa a | 321 |

<210> SEQ ID NO 298
<211> LENGTH: 107
<212> TYPE: PRT
<213> ORGANISM: Artificial Sequence
<220> FEATURE:
<223> OTHER INFORMATION: Synthetic

<400> SEQUENCE: 298

```
Asp Ile Gln Met Thr Gln Ser Pro Ser Ser Leu Ser Ala Ser Val Gly
  1               5                  10                  15

Asp Arg Val Thr Ile Thr Cys Arg Ala Arg Gln Gly Ile Ser Asn Tyr
             20                  25                  30

Leu Ala Trp Leu Gln Gln Lys Pro Gly Lys Ala Pro Lys Ser Leu Ile
         35                  40                  45

Tyr Ala Ala Ser Ser Leu Gln Ser Gly Val Pro Ser Lys Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Lys Ser Ser Pro Leu
             85                  90                  95

Thr Phe Gly Gly Gly Thr Lys Val Glu Ile Lys
            100                 105
```

<210> SEQ ID NO 299
<211> LENGTH: 18
<212> TYPE: DNA
<213> ORGANISM: Artificial Sequence
<220> FEATURE:
<223> OTHER INFORMATION: Synthetic

<400> SEQUENCE: 299
cagggcatta gtaattat                                                 18

<210> SEQ ID NO 300
<211> LENGTH: 6
<212> TYPE: PRT
<213> ORGANISM: Artificial Sequence
<220> FEATURE:
<223> OTHER INFORMATION: Synthetic

<400> SEQUENCE: 300

Gln Gly Ile Ser Asn Tyr
 1               5

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301 gctgcatcc                                                            9

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Ala Ala Ser
 1

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
caacaatata aagttcccc gctcact                                        27

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

Gln Gln Tyr Lys Ser Ser Pro Leu Thr
 1               5

<210> SEQ ID NO 305

<211> LENGTH: 357
<212> TYPE: DNA
<213> ORGANISM: Artificial Sequence
<220> FEATURE:
<223> OTHER INFORMATION: Synthetic

<400> SEQUENCE: 305

```
gaggtgcagc tgttggagtc tgggggaggc ttggtacagc ctggggggtc cctgagactc      60
tcctgtgcag cctctggatt cacctttagc agctatgcca tgacctgggt ccgccaggct     120
ccagggaagg ggctgtattg ggtctcagct attagtggta gtggtggtag cgcatactac     180
gcagactccg tgaagggccg gttcaccatc tccagagaca attccaagaa cacgctgtat     240
ctgcaaatga acagcctgag agccgaggac acggccgtat attactgtgc gaaagagggg     300
gatagtggct acgatttgga ctactggggc cggggaaccc tggtcaccgt ctcctca        357
```

<210> SEQ ID NO 306
<211> LENGTH: 119
<212> TYPE: PRT
<213> ORGANISM: Artificial Sequence
<220> FEATURE:
<223> OTHER INFORMATION: Synthetic

<400> SEQUENCE: 306

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Tyr Trp Val
        35                  40                  45

Ser Ala Ile Ser Gly Ser Gly Gly Ser Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Asp Ser Gly Tyr Asp Leu Asp Tyr Trp Gly Arg Gly
            100                 105                 110

Thr Leu Val Thr Val Ser Ser
        115
```

<210> SEQ ID NO 307
<211> LENGTH: 321
<212> TYPE: DNA
<213> ORGANISM: Artificial Sequence
<220> FEATURE:
<223> OTHER INFORMATION: Synthetic

<400> SEQUENCE: 307

```
gacatccaga tgacccagtc tccatcctca ctgtctgcat ctgtaggaga cagagtcacc      60
atcacttgtc gggcgaggca gggcattagt aattatttag cctggcttca gcagaaacca     120
gggaaagccc ctaagtccct gatctatgct gcatccagtt tgcaaagtgg ggtcccatca     180
aagttcagcg gcagtggatc tgggacagat ttcactctca ccatcagcag cctgcagcct     240
gaagattttg caacttatta ctgccaacaa tataaaagtt ccccgctcac tttcggcgga     300
gggaccaagg tggagatcaa a                                                321
```

<210> SEQ ID NO 308
<211> LENGTH: 107

```
<212> TYPE: PRT
<213> ORGANISM: Artificial Sequence
<220> FEATURE:
<223> OTHER INFORMATION: Synthetic

<400> SEQUENCE: 308

Asp Ile Gln Met Thr Gln Ser Pro Ser Ser Leu Ser Ala Ser Val Gly
1               5                   10                  15

Asp Arg Val Thr Ile Thr Cys Arg Ala Arg Gln Gly Ile Ser Asn Tyr
            20                  25                  30

Leu Ala Trp Leu Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Ser Ser Pro Leu
                85                  90                  95

Thr Phe Gly Gly Gly Thr Lys Val Glu Ile Lys
            100                 105

<210> SEQ ID NO 309
<211> LENGTH: 357
<212> TYPE: DNA
<213> ORGANISM: Artificial Sequence
<220> FEATURE:
<223> OTHER INFORMATION: Synthetic

<400> SEQUENCE: 309
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cgcatactac     180
gcagactccg tgaagggccg gttcaccatc tccagagaca attccaagaa cacgctgtat     240
ctgcaaatga acagcctgag agccgaggac acggccgtat attactgtgc gaaagagggg     300
gatagtggct acgatttgga ctactggggc cagggaaccc tggtcaccgt ctcctca        357

<210> SEQ ID NO 310
<211> LENGTH: 119
<212> TYPE: PRT
<213> ORGANISM: Artificial Sequence
<220> FEATURE:
<223> OTHER INFORMATION: Synthetic

<400> SEQUENCE: 310

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Ala Tyr Tyr Ala Asp Ser Val
50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Asp Ser Gly Tyr Asp Leu Asp Tyr Trp Gly Gln Gly
```

```
              100                 105                 110
Thr Leu Val Thr Val Ser Ser
        115

<210> SEQ ID NO 311
<211> LENGTH: 322
<212> TYPE: DNA
<213> ORGANISM: Artificial Sequence
<220> FEATURE:
<223> OTHER INFORMATION: Synthetic

<400> SEQUENCE: 311
gacatccaga tgacccagtc tccatcctca ctgtctgcat ctgtaggaga cagagtcacc     60
atcacttgtc gggcgagtca gggcattagt aattatttag cctggtttca gcagaaacca    120
gggaaagccc ctaagtccct gatctatgct gcatccagtt tgcaaagtgg ggtcccatca    180
aggttcagcg gcagtggatc tgggacagat ttcactctca ccatcagcag cctgcagcct    240
gaagattttg caacttatta ctgccaacaa tataaaagtt ccccgctcac tttcggcgga    300
gggaccaagg tggagatcaa ac                                             322

<210> SEQ ID NO 312
<211> LENGTH: 107
<212> TYPE: PRT
<213> ORGANISM: Artificial Sequence
<220> FEATURE:
<223> OTHER INFORMATION: Synthetic

<400> SEQUENCE: 312

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Asn Tyr
             20                  25                  30

Leu Ala Trp Phe Gln Gln Lys Pro Gly Lys Ala Pro Lys Ser Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Lys Ser Ser Pro Leu
                 85                  90                  95

Thr Phe Gly Gly Gly Thr Lys Val Glu Ile Lys
            100                 105

<210> SEQ ID NO 313
<211> LENGTH: 348
<212> TYPE: DNA
<213> ORGANISM: Artificial Sequence
<220> FEATURE:
<223> OTHER INFORMATION: Synthetic

<400> SEQUENCE: 313
gaagtgcagt tggtggagtc tgggggaggc ttggtacagc ctggcaggtc cctgagactc     60
tcctgtgcag cctctggatt cacctttgat gattatgcca tgcactgggt ccggcaagtt    120
ccagggaagg gcctggagtg ggtctcaggt attacttgga atagtggtag catagactat    180
gcggactctg tgaagggccg attcaccatc tccagagaca acgccaagaa ctccctgtat    240
ctgcaaatga acagtctgag agctgaggac acggccttct attattgtgt aaaagaagat    300
gaggcttttg actactgggg ccagggaacc ctggtcaccg tctcctca                 348
```

<210> SEQ ID NO 314
<211> LENGTH: 116
<212> TYPE: PRT
<213> ORGANISM: Artificial Sequence
<220> FEATURE:
<223> OTHER INFORMATION: Synthetic

<400> SEQUENCE: 314

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Thr Trp Asn Ser Gly Ser Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Phe Tyr Tyr Cys
                85                  90                  95

Val Lys Glu Asp Glu Ala Phe Asp Tyr Trp Gly Gln Gly Thr Leu Val
            100                 105                 110

Thr Val Ser Ser
        115

<210> SEQ ID NO 315
<211> LENGTH: 24
<212> TYPE: DNA
<213> ORGANISM: Artificial Sequence
<220> FEATURE:
<223> OTHER INFORMATION: Synthetic

<400> SEQUENCE: 315
ggattcacct ttgatgatta tgcc                                          24

<210> SEQ ID NO 316
<211> LENGTH: 8
<212> TYPE: PRT
<213> ORGANISM: Artificial Sequence
<220> FEATURE:
<223> OTHER INFORMATION: Synthetic

<400> SEQUENCE: 316

Gly Phe Thr Phe Asp Asp Tyr Ala
1               5

<210> SEQ ID NO 317
<211> LENGTH: 24
<212> TYPE: DNA
<213> ORGANISM: Artificial Sequence
<220> FEATURE:
<223> OTHER INFORMATION: Synthetic

<400> SEQUENCE: 317
attacttgga atagtggtag cata                                          24

<210> SEQ ID NO 318
<211> LENGTH: 8
<212> TYPE: PRT
<213> ORGANISM: Artificial Sequence
<220> FEATURE:
<223> OTHER INFORMATION: Synthetic

<400> SEQUENCE: 318

Ile Thr Trp Asn Ser Gly Ser Ile
 1               5

<210> SEQ ID NO 319
<211> LENGTH: 27
<212> TYPE: DNA
<213> ORGANISM: Artificial Sequence
<220> FEATURE:
<223> OTHER INFORMATION: Synthetic

<400> SEQUENCE: 319
gtaaaagaag atgaggcttt tgactac                                        27

<210> SEQ ID NO 320
<211> LENGTH: 9
<212> TYPE: PRT
<213> ORGANISM: Artificial Sequence
<220> FEATURE:
<223> OTHER INFORMATION: Synthetic

<400> SEQUENCE: 320

Val Lys Glu Asp Glu Ala Phe Asp Tyr
 1               5

<210> SEQ ID NO 321
<211> LENGTH: 336
<212> TYPE: DNA
<213> ORGANISM: Artificial Sequence
<220> FEATURE:
<223> OTHER INFORMATION: Synthetic

<400> SEQUENCE: 321
gatattgtga tgacccagac tccactctcc tcacctgtca cccttggaca gccggcctcc     60
atctcctgta ggtctagtca aagcctcgta cacagtgatg aaacaccta tttgagttgg    120 cttcagcaga ggccaggcca gcctccaaga ctcctaattt ataagatttc taaccggttc    180
tctggggtcc cagacagaat cagtggcagt ggggcaggga cagatttcac actgaaaatc    240
agcagggtgg aggctgagga tgtcggcgtt tattattgca tgcaagctac acaatttccg    300
tacacttttg gccaggggac caagctggag atcaaa                              336

<210> SEQ ID NO 322
<211> LENGTH: 112
<212> TYPE: PRT
<213> ORGANISM: Artificial Sequence
<220> FEATURE:
<223> OTHER INFORMATION: Synthetic

<400> SEQUENCE: 322

Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
                20                  25                  30

Asp Gly Asn Thr Tyr Leu Ser Trp Leu Gln Gln Arg Pro Gly Gln Pro
            35                  40                  45

Pro Arg Leu Leu Ile Tyr Lys Ile Ser Asn Arg Phe Ser Gly Val Pro
        50                  55                  60

Asp Arg Ile Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ala

```
                    85                  90                  95
Thr Gln Phe Pro Tyr Thr Phe Gly Gln Gly Thr Lys Leu Glu Ile Lys
            100                 105                 110

<210> SEQ ID NO 323
<211> LENGTH: 33
<212> TYPE: DNA
<213> ORGANISM: Artificial Sequence
<220> FEATURE:
<223> OTHER INFORMATION: Synthetic

<400> SEQUENCE: 323
caaagcctcg tacacagtga tggaaacacc tat                               33

<210> SEQ ID NO 324
<211> LENGTH: 11
<212> TYPE: PRT
<213> ORGANISM: Artificial Sequence
<220> FEATURE:
<223> OTHER INFORMATION: Synthetic

<400> SEQUENCE: 324

Gln Ser Leu Val His Ser Asp Gly Asn Thr Tyr
 1               5                  10

<210> SEQ ID NO 325
<211> LENGTH: 9
<212> TYPE: DNA
<213> ORGANISM: Artificial Sequence
<220> FEATURE:
<223> OTHER INFORMATION: Synthetic

<400> SEQUENCE: 325 aagatttct                                                          9

<210> SEQ ID NO 326
<211> LENGTH: 3
<212> TYPE: PRT
<213> ORGANISM: Artificial Sequence
<220> FEATURE:
<223> OTHER INFORMATION: Synthetic

<400> SEQUENCE: 326

Lys Ile Ser
 1

<210> SEQ ID NO 327
<211> LENGTH: 27
<212> TYPE: DNA
<213> ORGANISM: Artificial Sequence
<220> FEATURE:
<223> OTHER INFORMATION: Synthetic

<400> SEQUENCE: 327
atgcaagcta cacaatttcc gtacact                                      27

<210> SEQ ID NO 328
<211> LENGTH: 9
<212> TYPE: PRT
<213> ORGANISM: Artificial Sequence
<220> FEATURE:
<223> OTHER INFORMATION: Synthetic

<400> SEQUENCE: 328

Met Gln Ala Thr Gln Phe Pro Tyr Thr
 1               5
```

<210> SEQ ID NO 329
<211> LENGTH: 348
<212> TYPE: DNA
<213> ORGANISM: Artificial Sequence
<220> FEATURE:
<223> OTHER INFORMATION: Synthetic

<400> SEQUENCE: 329

```
gaagtgcagc tggtggagtc tgggggaggc ttggtacagc ctggcaggtc cctgagactc      60
tcctgtgcag cctctggatt cacctttgat gattatgcca tgcactgggt ccggcaagtt     120
ccagggaagg gcctggagtg ggtctcaggt attacttgga atagtggtag catagactat     180
gcggactctg tgaagggccg attcaccatc tccagagaca acgccaagaa ctccctgtat     240
ctgcaaatga acagtctgag agctgaggac acggccttct attattgtgt aaaagaagat     300
gaggcttttg actactgggg ccagggaacc ctggtcaccg tctcctca                 348
```

<210> SEQ ID NO 330
<211> LENGTH: 116
<212> TYPE: PRT
<213> ORGANISM: Artificial Sequence
<220> FEATURE:
<223> OTHER INFORMATION: Synthetic

<400> SEQUENCE: 330

```
Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Thr Trp Asn Ser Gly Ser Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Phe Tyr Tyr Cys
                85                  90                  95

Val Lys Glu Asp Glu Ala Phe Asp Tyr Trp Gly Gln Gly Thr Leu Val
            100                 105                 110

Thr Val Ser Ser
        115
```

<210> SEQ ID NO 331
<211> LENGTH: 336
<212> TYPE: DNA
<213> ORGANISM: Artificial Sequence
<220> FEATURE:
<223> OTHER INFORMATION: Synthetic

<400> SEQUENCE: 331

```
gatattgtga tgacccagac tccactctcc tcacctgtca cccttggaca gccggcctcc      60
atctcctgta ggtctagtca aagcctcgta cacagtgatg gaaacaccta tttgagttgg     120
cttcagcaga ggccaggcca gcctccaaga ctcctaattt ataagatttc taaccggttc     180
tctggggtcc cagacagaat cagtggcagt ggggcaggga cagatttcac actgaaaatc     240
agcagggtgg aggctgagga tgtcggcgtt tattattgca tgcaagctac acaatttccg     300
tacacttttg gccaggggac caagctggag atcaaa                               336
```

<210> SEQ ID NO 332
<211> LENGTH: 112
<212> TYPE: PRT
<213> ORGANISM: Artificial Sequence
<220> FEATURE:
<223> OTHER INFORMATION: Synthetic

<400> SEQUENCE: 332

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Ile Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Tyr Thr Phe Gly Gln Gly Thr Lys Leu Glu Ile Lys
            100                 105                 110

<210> SEQ ID NO 333
<211> LENGTH: 348
<212> TYPE: DNA
<213> ORGANISM: Artificial Sequence
<220> FEATURE:
<223> OTHER INFORMATION: Synthetic

<400> SEQUENCE: 333
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attacttgga atagtggtag cataggctat     180
gcggactctg tgaagggccg attcaccatc tccagagaca acgccaagaa ctccctgtat     240
ctgcaaatga acagtctgag agctgaggac acggccttgt attactgtgt aaaagaagat     300
gaggcttttg actactgggg ccagggaacc ctggtcaccg tctcctca                  348

<210> SEQ ID NO 334
<211> LENGTH: 116
<212> TYPE: PRT
<213> ORGANISM: Artificial Sequence
<220> FEATURE:
<223> OTHER INFORMATION: Synthetic

<400> SEQUENCE: 334

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Thr Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys

```
                    85                  90                  95
Val Lys Glu Asp Glu Ala Phe Asp Tyr Trp Gly Gln Gly Thr Leu Val
                100                 105                 110

Thr Val Ser Ser
        115

<210> SEQ ID NO 335
<211> LENGTH: 337
<212> TYPE: DNA
<213> ORGANISM: Artificial Sequence
<220> FEATURE:
<223> OTHER INFORMATION: Synthetic

<400> SEQUENCE: 335
gatattgtga tgacccagac tccactctcc tcacctgtca cccttggaca gccggcctcc      60
atctcctgca ggtctagtca aagcctcgta cacagtgatg gaaacaccta tttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tattactgca tgcaagctac acaatttccg     300
tacacttttg gccaggggac caagctggag atcaaac                              337

<210> SEQ ID NO 336
<211> LENGTH: 112
<212> TYPE: PRT
<213> ORGANISM: Artificial Sequence
<220> FEATURE:
<223> OTHER INFORMATION: Synthetic

<400> SEQUENCE: 336

Asp Ile Val Met Thr Gln Thr Pro Leu Ser Ser Pro Val Thr Leu Gly
  1               5                  10                  15

Gln Pro Ala Ser Ile Ser Cys Arg Ser Ser Gln Ser Leu Val His Ser
                 20                  25                  30

Asp Gly Asn Thr Tyr Leu Ser Trp Leu Gln Gln Arg Pro Gly Gln Pro
             35                  40                  45

Pro Arg Leu Leu Ile Tyr Lys Ile Ser Asn Arg Phe Ser Gly Val Pro
         50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Thr Gln Phe Pro Tyr Thr Phe Gly Gln Gly Thr Lys Leu Glu Ile Lys
                100                 105                 110

<210> SEQ ID NO 337
<211> LENGTH: 357
<212> TYPE: DNA
<213> ORGANISM: Artificial Sequence
<220> FEATURE:
<223> OTHER INFORMATION: Synthetic

<400> SEQUENCE: 337
gaggtgcaac tgttggagtc tgggggaggc ttggtacagc ctggggggtc cctgagactc      60
tcctgtgcag cctctggatt cacctttaga agttatacca tgacctgggt ccgccaggct     120
ccagggaagg gactggattg ggtctcaggt attactgata gtggtgctgg cacatactac     180
ggagactccg tgaagggccg gttcaccatc tccagagaca attccaagaa cacgctgtat     240
```

```
ctgcaaatga acagcctgag agccgaggac acggccgtgt attactgtgt gaaagagggg      300
gatagtggct acgatttgga ctactggggc cagggaaccc tggtcaccgt ctcctca          357
```

<210> SEQ ID NO 338
<211> LENGTH: 119
<212> TYPE: PRT
<213> ORGANISM: Artificial Sequence
<220> FEATURE:
<223> OTHER INFORMATION: Synthetic

<400> SEQUENCE: 338

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Ser Tyr
            20                  25                  30

Thr Met Thr Trp Val Arg Gln Ala Pro Gly Lys Gly Leu Asp Trp Val
        35                  40                  45

Ser Gly Ile Thr Asp Ser Gly Ala Gly Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Glu Gly Asp Ser Gly Tyr Asp Leu Asp Tyr Trp Gly Gln Gly
            100                 105                 110

Thr Leu Val Thr Val Ser Ser
        115
```

<210> SEQ ID NO 339
<211> LENGTH: 24
<212> TYPE: DNA
<213> ORGANISM: Artificial Sequence
<220> FEATURE:
<223> OTHER INFORMATION: Synthetic

<400> SEQUENCE: 339

```
ggattcacct ttagaagtta tacc                                              24
```

<210> SEQ ID NO 340
<211> LENGTH: 8
<212> TYPE: PRT
<213> ORGANISM: Artificial Sequence
<220> FEATURE:
<223> OTHER INFORMATION: Synthetic

<400> SEQUENCE: 340

```
Gly Phe Thr Phe Arg Ser Tyr Thr
 1               5
```

<210> SEQ ID NO 341
<211> LENGTH: 24
<212> TYPE: DNA
<213> ORGANISM: Artificial Sequence
<220> FEATURE:
<223> OTHER INFORMATION: Synthetic

<400> SEQUENCE: 341

```
attactgata gtggtgctgg caca                                              24
```

<210> SEQ ID NO 342
<211> LENGTH: 8
<212> TYPE: PRT

```
<213> ORGANISM: Artificial Sequence
<220> FEATURE:
<223> OTHER INFORMATION: Synthetic

<400> SEQUENCE: 342

Ile Thr Asp Ser Gly Ala Gly Thr
 1               5

<210> SEQ ID NO 343
<211> LENGTH: 36
<212> TYPE: DNA
<213> ORGANISM: Artificial Sequence
<220> FEATURE:
<223> OTHER INFORMATION: Synthetic

<400> SEQUENCE: 343
gtgaaagagg gggatagtgg ctacgatttg gactac                                 36

<210> SEQ ID NO 344
<211> LENGTH: 12
<212> TYPE: PRT
<213> ORGANISM: Artificial Sequence
<220> FEATURE:
<223> OTHER INFORMATION: Synthetic

<400> SEQUENCE: 344

Val Lys Glu Gly Asp Ser Gly Tyr Asp Leu Asp Tyr
 1               5                  10

<210> SEQ ID NO 345
<211> LENGTH: 321
<212> TYPE: DNA
<213> ORGANISM: Artificial Sequence
<220> FEATURE:
<223> OTHER INFORMATION: Synthetic

<400> SEQUENCE: 345
gacatccaga tgacccagtc tccatcctca ctgtctgcat ctgtaggaga cagagtcacc        60
atcacttgtc gggcgagtca gggcattagt acttatttag cctggcttca gcagaaacca      120
gggaaagccc ctaagtccct gatctatgct acatccagtt tgcaaagtgg ggtcccatca      180
aagttcagcg gcagtagatc tgggacagat ttcactctca ccatcagcag cctgcagcct      240
gaagattttg caacttatta ctgccaacaa tataagagtt ccccgctcac tttcggcgga      300
gggaccaagg tggagatcaa a                                                321

<210> SEQ ID NO 346
<211> LENGTH: 107
<212> TYPE: PRT
<213> ORGANISM: Artificial Sequence
<220> FEATURE:
<223> OTHER INFORMATION: Synthetic

<400> SEQUENCE: 346

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Thr Tyr
             20                  25                  30

Leu Ala Trp Leu Gln Gln Lys Pro Gly Lys Ala Pro Lys Ser Leu Ile
         35                  40                  45

Tyr Ala Thr Ser Ser Leu Gln Ser Gly Val Pro Ser Lys Phe Ser Gly
     50                  55                  60

Ser Arg Ser Gly Thr Asp Phe Thr Leu Thr Ile Ser Ser Leu Gln Pro
```

```
                65                  70                  75                  80
            Glu Asp Phe Ala Thr Tyr Tyr Cys Gln Gln Tyr Lys Ser Ser Pro Leu
                        85                  90                  95
            Thr Phe Gly Gly Gly Thr Lys Val Glu Ile Lys
                        100                 105
```

<210> SEQ ID NO 347
<211> LENGTH: 18
<212> TYPE: DNA
<213> ORGANISM: Artificial Sequence
<220> FEATURE:
<223> OTHER INFORMATION: Synthetic

<400> SEQUENCE: 347
cagggcatta gtacttat                                                        18

<210> SEQ ID NO 348
<211> LENGTH: 6
<212> TYPE: PRT
<213> ORGANISM: Artificial Sequence
<220> FEATURE:
<223> OTHER INFORMATION: Synthetic

<400> SEQUENCE: 348

Gln Gly Ile Ser Thr Tyr
1               5

<210> SEQ ID NO 349
<211> LENGTH: 9
<212> TYPE: DNA
<213> ORGANISM: Artificial Sequence
<220> FEATURE:
<223> OTHER INFORMATION: Synthetic

<400> SEQUENCE: 349 gctacatcc                                                                   9

<210> SEQ ID NO 350
<211> LENGTH: 3
<212> TYPE: PRT
<213> ORGANISM: Artificial Sequence
<220> FEATURE:
<223> OTHER INFORMATION: Synthetic

<400> SEQUENCE: 350

Ala Thr Ser
1

<210> SEQ ID NO 351
<211> LENGTH: 27
<212> TYPE: DNA
<213> ORGANISM: Artificial Sequence
<220> FEATURE:
<223> OTHER INFORMATION: Synthetic

<400> SEQUENCE: 351
caacaatata agagttcccc gctcact                                              27

<210> SEQ ID NO 352
<211> LENGTH: 9
<212> TYPE: PRT
<213> ORGANISM: Artificial Sequence
<220> FEATURE:
<223> OTHER INFORMATION: Synthetic

<400> SEQUENCE: 352

Gln Gln Tyr Lys Ser Ser Pro Leu Thr
 1               5

<210> SEQ ID NO 353
<211> LENGTH: 357
<212> TYPE: DNA
<213> ORGANISM: Artificial Sequence
<220> FEATURE:
<223> OTHER INFORMATION: Synthetic

<400> SEQUENCE: 353
gaggtgcagc tgttggagtc tggggggaggc ttggtacagc ctgggggtc cctgagactc      60 tcctgtgcag cctctggatt cacctttaga agttatacca tgacctgggt ccgccaggct     120
ccagggaagg gactggattg ggtctcaggt attactgata gtggtgctgg cacatactac     180
ggagactccg tgaagggccg gttcaccatc tccagagaca attccaagaa cacgctgtat     240
ctgcaaatga acagcctgag agccgaggac acggccgtgt attactgtgt gaaagagggg     300
gatagtggct acgatttgga ctactgggggc cagggaaccc tggtcaccgt ctcctca      357

<210> SEQ ID NO 354
<211> LENGTH: 119
<212> TYPE: PRT
<213> ORGANISM: Artificial Sequence
<220> FEATURE:
<223> OTHER INFORMATION: Synthetic

<400> SEQUENCE: 354

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Arg Ser Tyr
            20                  25                  30

Thr Met Thr Trp Val Arg Gln Ala Pro Gly Lys Gly Leu Asp Trp Val
        35                  40                  45

Ser Gly Ile Thr Asp Ser Gly Ala Gly Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Glu Gly Asp Ser Gly Tyr Asp Leu Asp Tyr Trp Gly Gln Gly
            100                 105                 110

Thr Leu Val Thr Val Ser Ser
        115

<210> SEQ ID NO 355
<211> LENGTH: 321
<212> TYPE: DNA
<213> ORGANISM: Artificial Sequence
<220> FEATURE:
<223> OTHER INFORMATION: Synthetic

<400> SEQUENCE: 355
gacatccaga tgacccagtc tccatcctca ctgtctgcat ctgtaggaga cagagtcacc      60
atcacttgtc gggcgagtca gggcattagt acttatttag cctggcttca gcagaaacca    120
gggaaagccc ctaagtccct gatctatgct acatccagtt tgcaaagtgg ggtcccatca    180 agttcagcg gcagtagatc tgggacagat ttcactctca ccatcagcag cctgcagcct    240
gaagattttg caacttatta ctgccaacaa tataagagtt ccccgctcac tttcggcgga    300
gggaccaagg tggagatcaa a    321

<210> SEQ ID NO 356
<211> LENGTH: 107
<212> TYPE: PRT
<213> ORGANISM: Artificial Sequence
<220> FEATURE:
<223> OTHER INFORMATION: Synthetic

<400> SEQUENCE: 356

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Thr Tyr
            20                  25                  30

Leu Ala Trp Leu Gln Gln Lys Pro Gly Lys Ala Pro Lys Ser Leu Ile
        35                  40                  45

Tyr Ala Thr Ser Ser Leu Gln Ser Gly Val Pro Ser Lys Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Ser Ser Pro Leu
                85                  90                  95

Thr Phe Gly Gly Gly Thr Lys Val Glu Ile Lys
            100                 105

<210> SEQ ID NO 357
<211> LENGTH: 357
<212> TYPE: DNA
<213> ORGANISM: Artificial Sequence
<220> FEATURE:
<223> OTHER INFORMATION: Synthetic

<400> SEQUENCE: 357
gaggtgcagc tgttggagtc tgggggaggc ttggtacagc ctggggggtc cctgagactc    60
tcctgtgcag cctctggatt cacctttaga agttatacca tgagctgggt ccgccaggct   120 ccagggaagg␣ggctggagtg␣gtctcagct attactgata gtggtgctgg cacatactac   180
gcagactccg tgaagggccg gttcaccatc tccagagaca attccaagaa cacgctgtat   240
ctgcaaatga acagcctgag agccgaggac acggccgtat attactgtgt gaaagagggg   300
gatagtggct acgatttgga ctactggggc cagggaaccc tggtcaccgt ctcctca     357

<210> SEQ ID NO 358
<211> LENGTH: 119
<212> TYPE: PRT
<213> ORGANISM: Artificial Sequence
<220> FEATURE:
<223> OTHER INFORMATION: Synthetic

<400> SEQUENCE: 358

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Thr Met Ser Trp Val Arg Gln Ala Pro Gly Lys Gly Leu Glu Trp Val
        35                  40                  45

Ser Ala Ile Thr Asp Ser Gly Ala Gly Thr Tyr Tyr Ala Asp Ser Val
    50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                    85                  90                  95

Val Lys Glu Gly Asp Ser Gly Tyr Asp Leu Asp Tyr Trp Gly Gln Gly
            100                 105                 110

Thr Leu Val Thr Val Ser Ser
        115

<210> SEQ ID NO 359
<211> LENGTH: 322
<212> TYPE: DNA
<213> ORGANISM: Artificial Sequence
<220> FEATURE:
<223> OTHER INFORMATION: Synthetic

<400> SEQUENCE: 359
gacatccaga tgacccagtc tccatcctca ctgtctgcat ctgtaggaga cagagtcacc      60
atcacttgtc gggcgagtca gggcattagt acttatttag cctggtttca gcagaaacca     120
gggaaagccc ctaagtccct gatctatgct acatccagtt tgcaaagtgg ggtcccatca     180
aggttcagcg gcagtggatc tgggacagat ttcactctca ccatcagcag cctgcagcct     240
gaagattttg caacttatta ctgccaacaa tataagagtt ccccgctcac tttcggcgga     300
gggaccaagg tggagatcaa ac                                              322

<210> SEQ ID NO 360
<211> LENGTH: 107
<212> TYPE: PRT
<213> ORGANISM: Artificial Sequence
<220> FEATURE:
<223> OTHER INFORMATION: Synthetic

<400> SEQUENCE: 360

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Thr Tyr
            20                  25                  30

Leu Ala Trp Phe Gln Gln Lys Pro Gly Lys Ala Pro Lys Ser Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Ser Ser Pro Leu
                85                  90                  95

Thr Phe Gly Gly Gly Thr Lys Val Glu Ile Lys
            100                 105

<210> SEQ ID NO 361
<211> LENGTH: 348
<212> TYPE: DNA
<213> ORGANISM: Artificial Sequence
<220> FEATURE:
<223> OTHER INFORMATION: Synthetic

<400> SEQUENCE: 361
gaagtgcaac tggtggagtc tgggggagac ttggtacagc ctggcaggtc cctgagactc      60
tcctgtgcag cctctggatt cacctttgat gattatgcca tgcactgggt ccggcaagct     120
ccagggaggg gcctagagtg ggtctcaggt attacttgga atagtggtac catggcctat     180
```
gcggactctg tggagggccg attcaccatc tccagagaca acgccaagaa ctccctgtat    240
ctacaaatga acagtctgag agctgaggac acggccttat attactgtgc aagagaaaac    300
tgggcctttg actactgggg ccagggaacc ctggtcaccg tctcctca                 348

<210> SEQ ID NO 362
<211> LENGTH: 116
<212> TYPE: PRT
<213> ORGANISM: Artificial Sequence
<220> FEATURE:
<223> OTHER INFORMATION: Synthetic

<400> SEQUENCE: 362

Glu Val Gln Leu Val Glu Ser Gly Gly Asp Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Arg Gly Leu Glu Trp Val
        35                  40                  45

Ser Gly Ile Thr Trp Asn Ser Gly Thr Met Ala Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Glu Asn Trp Ala Phe Asp Tyr Trp Gly Gln Gly Thr Leu Val
            100                 105                 110

Thr Val Ser Ser
        115

<210> SEQ ID NO 363
<211> LENGTH: 24
<212> TYPE: DNA
<213> ORGANISM: Artificial Sequence
<220> FEATURE:
<223> OTHER INFORMATION: Synthetic

<400> SEQUENCE: 363
ggattcacct ttgatgatta tgcc                                           24

<210> SEQ ID NO 364
<211> LENGTH: 8
<212> TYPE: PRT
<213> ORGANISM: Artificial Sequence
<220> FEATURE:
<223> OTHER INFORMATION: Synthetic

<400> SEQUENCE: 364

Gly Phe Thr Phe Asp Asp Tyr Ala
 1               5

<210> SEQ ID NO 365
<211> LENGTH: 24
<212> TYPE: DNA
<213> ORGANISM: Artificial Sequence
<220> FEATURE:
<223> OTHER INFORMATION: Synthetic

<400> SEQUENCE: 365
attacttgga atagtggtac catg                                           24

-continued

<210> SEQ ID NO 366
<211> LENGTH: 8
<212> TYPE: PRT
<213> ORGANISM: Artificial Sequence
<220> FEATURE:
<223> OTHER INFORMATION: Synthetic

<400> SEQUENCE: 366

Ile Thr Trp Asn Ser Gly Thr Met
1               5

<210> SEQ ID NO 367
<211> LENGTH: 27
<212> TYPE: DNA
<213> ORGANISM: Artificial Sequence
<220> FEATURE:
<223> OTHER INFORMATION: Synthetic

<400> SEQUENCE: 367
gcaagagaaa actgggcctt tgactac                                         27

<210> SEQ ID NO 368
<211> LENGTH: 9
<212> TYPE: PRT
<213> ORGANISM: Artificial Sequence
<220> FEATURE:
<223> OTHER INFORMATION: Synthetic

<400> SEQUENCE: 368

Ala Arg Glu Asn Trp Ala Phe Asp Tyr
1               5

<210> SEQ ID NO 369
<211> LENGTH: 336
<212> TYPE: DNA
<213> ORGANISM: Artificial Sequence
<220> FEATURE:
<223> OTHER INFORMATION: Synthetic

<400> SEQUENCE: 369
gatattgtga tgacccagac tccactctcc tcacctgtca cccttggaca gccggcctcc     60
atctcctgca ggtctagtca gcctcgtca cacagtgatg gaaacaccta cttgagttgg    120
cttcagcaga ggccaggcca gcctccaaga ctcctaattt ataagatttc taaccggttc    180
tctggggtcc cagacagatt cagtggcagt gggccaggga cagatttcac actgaaaatc    240
agcagggtgg aagctgagga tgtcggggtt tatttctgca tgcaagctac acaatttccg    300
tacacttttg gccaggggac caagctggag atcaaa                              336

<210> SEQ ID NO 370
<211> LENGTH: 112
<212> TYPE: PRT
<213> ORGANISM: Artificial Sequence
<220> FEATURE:
<223> OTHER INFORMATION: Synthetic

<400> SEQUENCE: 370

Asp Ile Val Met Thr Gln Thr Pro Leu Ser Ser Pro Val Thr Leu Gly
1               5                   10                  15

Gln Pro Ala Ser Ile Ser Cys Arg Ser Ser His Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro

```
                  50                  55                  60

Asp Arg Phe Ser Gly Ser Gly Pro Gly Thr Asp Phe Thr Leu Lys Ile
 65                  70                  75                  80

Ser Arg Val Glu Ala Glu Asp Val Gly Val Tyr Phe Cys Met Gln Ala
                 85                  90                  95

Thr Gln Phe Pro Tyr Thr Phe Gly Gln Gly Thr Lys Leu Glu Ile Lys
            100                 105                 110
```

<210> SEQ ID NO 371
<211> LENGTH: 33
<212> TYPE: DNA
<213> ORGANISM: Artificial Sequence
<220> FEATURE:
<223> OTHER INFORMATION: Synthetic

<400> SEQUENCE: 371
cacagcctcg tacacagtga tggaaacacc tac                                33

<210> SEQ ID NO 372
<211> LENGTH: 11
<212> TYPE: PRT
<213> ORGANISM: Artificial Sequence
<220> FEATURE:
<223> OTHER INFORMATION: Synthetic

<400> SEQUENCE: 372

```
His Ser Leu Val His Ser Asp Gly Asn Thr Tyr
 1               5                  10
```

<210> SEQ ID NO 373
<211> LENGTH: 9
<212> TYPE: DNA
<213> ORGANISM: Artificial Sequence
<220> FEATURE:
<223> OTHER INFORMATION: Synthetic

<400> SEQUENCE: 373 aagatttct                                                           9

<210> SEQ ID NO 374
<211> LENGTH: 3
<212> TYPE: PRT
<213> ORGANISM: Artificial Sequence
<220> FEATURE:
<223> OTHER INFORMATION: Synthetic

<400> SEQUENCE: 374

```
Lys Ile Ser
 1
```

<210> SEQ ID NO 375
<211> LENGTH: 27
<212> TYPE: DNA
<213> ORGANISM: Artificial Sequence
<220> FEATURE:
<223> OTHER INFORMATION: Synthetic

<400> SEQUENCE: 375
atgcaagcta cacaatttcc gtacact                                       27

<210> SEQ ID NO 376
<211> LENGTH: 9
<212> TYPE: PRT
<213> ORGANISM: Artificial Sequence
<220> FEATURE:

<223> OTHER INFORMATION: Synthetic

<400> SEQUENCE: 376

Met Gln Ala Thr Gln Phe Pro Tyr Thr
1               5

<210> SEQ ID NO 377
<211> LENGTH: 348
<212> TYPE: DNA
<213> ORGANISM: Artificial Sequence
<220> FEATURE:
<223> OTHER INFORMATION: Synthetic

<400> SEQUENCE: 377

```
gaagtgcagc tggtggagtc tgggggagac ttggtacagc ctggcaggtc cctgagactc      60
tcctgtgcag cctctggatt cacctttgat gattatgcca tgcactgggt ccggcaagct     120
ccagggaggg gcctagagtg ggtctcaggt attacttgga atagtggtac catggcctat     180
gcggactctg tggagggccg attcaccatc tccagagaca cgccaagaa ctccctgtat      240
ctacaaatga acagtctgag agctgaggac acggcttat attactgtgc aagagaaaac      300
tgggcctttg actactgggg ccagggaacc ctggtcaccg tctcctca                  348
```

<210> SEQ ID NO 378
<211> LENGTH: 116
<212> TYPE: PRT
<213> ORGANISM: Artificial Sequence
<220> FEATURE:
<223> OTHER INFORMATION: Synthetic

<400> SEQUENCE: 378

Glu Val Gln Leu Val Glu Ser Gly Gly Asp Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Arg Gly Leu Glu Trp Val
        35                  40                  45

Ser Gly Ile Thr Trp Asn Ser Gly Thr Met Ala Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Glu Asn Trp Ala Phe Asp Tyr Trp Gly Gln Gly Thr Leu Val
            100                 105                 110

Thr Val Ser Ser
        115

<210> SEQ ID NO 379
<211> LENGTH: 336
<212> TYPE: DNA
<213> ORGANISM: Artificial Sequence
<220> FEATURE:
<223> OTHER INFORMATION: Synthetic

<400> SEQUENCE: 379

```
gatattgtga tgacccagac tccactctcc tcacctgtca cccttggaca gccggcctcc      60
atctcctgca ggtctagtca gagcctcgta cacagtgatg aaacaccta cttgagttgg     120
cttcagcaga ggccaggcca gcctccaaga ctcctaattt ataagatttc taaccggttc    180
```

```
tctgggtcc cagacagatt cagtggcagt gggccaggga cagatttcac actgaaaatc    240 agcaggtgg aagctgagga tgtcggggtt tatttctgca tgcaagctac acaatttccg    300 tacactttg gccagggac caagctggag atcaaa                                336
```

<210> SEQ ID NO 380
<211> LENGTH: 112
<212> TYPE: PRT
<213> ORGANISM: Artificial Sequence
<220> FEATURE:
<223> OTHER INFORMATION: Synthetic

<400> SEQUENCE: 380

```
Asp Ile Val Met Thr Gln Thr Pro Leu Ser Ser Pro Val Thr Leu Gly
  1               5                  10                  15

Gln Pro Ala Ser Ile Ser Cys Arg Ser Ser His Ser Leu Val His Ser
             20                  25                  30

Asp Gly Asn Thr Tyr Leu Ser Trp Leu Gln Gln Arg Pro Gly Gln Pro
         35                  40                  45

Pro Arg Leu Leu Ile Tyr Lys Ile Ser Asn Arg Phe Ser Gly Val Pro
     50                  55                  60

Asp Arg Phe Ser Gly Ser Gly Pro Gly Thr Asp Phe Thr Leu Lys Ile
 65                  70                  75                  80

Ser Arg Val Glu Ala Glu Asp Val Gly Val Tyr Phe Cys Met Gln Ala
                 85                  90                  95

Thr Gln Phe Pro Tyr Thr Phe Gly Gln Gly Thr Lys Leu Glu Ile Lys
            100                 105                 110
```

<210> SEQ ID NO 381
<211> LENGTH: 348
<212> TYPE: DNA
<213> ORGANISM: Artificial Sequence
<220> FEATURE:
<223> OTHER INFORMATION: Synthetic

<400> SEQUENCE: 381

```
gaagtgcagc tggtggagtc tgggggaggc ttggtacagc ctggcaggtc cctgagactc    60
tcctgtgcag cctctggatt cacctttgat gattatgcca tgcactgggt ccggcaagct    120
ccagggaagg gcctggagtg ggtctcaggt attacttgga atagtggtac catgggctat    180
gcggactctg tgaagggccg attcaccatc tccagagaca cgccaagaa ctccctgtat    240 ctgcaaatga acagtctgag agctgaggac acggccttgt attactgtgc aagagaaaac    300 tgggccttg actactgggg ccagggaacc ctggtcaccg tctcctca                  348
```

<210> SEQ ID NO 382
<211> LENGTH: 116
<212> TYPE: PRT
<213> ORGANISM: Artificial Sequence
<220> FEATURE:
<223> OTHER INFORMATION: Synthetic

<400> SEQUENCE: 382

```
Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Gly Ile Thr Trp Asn Ser Gly Thr Met Gly Tyr Ala Asp Ser Val
```

```
                 50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Glu Asn Trp Ala Phe Asp Tyr Trp Gly Gln Gly Thr Leu Val
                100                 105                 110

Thr Val Ser Ser
        115

<210> SEQ ID NO 383
<211> LENGTH: 337
<212> TYPE: DNA
<213> ORGANISM: Artificial Sequence
<220> FEATURE:
<223> OTHER INFORMATION: Synthetic

<400> SEQUENCE: 383
gatattgtga tgacccagac tccactctcc tcacctgtca cccttggaca gccggcctcc     60
atctcctgca ggtctagtca gcctcgtaca cagtgatg gaaacaccta cttgagttgg     120
cttcagcaga ggccaggcca gcctccaaga ctcctaattt ataagatttc taaccggttc    180
tctggggtcc cagacagatt cagtggcagt ggggcaggga cagatttcac actgaaaatc    240
agcagggtgg aagctgagga tgtcgggggtt attactgca tgcaagctac acaatttccg    300
tacacttttg gccaggggac caagctggag atcaaac                             337

<210> SEQ ID NO 384
<211> LENGTH: 112
<212> TYPE: PRT
<213> ORGANISM: Artificial Sequence
<220> FEATURE:
<223> OTHER INFORMATION: Synthetic

<400> SEQUENCE: 384

Asp Ile Val Met Thr Gln Thr Pro Leu Ser Ser Pro Val Thr Leu Gly
  1               5                  10                  15

Gln Pro Ala Ser Ile Ser Cys Arg Ser Ser His Ser Leu Val His Ser
                 20                  25                  30

Asp Gly Asn Thr Tyr Leu Ser Trp Leu Gln Gln Arg Pro Gly Gln Pro
             35                  40                  45

Pro Arg Leu Leu Ile Tyr Lys Ile Ser Asn Arg Phe Ser Gly Val Pro
         50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Thr Gln Phe Pro Tyr Thr Phe Gly Gln Gly Thr Lys Leu Glu Ile Lys
                100                 105                 110

<210> SEQ ID NO 385
<211> LENGTH: 354
<212> TYPE: DNA
<213> ORGANISM: Artificial Sequence
<220> FEATURE:
<223> OTHER INFORMATION: Synthetic

<400> SEQUENCE: 385
gaggtgcaac tggtggagtc tgggggaaac gtggtacggc cggggggtc cctgagactc      60
```

```
tcctgtgcag cctctggatt cacctttgat gattatggca tgacctgggt ccgccaagtt    120
ccggggaagg ggctggagtg ggtctctggt attaattgga atggtggtag tacagattat    180
gcagactctg tgaagggccg attcaccata tctagagaca acgccaagaa ctccctgtat    240
ctgcaaatga atagtctgag agccgaggac acggccttat attactgtgc gagagataag    300
gggttctacg gtatggacgt ctggggccaa gggaccacgg tcaccgtctc ctca          354
```

<210> SEQ ID NO 386
<211> LENGTH: 118
<212> TYPE: PRT
<213> ORGANISM: Artificial Sequence
<220> FEATURE:
<223> OTHER INFORMATION: Synthetic

<400> SEQUENCE: 386

```
Glu Val Gln Leu Val Glu Ser Gly Gly Asn Val Val Arg Pro Gly Gly
 1               5                  10                  15

Ser Leu Arg Leu Ser Cys Ala Ala Ser Gly Phe Thr Phe Asp Asp Tyr
            20                  25                  30

Gly Met Thr Trp Val Arg Gln Val Pro Gly Lys Gly Leu Glu Trp Val
        35                  40                  45

Ser Gly Ile Asn Trp Asn Gly Gly Ser Thr Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Lys Gly Phe Tyr Gly Met Asp Val Trp Gly Gln Gly Thr
            100                 105                 110

Thr Val Thr Val Ser Ser
        115
```

<210> SEQ ID NO 387
<211> LENGTH: 24
<212> TYPE: DNA
<213> ORGANISM: Artificial Sequence
<220> FEATURE:
<223> OTHER INFORMATION: Synthetic

<400> SEQUENCE: 387

```
ggattcacct ttgatgatta tggc                                            24
```

<210> SEQ ID NO 388
<211> LENGTH: 8
<212> TYPE: PRT
<213> ORGANISM: Artificial Sequence
<220> FEATURE:
<223> OTHER INFORMATION: Synthetic

<400> SEQUENCE: 388

```
Gly Phe Thr Phe Asp Asp Tyr Gly
 1               5
```

<210> SEQ ID NO 389
<211> LENGTH: 24
<212> TYPE: DNA
<213> ORGANISM: Artificial Sequence
<220> FEATURE:
<223> OTHER INFORMATION: Synthetic

<400> SEQUENCE: 389

```
attaattgga atggtggtag taca                                              24
```

<210> SEQ ID NO 390
<211> LENGTH: 8
<212> TYPE: PRT
<213> ORGANISM: Artificial Sequence
<220> FEATURE:
<223> OTHER INFORMATION: Synthetic

<400> SEQUENCE: 390

Ile Asn Trp Asn Gly Gly Ser Thr
1               5

<210> SEQ ID NO 391
<211> LENGTH: 33
<212> TYPE: DNA
<213> ORGANISM: Artificial Sequence
<220> FEATURE:
<223> OTHER INFORMATION: Synthetic

<400> SEQUENCE: 391

```
gcgagagata aggggttcta cggtatggac gtc                                    33
```

<210> SEQ ID NO 392
<211> LENGTH: 11
<212> TYPE: PRT
<213> ORGANISM: Artificial Sequence
<220> FEATURE:
<223> OTHER INFORMATION: Synthetic

<400> SEQUENCE: 392

Ala Arg Asp Lys Gly Phe Tyr Gly Met Asp Val
1               5                   10

<210> SEQ ID NO 393
<211> LENGTH: 339
<212> TYPE: DNA
<213> ORGANISM: Artificial Sequence
<220> FEATURE:
<223> OTHER INFORMATION: Synthetic

<400> SEQUENCE: 393

```
gacatcgtga tgacccagtc tccagactcc ctggctgtgt ctctgggcga gagggccacc        60
atcaactgca gtccagcca gaatccttta tacaactcca caaaaagaa gtacttagct        120
tggtaccagc agaaaccagg acagccccct aagctggtca tttactgggc atctacccgg      180
gaatccgggg tccctgaccg attcagtggc agcgggtctg ggacagattt cactctcacc      240
atcaccagcc tacaggctga agatgtggca gtttattact gtcaacaata ttatagtact      300
ccgtacactt ttggccaggg gaccaagctg gagatcaaa                             339
```

<210> SEQ ID NO 394
<211> LENGTH: 113
<212> TYPE: PRT
<213> ORGANISM: Artificial Sequence
<220> FEATURE:
<223> OTHER INFORMATION: Synthetic

<400> SEQUENCE: 394

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Pro Leu Tyr Asn
            20                  25                  30

Ser Asn Lys Lys Lys Tyr Leu Ala Trp Tyr Gln Gln Lys Pro Gly Gln

```
            35                  40                  45
Pro Pro Lys Leu Val Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Thr Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys

<210> SEQ ID NO 395
<211> LENGTH: 36
<212> TYPE: DNA
<213> ORGANISM: Artificial Sequence
<220> FEATURE:
<223> OTHER INFORMATION: Synthetic

<400> SEQUENCE: 395
cagaatcctt tatacaactc caacaaaaag aagtac                              36

<210> SEQ ID NO 396
<211> LENGTH: 12
<212> TYPE: PRT
<213> ORGANISM: Artificial Sequence
<220> FEATURE:
<223> OTHER INFORMATION: Synthetic

<400> SEQUENCE: 396

Gln Asn Pro Leu Tyr Asn Ser Asn Lys Lys Lys Tyr
1               5                   10

<210> SEQ ID NO 397
<211> LENGTH: 9
<212> TYPE: DNA
<213> ORGANISM: Artificial Sequence
<220> FEATURE:
<223> OTHER INFORMATION: Synthetic

<400> SEQUENCE: 397 tgggcatct                                                             9

<210> SEQ ID NO 398
<211> LENGTH: 3
<212> TYPE: PRT
<213> ORGANISM: Artificial Sequence
<220> FEATURE:
<223> OTHER INFORMATION: Synthetic

<400> SEQUENCE: 398

Trp Ala Ser
1

<210> SEQ ID NO 399
<211> LENGTH: 27
<212> TYPE: DNA
<213> ORGANISM: Artificial Sequence
<220> FEATURE:
<223> OTHER INFORMATION: Synthetic

<400> SEQUENCE: 399
caacaatatt atagtactcc gtacact                                        27
```

```
<210> SEQ ID NO 400
<211> LENGTH: 9
<212> TYPE: PRT
<213> ORGANISM: Artificial Sequence
<220> FEATURE:
<223> OTHER INFORMATION: Synthetic

<400> SEQUENCE: 400

Gln Gln Tyr Tyr Ser Thr Pro Tyr Thr
 1               5

<210> SEQ ID NO 401
<211> LENGTH: 351
<212> TYPE: DNA
<213> ORGANISM: Artificial Sequence
<220> FEATURE:
<223> OTHER INFORMATION: Synthetic

<400> SEQUENCE: 401
gaggtgcagc tggtggagtc tgggggaaac gtggtacggc cggggggtc cctgagactc      60 tcctgtgcag cctctggatt cacctttgat gattatggca tgacctgggt ccgccaagtt    120
ccggggaagg ggctgagtg gtctctggt attaattgga atggtggtag tacagattat     180
gcagactctg tgaagggccg attcaccata tctagagaca cgccaagaa ctccctgtat    240 ctgcaaatga atagtctgag agccgaggac acggccttat attactgtgc gagagataag    300
gggttctacg gtatggacgt ctggggccaa gggaccacgg tcaccgtctc c             351

<210> SEQ ID NO 402
<211> LENGTH: 117
<212> TYPE: PRT
<213> ORGANISM: Artificial Sequence
<220> FEATURE:
<223> OTHER INFORMATION: Synthetic

<400> SEQUENCE: 402

Glu Val Gln Leu Val Glu Ser Gly Gly Asn Val Val Arg Pro Gly Gly
 1               5                  10                  15

Ser Leu Arg Leu Ser Cys Ala Ala Ser Gly Phe Thr Phe Asp Asp Tyr
             20                  25                  30

Gly Met Thr Trp Val Arg Gln Val Pro Gly Lys Gly Leu Glu Trp Val
         35                  40                  45

Ser Gly Ile Asn Trp Asn Gly Gly Ser Thr Asp Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Asp Lys Gly Phe Tyr Gly Met Asp Val Trp Gly Gln Gly Thr
            100                 105                 110

Thr Val Thr Val Ser
        115

<210> SEQ ID NO 403
<211> LENGTH: 339
<212> TYPE: DNA
<213> ORGANISM: Artificial Sequence
<220> FEATURE:
<223> OTHER INFORMATION: Synthetic

<400> SEQUENCE: 403
gacatcgtga tgacccagtc tccagactcc ctggctgtgt ctctgggcga gagggccacc      60
```

```
atcaactgca agtccagcca gaatccttta tacaactcca acaaaaagaa gtacttagct      120
tggtaccagc agaaaccagg acagccccct aagctggtca tttactgggc atctacccgg      180
gaatccgggg tccctgaccg attcagtggc agcgggtctg ggacagattt cactctcacc      240
atcaccagcc tacaggctga agatgtggca gtttattact gtcaacaata ttatagtact      300
ccgtacactt ttggccaggg gaccaagctg gagatcaaa                             339
```

```
<210> SEQ ID NO 404
<211> LENGTH: 113
<212> TYPE: PRT
<213> ORGANISM: Artificial Sequence
<220> FEATURE:
<223> OTHER INFORMATION: Synthetic

<400> SEQUENCE: 404
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Pro Leu Tyr Asn
            20                  25                  30

Ser Asn Lys Lys Lys Tyr Leu Ala Trp Tyr Gln Gln Lys Pro Gly Gln
        35                  40                  45

Pro Pro Lys Leu Val Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Thr Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys

```
<210> SEQ ID NO 405
<211> LENGTH: 352
<212> TYPE: DNA
<213> ORGANISM: Artificial Sequence
<220> FEATURE:
<223> OTHER INFORMATION: Synthetic

<400> SEQUENCE: 405
```

```
gaggtgcagc tggtggagtc tgggggaggt gtggtacggc ctgggggtc cctgagactc       60 tcctgtgcag cctctggatt cacctttgat gattatggca tgagctgggt ccgccaagct     120
ccagggaagg ggctggagtg ggtctctggt attaattgga tggtggtag tacaggttat      180 gcagactctg tgaagggccg attcaccatc tccagagaca acgccaagaa ctccctgtat     240
ctgcaaatga acagtctgag agccgaggac acggccttgt atcactgtgc gagagataag     300
gggttctacg gtatggacgt ctggggccaa gggaccacgg tcaccgtctc ct             352
```

```
<210> SEQ ID NO 406
<211> LENGTH: 117
<212> TYPE: PRT
<213> ORGANISM: Artificial Sequence
<220> FEATURE:
<223> OTHER INFORMATION: Synthetic

<400> SEQUENCE: 406
```

Glu Val Gln Leu Val Glu Ser Gly Gly Gly Val Val Arg Pro Gly Gly
1               5                   10                  15

```
Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Asp Lys Gly Phe Tyr Gly Met Asp Val Trp Gly Gln Gly Thr
            100                 105                 110

Thr Val Thr Val Ser
        115

<210> SEQ ID NO 407
<211> LENGTH: 340
<212> TYPE: DNA
<213> ORGANISM: Artificial Sequence
<220> FEATURE:
<223> OTHER INFORMATION: Synthetic

<400> SEQUENCE: 407
gacatcgtga tgacccagtc tccagactcc ctggctgtgt ctctgggcga gagggccacc      60
atcaactgca agtccagcca gaatcccttta tacaactcca acaaaaagaa gtacttagct    120
tggtaccagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtcaacaata ttatagtact    300
ccgtacactt ttggccaggg gaccaagctg gagatcaaac                            340

<210> SEQ ID NO 408
<211> LENGTH: 113
<212> TYPE: PRT
<213> ORGANISM: Artificial Sequence
<220> FEATURE:
<223> OTHER INFORMATION: Synthetic

<400> SEQUENCE: 408

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Pro Leu Tyr Asn
            20                  25                  30

Ser Asn Lys Lys Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys

<210> SEQ ID NO 409
<211> LENGTH: 384
```

<212> TYPE: DNA
<213> ORGANISM: Artificial Sequence
<220> FEATURE:
<223> OTHER INFORMATION: Synthetic

<400> SEQUENCE: 409

```
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg gtctcaggt attagttgga atagtggtag cataggctat     180
gcggactctg tgaagggccg attcaccatc tccagagaca acgccaagaa ctccctgtat     240
ctgcaaatga acagtctgag agctgaggac acggccttgt attactgtgc aaaagataga     300
ttccctccgt ataagtataa cagtggtggt ttttctgatg cttttgaaat ctggggccaa     360
gggacaatgg tcaccgtctc ttca                                            384
```

<210> SEQ ID NO 410
<211> LENGTH: 128
<212> TYPE: PRT
<213> ORGANISM: Artificial Sequence
<220> FEATURE:
<223> OTHER INFORMATION: Synthetic

<400> SEQUENCE: 410

```
Glu Val Gln Leu Val Glu Ser Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
             35                  40                  45

Ser Gly Ile Ser Trp Asn Ser Gly Ser Ile Gly Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Arg Phe Pro Pro Tyr Lys Tyr Asn Ser Gly Gly Phe Ser
            100                 105                 110

Asp Ala Phe Glu Ile Trp Gly Gln Gly Thr Met Val Thr Val Ser Ser
        115                 120                 125
```

<210> SEQ ID NO 411
<211> LENGTH: 24
<212> TYPE: DNA
<213> ORGANISM: Artificial Sequence
<220> FEATURE:
<223> OTHER INFORMATION: Synthetic

<400> SEQUENCE: 411

```
ggattcacct ttgatgatta tgcc                                             24
```

<210> SEQ ID NO 412
<211> LENGTH: 8
<212> TYPE: PRT
<213> ORGANISM: Artificial Sequence
<220> FEATURE:
<223> OTHER INFORMATION: Synthetic

<400> SEQUENCE: 412

```
Gly Phe Thr Phe Asp Asp Tyr Ala
 1               5
```

<210> SEQ ID NO 413
<211> LENGTH: 24
<212> TYPE: DNA
<213> ORGANISM: Artificial Sequence
<220> FEATURE:
<223> OTHER INFORMATION: Synthetic

<400> SEQUENCE: 413
attagttgga atagtggtag cata                                           24

<210> SEQ ID NO 414
<211> LENGTH: 8
<212> TYPE: PRT
<213> ORGANISM: Artificial Sequence
<220> FEATURE:
<223> OTHER INFORMATION: Synthetic

<400> SEQUENCE: 414

Ile Ser Trp Asn Ser Gly Ser Ile
 1               5

<210> SEQ ID NO 415
<211> LENGTH: 63
<212> TYPE: DNA
<213> ORGANISM: Artificial Sequence
<220> FEATURE:
<223> OTHER INFORMATION: Synthetic

<400> SEQUENCE: 415
gcaaaagata gattccctcc gtataagtat aacagtggtg gttttttctga tgcttttgaa    60 atc                                                                  63

<210> SEQ ID NO 416
<211> LENGTH: 21
<212> TYPE: PRT
<213> ORGANISM: Artificial Sequence
<220> FEATURE:
<223> OTHER INFORMATION: Synthetic

<400> SEQUENCE: 416

Ala Lys Asp Arg Phe Pro Pro Tyr Lys Tyr Asn Ser Gly Gly Phe Ser
 1               5                  10                  15

Asp Ala Phe Glu Ile
            20

<210> SEQ ID NO 417
<211> LENGTH: 324
<212> TYPE: DNA
<213> ORGANISM: Artificial Sequence
<220> FEATURE:
<223> OTHER INFORMATION: Synthetic

<400> SEQUENCE: 417
gaaattgtgt tgacgcagtc tccaggcacc ctgtctttgt ctccagggga aagagccacc    60
ctctcctgca gggccagtca gagttttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gttcaccgat caccttcggc   300
caagggacac gactggagat tgaa                                          324

<210> SEQ ID NO 418
<211> LENGTH: 108
<212> TYPE: PRT
<213> ORGANISM: Artificial Sequence
<220> FEATURE:
<223> OTHER INFORMATION: Synthetic

<400> SEQUENCE: 418

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Phe Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Ile Thr Phe Gly Gln Gly Thr Arg Leu Glu Ile Glu
            100                 105

<210> SEQ ID NO 419
<211> LENGTH: 21
<212> TYPE: DNA
<213> ORGANISM: Artificial Sequence
<220> FEATURE:
<223> OTHER INFORMATION: Synthetic

<400> SEQUENCE: 419
cagagtttta gcagcagcta c                                              21

<210> SEQ ID NO 420
<211> LENGTH: 7
<212> TYPE: PRT
<213> ORGANISM: Artificial Sequence
<220> FEATURE:
<223> OTHER INFORMATION: Synthetic

<400> SEQUENCE: 420

Gln Ser Phe Ser Ser Ser Tyr
1               5

<210> SEQ ID NO 421
<211> LENGTH: 9
<212> TYPE: DNA
<213> ORGANISM: Artificial Sequence
<220> FEATURE:
<223> OTHER INFORMATION: Synthetic

<400> SEQUENCE: 421 ggtgcatcc                                                             9

<210> SEQ ID NO 422
<211> LENGTH: 3
<212> TYPE: PRT
<213> ORGANISM: Artificial Sequence
<220> FEATURE:
<223> OTHER INFORMATION: Synthetic

<400> SEQUENCE: 422

Gly Ala Ser
1

<210> SEQ ID NO 423
<211> LENGTH: 27
<212> TYPE: DNA
<213> ORGANISM: Artificial Sequence
<220> FEATURE:
<223> OTHER INFORMATION: Synthetic

<400> SEQUENCE: 423

```
cagcagtatg gtagttcacc gatcacc                                             27
```

<210> SEQ ID NO 424
<211> LENGTH: 9
<212> TYPE: PRT
<213> ORGANISM: Artificial Sequence
<220> FEATURE:
<223> OTHER INFORMATION: Synthetic

<400> SEQUENCE: 424

Gln Gln Tyr Gly Ser Ser Pro Ile Thr
 1               5

<210> SEQ ID NO 425
<211> LENGTH: 384
<212> TYPE: DNA
<213> ORGANISM: Artificial Sequence
<220> FEATURE:
<223> OTHER INFORMATION: Synthetic

<400> SEQUENCE: 425

```
gaagtgcagc tggtggagtc tgggggaggc ttggtacagc ctggcaggtc cctgagactc         60
tcctgtgcag cctctggatt cacctttgat gattatgcca tgcactgggt ccggcaagct        120
ccagggaagg gcctggagtg ggtctcaggt attagttgga atagtggtag catagggctat       180
gcggactctg tgaagggccg attcaccatc tccagagaca acgccaagaa ctccctgtat        240
ctgcaaatga acagtctgag agctgaggac acggccttgt attactgtgc aaaagataga        300
ttccctccgt ataagtataa cagtggtggt ttttctgatg cttttgaaat ctggggccaa        360
gggacaatgg tcaccgtctc ttca                                               384
```

<210> SEQ ID NO 426
<211> LENGTH: 128
<212> TYPE: PRT
<213> ORGANISM: Artificial Sequence
<220> FEATURE:
<223> OTHER INFORMATION: Synthetic

<400> SEQUENCE: 426

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Gly Ile Ser Trp Asn Ser Gly Ser Ile Gly Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Arg Phe Pro Pro Tyr Lys Tyr Asn Ser Gly Gly Phe Ser

```
                 100                 105                 110
Asp Ala Phe Glu Ile Trp Gly Gln Gly Thr Met Val Thr Val Ser Ser
        115                 120                 125

<210> SEQ ID NO 427
<211> LENGTH: 324
<212> TYPE: DNA
<213> ORGANISM: Artificial Sequence
<220> FEATURE:
<223> OTHER INFORMATION: Synthetic

<400> SEQUENCE: 427
gaaattgtgt tgacgcagtc tccaggcacc ctgtctttgt ctccagggga aagagccacc    60
ctctcctgca gggccagtca gagttttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gttcaccgat caccttcggc   300
caagggacac gactggagat taaa                                          324

<210> SEQ ID NO 428
<211> LENGTH: 108
<212> TYPE: PRT
<213> ORGANISM: Artificial Sequence
<220> FEATURE:
<223> OTHER INFORMATION: Synthetic

<400> SEQUENCE: 428

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Phe Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Ile Thr Phe Gly Gln Gly Thr Arg Leu Glu Ile Lys
            100                 105

<210> SEQ ID NO 429
<211> LENGTH: 384
<212> TYPE: DNA
<213> ORGANISM: Artificial Sequence
<220> FEATURE:
<223> OTHER INFORMATION: Synthetic

<400> SEQUENCE: 429
gaagtgcagc tggtggagtc tgggggaggc ttggtacagc ctggcaggtc cctgagactc    60
tcctgtgcag cctctggatt cacctttgat gattatgcca tgcactgggt ccggcaagct   120
ccagggaagg gcctggagtg gtctcaggt attagttgga atagtggtag cataggctat   180
gcggactctg tgaagggccg attcaccatc tccagagaca acgccaagaa ctccctgtat   240
ctgcaaatga acagtctgag agctgaggac acggccttgt attactgtgc aaaagataga   300
ttccctccgt ataagtataa cagtggtggt ttttctgatg cttttgaaat ctggggccaa   360
```
gggacaatgg tcaccgtctc ttca  384

<210> SEQ ID NO 430
<211> LENGTH: 128
<212> TYPE: PRT
<213> ORGANISM: Artificial Sequence
<220> FEATURE:
<223> OTHER INFORMATION: Synthetic

<400> SEQUENCE: 430

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Arg Phe Pro Pro Tyr Lys Tyr Asn Ser Gly Gly Phe Ser
            100                 105                 110

Asp Ala Phe Glu Ile Trp Gly Gln Gly Thr Met Val Thr Val Ser Ser
        115                 120                 125

<210> SEQ ID NO 431
<211> LENGTH: 325
<212> TYPE: DNA
<213> ORGANISM: Artificial Sequence
<220> FEATURE:
<223> OTHER INFORMATION: Synthetic

<400> SEQUENCE: 431
gaaattgtgt tgacgcagtc tccaggcacc ctgtctttgt ctccagggga aagagccacc      60
ctctcctgca gggccagtca gagttttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gttcaccgat caccttcggc     300
caagggacac gactggagat taaac                                           325

<210> SEQ ID NO 432
<211> LENGTH: 108
<212> TYPE: PRT
<213> ORGANISM: Artificial Sequence
<220> FEATURE:
<223> OTHER INFORMATION: Synthetic

<400> SEQUENCE: 432

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Phe Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser

```
                50                   55                    60
Gly Ser Gly Ser Gly Thr Asp Phe Thr Leu Thr Ile Ser Arg Leu Glu
 65                  70                    75                    80

Pro Glu Asp Phe Ala Val Tyr Tyr Cys Gln Gln Tyr Gly Ser Ser Pro
                     85                    90                    95

Ile Thr Phe Gly Gln Gly Thr Arg Leu Glu Ile Lys
                100                 105
```

<210> SEQ ID NO 433
<211> LENGTH: 366
<212> TYPE: DNA
<213> ORGANISM: Artificial Sequence
<220> FEATURE:
<223> OTHER INFORMATION: Synthetic

<400> SEQUENCE: 433

```
gaggtgcagc tggtggagtc tgggggaggc ttggtacagc ctggggggtc cctgagactc      60
tcctgtgcag cctctggatt caccttcagt agctacgaca tgcactgggt ccgccaagtt     120
acaggaaaag gtctggaatg ggtctcagtc attggtactg ttggtgacac atactatcca     180
ggctccctga agggccgatt caccatctcc agagaaaatg ccaagaactc cttgtatctt     240
caaatgaaca ccctgagagc cggggacacg gctgtttatt actgtgcaag aactggagca     300 gcagccccact cgtactacta cggtatggac gtctggggcc aagggaccat ggtcaccgtc     360
tcctca                                                                366
```

<210> SEQ ID NO 434
<211> LENGTH: 122
<212> TYPE: PRT
<213> ORGANISM: Artificial Sequence
<220> FEATURE:
<223> OTHER INFORMATION: Synthetic

<400> SEQUENCE: 434

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Asp Met His Trp Val Arg Gln Val Thr Gly Lys Gly Leu Glu Trp Val
             35                  40                  45

Ser Val Ile Gly Thr Val Gly Asp Thr Tyr Tyr Pro Gly Ser Leu Lys
 50                  55                  60

Gly Arg Phe Thr Ile Ser Arg Glu Asn Ala Lys Asn Ser Leu Tyr Leu
 65                  70                  75                  80

Gln Met Asn Thr Leu Arg Ala Gly Asp Thr Ala Val Tyr Tyr Cys Ala
                 85                  90                  95

Arg Thr Gly Ala Ala Ala His Ser Tyr Tyr Tyr Gly Met Asp Val Trp
            100                 105                 110

Gly Gln Gly Thr Met Val Thr Val Ser Ser
            115                 120
```

<210> SEQ ID NO 435
<211> LENGTH: 24
<212> TYPE: DNA
<213> ORGANISM: Artificial Sequence
<220> FEATURE:
<223> OTHER INFORMATION: Synthetic

<400> SEQUENCE: 435

```
ggattcacct tcagtagcta cgac                                            24
```

<210> SEQ ID NO 436
<211> LENGTH: 8
<212> TYPE: PRT
<213> ORGANISM: Artificial Sequence
<220> FEATURE:
<223> OTHER INFORMATION: Synthetic

<400> SEQUENCE: 436

Gly Phe Thr Phe Ser Ser Tyr Asp
1               5

<210> SEQ ID NO 437
<211> LENGTH: 21
<212> TYPE: DNA
<213> ORGANISM: Artificial Sequence
<220> FEATURE:
<223> OTHER INFORMATION: Synthetic

<400> SEQUENCE: 437

```
attggtactg ttggtgacac a                                               21
```

<210> SEQ ID NO 438
<211> LENGTH: 7
<212> TYPE: PRT
<213> ORGANISM: Artificial Sequence
<220> FEATURE:
<223> OTHER INFORMATION: Synthetic

<400> SEQUENCE: 438

Ile Gly Thr Val Gly Asp Thr
1               5

<210> SEQ ID NO 439
<211> LENGTH: 48
<212> TYPE: DNA
<213> ORGANISM: Artificial Sequence
<220> FEATURE:
<223> OTHER INFORMATION: Synthetic

<400> SEQUENCE: 439

```
gcaagaactg gagcagcagc ccactcgtac tactacggta tggacgtc                  48
```

<210> SEQ ID NO 440
<211> LENGTH: 16
<212> TYPE: PRT
<213> ORGANISM: Artificial Sequence
<220> FEATURE:
<223> OTHER INFORMATION: Synthetic

<400> SEQUENCE: 440

Ala Arg Thr Gly Ala Ala Ala His Ser Tyr Tyr Tyr Gly Met Asp Val
1               5                   10                  15

<210> SEQ ID NO 441
<211> LENGTH: 321
<212> TYPE: DNA
<213> ORGANISM: Artificial Sequence
<220> FEATURE:
<223> OTHER INFORMATION: Synthetic

<400> SEQUENCE: 441

```
gaaattgtgt tgacgcagtc tccaggcacc ctgtctttgt ctccagggga aagagccacc     60
ctctcctgca gggccagtca gagtgttagc agcagctact tagcctggta ccagcagaaa    120
```

```
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcacccac tttcggcgga    300
gggaccaagg tggagatcaa a                                              321
```

<210> SEQ ID NO 442
<211> LENGTH: 107
<212> TYPE: PRT
<213> ORGANISM: Artificial Sequence
<220> FEATURE:
<223> OTHER INFORMATION: Synthetic

<400> SEQUENCE: 442

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Thr Phe Gly Gly Gly Thr Lys Val Glu Ile Lys
            100                 105
```

<210> SEQ ID NO 443
<211> LENGTH: 21
<212> TYPE: DNA
<213> ORGANISM: Artificial Sequence
<220> FEATURE:
<223> OTHER INFORMATION: Synthetic

<400> SEQUENCE: 443

```
cagagtgtta gcagcagcta c                                               21
```

<210> SEQ ID NO 444
<211> LENGTH: 7
<212> TYPE: PRT
<213> ORGANISM: Artificial Sequence
<220> FEATURE:
<223> OTHER INFORMATION: Synthetic

<400> SEQUENCE: 444

```
Gln Ser Val Ser Ser Ser Tyr
 1               5
```

<210> SEQ ID NO 445
<211> LENGTH: 9
<212> TYPE: DNA
<213> ORGANISM: Artificial Sequence
<220> FEATURE:
<223> OTHER INFORMATION: Synthetic

<400> SEQUENCE: 445

```
ggtgcatcc                                                              9
```

<210> SEQ ID NO 446
<211> LENGTH: 3

```
<212> TYPE: PRT
<213> ORGANISM: Artificial Sequence
<220> FEATURE:
<223> OTHER INFORMATION: Synthetic

<400> SEQUENCE: 446

Gly Ala Ser
 1

<210> SEQ ID NO 447
<211> LENGTH: 24
<212> TYPE: DNA
<213> ORGANISM: Artificial Sequence
<220> FEATURE:
<223> OTHER INFORMATION: Synthetic

<400> SEQUENCE: 447
cagcagtatg gtagctcacc cact                                           24

<210> SEQ ID NO 448
<211> LENGTH: 8
<212> TYPE: PRT
<213> ORGANISM: Artificial Sequence
<220> FEATURE:
<223> OTHER INFORMATION: Synthetic

<400> SEQUENCE: 448

Gln Gln Tyr Gly Ser Ser Pro Thr
 1               5

<210> SEQ ID NO 449
<211> LENGTH: 363
<212> TYPE: DNA
<213> ORGANISM: Artificial Sequence
<220> FEATURE:
<223> OTHER INFORMATION: Synthetic

<400> SEQUENCE: 449
gaggtgcagc tggtggagtc tgggggaggc ttggtacagc ctggggggtc cctgagactc    60
tcctgtgcag cctctggatt caccttcagt agctacgaca tgcactgggt ccgccaagtt   120
acaggaaaag gtctggaatg ggtctcagtc attggtactg ttggtgacac atactatcca   180
ggctccctga agggccgatt caccatctcc agagaaaatg ccaagaactc cttgtatctt   240
caaatgaaca ccctgagagc cggggacacg gctgtttatt actgtgcaag aactggagca   300
gcagcccact cgtactacta cggtatggac gtctggggcc aagggaccac ggtcaccgtc   360
tcc                                                                 363

<210> SEQ ID NO 450
<211> LENGTH: 121
<212> TYPE: PRT
<213> ORGANISM: Artificial Sequence
<220> FEATURE:
<223> OTHER INFORMATION: Synthetic

<400> SEQUENCE: 450

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met His Trp Val Arg Gln Val Thr Gly Lys Gly Leu Glu Trp Val
        35                  40                  45

Ser Val Ile Gly Thr Val Gly Asp Thr Tyr Tyr Pro Gly Ser Leu Lys
```

```
                    50                  55                  60

Gly Arg Phe Thr Ile Ser Arg Glu Asn Ala Lys Asn Ser Leu Tyr Leu
 65                  70                  75                  80

Gln Met Asn Thr Leu Arg Ala Gly Asp Thr Ala Val Tyr Tyr Cys Ala
                     85                  90                  95

Arg Thr Gly Ala Ala His Ser Tyr Tyr Gly Met Asp Val Trp
                100                 105                 110

Gly Gln Gly Thr Thr Val Thr Val Ser
            115                 120

<210> SEQ ID NO 451
<211> LENGTH: 321
<212> TYPE: DNA
<213> ORGANISM: Artificial Sequence
<220> FEATURE:
<223> OTHER INFORMATION: Synthetic

<400> SEQUENCE: 451
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacccac tttcggcgga     300
gggaccaagg tggagatcaa a                                                321

<210> SEQ ID NO 452
<211> LENGTH: 107
<212> TYPE: PRT
<213> ORGANISM: Artificial Sequence
<220> FEATURE:
<223> OTHER INFORMATION: Synthetic

<400> SEQUENCE: 452

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Thr Phe Gly Gly Gly Thr Lys Val Glu Ile Lys
            100                 105

<210> SEQ ID NO 453
<211> LENGTH: 364
<212> TYPE: DNA
<213> ORGANISM: Artificial Sequence
<220> FEATURE:
<223> OTHER INFORMATION: Synthetic

<400> SEQUENCE: 453
gaggtgcagc tggtggagtc tgggggaggc ttggtacagc ctggggggtc cctgagactc      60
```

```
tcctgtgcag cctctggatt caccttcagt agctacgaca tgcactgggt ccgccaagct        120
acaggaaaag gtctggagtg ggtctcagct attggtactg ttggtgacac atactatcca        180
ggctccgtga agggccgatt caccatctcc agagaaaatg ccaagaactc cttgtatctt        240
caaatgaaca gcctgagagc cggggacacg gctgtgtatt actgtgcaag aactggagca        300
gcagcccact cgtactacta cggtatggac gtctggggcc aagggaccac ggtcaccgtc        360
tcct                                                                     364
```

<210> SEQ ID NO 454
<211> LENGTH: 121
<212> TYPE: PRT
<213> ORGANISM: Artificial Sequence
<220> FEATURE:
<223> OTHER INFORMATION: Synthetic

<400> SEQUENCE: 454

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Val Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Thr Gly Ala Ala Ala His Ser Tyr Tyr Tyr Gly Met Asp Val Trp
            100                 105                 110

Gly Gln Gly Thr Thr Val Thr Val Ser
        115                 120
```

<210> SEQ ID NO 455
<211> LENGTH: 322
<212> TYPE: DNA
<213> ORGANISM: Artificial Sequence
<220> FEATURE:
<223> OTHER INFORMATION: Synthetic

<400> SEQUENCE: 455

```
gaaattgtgt tgacgcagtc tccaggcacc ctgtctttgt ctccagggga aagagccacc        60
ctctcctgca gggccagtca gagtgttagc agcagctact tagcctggta ccagcagaaa       120
cctggccagg ctcccaggct cctcatctat ggtgcatcca gcagggccac tggcatccca       180
gacaggttca gtggcagtgg gtctgggaca gacttcactc tcaccatcag cagactggag       240
cctgaagatt ttgcagtgta ttactgtcag cagtatggta gctcacccac tttcggcgga       300
gggaccaagg tggagatcaa ac                                                 322
```

<210> SEQ ID NO 456
<211> LENGTH: 107
<212> TYPE: PRT
<213> ORGANISM: Artificial Sequence
<220> FEATURE:
<223> OTHER INFORMATION: Synthetic

<400> SEQUENCE: 456

```
Glu Ile Val Leu Thr Gln Ser Pro Gly Thr Leu Ser Leu Ser Pro Gly
 1               5                  10                  15
```

```
            1               5                  10                 15
          Glu Arg Ala Thr Leu Ser Cys Arg Ala Ser Gln Ser Val Ser Ser
                         20                  25                  30

Tyr Leu Ala Trp Tyr Gln Gln Lys Pro Gly Gln Ala Pro Arg Leu Leu
                         35                  40                  45

Ile Tyr Gly Ala Ser Ser Arg Ala Thr Gly Ile Pro Asp Arg Phe Ser
           50                  55                  60

Gly Ser Gly Ser Gly Thr Asp Phe Thr Leu Thr Ile Ser Arg Leu Glu
           65                  70                  75                  80

Pro Glu Asp Phe Ala Val Tyr Tyr Cys Gln Gln Tyr Gly Ser Ser Pro
                              85                  90                  95

Thr Phe Gly Gly Gly Thr Lys Val Glu Ile Lys
                         100                 105

<210> SEQ ID NO 457
<211> LENGTH: 345
<212> TYPE: DNA
<213> ORGANISM: Artificial Sequence
<220> FEATURE:
<223> OTHER INFORMATION: synthetic

<400> SEQUENCE: 457
gaggtgcagc tggtggagtc tggggctgag gtgaagaagc ctggggcctc agtgaaggtc    60
tcctgtaagg cttctggatt caccttcacc gactactata tgcactgggt gcgacaggcc   120
cctggacaag ggcttgagtg gctgggatgg atcaacccta agagtggtgc gacaaagtat   180
gcacagaggt tcagggcag ggtcaccatg accaggaca cgtccatcag cacagcctac    240
atggaactga acggactaag atctgacgac acggccgttt tttactgtgc gcgaactgat   300 gctttgata tctggggcca aggacaatg gtcaccgtct cttca                     345

<210> SEQ ID NO 458
<211> LENGTH: 115
<212> TYPE: PRT
<213> ORGANISM: Artificial Sequence
<220> FEATURE:
<223> OTHER INFORMATION: Synthetic

<400> SEQUENCE: 458

Glu Val Gln Leu Val Glu Ser Gly Ala Glu Val Lys Lys Pro Gly Ala
           1               5                  10                  15

Ser Val Lys Val Ser Cys Lys Ala Ser Gly Phe Thr Phe Thr Asp Tyr
                         20                  25                  30

Tyr Met His Trp Val Arg Gln Ala Pro Gly Gln Gly Leu Glu Trp Leu
                         35                  40                  45

Gly Trp Ile Asn Pro Lys Ser Gly Ala Thr Lys Tyr Ala Gln Arg Phe
           50                  55                  60

Gln Gly Arg Val Thr Met Thr Arg Asp Thr Ser Ile Ser Thr Ala Tyr
           65                  70                  75                  80

Met Glu Leu Asn Gly Leu Arg Ser Asp Asp Thr Ala Val Phe Tyr Cys
                              85                  90                  95

Ala Arg Thr Asp Ala Phe Asp Ile Trp Gly Gln Gly Thr Met Val Thr
                         100                 105                 110

Val Ser Ser
                         115

<210> SEQ ID NO 459
<211> LENGTH: 24
```

```
<212> TYPE: DNA
<213> ORGANISM: Artificial Sequence
<220> FEATURE:
<223> OTHER INFORMATION: Synthetic

<400> SEQUENCE: 459
ggattcacct tcaccgacta ctat                                          24

<210> SEQ ID NO 460
<211> LENGTH: 8
<212> TYPE: PRT
<213> ORGANISM: Artificial Sequence
<220> FEATURE:
<223> OTHER INFORMATION: Synthetic

<400> SEQUENCE: 460

Gly Phe Thr Phe Thr Asp Tyr Tyr
 1               5

<210> SEQ ID NO 461
<211> LENGTH: 24
<212> TYPE: DNA
<213> ORGANISM: Artificial Sequence
<220> FEATURE:
<223> OTHER INFORMATION: Synthetic

<400> SEQUENCE: 461
atcaacccta agagtggtgc gaca                                          24

<210> SEQ ID NO 462
<211> LENGTH: 8
<212> TYPE: PRT
<213> ORGANISM: Artificial Sequence
<220> FEATURE:
<223> OTHER INFORMATION: Synthetic

<400> SEQUENCE: 462

Ile Asn Pro Lys Ser Gly Ala Thr
 1               5

<210> SEQ ID NO 463
<211> LENGTH: 24
<212> TYPE: DNA
<213> ORGANISM: Artificial Sequence
<220> FEATURE:
<223> OTHER INFORMATION: Synthetic

<400> SEQUENCE: 463
gcgcgaactg atgcttttga tatc                                          24

<210> SEQ ID NO 464
<211> LENGTH: 8
<212> TYPE: PRT
<213> ORGANISM: Artificial Sequence
<220> FEATURE:
<223> OTHER INFORMATION: Synthetic

<400> SEQUENCE: 464

Ala Arg Thr Asp Ala Phe Asp Ile
 1               5

<210> SEQ ID NO 465
<211> LENGTH: 321
<212> TYPE: DNA
<213> ORGANISM: Artificial Sequence
<220> FEATURE:
<223> OTHER INFORMATION: Synthetic
```

<400> SEQUENCE: 465

```
gacatccagt tgacccagtc tccttccacc ctgtctgcat ctgtaggaga cagagtcacc      60
atcacttgcc gggccagtca gagtgttagt aactggttgg cctggtatca gcagaaacca     120
gggaaagccc ctaaactcct gatctattcg cgtctactt tagaaagtgg ggtcccatca      180
aggttcagcg gcagtgaatc tgggacagaa ttcactctca ccatcagcag cctgcagcct     240
gatgattttg caacttatta ctgccaacac tataatagtt attggacgtt cggccaaggg     300
accaaggtgg aaatcaaacg a                                               321
```

<210> SEQ ID NO 466
<211> LENGTH: 107
<212> TYPE: PRT
<213> ORGANISM: Artificial Sequence
<220> FEATURE:
<223> OTHER INFORMATION: Synthetic

<400> SEQUENCE: 466

```
Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Val Ser Asn Trp
            20                  25                  30

Leu Ala Trp Tyr Gln Gln Lys Pro Gly Lys Ala Pro Lys Leu Leu Ile
        35                  40                  45

Tyr Ser Ala Ser Thr Leu Glu Ser Gly Val Pro Ser Arg Phe Ser Gly
    50                  55                  60

Ser Glu Ser Gly Thr Glu Phe Thr Leu Thr Ile Ser Ser Leu Gln Pro
65                  70                  75                  80

Asp Asp Phe Ala Thr Tyr Tyr Cys Gln His Tyr Asn Ser Tyr Trp Thr
                85                  90                  95

Phe Gly Gln Gly Thr Lys Val Glu Ile Lys Arg
            100                 105
```

<210> SEQ ID NO 467
<211> LENGTH: 18
<212> TYPE: DNA
<213> ORGANISM: Artificial Sequence
<220> FEATURE:
<223> OTHER INFORMATION: Synthetic

<400> SEQUENCE: 467

```
cagagtgtta gtaactgg                                                    18
```

<210> SEQ ID NO 468
<211> LENGTH: 6
<212> TYPE: PRT
<213> ORGANISM: Artificial Sequence
<220> FEATURE:
<223> OTHER INFORMATION: Synthetic

<400> SEQUENCE: 468

```
Gln Ser Val Ser Asn Trp
1               5
```

<210> SEQ ID NO 469
<211> LENGTH: 9
<212> TYPE: DNA
<213> ORGANISM: Artificial Sequence
<220> FEATURE:
<223> OTHER INFORMATION: Synthetic

```
<400> SEQUENCE: 469 tcggcgtct                                                                 9

<210> SEQ ID NO 470
<211> LENGTH: 3
<212> TYPE: PRT
<213> ORGANISM: Artificial Sequence
<220> FEATURE:
<223> OTHER INFORMATION: Synthetic

<400> SEQUENCE: 470

Ser Ala Ser
 1

<210> SEQ ID NO 471
<211> LENGTH: 24
<212> TYPE: DNA
<213> ORGANISM: Artificial Sequence
<220> FEATURE:
<223> OTHER INFORMATION: Synthetic

<400> SEQUENCE: 471
caacactata atagttattg gacg                                               24

<210> SEQ ID NO 472
<211> LENGTH: 8
<212> TYPE: PRT
<213> ORGANISM: Artificial Sequence
<220> FEATURE:
<223> OTHER INFORMATION: Synthetic

<400> SEQUENCE: 472

Gln His Tyr Asn Ser Tyr Trp Thr
 1               5

<210> SEQ ID NO 473
<211> LENGTH: 345
<212> TYPE: DNA
<213> ORGANISM: Artificial Sequence
<220> FEATURE:
<223> OTHER INFORMATION: Synthetic

<400> SEQUENCE: 473
caggtgcagc tggtgcagtc tggggctgag gtgaagaagc ctggggcctc agtgaaggtc         60
tcctgtaagg cttctggatt caccttcacc gactactata tgcactgggt gcgacaggcc        120
cctggacaag ggcttgagtg gctgggatgg atcaaccctc agagtggtgc gacaaagtat        180
gcacagaggt ttcagggcag ggtcaccatg accagggaca cgtccatcag cacagcctac        240
atggaactga acggactaag atctgacgac acggccgttt tttactgtgc gcgaactgat        300
gcttttgata tctggggcca agggacaatg gtcaccgtct cttca                        345

<210> SEQ ID NO 474
<211> LENGTH: 115
<212> TYPE: PRT
<213> ORGANISM: Artificial Sequence
<220> FEATURE:
<223> OTHER INFORMATION: Synthetic

<400> SEQUENCE: 474

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Thr Phe Thr Asp Tyr
             20                  25                  30
```

Tyr Met His Trp Val Arg Gln Ala Pro Gly Gln Gly Leu Glu Trp Leu
            35                  40                  45

Gly Trp Ile Asn Pro Lys Ser Gly Ala Thr Lys Tyr Ala Gln Arg Phe
 50                  55                  60

Gln Gly Arg Val Thr Met Thr Arg Asp Thr Ser Ile Ser Thr Ala Tyr
 65                  70                  75                  80

Met Glu Leu Asn Gly Leu Arg Ser Asp Thr Ala Val Phe Tyr Cys
            85                  90                  95

Ala Arg Thr Asp Ala Phe Asp Ile Trp Gly Gln Gly Thr Met Val Thr
                100                 105                 110

Val Ser Ser
    115

<210> SEQ ID NO 475
<211> LENGTH: 318
<212> TYPE: DNA
<213> ORGANISM: Artificial Sequence
<220> FEATURE:
<223> OTHER INFORMATION: Synthetic

<400> SEQUENCE: 475
gacatccaga tgacccagtc tccttccacc ctgtctgcat ctgtaggaga cagagtcacc    60
atcacttgcc gggccagtca gagtgttagt aactggttgg cctggtatca gcagaaacca   120
gggaaagccc ctaaactcct gatctattcg gcgtctactt tagaaagtgg ggtcccatca   180
aggttcagcg gcagtgaatc tgggacagaa ttcactctca ccatcagcag cctgcagcct   240
gatgattttg caacttatta ctgccaacac tataatagtt attggacgtt cggccaaggg   300
accaaggtgg aaatcaaa                                                 318

<210> SEQ ID NO 476
<211> LENGTH: 106
<212> TYPE: PRT
<213> ORGANISM: Artificial Sequence
<220> FEATURE:
<223> OTHER INFORMATION: Synthetic

<400> SEQUENCE: 476

Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Ser Val Ser Asn Trp
             20                  25                  30

Leu Ala Trp Tyr Gln Gln Lys Pro Gly Lys Ala Pro Lys Leu Leu Ile
         35                  40                  45

Tyr Ser Ala Ser Thr Leu Glu Ser Gly Val Pro Ser Arg Phe Ser Gly
 50                  55                  60

Ser Glu Ser Gly Thr Glu Phe Thr Leu Thr Ile Ser Ser Leu Gln Pro
 65                  70                  75                  80

Asp Asp Phe Ala Thr Tyr Tyr Cys Gln His Tyr Asn Ser Tyr Trp Thr
                 85                  90                  95

Phe Gly Gln Gly Thr Lys Val Glu Ile Lys
            100                 105

<210> SEQ ID NO 477
<211> LENGTH: 345
<212> TYPE: DNA
<213> ORGANISM: Artificial Sequence
<220> FEATURE:
<223> OTHER INFORMATION: Synthetic

<400> SEQUENCE: 477

```
caggtgcagc tggtgcagtc tggggctgag gtgaagaagc ctggggcctc agtgaaggtc      60
tcctgcaagg cttctggatt caccttcacc gactactata tgcactgggt gcgacaggcc     120
cctggacaag gcttgagtg gatgggatgg atcaaccct  agagtggtgc gacaaactat     180
gcacagaagt tcagggcag  ggtcaccatg accagggaca cgtccatcag cacagcctac     240
atggagctga gcaggctgag atctgacgac acggccgtgt attactgtgc gcgaactgat     300
gcttttgata tctggggcca aggacaatg  gtcaccgtct cttca                     345
```

<210> SEQ ID NO 478
<211> LENGTH: 115
<212> TYPE: PRT
<213> ORGANISM: Artificial Sequence
<220> FEATURE:
<223> OTHER INFORMATION: Synthetic

<400> SEQUENCE: 478

```
Gln Val Gln Leu Val Gln Ser Gly Ala Glu Val Lys Lys Pro Gly Ala
  1               5                  10                  15
Ser Val Lys Val Ser Cys Lys Ala Ser Gly Phe Thr Phe Thr Asp Tyr
             20                  25                  30
Tyr Met His Trp Val Arg Gln Ala Pro Gly Gln Gly Leu Glu Trp Met
         35                  40                  45
Gly Trp Ile Asn Pro Lys Ser Gly Ala Thr Asn Tyr Ala Gln Lys Phe
     50                  55                  60
Gln Gly Arg Val Thr Met Thr Arg Asp Thr Ser Ile Ser Thr Ala Tyr
 65                  70                  75                  80
Met Glu Leu Ser Arg Leu Arg Ser Asp Asp Thr Ala Val Tyr Tyr Cys
                 85                  90                  95
Ala Arg Thr Asp Ala Phe Asp Ile Trp Gly Gln Gly Thr Met Val Thr
            100                 105                 110
Val Ser Ser
        115
```

<210> SEQ ID NO 479
<211> LENGTH: 319
<212> TYPE: DNA
<213> ORGANISM: Artificial Sequence
<220> FEATURE:
<223> OTHER INFORMATION: Synthetic

<400> SEQUENCE: 479

```
gacatccaga tgacccagtc tccttccacc ctgtctgcat ctgtaggaga cagagtcacc      60
atcacttgcc gggccagtca gagtgttagt aactggttgg cctggtatca gcagaaacca     120
gggaaagccc ctaagctcct gatctattcg gcgtctagtt tagaaagtgg ggtcccatca     180
aggttcagcg gcagtggatc tgggacagaa ttcactctca ccatcagcag cctgcagcct     240
gatgattttg caacttatta ctgccaacac tataatagtt attggacgtt cggccaaggg     300
accaaggtgg aaatcaaac                                                  319
```

<210> SEQ ID NO 480
<211> LENGTH: 106
<212> TYPE: PRT
<213> ORGANISM: Artificial Sequence
<220> FEATURE:
<223> OTHER INFORMATION: Synthetic

<400> SEQUENCE: 480

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Ser Asn Trp
            20                  25                  30

Leu Ala Trp Tyr Gln Gln Lys Pro Gly Lys Ala Pro Lys Leu Leu Ile
        35                  40                  45

Tyr Ser Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Tyr Asn Ser Tyr Trp Thr
                85                  90                  95

Phe Gly Gln Gly Thr Lys Val Glu Ile Lys
            100                 105

<210> SEQ ID NO 481
<211> LENGTH: 354
<212> TYPE: DNA
<213> ORGANISM: Artificial Sequence
<220> FEATURE:
<223> OTHER INFORMATION: Synthetic

<400> SEQUENCE: 481
gaggtgcagc tggtggagtc tgggggaggc gtggtccagc ctggagggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagatgga     300
tatagtggct acgatgacta ctggggccag ggaaccctgg tcaccgtctc ctca           354

<210> SEQ ID NO 482
<211> LENGTH: 118
<212> TYPE: PRT
<213> ORGANISM: Artificial Sequence
<220> FEATURE:
<223> OTHER INFORMATION: Synthetic

<400> SEQUENCE: 482

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Ser Gly Tyr Asp Asp Tyr Trp Gly Gln Gly Thr
            100                 105                 110

Leu Val Thr Val Ser Ser
        115

```
<210> SEQ ID NO 483
<211> LENGTH: 24
<212> TYPE: DNA
<213> ORGANISM: Artificial Sequence
<220> FEATURE:
<223> OTHER INFORMATION: Synthetic

<400> SEQUENCE: 483
ggattcacct tcagtagcta tggc                                          24

<210> SEQ ID NO 484
<211> LENGTH: 8
<212> TYPE: PRT
<213> ORGANISM: Artificial Sequence
<220> FEATURE:
<223> OTHER INFORMATION: Synthetic

<400> SEQUENCE: 484

Gly Phe Thr Phe Ser Ser Tyr Gly
1               5

<210> SEQ ID NO 485
<211> LENGTH: 24
<212> TYPE: DNA
<213> ORGANISM: Artificial Sequence
<220> FEATURE:
<223> OTHER INFORMATION: Synthetic

<400> SEQUENCE: 485
atatggtatg atggaagtaa taaa                                          24

<210> SEQ ID NO 486
<211> LENGTH: 8
<212> TYPE: PRT
<213> ORGANISM: Artificial Sequence
<220> FEATURE:
<223> OTHER INFORMATION: Synthetic

<400> SEQUENCE: 486

Ile Trp Tyr Asp Gly Ser Asn Lys
1               5

<210> SEQ ID NO 487
<211> LENGTH: 33
<212> TYPE: DNA
<213> ORGANISM: Artificial Sequence
<220> FEATURE:
<223> OTHER INFORMATION: Synthetic

<400> SEQUENCE: 487
gcgagagatg gatatagtgg ctacgatgac tac                                33

<210> SEQ ID NO 488
<211> LENGTH: 11
<212> TYPE: PRT
<213> ORGANISM: Artificial Sequence
<220> FEATURE:
<223> OTHER INFORMATION: Synthetic

<400> SEQUENCE: 488

Ala Arg Asp Gly Tyr Ser Gly Tyr Asp Asp Tyr
1               5                   10

<210> SEQ ID NO 489
<211> LENGTH: 321
<212> TYPE: DNA
```

<213> ORGANISM: Artificial Sequence
<220> FEATURE:
<223> OTHER INFORMATION: Synthetic

<400> SEQUENCE: 489

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagctcct gatctatgct gcatccagtt tacaaagtgg ggtcccatca   180
aggttcagcg gcagtggatc tggcacagat ttcactctca ccatcagcag cctgcagcct   240
gaagattttg caacttatta ctgtctacaa gattacaatt accctcggac gttcggccaa   300
gggaccaagg tggaaatcaa a                                             321
```

<210> SEQ ID NO 490
<211> LENGTH: 107
<212> TYPE: PRT
<213> ORGANISM: Artificial Sequence
<220> FEATURE:
<223> OTHER INFORMATION: Synthetic

<400> SEQUENCE: 490

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Arg
                85                  90                  95

Thr Phe Gly Gln Gly Thr Lys Val Glu Ile Lys
            100                 105
```

<210> SEQ ID NO 491
<211> LENGTH: 18
<212> TYPE: DNA
<213> ORGANISM: Artificial Sequence
<220> FEATURE:
<223> OTHER INFORMATION: Synthetic

<400> SEQUENCE: 491

```
cagggcatta gaaatgat                                                  18
```

<210> SEQ ID NO 492
<211> LENGTH: 6
<212> TYPE: PRT
<213> ORGANISM: Artificial Sequence
<220> FEATURE:
<223> OTHER INFORMATION: Synthetic

<400> SEQUENCE: 492

```
Gln Gly Ile Arg Asn Asp
 1               5
```

<210> SEQ ID NO 493
<211> LENGTH: 9
<212> TYPE: DNA
<213> ORGANISM: Artificial Sequence

```
<220> FEATURE:
<223> OTHER INFORMATION: Synthetic

<400> SEQUENCE: 493 gctgcatcc                                                                9

<210> SEQ ID NO 494
<211> LENGTH: 3
<212> TYPE: PRT
<213> ORGANISM: Artificial Sequence
<220> FEATURE:
<223> OTHER INFORMATION: Synthetic

<400> SEQUENCE: 494

Ala Ala Ser
 1

<210> SEQ ID NO 495
<211> LENGTH: 27
<212> TYPE: DNA
<213> ORGANISM: Artificial Sequence
<220> FEATURE:
<223> OTHER INFORMATION: Synthetic

<400> SEQUENCE: 495
ctacaagatt acaattaccc tcggacg                                           27

<210> SEQ ID NO 496
<211> LENGTH: 9
<212> TYPE: PRT
<213> ORGANISM: Artificial Sequence
<220> FEATURE:
<223> OTHER INFORMATION: Synthetic

<400> SEQUENCE: 496

Leu Gln Asp Tyr Asn Tyr Pro Arg Thr
 1               5

<210> SEQ ID NO 497
<211> LENGTH: 354
<212> TYPE: DNA
<213> ORGANISM: Artificial Sequence
<220> FEATURE:
<223> OTHER INFORMATION: Synthetic

<400> SEQUENCE: 497
caggtgcagc tggtggagtc tgggggaggc gtggtccagc ctggggaggtc cctgagactc       60 tcctgtgcag cgtctggatt caccttcagt agctatggca tgcactgggt ccgccaggct      120
ccaggcaagg ggctggagtg ggtggcagtt atatggtatg atggaagtaa taaatactat      180
gcagactccg tgaagggccg attcaccatc tccagagaca attccaagaa cacgctgtat      240
ctgcaaatga acagcctgag agccgaggac acggctgtgt attactgtgc gagagatgga      300
tatagtggct acgatgacta ctggggccag ggaaccctgg tcaccgtctc ctca            354

<210> SEQ ID NO 498
<211> LENGTH: 118
<212> TYPE: PRT
<213> ORGANISM: Artificial Sequence
<220> FEATURE:
<223> OTHER INFORMATION: Synthetic

<400> SEQUENCE: 498

Gln Val Gln Leu Val Glu Ser Gly Gly Gly Val Val Gln Pro Gly Arg
 1               5                  10                  15
```

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Ser Gly Tyr Asp Asp Tyr Trp Gly Gln Gly Thr
            100                 105                 110

Leu Val Thr Val Ser Ser
            115

<210> SEQ ID NO 499
<211> LENGTH: 321
<212> TYPE: DNA
<213> ORGANISM: Artificial Sequence
<220> FEATURE:
<223> OTHER INFORMATION: Synthetic

<400> SEQUENCE: 499
gccatccaga tgacccagtc tccatcctcc ctgtctgcat ctgtaggaga cagagtcacc      60
atcacttgcc gggcaagtca gggcattaga aatgatttag ctggtatca gcagaaacca     120 gggaaagccc ctaagctcct gatctatgct gcatccagtt tacaaagtgg ggtcccatca    180
aggttcagcg gcagtggatc tggcacagat ttcactctca ccatcagcag cctgcagcct    240
gaagattttg caacttatta ctgtctacaa gattacaatt accctcggac gttcggccaa    300
gggaccaagg tggaaatcaa a                                              321

<210> SEQ ID NO 500
<211> LENGTH: 107
<212> TYPE: PRT
<213> ORGANISM: Artificial Sequence
<220> FEATURE:
<223> OTHER INFORMATION: Synthetic

<400> SEQUENCE: 500

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Arg
                85                  90                  95

Thr Phe Gly Gln Gly Thr Lys Val Glu Ile Lys
            100                 105

<210> SEQ ID NO 501
<211> LENGTH: 354
<212> TYPE: DNA

<213> ORGANISM: Artificial Sequence
<220> FEATURE:
<223> OTHER INFORMATION: Synthetic

<400> SEQUENCE: 501

```
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctagagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagatgga     300
tatagtggct acgatgacta ctggggccag ggaaccctgg tcaccgtctc ctca           354
```

<210> SEQ ID NO 502
<211> LENGTH: 118
<212> TYPE: PRT
<213> ORGANISM: Artificial Sequence
<220> FEATURE:
<223> OTHER INFORMATION: Synthetic

<400> SEQUENCE: 502

```
Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Trp Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Gly Tyr Ser Gly Tyr Asp Asp Tyr Trp Gly Gln Gly Thr
            100                 105                 110
Leu Val Thr Val Ser Ser
        115
```

<210> SEQ ID NO 503
<211> LENGTH: 322
<212> TYPE: DNA
<213> ORGANISM: Artificial Sequence
<220> FEATURE:
<223> OTHER INFORMATION: Synthetic

<400> SEQUENCE: 503

```
gccatccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagctcct gatctatgct gcatccagtt tacaaagtgg ggtcccatca     180
aggttcagcg gcagtggatc tggcacagat tcactctca  ccatcagcag cctgcagcct     240
gaagattttg caacttatta ctgtctacaa gattacaatt accctcggac gttcggccaa     300
gggaccaagg tggaaatcaa ac                                               322
```

<210> SEQ ID NO 504
<211> LENGTH: 107
<212> TYPE: PRT
<213> ORGANISM: Artificial Sequence
<220> FEATURE:
<223> OTHER INFORMATION: Synthetic

<400> SEQUENCE: 504

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Arg
                85                  90                  95

Thr Phe Gly Gln Gly Thr Lys Val Glu Ile Lys
            100                 105

<210> SEQ ID NO 505
<211> LENGTH: 348
<212> TYPE: DNA
<213> ORGANISM: Artificial Sequence
<220> FEATURE:
<223> OTHER INFORMATION: Synthetic

<400> SEQUENCE: 505
gaggtgcagc tggtgcagtc tgggggaggc ttggtacagc ctggcaggtc cctgagactc      60
tcctgtgcag cctctggatt cacctttgat gattatgcca tgcactgggt ccgacaaggt     120
ccagggaagg gcctggagtg gtctcaggt attagttgga tggtggtag cgcaggctat       180
gcggactctg tgaagggccg attcaccatc tccagagaca acgccaagaa ctccctgtat     240
ctgcaattga acagtctgag agctgaggac acggccttgt attactgtgc aaaagaagac     300
tatgctttg atatctgggg ccaagggaca atggtcaccg tctcctca                  348

<210> SEQ ID NO 506
<211> LENGTH: 116
<212> TYPE: PRT
<213> ORGANISM: Artificial Sequence
<220> FEATURE:
<223> OTHER INFORMATION: Synthetic

<400> SEQUENCE: 506

Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Gly Pro Gly Lys Gly Leu Glu Trp Val
        35                  40                  45

Ser Gly Ile Ser Trp Asn Gly Ser Ala Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Ala Lys Glu Asp Tyr Ala Phe Asp Ile Trp Gly Gln Gly Thr Met Val
            100                 105                 110

Thr Val Ser Ser
        115

<210> SEQ ID NO 507
<211> LENGTH: 24
<212> TYPE: DNA
<213> ORGANISM: Artificial Sequence
<220> FEATURE:
<223> OTHER INFORMATION: Synthetic

<400> SEQUENCE: 507
ggattcacct ttgatgatta tgcc                                          24

<210> SEQ ID NO 508
<211> LENGTH: 8
<212> TYPE: PRT
<213> ORGANISM: Artificial Sequence
<220> FEATURE:
<223> OTHER INFORMATION: Synthetic

<400> SEQUENCE: 508

Gly Phe Thr Phe Asp Asp Tyr Ala
1               5

<210> SEQ ID NO 509
<211> LENGTH: 24
<212> TYPE: DNA
<213> ORGANISM: Artificial Sequence
<220> FEATURE:
<223> OTHER INFORMATION: Synthetic

<400> SEQUENCE: 509
attagttgga atggtggtag cgca                                          24

<210> SEQ ID NO 510
<211> LENGTH: 8
<212> TYPE: PRT
<213> ORGANISM: Artificial Sequence
<220> FEATURE:
<223> OTHER INFORMATION: Synthetic

<400> SEQUENCE: 510

Ile Ser Trp Asn Gly Gly Ser Ala
1               5

<210> SEQ ID NO 511
<211> LENGTH: 27
<212> TYPE: DNA
<213> ORGANISM: Artificial Sequence
<220> FEATURE:
<223> OTHER INFORMATION: Synthetic

<400> SEQUENCE: 511
gcaaaagaag actatgcttt tgatatc                                       27

<210> SEQ ID NO 512
<211> LENGTH: 9
<212> TYPE: PRT
<213> ORGANISM: Artificial Sequence
<220> FEATURE:
<223> OTHER INFORMATION: Synthetic

<400> SEQUENCE: 512

Ala Lys Glu Asp Tyr Ala Phe Asp Ile
1               5

<210> SEQ ID NO 513
<211> LENGTH: 336
<212> TYPE: DNA
<213> ORGANISM: Artificial Sequence
<220> FEATURE:
<223> OTHER INFORMATION: Synthetic

<400> SEQUENCE: 513

```
gacatcgtga tgacccagac tccactctcc tcacctgtca cccttggaca gccggcctcc      60
atctcctgca ggtctagtca aagcctcgta cacagtgatg aaacaccta cttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tattactgca tgcaagctac acaatttccg     300
tacacttttg gccaggggac caaggtggag atcaaa                              336
```

<210> SEQ ID NO 514
<211> LENGTH: 112
<212> TYPE: PRT
<213> ORGANISM: Artificial Sequence
<220> FEATURE:
<223> OTHER INFORMATION: Synthetic

<400> SEQUENCE: 514

Asp Ile Val Met Thr Gln Thr Pro Leu Ser Ser Pro Val Thr Leu Gly
1               5                   10                  15
Gln Pro Ala Ser Ile Ser Cys Arg Ser Ser Gln Ser Leu Val His Ser
            20                  25                  30
Asp Gly Asn Thr Tyr Leu Ser Trp Leu Gln Gln Arg Pro Gly Gln Pro
        35                  40                  45
Pro Arg Leu Leu Ile Tyr Lys Ile Ser Asn Arg Phe Ser Gly Val Pro
    50                  55                  60
Asp Arg Phe Ser Gly Ser Gly Ala Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Thr Gln Phe Pro Tyr Thr Phe Gly Gln Gly Thr Lys Val Glu Ile Lys
            100                 105                 110

<210> SEQ ID NO 515
<211> LENGTH: 33
<212> TYPE: DNA
<213> ORGANISM: Artificial Sequence
<220> FEATURE:
<223> OTHER INFORMATION: Synthetic

<400> SEQUENCE: 515

```
caaagcctcg tacacagtga tggaaacacc tac                                  33
```

<210> SEQ ID NO 516
<211> LENGTH: 11
<212> TYPE: PRT
<213> ORGANISM: Artificial Sequence
<220> FEATURE:
<223> OTHER INFORMATION: Synthetic

<400> SEQUENCE: 516

Gln Ser Leu Val His Ser Asp Gly Asn Thr Tyr
1               5                   10

<210> SEQ ID NO 517

```
<211> LENGTH: 9
<212> TYPE: DNA
<213> ORGANISM: Artificial Sequence
<220> FEATURE:
<223> OTHER INFORMATION: Synthetic

<400> SEQUENCE: 517 aagatttct                                                                 9

<210> SEQ ID NO 518
<211> LENGTH: 3
<212> TYPE: PRT
<213> ORGANISM: Artificial Sequence
<220> FEATURE:
<223> OTHER INFORMATION: Synthetic

<400> SEQUENCE: 518

Lys Ile Ser
 1

<210> SEQ ID NO 519
<211> LENGTH: 27
<212> TYPE: DNA
<213> ORGANISM: Artificial Sequence
<220> FEATURE:
<223> OTHER INFORMATION: Synthetic

<400> SEQUENCE: 519
atgcaagcta cacaatttcc gtacact                                            27

<210> SEQ ID NO 520
<211> LENGTH: 9
<212> TYPE: PRT
<213> ORGANISM: Artificial Sequence
<220> FEATURE:
<223> OTHER INFORMATION: Synthetic

<400> SEQUENCE: 520

Met Gln Ala Thr Gln Phe Pro Tyr Thr
 1               5

<210> SEQ ID NO 521
<211> LENGTH: 348
<212> TYPE: DNA
<213> ORGANISM: Artificial Sequence
<220> FEATURE:
<223> OTHER INFORMATION: Synthetic

<400> SEQUENCE: 521
gaagtgcagc tggtggagtc tgggggaggc ttggtacagc ctggcaggtc cctgagactc        60
tcctgtgcag cctctggatt caccttttgat gattatgcca tgcactgggt ccgacaaggt      120
ccagggaagg gcctggagtg ggtctcaggt attagttgga atggtggtag cgcaggctat       180
gcggactctg tgaagggccg attcaccatc tccagagaca cgccaagaa ctccctgtat        240 ctgcaattga acagtctgag agctgaggac acggccttgt attactgtgc aaaagaagac       300
tatgcttttg atatctgggg ccaagggaca atggtcaccg tctcttca                    348

<210> SEQ ID NO 522
<211> LENGTH: 116
<212> TYPE: PRT
<213> ORGANISM: Artificial Sequence
<220> FEATURE:
<223> OTHER INFORMATION: Synthetic

<400> SEQUENCE: 522
```

```
Glu Val Gln Leu Val Glu Ser Gly Gly Gly Leu Val Gln Pro Gly Arg
 1               5                  10                 15

Ser Leu Arg Leu Ser Cys Ala Ala Ser Gly Phe Thr Phe Asp Asp Tyr
            20                  25                  30

Ala Met His Trp Val Arg Gln Gly Pro Gly Lys Gly Leu Glu Trp Val
        35                  40                  45

Ser Gly Ile Ser Trp Asn Gly Gly Ser Ala Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Ala Lys Glu Asp Tyr Ala Phe Asp Ile Trp Gly Gln Gly Thr Met Val
            100                 105                 110

Thr Val Ser Ser
        115
```

```
<210> SEQ ID NO 523
<211> LENGTH: 336
<212> TYPE: DNA
<213> ORGANISM: Artificial Sequence
<220> FEATURE:
<223> OTHER INFORMATION: Synthetic

<400> SEQUENCE: 523
gatattgtga tgacccagac tccactctcc tcacctgtca cccttggaca gccggcctcc      60
atctcctgca ggtctagtca aagcctcgta cacagtgatg gaaacaccta cttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tattactgca tgcaagctac acaatttccg     300
tacacttttg gccaggggac caagctggag atcaaa                               336
```

```
<210> SEQ ID NO 524
<211> LENGTH: 112
<212> TYPE: PRT
<213> ORGANISM: Artificial Sequence
<220> FEATURE:
<223> OTHER INFORMATION: Synthetic

<400> SEQUENCE: 524

Asp Ile Val Met Thr Gln Thr Pro Leu Ser Ser Pro Val Thr Leu Gly
 1               5                  10                 15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Tyr Thr Phe Gly Gln Gly Thr Lys Leu Glu Ile Lys
            100                 105                 110
```

-continued

<210> SEQ ID NO 525
<211> LENGTH: 348
<212> TYPE: DNA
<213> ORGANISM: Artificial Sequence
<220> FEATURE:
<223> OTHER INFORMATION: Synthetic

<400> SEQUENCE: 525
gaagtgcagc tggtggagtc tgggggaggc ttggtacagc ctggcaggtc cctgagactc        60
tcctgtgcag cctctggatt cacctttgat gattatgcca tgcactgggt ccggcaagct       120
ccagggaagg gcctggagtg ggtctcaggt attagttgga atggtggtag cgcaggctat       180
gcggactctg tgaagggccg attcaccatc tccagagaca cgccaagaa ctccctgtat        240 ctgcaaatga acagtctgag agctgaggac acggccttgt attactgtgc aaaagaagac       300
tatgcttttg atatctgggg ccaagggaca atggtcaccg tctcttca                   348

<210> SEQ ID NO 526
<211> LENGTH: 116
<212> TYPE: PRT
<213> ORGANISM: Artificial Sequence
<220> FEATURE:
<223> OTHER INFORMATION: Synthetic

<400> SEQUENCE: 526

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Gly Gly Ser Ala Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Asp Tyr Ala Phe Asp Ile Trp Gly Gln Gly Thr Met Val
            100                 105                 110

Thr Val Ser Ser
        115

<210> SEQ ID NO 527
<211> LENGTH: 337
<212> TYPE: DNA
<213> ORGANISM: Artificial Sequence
<220> FEATURE:
<223> OTHER INFORMATION: Synthetic

<400> SEQUENCE: 527
gatattgtga tgacccagac tccactctcc tcacctgtca cccttggaca gccggcctcc        60
atctcctgca ggtctagtca agcctcgta cacagtgatg gaaacaccta cttgagttgg       120
cttcagcaga ggccaggcca gcctccaaga ctcctaattt ataagatttc taaccggttc       180
tctggggtcc cagacagatt cagtggcagt ggggcaggga cagatttcac actgaaaatc       240
agcagggtgg aagctgagga tgtcggggtt tattactgca tgcaagctac acaatttccg       300
tacacttttg gccaggggac caagctggag atcaaac                                337

<210> SEQ ID NO 528

<211> LENGTH: 112
<212> TYPE: PRT
<213> ORGANISM: Artificial Sequence
<220> FEATURE:
<223> OTHER INFORMATION: Synthetic

<400> SEQUENCE: 528

```
Asp Ile Val Met Thr Gln Thr Pro Leu Ser Ser Val Thr Leu Gly
 1               5                  10                  15
Gln Pro Ala Ser Ile Ser Cys Arg Ser Ser Gln Ser Leu Val His Ser
            20                  25                  30
Asp Gly Asn Thr Tyr Leu Ser Trp Leu Gln Gln Arg Pro Gly Gln Pro
        35                  40                  45
Pro Arg Leu Leu Ile Tyr Lys Ile Ser Asn Arg Phe Ser Gly Val Pro
    50                  55                  60
Asp Arg Phe Ser Gly Ser Gly Ala Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Thr Gln Phe Pro Tyr Thr Phe Gly Gln Gly Thr Lys Leu Glu Ile Lys
            100                 105                 110
```

<210> SEQ ID NO 529
<211> LENGTH: 348
<212> TYPE: DNA
<213> ORGANISM: Artificial Sequence
<220> FEATURE:
<223> OTHER INFORMATION: Synthetic

<400> SEQUENCE: 529

```
gaggtgcagc tggtggagtc tgggggaggc ttggtacagc ctggcaggtc cctgagactc      60
tcctgtgcag cctctggatt cacctttgaa gattatgcca tgcactgggt ccggcaagct     120
ccagggaagg gcctggaatg ggtctcaggt attacttgga atagtgataa taaggctat      180
gcggactctg tgaagggccg attcaccatc tccagagaca cgccaagta ctccctgtat      240
ctgcaaatga acagtctgag agctgaggac acggccttgt attactgtgc aaaagaggac     300
tgggcgtttg actactgggg ccagggaacc ctggtcaccg tctcctca                  348
```

<210> SEQ ID NO 530
<211> LENGTH: 116
<212> TYPE: PRT
<213> ORGANISM: Artificial Sequence
<220> FEATURE:
<223> OTHER INFORMATION: Synthetic

<400> SEQUENCE: 530

```
Glu Val Gln Leu Val Glu Ser Gly Gly Gly Leu Val Gln Pro Gly Arg
 1               5                  10                  15
Ser Leu Arg Leu Ser Cys Ala Ala Ser Gly Phe Thr Phe Glu Asp Tyr
            20                  25                  30
Ala Met His Trp Val Arg Gln Ala Pro Gly Lys Gly Leu Glu Trp Val
        35                  40                  45
Ser Gly Ile Thr Trp Asn Ser Asp Asn Lys Gly Tyr Ala Asp Ser Val
    50                  55                  60
Lys Gly Arg Phe Thr Ile Ser Arg Asp Asn Ala Lys Tyr Ser Leu Tyr
65                  70                  75                  80
Leu Gln Met Asn Ser Leu Arg Ala Glu Asp Thr Ala Leu Tyr Tyr Cys
                85                  90                  95
```

Ala Lys Glu Asp Trp Ala Phe Asp Tyr Trp Gly Gln Gly Thr Leu Val
            100                 105                 110

Thr Val Ser Ser
        115

<210> SEQ ID NO 531
<211> LENGTH: 24
<212> TYPE: DNA
<213> ORGANISM: Artificial Sequence
<220> FEATURE:
<223> OTHER INFORMATION: Synthetic

<400> SEQUENCE: 531
ggattcacct ttgaagatta tgcc                                          24

<210> SEQ ID NO 532
<211> LENGTH: 8
<212> TYPE: PRT
<213> ORGANISM: Artificial Sequence
<220> FEATURE:
<223> OTHER INFORMATION: Synthetic

<400> SEQUENCE: 532

Gly Phe Thr Phe Glu Asp Tyr Ala
1               5

<210> SEQ ID NO 533
<211> LENGTH: 24
<212> TYPE: DNA
<213> ORGANISM: Artificial Sequence
<220> FEATURE:
<223> OTHER INFORMATION: Synthetic

<400> SEQUENCE: 533
attacttgga atagtgataa taaa                                          24

<210> SEQ ID NO 534
<211> LENGTH: 8
<212> TYPE: PRT
<213> ORGANISM: Artificial Sequence
<220> FEATURE:
<223> OTHER INFORMATION: Synthetic

<400> SEQUENCE: 534

Ile Thr Trp Asn Ser Asp Asn Lys
1               5

<210> SEQ ID NO 535
<211> LENGTH: 27
<212> TYPE: DNA
<213> ORGANISM: Artificial Sequence
<220> FEATURE:
<223> OTHER INFORMATION: Synthetic

<400> SEQUENCE: 535
gcaaaagagg actgggcgtt tgactac                                       27

<210> SEQ ID NO 536
<211> LENGTH: 9
<212> TYPE: PRT
<213> ORGANISM: Artificial Sequence
<220> FEATURE:
<223> OTHER INFORMATION: Synthetic

<400> SEQUENCE: 536

Ala Lys Glu Asp Trp Ala Phe Asp Tyr

<210> SEQ ID NO 537
<211> LENGTH: 321
<212> TYPE: DNA
<213> ORGANISM: Artificial Sequence
<220> FEATURE:
<223> OTHER INFORMATION: Synthetic

<400> SEQUENCE: 537

```
gacatccaga tgacccagtc tccatcttcc gtgtctgcat ctgtaggaga cagagtcacc      60
atcacttgtc gtgcgagtca gggtattaac agttggttag cctggtatca gcagaaacca     120
gggaaagccc ctaagctcct gatctacgct gcatccagtt tgcagagtgg ggtcccatca     180
aggttcagcg gcagtggatc tgggacagat tcactctcac catcagcgg cctccagcct      240
gaagattttg caacttacta ttgtcaacag gctaacagtt tcccgtacac ttttggccag     300
gggaccaagg tggaaatcaa a                                               321
```

<210> SEQ ID NO 538
<211> LENGTH: 107
<212> TYPE: PRT
<213> ORGANISM: Artificial Sequence
<220> FEATURE:
<223> OTHER INFORMATION: Synthetic

<400> SEQUENCE: 538

Asp Ile Gln Met Thr Gln Ser Pro Ser Ser Val Ser Ala Ser Val Gly
1               5                   10                  15
Asp Arg Val Thr Ile Thr Cys Arg Ala Ser Gln Gly Ile Asn Ser Trp
            20                  25                  30
Leu Ala Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Gly Leu Gln Pro
65                  70                  75                  80
Glu Asp Phe Ala Thr Tyr Tyr Cys Gln Gln Ala Asn Ser Phe Pro Tyr
                85                  90                  95
Thr Phe Gly Gln Gly Thr Lys Val Glu Ile Lys
            100                 105

<210> SEQ ID NO 539
<211> LENGTH: 18
<212> TYPE: DNA
<213> ORGANISM: Artificial Sequence
<220> FEATURE:
<223> OTHER INFORMATION: Synthetic

<400> SEQUENCE: 539

```
cagggtatta acagttgg                                                    18
```

<210> SEQ ID NO 540
<211> LENGTH: 6
<212> TYPE: PRT
<213> ORGANISM: Artificial Sequence
<220> FEATURE:
<223> OTHER INFORMATION: Synthetic

<400> SEQUENCE: 540

Gln Gly Ile Asn Ser Trp
1               5

<210> SEQ ID NO 541
<211> LENGTH: 9
<212> TYPE: DNA
<213> ORGANISM: Artificial Sequence
<220> FEATURE:
<223> OTHER INFORMATION: Synthetic

<400> SEQUENCE: 541 gctgcatcc                                                                 9

<210> SEQ ID NO 542
<211> LENGTH: 3
<212> TYPE: PRT
<213> ORGANISM: Artificial Sequence
<220> FEATURE:
<223> OTHER INFORMATION: Synthetic

<400> SEQUENCE: 542

Ala Ala Ser
 1

<210> SEQ ID NO 543
<211> LENGTH: 27
<212> TYPE: DNA
<213> ORGANISM: Artificial Sequence
<220> FEATURE:
<223> OTHER INFORMATION: Synthetic

<400> SEQUENCE: 543
caacaggcta acagtttccc gtacact                                             27

<210> SEQ ID NO 544
<211> LENGTH: 9
<212> TYPE: PRT
<213> ORGANISM: Artificial Sequence
<220> FEATURE:
<223> OTHER INFORMATION: Synthetic

<400> SEQUENCE: 544

Gln Gln Ala Asn Ser Phe Pro Tyr Thr
 1               5

<210> SEQ ID NO 545
<211> LENGTH: 348
<212> TYPE: DNA
<213> ORGANISM: Artificial Sequence
<220> FEATURE:
<223> OTHER INFORMATION: Synthetic

<400> SEQUENCE: 545
gaagtgcagc tggtggagtc tgggggaggc ttggtacagc ctggcaggtc cctgagactc         60
tcctgtgcag cctctggatt caccttttgaa gattatgcca tgcactgggt ccggcaagct       120
ccagggaagg gcctggaatg ggtctcaggt attacttgga atagtgataa taaaggctat       180
gcggactctg tgaagggccg attcaccatc tccagagaca acgccaagta ctccctgtat       240
ctgcaaatga acagtctgag agctgaggac acggccttgt attactgtgc aaaagaggac       300
tgggcgtttg actactgggg ccagggaacc ctggtcaccg tctcctca                    348

<210> SEQ ID NO 546
<211> LENGTH: 116
<212> TYPE: PRT
<213> ORGANISM: Artificial Sequence
<220> FEATURE:

<223> OTHER INFORMATION: Synthetic

<400> SEQUENCE: 546

Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Glu Asp Tyr
            20                  25                  30
Ala Met His Trp Val Arg Gln Ala Pro Gly Lys Gly Leu Glu Trp Val
        35                  40                  45
Ser Gly Ile Thr Trp Asn Ser Asp Asn Lys Gly Tyr Ala Asp Ser Val
    50                  55                  60
Lys Gly Arg Phe Thr Ile Ser Arg Asp Asn Ala Lys Tyr Ser Leu Tyr
65                  70                  75                  80
Leu Gln Met Asn Ser Leu Arg Ala Glu Asp Thr Ala Leu Tyr Tyr Cys
                85                  90                  95
Ala Lys Glu Asp Trp Ala Phe Asp Tyr Trp Gly Gln Gly Thr Leu Val
            100                 105                 110
Thr Val Ser Ser
        115

<210> SEQ ID NO 547
<211> LENGTH: 321
<212> TYPE: DNA
<213> ORGANISM: Artificial Sequence
<220> FEATURE:
<223> OTHER INFORMATION: Synthetic

<400> SEQUENCE: 547
gacatccaga tgacccagtc tccatcttcc gtgtctgcat ctgtaggaga cagagtcacc    60
atcacttgtc gtgcgagtca gggtattaac agttggttag cctggtatca gcagaaacca   120
gggaaagccc ctaagctcct gatctacgct gcatccagtt tgcagagtgg ggtcccatca   180
aggttcagcg gcagtggatc tgggacagat ttcactctca ccatcagcgg cctccagcct   240
gaagattttg caacttacta ttgtcaacag gctaacagtt tcccgtacac ttttggccag   300
gggaccaagc tggagatcaa a                                             321

<210> SEQ ID NO 548
<211> LENGTH: 107
<212> TYPE: PRT
<213> ORGANISM: Artificial Sequence
<220> FEATURE:
<223> OTHER INFORMATION: Synthetic

<400> SEQUENCE: 548

Asp Ile Gln Met Thr Gln Ser Pro Ser Ser Val Ser Ala Ser Val Gly
1               5                   10                  15
Asp Arg Val Thr Ile Thr Cys Arg Ala Ser Gln Gly Ile Asn Ser Trp
            20                  25                  30
Leu Ala Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Gly Leu Gln Pro
65                  70                  75                  80
Glu Asp Phe Ala Thr Tyr Tyr Cys Gln Gln Ala Asn Ser Phe Pro Tyr
                85                  90                  95
Thr Phe Gly Gln Gly Thr Lys Leu Glu Ile Lys

<210> SEQ ID NO 549
<211> LENGTH: 348
<212> TYPE: DNA
<213> ORGANISM: Artificial Sequence
<220> FEATURE:
<223> OTHER INFORMATION: Synthetic

<400> SEQUENCE: 549

```
gaagtgcagc tggtggagtc tgggggaggc ttggtacagc ctggcaggtc cctgagactc      60
tcctgtgcag cctctggatt cacctttgaa gattatgcca tgcactgggt ccggcaagct     120
ccagggaagg gcctggagtg ggtctcaggt attacttgga atagtgataa taaaggctat     180
gcggactctg tgaagggccg attcaccatc tccagagaca cgccaagaa ctccctgtat      240
ctgcaaatga acagtctgag agctgaggac acggccttgt attactgtgc aaaagaggac     300
tgggcgtttg actactgggg ccagggaacc ctggtcaccg tctcctca                  348
```

<210> SEQ ID NO 550
<211> LENGTH: 116
<212> TYPE: PRT
<213> ORGANISM: Artificial Sequence
<220> FEATURE:
<223> OTHER INFORMATION: Synthetic

<400> SEQUENCE: 550

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Glu Asp Tyr
            20                  25                  30

Ala Met His Trp Val Arg Gln Ala Pro Gly Lys Gly Leu Glu Trp Val
        35                  40                  45

Ser Gly Ile Thr Trp Asn Ser Asp Asn Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Asp Trp Ala Phe Asp Tyr Trp Gly Gln Gly Thr Leu Val
            100                 105                 110

Thr Val Ser Ser
        115

<210> SEQ ID NO 551
<211> LENGTH: 322
<212> TYPE: DNA
<213> ORGANISM: Artificial Sequence
<220> FEATURE:
<223> OTHER INFORMATION: Synthetic

<400> SEQUENCE: 551

```
gacatccaga tgacccagtc tccatcttct gtgtctgcat ctgtaggaga cagagtcacc      60
atcacttgtc gggcgagtca gggtattaac agttggttag cctggtatca gcagaaacca     120
gggaaagccc ctaagctcct gatctatgct gcatccagtt tgcaaagtgg ggtcccatca     180
aggttcagcg gcagtggatc tgggacagat ttcactctca ctatcagcag cctgcagcct     240
gaagattttg caacttacta ttgtcaacag gctaacagtt tcccgtacac ttttggccag     300
gggaccaagc tggagatcaa ac                                              322
```

<210> SEQ ID NO 552
<211> LENGTH: 107
<212> TYPE: PRT
<213> ORGANISM: Artificial Sequence
<220> FEATURE:
<223> OTHER INFORMATION: Synthetic

<400> SEQUENCE: 552

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asn Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Leu Glu Ile Lys
            100                 105

<210> SEQ ID NO 553
<211> LENGTH: 348
<212> TYPE: DNA
<213> ORGANISM: Artificial Sequence
<220> FEATURE:
<223> OTHER INFORMATION: Synthetic

<400> SEQUENCE: 553
gaggtgcagc tggtgcagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagtggtag caaaggctat     180
gcggactctg tgaagggccg attcaccatc tccagagaca acgccaagaa ctccctgtat     240
ctgcaaatga acagtctgag acgtgaggac acggccttgt attactgtgt aaaagaggac     300
tgggcgtttg actactgggg ccagggaacc ctggtcaccg tctcctca                  348

<210> SEQ ID NO 554
<211> LENGTH: 116
<212> TYPE: PRT
<213> ORGANISM: Artificial Sequence
<220> FEATURE:
<223> OTHER INFORMATION: Synthetic

<400> SEQUENCE: 554

Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Arg Glu Asp Thr Ala Leu Tyr Tyr Cys
            85                  90                  95

Val Lys Glu Asp Trp Ala Phe Asp Tyr Trp Gly Gln Gly Thr Leu Val
        100                 105                 110

Thr Val Ser Ser
        115

<210> SEQ ID NO 555
<211> LENGTH: 24
<212> TYPE: DNA
<213> ORGANISM: Artificial Sequence
<220> FEATURE:
<223> OTHER INFORMATION: Synthetic

<400> SEQUENCE: 555
ggattcacct ttgatgatta tgcc                                          24

<210> SEQ ID NO 556
<211> LENGTH: 8
<212> TYPE: PRT
<213> ORGANISM: Artificial Sequence
<220> FEATURE:
<223> OTHER INFORMATION: Synthetic

<400> SEQUENCE: 556

Gly Phe Thr Phe Asp Asp Tyr Ala
1               5

<210> SEQ ID NO 557
<211> LENGTH: 24
<212> TYPE: DNA
<213> ORGANISM: Artificial Sequence
<220> FEATURE:
<223> OTHER INFORMATION: Synthetic

<400> SEQUENCE: 557
attagttgga atagtggtag caaa                                          24

<210> SEQ ID NO 558
<211> LENGTH: 8
<212> TYPE: PRT
<213> ORGANISM: Artificial Sequence
<220> FEATURE:
<223> OTHER INFORMATION: Synthetic

<400> SEQUENCE: 558

Ile Ser Trp Asn Ser Gly Ser Lys
1               5

<210> SEQ ID NO 559
<211> LENGTH: 27
<212> TYPE: DNA
<213> ORGANISM: Artificial Sequence
<220> FEATURE:
<223> OTHER INFORMATION: Synthetic

<400> SEQUENCE: 559
gtaaaagagg actgggcgtt tgactac                                       27

<210> SEQ ID NO 560
<211> LENGTH: 9
<212> TYPE: PRT
<213> ORGANISM: Artificial Sequence
<220> FEATURE:
<223> OTHER INFORMATION: Synthetic -continued

<400> SEQUENCE: 560

Val Lys Glu Asp Trp Ala Phe Asp Tyr
 1               5

<210> SEQ ID NO 561
<211> LENGTH: 315
<212> TYPE: DNA
<213> ORGANISM: Artificial Sequence
<220> FEATURE:
<223> OTHER INFORMATION: Synthetic

<400> SEQUENCE: 561
gacatccaga tgacccagtc tccatcctcc ctgtctgcat ctgtaggaga cagagtcacc     60
atcacttgcc aggcgagtca ggacattagc aactatttaa attggtatca acaaaaacca    120
gggaaagccc ctaagttcct gatctacgat gcatccaatt tgggaacagg ggtcccatca    180
aggttcagtg gaagtggatc tgggacagat tttactttca ccatcagcag cctgcagcct    240
gaagatattg cgacatatta ctgtcaacag tatgataatc tccctttcgg cggagggacc    300
aaggtggaaa tcaaa                                                     315

<210> SEQ ID NO 562
<211> LENGTH: 105
<212> TYPE: PRT
<213> ORGANISM: Artificial Sequence
<220> FEATURE:
<223> OTHER INFORMATION: Synthetic

<400> SEQUENCE: 562

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Phe Leu Ile
        35                  40                  45

Tyr Asp Ala Ser Asn Leu Gly Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Phe
                85                  90                  95

Gly Gly Gly Thr Lys Val Glu Ile Lys
            100                 105

<210> SEQ ID NO 563
<211> LENGTH: 18
<212> TYPE: DNA
<213> ORGANISM: Artificial Sequence
<220> FEATURE:
<223> OTHER INFORMATION: Synthetic

<400> SEQUENCE: 563
caggacatta gcaactat                                                   18

<210> SEQ ID NO 564
<211> LENGTH: 6
<212> TYPE: PRT
<213> ORGANISM: Artificial Sequence
<220> FEATURE:
<223> OTHER INFORMATION: Synthetic

<400> SEQUENCE: 564

```
<210> SEQ ID NO 565
<211> LENGTH: 9
<212> TYPE: DNA
<213> ORGANISM: Artificial Sequence
<220> FEATURE:
<223> OTHER INFORMATION: Synthetic

<400> SEQUENCE: 565 gatgcatcc                                                                      9

<210> SEQ ID NO 566
<211> LENGTH: 3
<212> TYPE: PRT
<213> ORGANISM: Artificial Sequence
<220> FEATURE:
<223> OTHER INFORMATION: Synthetic

<400> SEQUENCE: 566

Asp Ala Ser
 1

<210> SEQ ID NO 567
<211> LENGTH: 21
<212> TYPE: DNA
<213> ORGANISM: Artificial Sequence
<220> FEATURE:
<223> OTHER INFORMATION: Synthetic

<400> SEQUENCE: 567
caacagtatg ataatctccc t                                                       21

<210> SEQ ID NO 568
<211> LENGTH: 7
<212> TYPE: PRT
<213> ORGANISM: Artificial Sequence
<220> FEATURE:
<223> OTHER INFORMATION: Synthetic

<400> SEQUENCE: 568

Gln Gln Tyr Asp Asn Leu Pro
 1               5

<210> SEQ ID NO 569
<211> LENGTH: 348
<212> TYPE: DNA
<213> ORGANISM: Artificial Sequence
<220> FEATURE:
<223> OTHER INFORMATION: Synthetic

<400> SEQUENCE: 569
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagtggtag caaaggctat     180
gcggactctg tgaagggccg attcaccatc tccagagaca cgccaagaa ctccctgtat      240 ctgcaaatga acagtctgag acgtgaggac acggccttgt attactgtgt aaaagaggac     300
tgggcgtttg actactgggg ccagggaacc ctggtcaccg tctcctca                  348

<210> SEQ ID NO 570
<211> LENGTH: 116
```

(Gln Asp Ile Ser Asn Tyr continued from previous page:)

Gln Asp Ile Ser Asn Tyr
 1               5

<212> TYPE: PRT
<213> ORGANISM: Artificial Sequence
<220> FEATURE:
<223> OTHER INFORMATION: Synthetic

<400> SEQUENCE: 570

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Arg Glu Asp Thr Ala Leu Tyr Tyr Cys
                85                  90                  95

Val Lys Glu Asp Trp Ala Phe Asp Tyr Trp Gly Gln Gly Thr Leu Val
            100                 105                 110

Thr Val Ser Ser
        115

<210> SEQ ID NO 571
<211> LENGTH: 315
<212> TYPE: DNA
<213> ORGANISM: Artificial Sequence
<220> FEATURE:
<223> OTHER INFORMATION: Synthetic

<400> SEQUENCE: 571
gacatccaga tgacccagtc tccatcctcc ctgtctgcat ctgtaggaga cagagtcacc      60
atcacttgcc aggcgagtca ggacattagc aactatttaa attggtatca acaaaaacca     120
gggaaagccc ctaagttcct gatctacgat gcatccaatt tgggaacagg ggtcccatca     180
aggttcagtg gaagtggatc tgggacagat tttactttca ccatcagcag cctgcagcct     240
gaagatattg cgacatatta ctgtcaacag tatgataatc tccctttcgg cggagggacc     300
aaggtggaga tcaaa                                                      315

<210> SEQ ID NO 572
<211> LENGTH: 105
<212> TYPE: PRT
<213> ORGANISM: Artificial Sequence
<220> FEATURE:
<223> OTHER INFORMATION: Synthetic

<400> SEQUENCE: 572

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Phe Leu Ile
        35                  40                  45

Tyr Asp Ala Ser Asn Leu Gly Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Phe

Gly Gly Gly Thr Lys Val Glu Ile Lys
           100                 105

<210> SEQ ID NO 573
<211> LENGTH: 348
<212> TYPE: DNA
<213> ORGANISM: Artificial Sequence
<220> FEATURE:
<223> OTHER INFORMATION: Synthetic

<400> SEQUENCE: 573
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg gtctcaggt attagttgga atagtggtag caaaggctat     180
gcggactctg tgaagggccg attcaccatc tccagagaca acgccaagaa ctccctgtat     240
ctgcaaatga acagtctgag agctgaggac acggccttgt attactgtgt aaaagaggac     300
tgggcgtttg actactgggg ccagggaacc ctggtcaccg tctcctca                  348

<210> SEQ ID NO 574
<211> LENGTH: 116
<212> TYPE: PRT
<213> ORGANISM: Artificial Sequence
<220> FEATURE:
<223> OTHER INFORMATION: Synthetic

<400> SEQUENCE: 574

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Glu Asp Trp Ala Phe Asp Tyr Trp Gly Gln Gly Thr Leu Val
            100                 105                 110

Thr Val Ser Ser
        115

<210> SEQ ID NO 575
<211> LENGTH: 316
<212> TYPE: DNA
<213> ORGANISM: Artificial Sequence
<220> FEATURE:
<223> OTHER INFORMATION: Synthetic

<400> SEQUENCE: 575
gacatccaga tgacccagtc tccatcctcc ctgtctgcat ctgtaggaga cagagtcacc      60
atcacttgcc aggcgagtca ggacattagc aactatttaa attggtatca gcagaaacca     120
gggaaagccc ctaagctcct gatctacgat gcatccaatt tggaaacagg ggtcccatca     180
aggttcagtg gaagtggatc tgggacagat tttactttca ccatcagcag cctgcagcct     240
gaagatattg caacatatta ctgtcaacag tatgataatc tcccttttcgg cggagggacc    300 aaggtggaga tcaaac                                                    316

<210> SEQ ID NO 576
<211> LENGTH: 105
<212> TYPE: PRT
<213> ORGANISM: Artificial Sequence
<220> FEATURE:
<223> OTHER INFORMATION: Synthetic

<400> SEQUENCE: 576

Asp Ile Gln Met Thr Gln Ser Pro Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Phe
                85                  90                  95

Gly Gly Gly Thr Lys Val Glu Ile Lys
            100                 105

<210> SEQ ID NO 577
<211> LENGTH: 375
<212> TYPE: DNA
<213> ORGANISM: Artificial Sequence
<220> FEATURE:
<223> OTHER INFORMATION: Synthetic

<400> SEQUENCE: 577
caggtgcagc tggtgcagtc aggtccagga ctggtgaagc cctcgcagac cctctcactc     60
acctgtgcca tctccgggga cagtgtctct agcaacagtg ctgcttggaa ctggatcagg    120
cagtccccat cgagaggcct tgagtggctg ggaaggacta ctacaggtc caagtggtat     180 aatgattatg cagtatctgt gaaaagtcga ataaccatca cccagacac atccaagaac     240 cagttctccc tgcagctgaa ctctgtgact cccgaggaca cggctgtgta ttactgtgca    300
agagggtata gcagcagctg gtacggggt gcttttgata tctggggcca agggacaatg    360
gtcaccgtct cttca                                                    375

<210> SEQ ID NO 578
<211> LENGTH: 125
<212> TYPE: PRT
<213> ORGANISM: Artificial Sequence
<220> FEATURE:
<223> OTHER INFORMATION: Synthetic

<400> SEQUENCE: 578

Gln Val Gln Leu Val Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala

```
                50                  55                  60
Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Gly Tyr Ser Ser Ser Trp Tyr Gly Gly Ala Phe
            100                 105                 110

Asp Ile Trp Gly Gln Gly Thr Met Val Thr Val Ser Ser
        115                 120                 125

<210> SEQ ID NO 579
<211> LENGTH: 30
<212> TYPE: DNA
<213> ORGANISM: Artificial Sequence
<220> FEATURE:
<223> OTHER INFORMATION: Synthetic

<400> SEQUENCE: 579
ggggacagtg tctctagcaa cagtgctgct                                        30

<210> SEQ ID NO 580
<211> LENGTH: 10
<212> TYPE: PRT
<213> ORGANISM: Artificial Sequence
<220> FEATURE:
<223> OTHER INFORMATION: Synthetic

<400> SEQUENCE: 580

Gly Asp Ser Val Ser Ser Asn Ser Ala Ala
 1               5                  10

<210> SEQ ID NO 581
<211> LENGTH: 27
<212> TYPE: DNA
<213> ORGANISM: Artificial Sequence
<220> FEATURE:
<223> OTHER INFORMATION: Synthetic

<400> SEQUENCE: 581
acatactaca ggtccaagtg gtataat                                           27

<210> SEQ ID NO 582
<211> LENGTH: 9
<212> TYPE: PRT
<213> ORGANISM: Artificial Sequence
<220> FEATURE:
<223> OTHER INFORMATION: Synthetic

<400> SEQUENCE: 582

Thr Tyr Tyr Arg Ser Lys Trp Tyr Asn
 1               5

<210> SEQ ID NO 583
<211> LENGTH: 45
<212> TYPE: DNA
<213> ORGANISM: Artificial Sequence
<220> FEATURE:
<223> OTHER INFORMATION: Synthetic

<400> SEQUENCE: 583
gcaagagggt atagcagcag ctggtacggg ggtgcttttg atatc                       45

<210> SEQ ID NO 584
<211> LENGTH: 15
```

```
<212> TYPE: PRT
<213> ORGANISM: Artificial Sequence
<220> FEATURE:
<223> OTHER INFORMATION: Synthetic

<400> SEQUENCE: 584

Ala Arg Gly Tyr Ser Ser Ser Trp Tyr Gly Gly Ala Phe Asp Ile
 1               5                  10                  15

<210> SEQ ID NO 585
<211> LENGTH: 321
<212> TYPE: DNA
<213> ORGANISM: Artificial Sequence
<220> FEATURE:
<223> OTHER INFORMATION: Synthetic

<400> SEQUENCE: 585
gacatccaga tgacccagtc tccatcctcc ctgtctgcat ctgtaggaga cagagtcacc     60
atcacttgcc gggcaagtca gagcattagc agttatttaa gttggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccccattca ctttcggccct    300 gggaccaagg tggaaatcaa a                                              321

<210> SEQ ID NO 586
<211> LENGTH: 107
<212> TYPE: PRT
<213> ORGANISM: Artificial Sequence
<220> FEATURE:
<223> OTHER INFORMATION: Synthetic

<400> SEQUENCE: 586

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Ser Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Phe
                 85                  90                  95

Thr Phe Gly Pro Gly Thr Lys Val Glu Ile Lys
            100                 105

<210> SEQ ID NO 587
<211> LENGTH: 18
<212> TYPE: DNA
<213> ORGANISM: Artificial Sequence
<220> FEATURE:
<223> OTHER INFORMATION: Synthetic

<400> SEQUENCE: 587
cagagcatta gcagttat                                                   18

<210> SEQ ID NO 588
<211> LENGTH: 6
<212> TYPE: PRT
```

```
<213> ORGANISM: Artificial Sequence
<220> FEATURE:
<223> OTHER INFORMATION: Synthetic

<400> SEQUENCE: 588

Gln Ser Ile Ser Ser Tyr
  1               5

<210> SEQ ID NO 589
<211> LENGTH: 9
<212> TYPE: DNA
<213> ORGANISM: Artificial Sequence
<220> FEATURE:
<223> OTHER INFORMATION: Synthetic

<400> SEQUENCE: 589 gctgcatcc                                                                  9

<210> SEQ ID NO 590
<211> LENGTH: 3
<212> TYPE: PRT
<213> ORGANISM: Artificial Sequence
<220> FEATURE:
<223> OTHER INFORMATION: Synthetic

<400> SEQUENCE: 590

Ala Ala Ser
  1

<210> SEQ ID NO 591
<211> LENGTH: 27
<212> TYPE: DNA
<213> ORGANISM: Artificial Sequence
<220> FEATURE:
<223> OTHER INFORMATION: Synthetic

<400> SEQUENCE: 591
caacagagtt acagtacccc attcact                                             27

<210> SEQ ID NO 592
<211> LENGTH: 9
<212> TYPE: PRT
<213> ORGANISM: Artificial Sequence
<220> FEATURE:
<223> OTHER INFORMATION: Synthetic

<400> SEQUENCE: 592

Gln Gln Ser Tyr Ser Thr Pro Phe Thr
  1               5

<210> SEQ ID NO 593
<211> LENGTH: 375
<212> TYPE: DNA
<213> ORGANISM: Artificial Sequence
<220> FEATURE:
<223> OTHER INFORMATION: Synthetic

<400> SEQUENCE: 593
caggtacagc tgcagcagtc aggtccagga ctggtgaagc cctcgcagac cctctcactc         60
acctgtgcca tctccgggga cagtgtctct agcaacagtg ctgcttggaa ctggatcagg        120
cagtccccat cgagaggcct tgagtggctg ggaaggacat actacaggtc caagtggtat        180
aatgattatg cagtatctgt gaaaagtcga ataaccatca acccagacac atccaagaac        240
cagttctccc tgcagctgaa ctctgtgact cccgaggaca cggctgtgta ttactgtgca        300
```

```
agagggtata gcagcagctg gtacgggggt gcttttgata tctggggcca agggacaatg    360
gtcaccgtct cttca                                                      375
```

<210> SEQ ID NO 594
<211> LENGTH: 125
<212> TYPE: PRT
<213> ORGANISM: Artificial Sequence
<220> FEATURE:
<223> OTHER INFORMATION: Synthetic

<400> SEQUENCE: 594

```
Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30

Ser Ala Ala Trp Asn Trp Ile Arg Gln Ser Pro Ser Arg Gly Leu Glu
         35                  40                  45

Trp Leu Gly Arg Thr Tyr Tyr Arg Ser Lys Trp Tyr Asn Asp Tyr Ala
     50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Gly Tyr Ser Ser Trp Tyr Gly Gly Ala Phe
            100                 105                 110

Asp Ile Trp Gly Gln Gly Thr Met Val Thr Val Ser Ser
        115                 120                 125
```

<210> SEQ ID NO 595
<211> LENGTH: 321
<212> TYPE: DNA
<213> ORGANISM: Artificial Sequence
<220> FEATURE:
<223> OTHER INFORMATION: Synthetic

<400> SEQUENCE: 595

```
gacatccaga tgacccagtc tccatcctcc ctgtctgcat ctgtaggaga cagagtcacc     60
atcacttgcc gggcaagtca gagcattagc agttatttaa gttggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccccattcac tttcggccct    300
gggaccaaag tggatatcaa a                                              321
```

<210> SEQ ID NO 596
<211> LENGTH: 107
<212> TYPE: PRT
<213> ORGANISM: Artificial Sequence
<220> FEATURE:
<223> OTHER INFORMATION: Synthetic

<400> SEQUENCE: 596

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
             20                  25                  30

Leu Ser Trp Tyr Gln Gln Lys Pro Gly Lys Ala Pro Lys Leu Leu Ile
         35                  40                  45
```

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
                100                 105

<210> SEQ ID NO 597
<211> LENGTH: 375
<212> TYPE: DNA
<213> ORGANISM: Artificial Sequence
<220> FEATURE:
<223> OTHER INFORMATION: Synthetic

<400> SEQUENCE: 597
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg ggaaggacat actacaggtc caagtggtat     180
aatgattatg cagtatctgt gaaaagtcga ataaccatca acccagacac atccaagaac     240
cagttctccc tgcagctgaa ctctgtgact cccgaggaca cggctgtgta ttactgtgca     300
agagggtata gcagcagctg gtacgggggt gcttttgata tctggggcca agggacaatg     360
gtcaccgtct cttca                                                     375

<210> SEQ ID NO 598
<211> LENGTH: 125
<212> TYPE: PRT
<213> ORGANISM: Artificial Sequence
<220> FEATURE:
<223> OTHER INFORMATION: Synthetic

<400> SEQUENCE: 598

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Tyr Ser Ser Ser Trp Tyr Gly Gly Ala Phe
            100                 105                 110

Asp Ile Trp Gly Gln Gly Thr Met Val Thr Val Ser Ser
        115                 120                 125

<210> SEQ ID NO 599
<211> LENGTH: 322
<212> TYPE: DNA
<213> ORGANISM: Artificial Sequence
<220> FEATURE:
<223> OTHER INFORMATION: Synthetic

<400> SEQUENCE: 599

```
gacatccaga tgacccagtc tccatcctcc ctgtctgcat ctgtaggaga cagagtcacc    60
atcacttgcc gggcaagtca gagcattagc agttatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ccccattcac tttcggccct   300
gggaccaaag tggatatcaa ac                                             322
```

<210> SEQ ID NO 600
<211> LENGTH: 107
<212> TYPE: PRT
<213> ORGANISM: Artificial Sequence
<220> FEATURE:
<223> OTHER INFORMATION: Synthetic

<400> SEQUENCE: 600

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 601
<211> LENGTH: 357
<212> TYPE: DNA
<213> ORGANISM: Artificial Sequence
<220> FEATURE:
<223> OTHER INFORMATION: Synthetic

<400> SEQUENCE: 601

```
caggtgcagc tgcaggagtc tgggggaggc tcggtacagc ctggggggtc cctgcgactc    60
tcctgtgcaa cctctggatt caccttta cc aactttgcca taagctgggt ccgccaggct   120
ccaggcagtg ggctggagtg ggtctcatct attactggta gtggtgatta cgcatactac   180
gcagactccg tgaagggccg gttcaccatc tccagagaca gttccaagaa cacgctctat   240
ctacaaatga acagcctgag agccgacgac acggccgtat atttctgtac gagagaagac   300
tatattaact cgtcctttga ctactggggc cagggaacca cggtcaccgt ctcctca      357
```

<210> SEQ ID NO 602
<211> LENGTH: 119
<212> TYPE: PRT
<213> ORGANISM: Artificial Sequence
<220> FEATURE:
<223> OTHER INFORMATION: Synthetic

<400> SEQUENCE: 602

Gln Val Gln Leu Gln Glu Ser Gly Gly Gly Ser Val Gln Pro Gly Gly
1               5                   10                  15

Ser Leu Arg Leu Ser Cys Ala Thr Ser Gly Phe Thr Phe Thr Asn Phe
             20                  25                  30

Ala Ile Ser Trp Val Arg Gln Ala Pro Gly Ser Gly Leu Glu Trp Val
         35                  40                  45

Ser Ser Ile Thr Gly Ser Gly Asp Tyr Ala Tyr Tyr Ala Asp Ser Val
     50                  55                  60

Lys Gly Arg Phe Thr Ile Ser Arg Asp Ser Ser Lys Asn Thr Leu Tyr
 65                  70                  75                  80

Leu Gln Met Asn Ser Leu Arg Ala Asp Asp Thr Ala Val Tyr Phe Cys
                 85                  90                  95

Thr Arg Glu Asp Tyr Ile Asn Ser Ser Phe Asp Tyr Trp Gly Gln Gly
             100                 105                 110

Thr Thr Val Thr Val Ser Ser
        115

<210> SEQ ID NO 603
<211> LENGTH: 24
<212> TYPE: DNA
<213> ORGANISM: Artificial Sequence
<220> FEATURE:
<223> OTHER INFORMATION: Synthetic

<400> SEQUENCE: 603
ggattcacct ttaccaactt tgcc                                            24

<210> SEQ ID NO 604
<211> LENGTH: 8
<212> TYPE: PRT
<213> ORGANISM: Artificial Sequence
<220> FEATURE:
<223> OTHER INFORMATION: Synthetic

<400> SEQUENCE: 604

Gly Phe Thr Phe Thr Asn Phe Ala
 1               5

<210> SEQ ID NO 605
<211> LENGTH: 24
<212> TYPE: DNA
<213> ORGANISM: Artificial Sequence
<220> FEATURE:
<223> OTHER INFORMATION: Synthetic

<400> SEQUENCE: 605
attactggta gtggtgatta cgca                                            24

<210> SEQ ID NO 606
<211> LENGTH: 8
<212> TYPE: PRT
<213> ORGANISM: Artificial Sequence
<220> FEATURE:
<223> OTHER INFORMATION: Synthetic

<400> SEQUENCE: 606

Ile Thr Gly Ser Gly Asp Tyr Ala
 1               5

<210> SEQ ID NO 607
<211> LENGTH: 36
<212> TYPE: DNA
<213> ORGANISM: Artificial Sequence
<220> FEATURE:
<223> OTHER INFORMATION: Synthetic

<400> SEQUENCE: 607
acgagagaag actatattaa ctcgtccttt gactac    36

<210> SEQ ID NO 608
<211> LENGTH: 12
<212> TYPE: PRT
<213> ORGANISM: Artificial Sequence
<220> FEATURE:
<223> OTHER INFORMATION: Synthetic

<400> SEQUENCE: 608

Thr Arg Glu Asp Tyr Ile Asn Ser Ser Phe Asp Tyr
1               5                   10

<210> SEQ ID NO 609
<211> LENGTH: 333
<212> TYPE: DNA
<213> ORGANISM: Artificial Sequence
<220> FEATURE:
<223> OTHER INFORMATION: Synthetic

<400> SEQUENCE: 609
gacatccaga tgacccagac tccactctcc tcacctgtca cccttggaca gccggcctcc    60
atctcctgta ggtctagtca gagcctcgta cacagtgatg gaaataccta cttgagttgg   120
cttcagcgga ggccaggcca gcctccaaga ctcctaattt ataagatttc taaccggttc   180
tctggggtcc cagacagatt cagtggcagt ggggcaggga cagatttcac actgaaaatc   240
agcagggtgg aagctgagga tgtcggggtt tattactgca tgcaagctac acaacttccg   300
acgttcggcc aagggaccaa ggtggaaatc aaa                                333

<210> SEQ ID NO 610
<211> LENGTH: 111
<212> TYPE: PRT
<213> ORGANISM: Artificial Sequence
<220> FEATURE:
<223> OTHER INFORMATION: Synthetic

<400> SEQUENCE: 610

Asp Ile Gln Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Arg Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Leu Pro Thr Phe Gly Gln Gly Thr Lys Val Glu Ile Lys
            100                 105                 110

<210> SEQ ID NO 611
<211> LENGTH: 33
<212> TYPE: DNA
<213> ORGANISM: Artificial Sequence
<220> FEATURE:
<223> OTHER INFORMATION: Synthetic

<400> SEQUENCE: 611

```
cagagcctcg tacacagtga tggaaatacc tac                                    33
```

<210> SEQ ID NO 612
<211> LENGTH: 11
<212> TYPE: PRT
<213> ORGANISM: Artificial Sequence
<220> FEATURE:
<223> OTHER INFORMATION: Synthetic

<400> SEQUENCE: 612

```
Gln Ser Leu Val His Ser Asp Gly Asn Thr Tyr
 1               5                  10
```

<210> SEQ ID NO 613
<211> LENGTH: 9
<212> TYPE: DNA
<213> ORGANISM: Artificial Sequence
<220> FEATURE:
<223> OTHER INFORMATION: Synthetic

<400> SEQUENCE: 613

```
aagatttct                                                               9
```

<210> SEQ ID NO 614
<211> LENGTH: 3
<212> TYPE: PRT
<213> ORGANISM: Artificial Sequence
<220> FEATURE:
<223> OTHER INFORMATION: Synthetic

<400> SEQUENCE: 614

```
Lys Ile Ser
 1
```

<210> SEQ ID NO 615
<211> LENGTH: 24
<212> TYPE: DNA
<213> ORGANISM: Artificial Sequence
<220> FEATURE:
<223> OTHER INFORMATION: Synthetic

<400> SEQUENCE: 615

```
atgcaagcta cacaacttcc gacg                                              24
```

<210> SEQ ID NO 616
<211> LENGTH: 8
<212> TYPE: PRT
<213> ORGANISM: Artificial Sequence
<220> FEATURE:
<223> OTHER INFORMATION: Synthetic

<400> SEQUENCE: 616

```
Met Gln Ala Thr Gln Leu Pro Thr
 1               5
```

<210> SEQ ID NO 617
<211> LENGTH: 357
<212> TYPE: DNA
<213> ORGANISM: Artificial Sequence
<220> FEATURE:
<223> OTHER INFORMATION: Synthetic

<400> SEQUENCE: 617

```
gaggtgcagc tgttggagtc tgggggaggc tcggtacagc ctggggggtc cctgcgactc       60
tcctgtgcaa cctctggatt caccttttacc aactttgcca taagctgggt ccgccaggct     120
```

```
ccaggcagtg ggctggagtg ggtctcatct attactggta gtggtgatta cgcatactac    180
gcagactccg tgaagggccg gttcaccatc tccagagaca gttccaagaa cacgctctat    240
ctacaaatga acagcctgag agccgacgac acggccgtat atttctgtac gagagaagac    300
tatattaact cgtcctttga ctactggggc cagggaaccc tggtcaccgt ctcctca      357
```

<210> SEQ ID NO 618
<211> LENGTH: 119
<212> TYPE: PRT
<213> ORGANISM: Artificial Sequence
<220> FEATURE:
<223> OTHER INFORMATION: Synthetic

<400> SEQUENCE: 618

```
Glu Val Gln Leu Leu Glu Ser Gly Gly Gly Ser Val Gln Pro Gly Gly
 1               5                  10                  15

Ser Leu Arg Leu Ser Cys Ala Thr Ser Gly Phe Thr Phe Thr Asn Phe
            20                  25                  30

Ala Ile Ser Trp Val Arg Gln Ala Pro Gly Ser Gly Leu Glu Trp Val
        35                  40                  45

Ser Ser Ile Thr Gly Ser Gly Asp Tyr Ala Tyr Tyr Ala Asp Ser Val
    50                  55                  60

Lys Gly Arg Phe Thr Ile Ser Arg Asp Ser Ser Lys Asn Thr Leu Tyr
65                  70                  75                  80

Leu Gln Met Asn Ser Leu Arg Ala Asp Asp Thr Ala Val Tyr Phe Cys
                85                  90                  95

Thr Arg Glu Asp Tyr Ile Asn Ser Ser Phe Asp Tyr Trp Gly Gln Gly
            100                 105                 110

Thr Leu Val Thr Val Ser Ser
        115
```

<210> SEQ ID NO 619
<211> LENGTH: 333
<212> TYPE: DNA
<213> ORGANISM: Artificial Sequence
<220> FEATURE:
<223> OTHER INFORMATION: Synthetic

<400> SEQUENCE: 619

```
gatattgtga tgacccagac tccactctcc tcacctgtca cccttggaca gccggcctcc    60
atctcctgta ggtctagtca gagcctcgta cacagtgatg aaataccta cttgagttgg    120 cttcagcgga ggccaggcca gcctccaaga ctcctaattt ataagatttc taaccggttc    180
tctggggtcc cagacagatt cagtggcagt ggggcaggga cagatttcac actgaaaatc    240
agcagggtgg aagctgagga tgtcggggtt tattactgca tgcaagctac acaacttccg    300
acgttcggcc aagggaccaa ggtggaaatc aaa                                333
```

<210> SEQ ID NO 620
<211> LENGTH: 111
<212> TYPE: PRT
<213> ORGANISM: Artificial Sequence
<220> FEATURE:
<223> OTHER INFORMATION: Synthetic

<400> SEQUENCE: 620

```
Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
```

```
                    20                  25                  30
Asp Gly Asn Thr Tyr Leu Ser Trp Leu Gln Arg Arg Pro Gly Gln Pro
                35                  40                  45

Pro Arg Leu Leu Ile Tyr Lys Ile Ser Asn Arg Phe Ser Gly Val Pro
         50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Thr Gln Leu Pro Thr Phe Gly Gln Gly Thr Lys Val Glu Ile Lys
            100                 105                 110

<210> SEQ ID NO 621
<211> LENGTH: 357
<212> TYPE: DNA
<213> ORGANISM: Artificial Sequence
<220> FEATURE:
<223> OTHER INFORMATION: Synthetic

<400> SEQUENCE: 621
gaggtgcagc tgttggagtc tgggggaggc ttggtacagc ctggggggtc cctgagactc     60
tcctgtgcag cctctggatt cacctttacc aactttgcca tgagctgggt ccgccaggct    120
ccagggaagg ggctggagtg ggtctcagct attactggta gtggtgatta cgcatactac    180
gcagactccg tgaagggccg gttcaccatc tccagagaca attccaagaa cacgctgtat    240
ctgcaaatga acagcctgag agccgaggac acggccgtat attactgtac gagagaagac    300
tatattaact cgtcctttga ctactggggc cagggaaccc tggtcaccgt ctcctca      357

<210> SEQ ID NO 622
<211> LENGTH: 119
<212> TYPE: PRT
<213> ORGANISM: Artificial Sequence
<220> FEATURE:
<223> OTHER INFORMATION: Synthetic

<400> SEQUENCE: 622

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Asn Phe
            20                  25                  30

Ala Met Ser Trp Val Arg Gln Ala Pro Gly Lys Gly Leu Glu Trp Val
         35                  40                  45

Ser Ala Ile Thr Gly Ser Gly Asp Tyr Ala Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Glu Asp Tyr Ile Asn Ser Ser Phe Asp Tyr Trp Gly Gln Gly
            100                 105                 110

Thr Leu Val Thr Val Ser Ser
        115

<210> SEQ ID NO 623
<211> LENGTH: 334
<212> TYPE: DNA
<213> ORGANISM: Artificial Sequence
<220> FEATURE:
```

<223> OTHER INFORMATION: Synthetic

<400> SEQUENCE: 623

```
gatattgtga tgacccagac tccactctcc tcacctgtca cccttggaca gccggcctcc    60
atctcctgca ggtctagtca gagcctcgta cacagtgatg gaaataccta cttgagttgg   120
cttcagcaga ggccaggcca gcctccaaga ctcctaattt ataagatttc taaccggttc   180
tctggggtcc cagacagatt cagtggcagt ggggcaggga cagatttcac actgaaaatc   240
agcagggtgg aagctgagga tgtcggggtt tattactgca tgcaagctac acaacttccg   300
acgttcggcc aagggaccaa ggtggaaatc aaac                               334
```

<210> SEQ ID NO 624
<211> LENGTH: 111
<212> TYPE: PRT
<213> ORGANISM: Artificial Sequence
<220> FEATURE:
<223> OTHER INFORMATION: Synthetic

<400> SEQUENCE: 624

```
Asp Ile Val Met Thr Gln Thr Pro Leu Ser Ser Pro Val Thr Leu Gly
 1               5                  10                  15
Gln Pro Ala Ser Ile Ser Cys Arg Ser Ser Gln Ser Leu Val His Ser
            20                  25                  30
Asp Gly Asn Thr Tyr Leu Ser Trp Leu Gln Arg Pro Gly Gln Pro
        35                  40                  45
Pro Arg Leu Leu Ile Tyr Lys Ile Ser Asn Arg Phe Ser Gly Val Pro
    50                  55                  60
Asp Arg Phe Ser Gly Ser Gly Ala Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Thr Gln Leu Pro Thr Phe Gly Gln Gly Thr Lys Val Glu Ile Lys
            100                 105                 110
```

<210> SEQ ID NO 625
<211> LENGTH: 357
<212> TYPE: DNA
<213> ORGANISM: Artificial Sequence
<220> FEATURE:
<223> OTHER INFORMATION: Synthetic

<400> SEQUENCE: 625

```
caggtgcagc tggtggagtc tgggggaggc gtggtccagc ctgggatgtc cctgagactc    60
tcctgtgcag cgtccggatt taccttcagg agatatggca tgcactgggt ccgccaggct   120
ccaggcaagg ggctggagtg gtggcagtt atatggtatg atggaagtaa taaatattat   180
gtagattccg tgaagggccg attcaccatc tccagagaca attccaagaa cacgctgtat   240
ctgcaaatga acagcctgag agccgaggac acggctgtgt attactgtgc gagcgaaatt   300
acagttgggg actggttcga cccctggggc cagggaaccc tggtcaccgt ctcctca      357
```

<210> SEQ ID NO 626
<211> LENGTH: 119
<212> TYPE: PRT
<213> ORGANISM: Artificial Sequence
<220> FEATURE:
<223> OTHER INFORMATION: Synthetic

<400> SEQUENCE: 626

```
Gln Val Gln Leu Val Glu Ser Gly Gly Val Val Gln Pro Gly Met
1               5                   10                  15

Ser Leu Arg Leu Ser Cys Ala Ala Ser Gly Phe Thr Phe Arg Arg Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Glu Ile Thr Val Gly Asp Trp Phe Asp Pro Trp Gly Gln Gly
            100                 105                 110

Thr Leu Val Thr Val Ser Ser
        115
```

<210> SEQ ID NO 627
<211> LENGTH: 24
<212> TYPE: DNA
<213> ORGANISM: Artificial Sequence
<220> FEATURE:
<223> OTHER INFORMATION: Synthetic

<400> SEQUENCE: 627
ggatttacct tcaggagata tggc                                          24

<210> SEQ ID NO 628
<211> LENGTH: 8
<212> TYPE: PRT
<213> ORGANISM: Artificial Sequence
<220> FEATURE:
<223> OTHER INFORMATION: Synthetic

<400> SEQUENCE: 628

```
Gly Phe Thr Phe Arg Arg Tyr Gly
1               5
```

<210> SEQ ID NO 629
<211> LENGTH: 24
<212> TYPE: DNA
<213> ORGANISM: Artificial Sequence
<220> FEATURE:
<223> OTHER INFORMATION: Synthetic

<400> SEQUENCE: 629
atatggtatg atggaagtaa taaa                                          24

<210> SEQ ID NO 630
<211> LENGTH: 8
<212> TYPE: PRT
<213> ORGANISM: Artificial Sequence
<220> FEATURE:
<223> OTHER INFORMATION: Synthetic

<400> SEQUENCE: 630

```
Ile Trp Tyr Asp Gly Ser Asn Lys
1               5
```

<210> SEQ ID NO 631
<211> LENGTH: 36
<212> TYPE: DNA
<213> ORGANISM: Artificial Sequence
<220> FEATURE:
<223> OTHER INFORMATION: Synthetic

<400> SEQUENCE: 631
gcgagcgaaa ttacagttgg ggactggttc gacccc        36

<210> SEQ ID NO 632
<211> LENGTH: 12
<212> TYPE: PRT
<213> ORGANISM: Artificial Sequence
<220> FEATURE:
<223> OTHER INFORMATION: Synthetic

<400> SEQUENCE: 632

Ala Ser Glu Ile Thr Val Gly Asp Trp Phe Asp Pro
1               5                   10

<210> SEQ ID NO 633
<211> LENGTH: 321
<212> TYPE: DNA
<213> ORGANISM: Artificial Sequence
<220> FEATURE:
<223> OTHER INFORMATION: Synthetic

<400> SEQUENCE: 633
gacatccaga tgacccagtc tccatcctcc ctgtctgcat ctgtaggaga cagagtcacc        60
atcacttgtc gggcaagtca gggcattaga aatgatttag cctggtatca gcagaaacca       120
gggaaagccc ctaaactcct gatctatgct gcatccagtt tacacagtgg ggtcccatca       180
aggttcagcg gcagtggatc tggcacagat ttcactctca ccatcagcag cctgcagcct       240
gaagattttg caacttatta ctgtctacag gatttcaatt accctctcac tttcggcgga       300
gggaccaagg tggagatcaa a                                                 321

<210> SEQ ID NO 634
<211> LENGTH: 107
<212> TYPE: PRT
<213> ORGANISM: Artificial Sequence
<220> FEATURE:
<223> OTHER INFORMATION: Synthetic

<400> SEQUENCE: 634

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Leu
                85                  90                  95

Thr Phe Gly Gly Gly Thr Lys Val Glu Ile Lys
            100                 105

<210> SEQ ID NO 635
<211> LENGTH: 18
<212> TYPE: DNA
<213> ORGANISM: Artificial Sequence
<220> FEATURE:

<223> OTHER INFORMATION: Synthetic

<400> SEQUENCE: 635
cagggcatta gaaatgat								18

<210> SEQ ID NO 636
<211> LENGTH: 6
<212> TYPE: PRT
<213> ORGANISM: Artificial Sequence
<220> FEATURE:
<223> OTHER INFORMATION: Synthetic

<400> SEQUENCE: 636

Gln Gly Ile Arg Asn Asp
 1               5

<210> SEQ ID NO 637
<211> LENGTH: 9
<212> TYPE: DNA
<213> ORGANISM: Artificial Sequence
<220> FEATURE:
<223> OTHER INFORMATION: Synthetic

<400> SEQUENCE: 637 gctgcatcc								9

<210> SEQ ID NO 638
<211> LENGTH: 3
<212> TYPE: PRT
<213> ORGANISM: Artificial Sequence
<220> FEATURE:
<223> OTHER INFORMATION: Synthetic

<400> SEQUENCE: 638

Ala Ala Ser
 1

<210> SEQ ID NO 639
<211> LENGTH: 27
<212> TYPE: DNA
<213> ORGANISM: Artificial Sequence
<220> FEATURE:
<223> OTHER INFORMATION: Synthetic

<400> SEQUENCE: 639
ctacaggatt tcaattaccc tctcact								27

<210> SEQ ID NO 640
<211> LENGTH: 9
<212> TYPE: PRT
<213> ORGANISM: Artificial Sequence
<220> FEATURE:
<223> OTHER INFORMATION: Synthetic

<400> SEQUENCE: 640

Leu Gln Asp Phe Asn Tyr Pro Leu Thr
 1               5

<210> SEQ ID NO 641
<211> LENGTH: 357
<212> TYPE: DNA
<213> ORGANISM: Artificial Sequence
<220> FEATURE:
<223> OTHER INFORMATION: Synthetic

<400> SEQUENCE: 641

| | |
|---|---|
| caggtgcagc tggtggagtc tggggggaggc gtggtccagc ctgggatgtc cctgagactc | 60 |
| tcctgtgcag cgtccggatt taccttcagg agatatggca tgcactgggt ccgccaggct | 120 |
| ccaggcaagg ggctggagtg ggtggcagtt atatggtatg atggaagtaa taaatattat | 180 |
| gtagattccg tgaagggccg attcaccatc tccagagaca attccaagaa cacgctgtat | 240 |
| ctgcaaatga acagcctgag agccgaggac acggctgtgt attactgtgc gagcgaaatt | 300 |
| acagttgggg actggttcga cccctggggc cagggaaccc tggtcaccgt ctcctca | 357 |

```
<210> SEQ ID NO 642
<211> LENGTH: 119
<212> TYPE: PRT
<213> ORGANISM: Artificial Sequence
<220> FEATURE:
<223> OTHER INFORMATION: Synthetic

<400> SEQUENCE: 642
```

Gln Val Gln Leu Val Glu Ser Gly Gly Gly Val Val Gln Pro Gly Met
1               5                   10                  15

Ser Leu Arg Leu Ser Cys Ala Ala Ser Gly Phe Thr Phe Arg Arg Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Glu Ile Thr Val Gly Asp Trp Phe Asp Pro Trp Gly Gln Gly
            100                 105                 110

Thr Leu Val Thr Val Ser Ser
        115

```
<210> SEQ ID NO 643
<211> LENGTH: 321
<212> TYPE: DNA
<213> ORGANISM: Artificial Sequence
<220> FEATURE:
<223> OTHER INFORMATION: Synthetic

<400> SEQUENCE: 643
```

| | |
|---|---|
| gccatccaga tgacccagtc tccatcctcc ctgtctgcat ctgtaggaga cagagtcacc | 60 |
| atcacttgtc gggcaagtca gggcattaga aatgatttag gctggtatca gcagaaacca | 120 |
| gggaaagccc ctaaactcct gatctatgct gcatccagtt tacacagtgg ggtcccatca | 180 |
| aggttcagcg gcagtggatc tgggacagat ttcactctca ccatcagcag cctgcagcct | 240 |
| gaagattttg caacttatta ctgtctacag gatttcaatt accctctcac tttcggcgga | 300 |
| gggaccaagg tggagatcaa a | 321 |

```
<210> SEQ ID NO 644
<211> LENGTH: 107
<212> TYPE: PRT
<213> ORGANISM: Artificial Sequence
<220> FEATURE:
<223> OTHER INFORMATION: Synthetic

<400> SEQUENCE: 644
```

Ala Ile Gln Met Thr Gln Ser Pro Ser Ser Leu Ser Ala Ser Val Gly

```
                1               5                  10                 15
            Asp Arg Val Thr Ile Thr Cys Arg Ala Ser Gln Gly Ile Arg Asn Asp
                            20                  25                  30

Leu Gly Trp Tyr Gln Gln Lys Pro Gly Lys Ala Pro Lys Leu Leu Ile
                        35                  40                  45

Tyr Ala Ala Ser Ser Leu His Ser Gly Val Pro Ser Arg Phe Ser Gly
                    50                  55                  60

Ser Gly Ser Gly Thr Asp Phe Thr Leu Thr Ile Ser Ser Leu Gln Pro
            65                  70                  75                  80

Glu Asp Phe Ala Thr Tyr Tyr Cys Leu Gln Asp Phe Asn Tyr Pro Leu
                                85                  90                  95

Thr Phe Gly Gly Gly Thr Lys Val Glu Ile Lys
                        100                 105

<210> SEQ ID NO 645
            <211> LENGTH: 357
            <212> TYPE: DNA
            <213> ORGANISM: Artificial Sequence
            <220> FEATURE:
            <223> OTHER INFORMATION: Synthetic

<400> SEQUENCE: 645
caggtgcagc tggtggagtc tgggggaggc gtggtccagc ctggagggtc cctgagactc        60
tcctgtgcag cgtctggatt taccttcagg agatatggca tgcactgggt ccgccaggct       120
ccaggcaagg ggctggagtg ggtggcagtt atatggtatg atggaagtaa taaatactat       180
gcagactccg tgaagggccg attcaccatc tccagagaca actccaagaa cacgctgtat       240
ctgcaaatga acagcctgag agccgaggac acggctgtgt attactgtgc gagcgaaatt       300
acagttgggg actggttcga ccctgggggc cagggaaccc tggtcaccgt ctcctca          357

<210> SEQ ID NO 646
            <211> LENGTH: 119
            <212> TYPE: PRT
            <213> ORGANISM: Artificial Sequence
            <220> FEATURE:
            <223> OTHER INFORMATION: Synthetic

<400> SEQUENCE: 646

Gln Val Gln Leu Val Glu Ser Gly Gly Gly Val Val Gln Pro Gly Arg
            1               5                   10                  15

Ser Leu Arg Leu Ser Cys Ala Ala Ser Gly Phe Thr Phe Arg Arg Tyr
                            20                  25                  30

Gly Met His Trp Val Arg Gln Ala Pro Gly Lys Gly Leu Glu Trp Val
                        35                  40                  45

Ala Val Ile Trp Tyr Asp Gly Ser Asn Lys Tyr Tyr Ala Asp Ser Val
                    50                  55                  60

Lys Gly Arg Phe Thr Ile Ser Arg Asp Asn Ser Lys Asn Thr Leu Tyr
            65                  70                  75                  80

Leu Gln Met Asn Ser Leu Arg Ala Glu Asp Thr Ala Val Tyr Tyr Cys
                                85                  90                  95

Ala Ser Glu Ile Thr Val Gly Asp Trp Phe Asp Pro Trp Gly Gln Gly
                        100                 105                 110

Thr Leu Val Thr Val Ser Ser
                    115

<210> SEQ ID NO 647
            <211> LENGTH: 322
```

<212> TYPE: DNA
<213> ORGANISM: Artificial Sequence
<220> FEATURE:
<223> OTHER INFORMATION: Synthetic

<400> SEQUENCE: 647

```
gccatccaga tgacccagtc tccatcctcc ctgtctgcat ctgtaggaga cagagtcacc      60
atcacttgcc gggcaagtca gggcattaga aatgatttag ctggtatca gcagaaacca     120
gggaaagccc ctaagctcct gatctatgct gcatccagtt tacaaagtgg ggtcccatca    180
aggttcagcg gcagtggatc tggcacagat tcactctca ccatcagcag cctgcagcct     240
gaagattttg caacttatta ctgtctacag gatttcaatt accctctcac tttcggcgga    300
gggaccaagg tggagatcaa ac                                              322
```

<210> SEQ ID NO 648
<211> LENGTH: 107
<212> TYPE: PRT
<213> ORGANISM: Artificial Sequence
<220> FEATURE:
<223> OTHER INFORMATION: Synthetic

<400> SEQUENCE: 648

```
Ala Ile Gln Met Thr Gln Ser Pro Ser Ser Leu Ser Ala Ser Val Gly
 1               5                  10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Leu Gln Asp Phe Asn Tyr Pro Leu
                85                  90                  95
Thr Phe Gly Gly Gly Thr Lys Val Glu Ile Lys
            100                 105
```

<210> SEQ ID NO 649
<211> LENGTH: 357
<212> TYPE: DNA
<213> ORGANISM: Artificial Sequence
<220> FEATURE:
<223> OTHER INFORMATION: Synthetic

<400> SEQUENCE: 649

```
caggtgcagc tggtggagtc tgggggaggc gtggtccagc ctggggggtc cctgagactc     60
tcctgtgtag cctctggatt caccttcagt agatatggca tgcactgggt ccgccaggct    120
ccaggcaagg ggctggagtg gctgatagtt atatcatatg atggaattaa taaatactat    180
gcagactccg tgaagggccg attcaccatc tccagagaca attccaagaa cacggtgtat    240
ctgcaaatga acagcctgag agctgaggac acggagtgt attactgtgc gaaggggac      300
ttttggagtg gttactttga ctactggggc cagggaaccc tggtcactgt ctcctca       357
```

<210> SEQ ID NO 650
<211> LENGTH: 119
<212> TYPE: PRT
<213> ORGANISM: Artificial Sequence
<220> FEATURE:
<223> OTHER INFORMATION: Synthetic

<400> SEQUENCE: 650

Gln Val Gln Leu Val Glu Ser Gly Gly Val Val Gln Pro Gly Arg
1               5                   10                  15

Ser Leu Arg Leu Ser Cys Val Ala Ser Gly Phe Thr Phe Ser Arg Tyr
            20                  25                  30

Gly Met His Trp Val Arg Gln Ala Pro Gly Lys Gly Leu Glu Trp Leu
        35                  40                  45

Ile Val Ile Ser Tyr Asp Gly Ile Asn Lys Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Gly Val Tyr Tyr Cys
                85                  90                  95

Ala Lys Gly Asp Phe Trp Ser Gly Tyr Phe Asp Tyr Trp Gly Gln Gly
            100                 105                 110

Thr Leu Val Thr Val Ser Ser
        115

<210> SEQ ID NO 651
<211> LENGTH: 24
<212> TYPE: DNA
<213> ORGANISM: Artificial Sequence
<220> FEATURE:
<223> OTHER INFORMATION: Synthetic

<400> SEQUENCE: 651
ggattcacct tcagtagata tggc                                      24

<210> SEQ ID NO 652
<211> LENGTH: 8
<212> TYPE: PRT
<213> ORGANISM: Artificial Sequence
<220> FEATURE:
<223> OTHER INFORMATION: Synthetic

<400> SEQUENCE: 652

Gly Phe Thr Phe Ser Arg Tyr Gly
1               5

<210> SEQ ID NO 653
<211> LENGTH: 24
<212> TYPE: DNA
<213> ORGANISM: Artificial Sequence
<220> FEATURE:
<223> OTHER INFORMATION: Synthetic

<400> SEQUENCE: 653
atatcatatg atggaattaa taaa                                      24

<210> SEQ ID NO 654
<211> LENGTH: 8
<212> TYPE: PRT
<213> ORGANISM: Artificial Sequence
<220> FEATURE:
<223> OTHER INFORMATION: Synthetic

<400> SEQUENCE: 654

Ile Ser Tyr Asp Gly Ile Asn Lys
1               5

<210> SEQ ID NO 655

```
<211> LENGTH: 36
<212> TYPE: DNA
<213> ORGANISM: Artificial Sequence
<220> FEATURE:
<223> OTHER INFORMATION: Synthetic

<400> SEQUENCE: 655
gcgaaagggg actttggag tggttacttt gactac                                  36

<210> SEQ ID NO 656
<211> LENGTH: 12
<212> TYPE: PRT
<213> ORGANISM: Artificial Sequence
<220> FEATURE:
<223> OTHER INFORMATION: Synthetic

<400> SEQUENCE: 656

Ala Lys Gly Asp Phe Trp Ser Gly Tyr Phe Asp Tyr
 1               5                  10

<210> SEQ ID NO 657
<211> LENGTH: 336
<212> TYPE: DNA
<213> ORGANISM: Artificial Sequence
<220> FEATURE:
<223> OTHER INFORMATION: Synthetic

<400> SEQUENCE: 657
gacatcgtga tgacccagac tccactctcc tcacctgtca cccttggaca gccggcctcc        60
atctcctgca ggtctagtca aagcctcgtc cacagtgatg gaaacaccta cttgagttgg       120
cttcaccaga ggccaggcca gcctccaaga ctcctaattt ataagatttc taaccggttc       180
tctggggtcc cagacagatt cagtggcagt ggggcaggga cagatttcac actgcaaatc       240
agcagggtgg aagctgagga tgtcgggatt tattactgca tgcaaggtac acaatttccg       300
actttcggcg agggaccaa ggtggagatc aaacga                                 336

<210> SEQ ID NO 658
<211> LENGTH: 112
<212> TYPE: PRT
<213> ORGANISM: Artificial Sequence
<220> FEATURE:
<223> OTHER INFORMATION: Synthetic

<400> SEQUENCE: 658

Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
                20                  25                  30

Asp Gly Asn Thr Tyr Leu Ser Trp Leu His Gln Arg Pro Gly Gln Pro
            35                  40                  45

Pro Arg Leu Leu Ile Tyr Lys Ile Ser Asn Arg Phe Ser Gly Val Pro
        50                  55                  60

Asp Arg Phe Ser Gly Ser Gly Ala Gly Thr Asp Phe Thr Leu Gln Ile
 65                 70                  75                  80

Ser Arg Val Glu Ala Glu Asp Val Gly Ile Tyr Tyr Cys Met Gln Gly
                85                  90                  95

Thr Gln Phe Pro Thr Phe Gly Gly Gly Thr Lys Val Glu Ile Lys Arg
                100                 105                 110

<210> SEQ ID NO 659
<211> LENGTH: 33
```

```
<212> TYPE: DNA
<213> ORGANISM: Artificial Sequence
<220> FEATURE:
<223> OTHER INFORMATION: Synthetic

<400> SEQUENCE: 659
caaagcctcg tccacagtga tggaaacacc tac                                    33

<210> SEQ ID NO 660
<211> LENGTH: 11
<212> TYPE: PRT
<213> ORGANISM: Artificial Sequence
<220> FEATURE:
<223> OTHER INFORMATION: Synthetic

<400> SEQUENCE: 660

Gln Ser Leu Val His Ser Asp Gly Asn Thr Tyr
 1               5                  10

<210> SEQ ID NO 661
<211> LENGTH: 9
<212> TYPE: DNA
<213> ORGANISM: Artificial Sequence
<220> FEATURE:
<223> OTHER INFORMATION: Synthetic

<400> SEQUENCE: 661 aagatttct                                                                9

<210> SEQ ID NO 662
<211> LENGTH: 3
<212> TYPE: PRT
<213> ORGANISM: Artificial Sequence
<220> FEATURE:
<223> OTHER INFORMATION: Synthetic

<400> SEQUENCE: 662

Lys Ile Ser
 1

<210> SEQ ID NO 663
<211> LENGTH: 24
<212> TYPE: DNA
<213> ORGANISM: Artificial Sequence
<220> FEATURE:
<223> OTHER INFORMATION: Synthetic

<400> SEQUENCE: 663
atgcaaggta cacaatttcc gact                                              24

<210> SEQ ID NO 664
<211> LENGTH: 8
<212> TYPE: PRT
<213> ORGANISM: Artificial Sequence
<220> FEATURE:
<223> OTHER INFORMATION: Synthetic

<400> SEQUENCE: 664

Met Gln Gly Thr Gln Phe Pro Thr
 1               5

<210> SEQ ID NO 665
<211> LENGTH: 357
<212> TYPE: DNA
<213> ORGANISM: Artificial Sequence
<220> FEATURE:
<223> OTHER INFORMATION: Synthetic
```

<400> SEQUENCE: 665

```
caggtgcagc tggtggagtc tgggggaggc gtggtccagc ctggagggtc cctgagactc    60
tcctgtgtag cctctggatt caccttcagt agatatggca tgcactgggt ccgccaggct   120
ccaggcaagg ggctggagtg gctgatagtt atatcatatg atggaattaa taaatactat   180
gcagactccg tgaagggccg attcaccatc tccagagaca attccaagaa cacggtgtat   240
ctgcaaatga acagcctgag agctgaggac acggagtgt attactgtgc gaaggggac    300
ttttggagtg gttactttga ctactggggc cagggaaccc tggtcaccgt ctcctca     357
```

<210> SEQ ID NO 666
<211> LENGTH: 119
<212> TYPE: PRT
<213> ORGANISM: Artificial Sequence
<220> FEATURE:
<223> OTHER INFORMATION: Synthetic

<400> SEQUENCE: 666

```
Gln Val Gln Leu Val Glu Ser Gly Gly Gly Val Val Gln Pro Gly Arg
  1               5                  10                  15
Ser Leu Arg Leu Ser Cys Val Ala Ser Gly Phe Thr Phe Ser Arg Tyr
             20                  25                  30
Gly Met His Trp Val Arg Gln Ala Pro Gly Lys Gly Leu Glu Trp Leu
         35                  40                  45
Ile Val Ile Ser Tyr Asp Gly Ile Asn Lys Tyr Tyr Ala Asp Ser Val
     50                  55                  60
Lys Gly Arg Phe Thr Ile Ser Arg Asp Asn Ser Lys Asn Thr Val Tyr
 65                  70                  75                  80
Leu Gln Met Asn Ser Leu Arg Ala Glu Asp Thr Gly Val Tyr Tyr Cys
                 85                  90                  95
Ala Lys Gly Asp Phe Trp Ser Gly Tyr Phe Asp Tyr Trp Gly Gln Gly
            100                 105                 110
Thr Leu Val Thr Val Ser Ser
        115
```

<210> SEQ ID NO 667
<211> LENGTH: 333
<212> TYPE: DNA
<213> ORGANISM: Artificial Sequence
<220> FEATURE:
<223> OTHER INFORMATION: Synthetic

<400> SEQUENCE: 667

```
gatattgtga tgacccagac tccactctcc tcacctgtca cccttggaca gccggcctcc    60
atctcctgca ggtctagtca aagcctcgtc cacagtgatg aaacacccta cttgagttgg   120
cttcaccaga ggccaggcca gcctccaaga ctcctaattt ataagatttc taaccggttc   180
tctggggtcc cagacagatt cagtggcagt ggggcaggga cagatttcac actgcaaatc   240
agcagggtgg aagctgagga tgtcggggatt tattactgca tgcaaggtac acaatttccg   300
actttcggcg gagggaccaa ggtggagatc aaa                                333
```

<210> SEQ ID NO 668
<211> LENGTH: 111
<212> TYPE: PRT
<213> ORGANISM: Artificial Sequence
<220> FEATURE:
<223> OTHER INFORMATION: Synthetic

<400> SEQUENCE: 668

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu His Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Gln Ile
65                  70                  75                  80

Ser Arg Val Glu Ala Glu Asp Val Gly Ile Tyr Tyr Cys Met Gln Gly
                85                  90                  95

Thr Gln Phe Pro Thr Phe Gly Gly Gly Thr Lys Val Glu Ile Lys
            100                 105                 110

<210> SEQ ID NO 669
<211> LENGTH: 357
<212> TYPE: DNA
<213> ORGANISM: Artificial Sequence
<220> FEATURE:
<223> OTHER INFORMATION: Synthetic

<400> SEQUENCE: 669

```
caggtgcagc tggtggagtc tgggggaggc gtggtccagc ctggagggtc cctgagactc      60
tcctgtgcag cctctggatt caccttcagt agatatggca tgcactgggt ccgccaggct     120
ccaggcaagg ggctggagtg ggtggcagtt atatcatatg atggaattaa taaatactat     180
gcagactccg tgaagggccg attcaccatc tccagagaca attccaagaa cacgctgtat     240
ctgcaaatga acagcctgag agctgaggac acggctgtgt attactgtgc gaaaggggac     300
ttttggagtg gttactttga ctactggggc cagggaaccc tggtcaccgt ctcctca       357
```

<210> SEQ ID NO 670
<211> LENGTH: 119
<212> TYPE: PRT
<213> ORGANISM: Artificial Sequence
<220> FEATURE:
<223> OTHER INFORMATION: Synthetic

<400> SEQUENCE: 670

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ile Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Phe Trp Ser Gly Tyr Phe Asp Tyr Trp Gly Gln Gly
            100                 105                 110

Thr Leu Val Thr Val Ser Ser
        115

<210> SEQ ID NO 671
<211> LENGTH: 334
<212> TYPE: DNA
<213> ORGANISM: Artificial Sequence
<220> FEATURE:
<223> OTHER INFORMATION: Synthetic

<400> SEQUENCE: 671

```
gatattgtga tgacccagac tccactctcc tcacctgtca cccttggaca gccggcctcc      60
atctcctgca ggtctagtca aagcctcgtc cacagtgatg gaaacaccta cttgagttgg     120
cttcagcaga ggccaggcca gcctccaaga ctcctaattt ataagatttc taaccggttc     180 tctgggtcc cagacagatt cagtggcagt ggggcaggga cagatttcac actgaaaatc      240
agcagggtgg aagctgagga tgtcggggtt tattactgca tgcaaggtac acaatttccg     300
actttcggcg gagggaccaa ggtggagatc aaac                                 334
```

<210> SEQ ID NO 672
<211> LENGTH: 111
<212> TYPE: PRT
<213> ORGANISM: Artificial Sequence
<220> FEATURE:
<223> OTHER INFORMATION: Synthetic

<400> SEQUENCE: 672

Asp Ile Val Met Thr Gln Thr Pro Leu Ser Ser Pro Val Thr Leu Gly
1               5                   10                  15
Gln Pro Ala Ser Ile Ser Cys Arg Ser Ser Gln Ser Leu Val His Ser
            20                  25                  30
Asp Gly Asn Thr Tyr Leu Ser Trp Leu Gln Gln Arg Pro Gly Gln Pro
        35                  40                  45
Pro Arg Leu Leu Ile Tyr Lys Ile Ser Asn Arg Phe Ser Gly Val Pro
    50                  55                  60
Asp Arg Phe Ser Gly Ser Gly Ala Gly Thr Asp Phe Thr Leu Lys Ile
65                  70                  75                  80
Ser Arg Val Glu Ala Glu Asp Val Gly Val Tyr Tyr Cys Met Gln Gly
                85                  90                  95
Thr Gln Phe Pro Thr Phe Gly Gly Gly Thr Lys Val Glu Ile Lys
            100                 105                 110

<210> SEQ ID NO 673
<211> LENGTH: 357
<212> TYPE: DNA
<213> ORGANISM: Artificial Sequence
<220> FEATURE:
<223> OTHER INFORMATION: Synthetic

<400> SEQUENCE: 673

```
caggtgcagc tggtgcagtc tgggggaggc gtggtccagc ctggagggtc cctgagactc      60
tcctgtgtag cctctggatt caccttcagt agatatggca tgcactgggt ccgccaggct     120
ccaggcaagg ggctggagtg ggtggtagtt atatcatatg atggaattaa taatactat      180 gcagactccg tgaagggccg attcaccatc tccagagaca attccaagaa cacggtgtat     240
ctgcaaatga acagcctgag agctgaggac acggctgtgt atcactgtgc gaaggggac      300 ttttggagtg gttactttga ctactggggc cagggaaccc tggtcaccgt ctcctca        357
```

<210> SEQ ID NO 674
<211> LENGTH: 119
<212> TYPE: PRT

<213> ORGANISM: Artificial Sequence
<220> FEATURE:
<223> OTHER INFORMATION: Synthetic

<400> SEQUENCE: 674

```
Gln Val Gln Leu Val Gln Ser Gly Gly Val Val Gln Pro Gly Arg
 1               5                  10                  15
Ser Leu Arg Leu Ser Cys Val Ala Ser Gly Phe Thr Phe Ser Arg Tyr
                20                  25                  30
Gly Met His Trp Val Arg Gln Ala Pro Gly Lys Gly Leu Glu Trp Val
             35                  40                  45
Val Val Ile Ser Tyr Asp Gly Ile Asn Lys Tyr Tyr Ala Asp Ser Val
 50                  55                  60
Lys Gly Arg Phe Thr Ile Ser Arg Asp Asn Ser Lys Asn Thr Val Tyr
 65                  70                  75                  80
Leu Gln Met Asn Ser Leu Arg Ala Glu Asp Thr Ala Val Tyr His Cys
                 85                  90                  95
Ala Lys Gly Asp Phe Trp Ser Gly Tyr Phe Asp Tyr Trp Gly Gln Gly
            100                 105                 110
Thr Leu Val Thr Val Ser Ser
            115
```

<210> SEQ ID NO 675
<211> LENGTH: 24
<212> TYPE: DNA
<213> ORGANISM: Artificial Sequence
<220> FEATURE:
<223> OTHER INFORMATION: Synthetic

<400> SEQUENCE: 675
ggattcacct tcagtagata tggc        24

<210> SEQ ID NO 676
<211> LENGTH: 8
<212> TYPE: PRT
<213> ORGANISM: Artificial Sequence
<220> FEATURE:
<223> OTHER INFORMATION: Synthetic

<400> SEQUENCE: 676

```
Gly Phe Thr Phe Ser Arg Tyr Gly
 1               5
```

<210> SEQ ID NO 677
<211> LENGTH: 24
<212> TYPE: DNA
<213> ORGANISM: Artificial Sequence
<220> FEATURE:
<223> OTHER INFORMATION: Synthetic

<400> SEQUENCE: 677
atatcatatg atggaattaa taaa        24

<210> SEQ ID NO 678
<211> LENGTH: 8
<212> TYPE: PRT
<213> ORGANISM: Artificial Sequence
<220> FEATURE:
<223> OTHER INFORMATION: Synthetic

<400> SEQUENCE: 678

```
Ile Ser Tyr Asp Gly Ile Asn Lys
 1               5
```

<210> SEQ ID NO 679
<211> LENGTH: 36
<212> TYPE: DNA
<213> ORGANISM: Artificial Sequence
<220> FEATURE:
<223> OTHER INFORMATION: Synthetic

<400> SEQUENCE: 679
gcgaaagggg acttttggag tggttacttt gactac              36

<210> SEQ ID NO 680
<211> LENGTH: 12
<212> TYPE: PRT
<213> ORGANISM: Artificial Sequence
<220> FEATURE:
<223> OTHER INFORMATION: Synthetic

<400> SEQUENCE: 680

Ala Lys Gly Asp Phe Trp Ser Gly Tyr Phe Asp Tyr
1               5                   10

<210> SEQ ID NO 681
<211> LENGTH: 336
<212> TYPE: DNA
<213> ORGANISM: Artificial Sequence
<220> FEATURE:
<223> OTHER INFORMATION: Synthetic

<400> SEQUENCE: 681
gacatcgtga tgacccagac tccactctcc tcacctgtca cccttggaca gccggcctcc    60
atctcctgca ggtctagtca agcctcgta cacagtgatg aaacaccta cttgagttgg    120 cttcaccaga ggccaggcca gcctccaaga ctcctaattt ataagatttc taaccggttc    180
tctggggtcc cagacagatt cagtggcagt ggggcaggga cagatttcac actgcaaatc    240
agcagggtgg aagctgagga tgtcgggatt tattactgca tgcaagcaac acaatttccg    300
actttcggcg gagggaccaa ggtggaaatc aaacga                              336

<210> SEQ ID NO 682
<211> LENGTH: 112
<212> TYPE: PRT
<213> ORGANISM: Artificial Sequence
<220> FEATURE:
<223> OTHER INFORMATION: Synthetic

<400> SEQUENCE: 682

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu His Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Gln Ile
65                  70                  75                  80

Ser Arg Val Glu Ala Glu Asp Val Gly Ile Tyr Tyr Cys Met Gln Ala
                85                  90                  95

Thr Gln Phe Pro Thr Phe Gly Gly Gly Thr Lys Val Glu Ile Lys Arg
            100                 105                 110

<210> SEQ ID NO 683
<211> LENGTH: 33
<212> TYPE: DNA
<213> ORGANISM: Artificial Sequence
<220> FEATURE:
<223> OTHER INFORMATION: Synthetic

<400> SEQUENCE: 683
caaagcctcg tacacagtga tggaaacacc tac                                   33

<210> SEQ ID NO 684
<211> LENGTH: 11
<212> TYPE: PRT
<213> ORGANISM: Artificial Sequence
<220> FEATURE:
<223> OTHER INFORMATION: Synthetic

<400> SEQUENCE: 684

Gln Ser Leu Val His Ser Asp Gly Asn Thr Tyr
 1               5                  10

<210> SEQ ID NO 685
<211> LENGTH: 9
<212> TYPE: DNA
<213> ORGANISM: Artificial Sequence
<220> FEATURE:
<223> OTHER INFORMATION: Synthetic

<400> SEQUENCE: 685 aagatttct                                                              9

<210> SEQ ID NO 686
<211> LENGTH: 3
<212> TYPE: PRT
<213> ORGANISM: Artificial Sequence
<220> FEATURE:
<223> OTHER INFORMATION: Synthetic

<400> SEQUENCE: 686

Lys Ile Ser
 1

<210> SEQ ID NO 687
<211> LENGTH: 24
<212> TYPE: DNA
<213> ORGANISM: Artificial Sequence
<220> FEATURE:
<223> OTHER INFORMATION: Synthetic

<400> SEQUENCE: 687
atgcaagcaa cacaatttcc gact                                             24

<210> SEQ ID NO 688
<211> LENGTH: 8
<212> TYPE: PRT
<213> ORGANISM: Artificial Sequence
<220> FEATURE:
<223> OTHER INFORMATION: Synthetic

<400> SEQUENCE: 688

Met Gln Ala Thr Gln Phe Pro Thr
 1               5

<210> SEQ ID NO 689
<211> LENGTH: 357
<212> TYPE: DNA

<213> ORGANISM: Artificial Sequence
<220> FEATURE:
<223> OTHER INFORMATION: Synthetic

<400> SEQUENCE: 689

```
caggtgcagc tggtggagtc tgggggaggc gtggtccagc ctggggaggtc cctgagactc      60
tcctgtgtag cctctggatt caccttcagt agatatggca tgcactgggt ccgccaggct     120
ccaggcaagg ggctggagtg ggtggtagtt atatcatatg atggaattaa taaatactat     180
gcagactccg tgaagggccg attcaccatc tccagagaca attccaagaa cacggtgtat     240
ctgcaaatga acagcctgag agctgaggac acggctgtgt atcactgtgc gaaaggggac     300
ttttggagtg gttactttga ctactggggc cagggaaccc tggtcaccgt ctcctca        357
```

<210> SEQ ID NO 690
<211> LENGTH: 119
<212> TYPE: PRT
<213> ORGANISM: Artificial Sequence
<220> FEATURE:
<223> OTHER INFORMATION: Synthetic

<400> SEQUENCE: 690

```
Gln Val Gln Leu Val Glu Ser Gly Gly Gly Val Val Gln Pro Gly Arg
1               5                   10                  15
Ser Leu Arg Leu Ser Cys Val Ala Ser Gly Phe Thr Phe Ser Arg Tyr
            20                  25                  30
Gly Met His Trp Val Arg Gln Ala Pro Gly Lys Gly Leu Glu Trp Val
        35                  40                  45
Val Val Ile Ser Tyr Asp Gly Ile Asn Lys Tyr Tyr Ala Asp Ser Val
    50                  55                  60
Lys Gly Arg Phe Thr Ile Ser Arg Asp Asn Ser Lys Asn Thr Val Tyr
65                  70                  75                  80
Leu Gln Met Asn Ser Leu Arg Ala Glu Asp Thr Ala Val Tyr His Cys
                85                  90                  95
Ala Lys Gly Asp Phe Trp Ser Gly Tyr Phe Asp Tyr Trp Gly Gln Gly
            100                 105                 110
Thr Leu Val Thr Val Ser Ser
        115
```

<210> SEQ ID NO 691
<211> LENGTH: 333
<212> TYPE: DNA
<213> ORGANISM: Artificial Sequence
<220> FEATURE:
<223> OTHER INFORMATION: Synthetic

<400> SEQUENCE: 691

```
gatattgtga tgacccagac tccactctcc tcacctgtca cccttggaca gccggcctcc      60
atctcctgca ggtctagtca aagcctcgta cacagtgatg aaacacccta cttgagttgg     120
cttcaccaga ggccaggcca gcctccaaga ctcctaattt ataagatttc taaccggttc     180
tctggggtcc cagacagatt cagtggcagt ggggcaggga cagatttcac actgcaaatc     240
agcagggtgg aagctgagga tgtcgggatt tattactgca tgcaagcaac acaatttccg     300
actttcggcg agggaccaa ggtggagatc aaa                                   333
```

<210> SEQ ID NO 692
<211> LENGTH: 111
<212> TYPE: PRT
<213> ORGANISM: Artificial Sequence
<220> FEATURE:
<223> OTHER INFORMATION: Synthetic

<400> SEQUENCE: 692

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu His Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Gln Ile
65                  70                  75                  80

Ser Arg Val Glu Ala Glu Asp Val Gly Ile Tyr Tyr Cys Met Gln Ala
                85                  90                  95

Thr Gln Phe Pro Thr Phe Gly Gly Gly Thr Lys Val Glu Ile Lys
            100                 105                 110

<210> SEQ ID NO 693
<211> LENGTH: 357
<212> TYPE: DNA
<213> ORGANISM: Artificial Sequence
<220> FEATURE:
<223> OTHER INFORMATION: Synthetic

<400> SEQUENCE: 693
caggtgcagc tggtggagtc tgggggaggc gtggtccagc ctggggaggtc cctgagactc      60
tcctgtgcag cctctggatt caccttcagt agatatggca tgcactgggt ccgccaggct     120
ccaggcaagg gctggagtg gtggcagtt atatcatatg atggaattaa taaatactat     180
gcagactccg tgaagggccg attcaccatc tccagagaca attccaagaa cacgctgtat     240
ctgcaaatga acagcctgag agctgaggac acggctgtgt attactgtgc gaaaggggac     300
ttttggagtg gttactttga ctactggggc cagggaaccc tggtcaccgt ctcctca       357

<210> SEQ ID NO 694
<211> LENGTH: 119
<212> TYPE: PRT
<213> ORGANISM: Artificial Sequence
<220> FEATURE:
<223> OTHER INFORMATION: Synthetic

<400> SEQUENCE: 694

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ile Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Phe Trp Ser Gly Tyr Phe Asp Tyr Trp Gly Gln Gly
            100                 105                 110

Thr Leu Val Thr Val Ser Ser
        115

<210> SEQ ID NO 695
<211> LENGTH: 334
<212> TYPE: DNA
<213> ORGANISM: Artificial Sequence
<220> FEATURE:
<223> OTHER INFORMATION: Synthetic

<400> SEQUENCE: 695
gatattgtga tgacccagac tccactctcc tcacctgtca cccttggaca gccggcctcc      60
atctcctgca ggtctagtca aagcctcgta cacagtgatg gaaacaccta cttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tattactgca tgcaagcaac acaatttccg     300
actttcggcg agggaccaa ggtggagatc aaac                                  334

<210> SEQ ID NO 696
<211> LENGTH: 111
<212> TYPE: PRT
<213> ORGANISM: Artificial Sequence
<220> FEATURE:
<223> OTHER INFORMATION: Synthetic

<400> SEQUENCE: 696

Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Thr Phe Gly Gly Gly Thr Lys Val Glu Ile Lys
            100                 105                 110

<210> SEQ ID NO 697
<211> LENGTH: 357
<212> TYPE: DNA
<213> ORGANISM: Artificial Sequence
<220> FEATURE:
<223> OTHER INFORMATION: Synthetic

<400> SEQUENCE: 697
caggtgcagc tggtgcagtc tgggggaggc gtggtccagc ctgggaggtc cctgagactc      60
tcctgtgtag cctctggatt caccttcagt agatatggca tacactgggt ccgccaggct     120
ccaggcaagg ggctggagtg ggtgatagtt atatcatatg atggaattaa taaatactat     180
gcagactccg tgaagggccg attcaccatc tccagagaca attccaagaa cacggtatat     240
ctgcaaatga acagcctgag agccgaggac acggctgtgt attactgtgc gaaaggggac     300
ttttggagtg gttactttga ctattggggc caggaaccc tggtcaccgt ctcctca         357

```
<210> SEQ ID NO 698
<211> LENGTH: 119
<212> TYPE: PRT
<213> ORGANISM: Artificial Sequence
<220> FEATURE:
<223> OTHER INFORMATION: Synthetic

<400> SEQUENCE: 698
```

Gln Val Gln Leu Val Gln Ser Gly Gly Val Val Gln Pro Gly Arg
1               5                   10                  15

Ser Leu Arg Leu Ser Cys Val Ala Ser Gly Phe Thr Phe Ser Arg Tyr
            20                  25                  30

Gly Ile His Trp Val Arg Gln Ala Pro Gly Lys Gly Leu Glu Trp Val
        35                  40                  45

Ile Val Ile Ser Tyr Asp Gly Ile Asn Lys Tyr Tyr Ala Asp Ser Val
50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Gly Asp Phe Trp Ser Gly Tyr Phe Asp Tyr Trp Gly Gln Gly
            100                 105                 110

Thr Leu Val Thr Val Ser Ser
        115

```
<210> SEQ ID NO 699
<211> LENGTH: 24
<212> TYPE: DNA
<213> ORGANISM: Artificial Sequence
<220> FEATURE:
<223> OTHER INFORMATION: Synthetic

<400> SEQUENCE: 699
```
ggattcacct tcagtagata tggc                                  24

```
<210> SEQ ID NO 700
<211> LENGTH: 8
<212> TYPE: PRT
<213> ORGANISM: Artificial Sequence
<220> FEATURE:
<223> OTHER INFORMATION: Synthetic

<400> SEQUENCE: 700
```

Gly Phe Thr Phe Ser Arg Tyr Gly
1               5

```
<210> SEQ ID NO 701
<211> LENGTH: 24
<212> TYPE: DNA
<213> ORGANISM: Artificial Sequence
<220> FEATURE:
<223> OTHER INFORMATION: Synthetic

<400> SEQUENCE: 701
```
atatcatatg atggaattaa taaa                                  24

```
<210> SEQ ID NO 702
<211> LENGTH: 8
<212> TYPE: PRT
<213> ORGANISM: Artificial Sequence
<220> FEATURE:
<223> OTHER INFORMATION: Synthetic

<400> SEQUENCE: 702
```

Ile Ser Tyr Asp Gly Ile Asn Lys
1               5

<210> SEQ ID NO 703
<211> LENGTH: 36
<212> TYPE: DNA
<213> ORGANISM: Artificial Sequence
<220> FEATURE:
<223> OTHER INFORMATION: Synthetic

<400> SEQUENCE: 703
gcgaaagggg acttttggag tggttacttt gactat         36

<210> SEQ ID NO 704
<211> LENGTH: 12
<212> TYPE: PRT
<213> ORGANISM: Artificial Sequence
<220> FEATURE:
<223> OTHER INFORMATION: Synthetic

<400> SEQUENCE: 704

Ala Lys Gly Asp Phe Trp Ser Gly Tyr Phe Asp Tyr
1               5                   10

<210> SEQ ID NO 705
<211> LENGTH: 336
<212> TYPE: DNA
<213> ORGANISM: Artificial Sequence
<220> FEATURE:
<223> OTHER INFORMATION: Synthetic

<400> SEQUENCE: 705
gaaattgtgc tgactcagac tccactctct tcacctgtca cccttggaca gccggcctcc         60
atctcctgta ggtctaatca aagcctcgta cacagtgatg gaaacaccta cttgagttgg        120
cttcaccaga ggccaggcca gcctccaaga ctcctaattt ataagatttc taaccggttc        180
tctggggtcc cagacagatt cagtggcagt ggggcaggga cagatttcac actgcaaatc        240
agcagggtgg aagctgagga tgtcggtatt tattactgca tgcaagctac acaatttccg        300
actttcggcg agggaccaa ggtggaaatc aaacga                                  336

<210> SEQ ID NO 706
<211> LENGTH: 112
<212> TYPE: PRT
<213> ORGANISM: Artificial Sequence
<220> FEATURE:
<223> OTHER INFORMATION: Synthetic

<400> SEQUENCE: 706

Glu Ile Val Leu Thr Gln Thr Pro Leu Ser Ser Pro Val Thr Leu Gly
1               5                   10                  15

Gln Pro Ala Ser Ile Ser Cys Arg Ser Asn Gln Ser Leu Val His Ser
            20                  25                  30

Asp Gly Asn Thr Tyr Leu Ser Trp Leu His Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Gln Ile
65                  70                  75                  80

Ser Arg Val Glu Ala Glu Asp Val Gly Ile Tyr Tyr Cys Met Gln Ala
                85                  90                  95

```
Thr Gln Phe Pro Thr Phe Gly Gly Gly Thr Lys Val Glu Ile Lys Arg
            100                 105                 110
```

<210> SEQ ID NO 707
<211> LENGTH: 33
<212> TYPE: DNA
<213> ORGANISM: Artificial Sequence
<220> FEATURE:
<223> OTHER INFORMATION: Synthetic

<400> SEQUENCE: 707
caaagcctcg tacacagtga tggaaacacc tac        33

<210> SEQ ID NO 708
<211> LENGTH: 11
<212> TYPE: PRT
<213> ORGANISM: Artificial Sequence
<220> FEATURE:
<223> OTHER INFORMATION: Synthetic

<400> SEQUENCE: 708

```
Gln Ser Leu Val His Ser Asp Gly Asn Thr Tyr
  1               5                  10
```

<210> SEQ ID NO 709
<211> LENGTH: 9
<212> TYPE: DNA
<213> ORGANISM: Artificial Sequence
<220> FEATURE:
<223> OTHER INFORMATION: Synthetic

<400> SEQUENCE: 709 aagatttct        9

<210> SEQ ID NO 710
<211> LENGTH: 3
<212> TYPE: PRT
<213> ORGANISM: Artificial Sequence
<220> FEATURE:
<223> OTHER INFORMATION: Synthetic

<400> SEQUENCE: 710

```
Lys Ile Ser
  1
```

<210> SEQ ID NO 711
<211> LENGTH: 24
<212> TYPE: DNA
<213> ORGANISM: Artificial Sequence
<220> FEATURE:
<223> OTHER INFORMATION: Synthetic

<400> SEQUENCE: 711
atgcaagcta cacaatttcc gact        24

<210> SEQ ID NO 712
<211> LENGTH: 8
<212> TYPE: PRT
<213> ORGANISM: Artificial Sequence
<220> FEATURE:
<223> OTHER INFORMATION: Synthetic

<400> SEQUENCE: 712

```
Met Gln Ala Thr Gln Phe Pro Thr
  1               5
```

<210> SEQ ID NO 713
<211> LENGTH: 357
<212> TYPE: DNA
<213> ORGANISM: Artificial Sequence
<220> FEATURE:
<223> OTHER INFORMATION: Synthetic

<400> SEQUENCE: 713

```
caggtgcagc tggtggagtc tgggggaggc gtggtccagc ctggagggtc cctgagactc      60
tcctgtgtag cctctggatt caccttcagt agatatggca tacactgggt ccgccaggct     120
ccaggcaagg ggctggagtg ggtgatagtt atatcatatg atggaattaa taaatactat     180
gcagactccg tgaagggccg attcaccatc tccagagaca attccaagaa cacggtatat     240
ctgcaaatga acagcctgag agccgaggac acggctgtgt attactgtgc gaaggggac     300
ttttggagtg gttactttga ctattggggc cagggaaccc tggtcaccgt ctcctca       357
```

<210> SEQ ID NO 714
<211> LENGTH: 119
<212> TYPE: PRT
<213> ORGANISM: Artificial Sequence
<220> FEATURE:
<223> OTHER INFORMATION: Synthetic

<400> SEQUENCE: 714

```
Gln Val Gln Leu Val Glu Ser Gly Gly Gly Val Val Gln Pro Gly Arg
 1               5                  10                  15
Ser Leu Arg Leu Ser Cys Val Ala Ser Gly Phe Thr Phe Ser Arg Tyr
                20                  25                  30
Gly Ile His Trp Val Arg Gln Ala Pro Gly Lys Gly Leu Glu Trp Val
            35                  40                  45
Ile Val Ile Ser Tyr Asp Gly Ile Asn Lys Tyr Tyr Ala Asp Ser Val
        50                  55                  60
Lys Gly Arg Phe Thr Ile Ser Arg Asp Asn Ser Lys Asn Thr Val Tyr
 65                  70                  75                  80
Leu Gln Met Asn Ser Leu Arg Ala Glu Asp Thr Ala Val Tyr Tyr Cys
                85                  90                  95
Ala Lys Gly Asp Phe Trp Ser Gly Tyr Phe Asp Tyr Trp Gly Gln Gly
            100                 105                 110
Thr Leu Val Thr Val Ser Ser
        115
```

<210> SEQ ID NO 715
<211> LENGTH: 333
<212> TYPE: DNA
<213> ORGANISM: Artificial Sequence
<220> FEATURE:
<223> OTHER INFORMATION: Synthetic

<400> SEQUENCE: 715

```
gatattgtga tgacccagac tccactctct tcacctgtca cccttggaca gccggcctcc      60
atctcctgta ggtctaatca aagcctcgta cacagtgatg gaaacaccta cttgagttgg     120
cttcaccaga ggccaggcca gcctccaaga ctcctaattt ataagatttc taaccggttc     180
tctggggtcc cagacagatt cagtggcagt ggggcaggga cagatttcac actgcaaatc     240
agcagggtgg aagctgagga tgtcggtatt tattactgca tgcaagctac acaatttccg     300
actttcggcg gagggaccaa ggtggagatc aaa                                  333
```

<210> SEQ ID NO 716

<211> LENGTH: 111
<212> TYPE: PRT
<213> ORGANISM: Artificial Sequence
<220> FEATURE:
<223> OTHER INFORMATION: Synthetic

<400> SEQUENCE: 716

```
Asp Ile Val Met Thr Gln Thr Pro Leu Ser Ser Val Thr Leu Gly
 1               5                  10                  15

Gln Pro Ala Ser Ile Ser Cys Arg Ser Asn Gln Ser Leu Val His Ser
             20                  25                  30

Asp Gly Asn Thr Tyr Leu Ser Trp Leu His Gln Arg Pro Gly Gln Pro
         35                  40                  45

Pro Arg Leu Leu Ile Tyr Lys Ile Ser Asn Arg Phe Ser Gly Val Pro
     50                  55                  60

Asp Arg Phe Ser Gly Ser Gly Ala Gly Thr Asp Phe Thr Leu Gln Ile
 65                  70                  75                  80

Ser Arg Val Glu Ala Glu Asp Val Gly Ile Tyr Tyr Cys Met Gln Ala
                 85                  90                  95

Thr Gln Phe Pro Thr Phe Gly Gly Gly Thr Lys Val Glu Ile Lys
            100                 105                 110
```

<210> SEQ ID NO 717
<211> LENGTH: 357
<212> TYPE: DNA
<213> ORGANISM: Artificial Sequence
<220> FEATURE:
<223> OTHER INFORMATION: Synthetic

<400> SEQUENCE: 717

```
caggtgcagc tggtggagtc tggggggaggc gtggtccagc ctgggaggtc cctgagactc    60
tcctgtgcag cctctggatt caccttcagt agatatggca tgcactgggt ccgccaggct   120
ccaggcaagg ggctggagtg ggtggcagtt atatcatatg atggaattaa taaatactat   180
gcagactccg tgaagggccg attcaccatc tccagagaca attccaagaa cacgctgtat   240
ctgcaaatga acagcctgag agctgaggac acggctgtgt attactgtgc gaaaggggac   300
ttttggagtg gttactttga ctattggggc cagggaaccc tggtcaccgt ctcctca     357
```

<210> SEQ ID NO 718
<211> LENGTH: 119
<212> TYPE: PRT
<213> ORGANISM: Artificial Sequence
<220> FEATURE:
<223> OTHER INFORMATION: Synthetic

<400> SEQUENCE: 718

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Arg Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ile Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

Ala Lys Gly Asp Phe Trp Ser Gly Tyr Phe Asp Tyr Trp Gly Gln Gly
            100                 105                 110
Thr Leu Val Thr Val Ser Ser
        115

<210> SEQ ID NO 719
<211> LENGTH: 334
<212> TYPE: DNA
<213> ORGANISM: Artificial Sequence
<220> FEATURE:
<223> OTHER INFORMATION: Synthetic

<400> SEQUENCE: 719
gatattgtga tgacccagac tccactctcc tcacctgtca cccttggaca gccggcctcc      60
atctcctgca ggtctagtca aagcctcgta cacagtgatg gaaacaccta cttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcgggggtt tattactgca tgcaagctac acaatttccg     300
actttcggcg gagggaccaa ggtggagatc aaac                                  334

<210> SEQ ID NO 720
<211> LENGTH: 111
<212> TYPE: PRT
<213> ORGANISM: Artificial Sequence
<220> FEATURE:
<223> OTHER INFORMATION: Synthetic

<400> SEQUENCE: 720

Asp Ile Val Met Thr Gln Thr Pro Leu Ser Ser Pro Val Thr Leu Gly
  1               5                  10                  15

Gln Pro Ala Ser Ile Ser Cys Arg Ser Ser Gln Ser Leu Val His Ser
             20                  25                  30

Asp Gly Asn Thr Tyr Leu Ser Trp Leu Gln Gln Arg Pro Gly Gln Pro
         35                  40                  45

Pro Arg Leu Leu Ile Tyr Lys Ile Ser Asn Arg Phe Ser Gly Val Pro
     50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Thr Gln Phe Pro Thr Phe Gly Gly Gly Thr Lys Val Glu Ile Lys
            100                 105                 110

<210> SEQ ID NO 721
<211> LENGTH: 357
<212> TYPE: DNA
<213> ORGANISM: Artificial Sequence
<220> FEATURE:
<223> OTHER INFORMATION: Synthetic

<400> SEQUENCE: 721
caggtgcagc tggtggagtc tgggggaggc gtggtccagc ctgggatgtc cctgagactc      60
tcctgtacag cgtccggatt tacgttcagg agatatggca tgcactgggt ccgccaggct     120
ccaggcaagg ggctggagtg ggtggcagtt atttggtatg atggaagtaa taaatattat     180
gcagactccg tgaagggacg attcaccata accagagaca attccaagaa cacgttgtat     240
ctgcaaatga acagcctgag agccgaggac acggctatat attttgtgc gagcgaaata      300

```
acaattgggg actggttcga cccccggggc cagggaaccc tggtcaccgt ctcctca        357
```

<210> SEQ ID NO 722
<211> LENGTH: 119
<212> TYPE: PRT
<213> ORGANISM: Artificial Sequence
<220> FEATURE:
<223> OTHER INFORMATION: Synthetic

<400> SEQUENCE: 722

```
Gln Val Gln Leu Val Glu Ser Gly Gly Val Val Gln Pro Gly Met
 1               5                  10                  15

Ser Leu Arg Leu Ser Cys Thr Ala Ser Gly Phe Thr Phe Arg Arg Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Thr Arg Asp Asn Ser Lys Asn Thr Leu Tyr
65                  70                  75                  80

Leu Gln Met Asn Ser Leu Arg Ala Glu Asp Thr Ala Ile Tyr Phe Cys
                85                  90                  95

Ala Ser Glu Ile Thr Ile Gly Asp Trp Phe Asp Pro Arg Gly Gln Gly
            100                 105                 110

Thr Leu Val Thr Val Ser Ser
        115
```

<210> SEQ ID NO 723
<211> LENGTH: 24
<212> TYPE: DNA
<213> ORGANISM: Artificial Sequence
<220> FEATURE:
<223> OTHER INFORMATION: Synthetic

<400> SEQUENCE: 723

```
ggatttacgt tcaggagata tggc                                              24
```

<210> SEQ ID NO 724
<211> LENGTH: 8
<212> TYPE: PRT
<213> ORGANISM: Artificial Sequence
<220> FEATURE:
<223> OTHER INFORMATION: Synthetic

<400> SEQUENCE: 724

```
Gly Phe Thr Phe Arg Arg Tyr Gly
 1               5
```

<210> SEQ ID NO 725
<211> LENGTH: 24
<212> TYPE: DNA
<213> ORGANISM: Artificial Sequence
<220> FEATURE:
<223> OTHER INFORMATION: Synthetic

<400> SEQUENCE: 725

```
atttggtatg atggaagtaa taaa                                              24
```

<210> SEQ ID NO 726
<211> LENGTH: 8
<212> TYPE: PRT
<213> ORGANISM: Artificial Sequence
<220> FEATURE:

<223> OTHER INFORMATION: Synthetic

<400> SEQUENCE: 726

Ile Trp Tyr Asp Gly Ser Asn Lys
1               5

<210> SEQ ID NO 727
<211> LENGTH: 36
<212> TYPE: DNA
<213> ORGANISM: Artificial Sequence
<220> FEATURE:
<223> OTHER INFORMATION: Synthetic

<400> SEQUENCE: 727
gcgagcgaaa taacaattgg ggactggttc gacccc                                    36

<210> SEQ ID NO 728
<211> LENGTH: 12
<212> TYPE: PRT
<213> ORGANISM: Artificial Sequence
<220> FEATURE:
<223> OTHER INFORMATION: Synthetic

<400> SEQUENCE: 728

Ala Ser Glu Ile Thr Ile Gly Asp Trp Phe Asp Pro
1               5                   10

<210> SEQ ID NO 729
<211> LENGTH: 324
<212> TYPE: DNA
<213> ORGANISM: Artificial Sequence
<220> FEATURE:
<223> OTHER INFORMATION: Synthetic

<400> SEQUENCE: 729
gccatccaga tgacccagtc tccatcctcc ctgtctgcat ctgttggaga cagagtcacc          60
atcacttgtc gggcaagtca gggcattaga aatgatttag ctggtttca acagaaacca         120
gggaaagtcc ctaaactcct gatctatgct gcatccactt tacacagtgg ggtcccatca         180
aggttcagcg gcagtggatt tggcacagat ttcactctca ccatcagcag cctgcagcct         240
gaagattttg caacttatta ctgtctacag gatttcaatt accctctcac tttcggcgga         300
gggaccaagg tggagatcaa acga                                                324

<210> SEQ ID NO 730
<211> LENGTH: 108
<212> TYPE: PRT
<213> ORGANISM: Artificial Sequence
<220> FEATURE:
<223> OTHER INFORMATION: Synthetic

<400> SEQUENCE: 730

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Phe Gln Gln Lys Pro Gly Lys Val Pro Lys Leu Leu Ile
        35                  40                  45

Tyr Ala Ala Ser Thr Leu His Ser Gly Val Pro Ser Arg Phe Ser Gly
    50                  55                  60

Ser Gly Phe Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Leu
                85                  90                  95

Thr Phe Gly Gly Gly Thr Lys Val Glu Ile Lys Arg
            100                 105

<210> SEQ ID NO 731
<211> LENGTH: 18
<212> TYPE: DNA
<213> ORGANISM: Artificial Sequence
<220> FEATURE:
<223> OTHER INFORMATION: Synthetic

<400> SEQUENCE: 731
cagggcatta gaaatgat                                                       18

<210> SEQ ID NO 732
<211> LENGTH: 6
<212> TYPE: PRT
<213> ORGANISM: Artificial Sequence
<220> FEATURE:
<223> OTHER INFORMATION: Synthetic

<400> SEQUENCE: 732

Gln Gly Ile Arg Asn Asp
1               5

<210> SEQ ID NO 733
<211> LENGTH: 9
<212> TYPE: DNA
<213> ORGANISM: Artificial Sequence
<220> FEATURE:
<223> OTHER INFORMATION: Synthetic

<400> SEQUENCE: 733 gctgcatcc                                                                  9

<210> SEQ ID NO 734
<211> LENGTH: 3
<212> TYPE: PRT
<213> ORGANISM: Artificial Sequence
<220> FEATURE:
<223> OTHER INFORMATION: Synthetic

<400> SEQUENCE: 734

Ala Ala Ser
1

<210> SEQ ID NO 735
<211> LENGTH: 27
<212> TYPE: DNA
<213> ORGANISM: Artificial Sequence
<220> FEATURE:
<223> OTHER INFORMATION: Synthetic

<400> SEQUENCE: 735
ctacaggatt tcaattaccc tctcact                                             27

<210> SEQ ID NO 736
<211> LENGTH: 9
<212> TYPE: PRT
<213> ORGANISM: Artificial Sequence
<220> FEATURE:
<223> OTHER INFORMATION: Synthetic

<400> SEQUENCE: 736

Leu Gln Asp Phe Asn Tyr Pro Leu Thr

<210> SEQ ID NO 737
<211> LENGTH: 357
<212> TYPE: DNA
<213> ORGANISM: Artificial Sequence
<220> FEATURE:
<223> OTHER INFORMATION: Synthetic

<400> SEQUENCE: 737

```
caggtgcagc tggtggagtc tgggggaggc gtggtccagc ctgggatgtc cctgagactc      60
tcctgtacag cgtccggatt tacgttcagg agatatggca tgcactgggt ccgccaggct     120
ccaggcaagg ggctggagtg ggtggcagtt atttggtatg atggaagtaa taaatattat     180
gcagactccg tgaagggacg attcaccata accagagaca attccaagaa cacgttgtat     240
ctgcaaatga acagcctgag agccgaggac acggctatat attttgtgc gagcgaaata      300
acaattgggg actggttcga ccccggggc cagggaaccc tggtcaccgt ctcctca         357
```

<210> SEQ ID NO 738
<211> LENGTH: 119
<212> TYPE: PRT
<213> ORGANISM: Artificial Sequence
<220> FEATURE:
<223> OTHER INFORMATION: Synthetic

<400> SEQUENCE: 738

Gln Val Gln Leu Val Glu Ser Gly Gly Gly Val Val Gln Pro Gly Met
1               5                   10                  15
Ser Leu Arg Leu Ser Cys Thr Ala Ser Gly Phe Thr Phe Arg Arg Tyr
            20                  25                  30
Gly Met His Trp Val Arg Gln Ala Pro Gly Lys Gly Leu Glu Trp Val
        35                  40                  45
Ala Val Ile Trp Tyr Asp Gly Ser Asn Lys Tyr Tyr Ala Asp Ser Val
    50                  55                  60
Lys Gly Arg Phe Thr Ile Thr Arg Asp Asn Ser Lys Asn Thr Leu Tyr
65                  70                  75                  80
Leu Gln Met Asn Ser Leu Arg Ala Glu Asp Thr Ala Ile Tyr Phe Cys
                85                  90                  95
Ala Ser Glu Ile Thr Ile Gly Asp Trp Phe Asp Pro Arg Gly Gln Gly
            100                 105                 110
Thr Leu Val Thr Val Ser Ser
        115

<210> SEQ ID NO 739
<211> LENGTH: 321
<212> TYPE: DNA
<213> ORGANISM: Artificial Sequence
<220> FEATURE:
<223> OTHER INFORMATION: Synthetic

<400> SEQUENCE: 739

```
gccatccaga tgacccagtc tccatcctcc ctgtctgcat ctgttggaga cagagtcacc      60
atcacttgtc gggcaagtca gggcattaga aatgatttag ctggtttca acagaaacca     120
gggaaagtcc ctaaactcct gatctatgct gcatccactt tacacagtgg ggtcccatca     180
aggttcagcg gcagtggatt tggcacagat ttcactctca ccatcagcag cctgcagcct     240
gaagattttg caacttatta ctgtctacag gatttcaatt accctctcac tttcggcgga     300
gggaccaagg tggagatcaa a                                                321
```

<210> SEQ ID NO 740
<211> LENGTH: 107
<212> TYPE: PRT
<213> ORGANISM: Artificial Sequence
<220> FEATURE:
<223> OTHER INFORMATION: Synthetic

<400> SEQUENCE: 740

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Phe Gln Gln Lys Pro Gly Lys Val Pro Lys Leu Leu Ile
        35                  40                  45

Tyr Ala Ala Ser Thr Leu His Ser Gly Val Pro Ser Arg Phe Ser Gly
    50                  55                  60

Ser Gly Phe Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Leu
                85                  90                  95

Thr Phe Gly Gly Gly Thr Lys Val Glu Ile Lys
            100                 105

<210> SEQ ID NO 741
<211> LENGTH: 357
<212> TYPE: DNA
<213> ORGANISM: Artificial Sequence
<220> FEATURE:
<223> OTHER INFORMATION: Synthetic

<400> SEQUENCE: 741
caggtgcagc tggtggagtc tgggggaggc gtggtccagc ctggagggtc cctgagactc      60
tcctgtgcag cgtctggatt tacgttcagg agatatggca tgcactgggt ccgccaggct     120
ccaggcaagg ggctggagtg ggtggcagtt atttggtatg atggaagtaa taaatactat     180
gcagactccg tgaagggccg attcaccatc tccagagaca actccaagaa cacgctgtat     240
ctgcaaatga acagcctgag agccgaggac acggctgtgt attactgtgc gagcgaaata     300
acaattgggg actggttcga cccccggggc cagggaaccc tggtcaccgt ctcctca        357

<210> SEQ ID NO 742
<211> LENGTH: 119
<212> TYPE: PRT
<213> ORGANISM: Artificial Sequence
<220> FEATURE:
<223> OTHER INFORMATION: Synthetic

<400> SEQUENCE: 742

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Arg Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Ser Glu Ile Thr Ile Gly Asp Trp Phe Asp Pro Arg Gly Gln Gly
        100                 105                 110

Thr Leu Val Thr Val Ser Ser
        115

<210> SEQ ID NO 743
<211> LENGTH: 322
<212> TYPE: DNA
<213> ORGANISM: Artificial Sequence
<220> FEATURE:
<223> OTHER INFORMATION: Synthetic

<400> SEQUENCE: 743
gccatccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagctcct gatctatgct gcatccagtt tacaaagtgg ggtcccatca     180
aggttcagcg gcagtggatc tggcacagat ttcactctca ccatcagcag cctgcagcct     240
gaagattttg caacttatta ctgtctacag gatttcaatt accctctcac tttcggcgga     300
gggaccaagg tggagatcaa ac                                              322

<210> SEQ ID NO 744
<211> LENGTH: 107
<212> TYPE: PRT
<213> ORGANISM: Artificial Sequence
<220> FEATURE:
<223> OTHER INFORMATION: Synthetic

<400> SEQUENCE: 744

Ala Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Leu
                85                  90                  95

Thr Phe Gly Gly Gly Thr Lys Val Glu Ile Lys
            100                 105

<210> SEQ ID NO 745
<211> LENGTH: 357
<212> TYPE: DNA
<213> ORGANISM: Artificial Sequence
<220> FEATURE:
<223> OTHER INFORMATION: Synthetic

<400> SEQUENCE: 745
caggtgcagc tggtgcagtc tggggggaggc gtggtccagc ctggggaggtc cctgagactc      60 tcctgtgtag cctctggatt caccttcagt agatatggca tgcactgggt ccgccaggct     120
ccaggcaagg ggctggagtg ggtggtagtt atatcatatg atggaattaa taaatactat     180
gcagactccg tgaagggccg attcaccatc tccagagaca attccaagaa cacggtgtat     240

```
ctgcaaatga acagcctgag agctgaggac acggctgtgt attactgtgc gaaagggac      300 ttttggagtg gttactttga ctactggggc cagggaaccc tggtcaccgt ctcctca       357
```

<210> SEQ ID NO 746
<211> LENGTH: 119
<212> TYPE: PRT
<213> ORGANISM: Artificial Sequence
<220> FEATURE:
<223> OTHER INFORMATION: Synthetic

<400> SEQUENCE: 746

```
Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Val Val Ile Ser Tyr Asp Gly Ile Asn Lys Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Gly Asp Phe Trp Ser Gly Tyr Phe Asp Tyr Trp Gly Gln Gly
            100                 105                 110

Thr Leu Val Thr Val Ser Ser
        115
```

<210> SEQ ID NO 747
<211> LENGTH: 24
<212> TYPE: DNA
<213> ORGANISM: Artificial Sequence
<220> FEATURE:
<223> OTHER INFORMATION: Synthetic

<400> SEQUENCE: 747

```
ggattcacct tcagtagata tggc                                            24
```

<210> SEQ ID NO 748
<211> LENGTH: 8
<212> TYPE: PRT
<213> ORGANISM: Artificial Sequence
<220> FEATURE:
<223> OTHER INFORMATION: Synthetic

<400> SEQUENCE: 748

```
Gly Phe Thr Phe Ser Arg Tyr Gly
1               5
```

<210> SEQ ID NO 749
<211> LENGTH: 24
<212> TYPE: DNA
<213> ORGANISM: Artificial Sequence
<220> FEATURE:
<223> OTHER INFORMATION: Synthetic

<400> SEQUENCE: 749

```
atatcatatg atggaattaa taaa                                            24
```

<210> SEQ ID NO 750
<211> LENGTH: 8

```
<212> TYPE: PRT
<213> ORGANISM: Artificial Sequence
<220> FEATURE:
<223> OTHER INFORMATION: Synthetic

<400> SEQUENCE: 750

Ile Ser Tyr Asp Gly Ile Asn Lys
 1               5

<210> SEQ ID NO 751
<211> LENGTH: 36
<212> TYPE: DNA
<213> ORGANISM: Artificial Sequence
<220> FEATURE:
<223> OTHER INFORMATION: Synthetic

<400> SEQUENCE: 751
gcgaaagggg actttggag tggttacttt gactac                              36

<210> SEQ ID NO 752
<211> LENGTH: 12
<212> TYPE: PRT
<213> ORGANISM: Artificial Sequence
<220> FEATURE:
<223> OTHER INFORMATION: Synthetic

<400> SEQUENCE: 752

Ala Lys Gly Asp Phe Trp Ser Gly Tyr Phe Asp Tyr
 1               5                  10

<210> SEQ ID NO 753
<211> LENGTH: 336
<212> TYPE: DNA
<213> ORGANISM: Artificial Sequence
<220> FEATURE:
<223> OTHER INFORMATION: Synthetic

<400> SEQUENCE: 753
gaaattgtgc tgactcagac tccactctcc tcacctgtca cccttggaca gccggcctcc    60
atctcctgca ggtctagtca aagcctcgta cacagtgatg gaaacaccta cttgagttgg   120
cttcaccaga ggccaggcca gcctccaaga ctcctaattt ataagatttc taaccggttc   180
tctggggtcc cagacagatt cagtggcagt ggggcaggga cagatttcac actgcaaatc   240
agcagggtgg aagctgagga tgtcgggatt tattactgca tgcaagctac acaatttccg   300
actttcggcg gagggaccaa ggtggagatc aaacga                             336

<210> SEQ ID NO 754
<211> LENGTH: 112
<212> TYPE: PRT
<213> ORGANISM: Artificial Sequence
<220> FEATURE:
<223> OTHER INFORMATION: Synthetic

<400> SEQUENCE: 754

Glu Ile Val Leu Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
             20                  25                  30

Asp Gly Asn Thr Tyr Leu Ser Trp Leu His Gln Arg Pro Gly Gln Pro
         35                  40                  45

Pro Arg Leu Leu Ile Tyr Lys Ile Ser Asn Arg Phe Ser Gly Val Pro
     50                  55                  60
```

Asp Arg Phe Ser Gly Ser Gly Ala Gly Thr Asp Phe Thr Leu Gln Ile
65                  70                  75                  80

Ser Arg Val Glu Ala Glu Asp Val Gly Ile Tyr Tyr Cys Met Gln Ala
                85                  90                  95

Thr Gln Phe Pro Thr Phe Gly Gly Gly Thr Lys Val Glu Ile Lys Arg
            100                 105                 110

<210> SEQ ID NO 755
<211> LENGTH: 33
<212> TYPE: DNA
<213> ORGANISM: Artificial Sequence
<220> FEATURE:
<223> OTHER INFORMATION: Synthetic

<400> SEQUENCE: 755
caaagcctcg tacacagtga tggaaacacc tac            33

<210> SEQ ID NO 756
<211> LENGTH: 11
<212> TYPE: PRT
<213> ORGANISM: Artificial Sequence
<220> FEATURE:
<223> OTHER INFORMATION: Synthetic

<400> SEQUENCE: 756

Gln Ser Leu Val His Ser Asp Gly Asn Thr Tyr
1               5                   10

<210> SEQ ID NO 757
<211> LENGTH: 9
<212> TYPE: DNA
<213> ORGANISM: Artificial Sequence
<220> FEATURE:
<223> OTHER INFORMATION: Synthetic

<400> SEQUENCE: 757 aagatttct            9

<210> SEQ ID NO 758
<211> LENGTH: 3
<212> TYPE: PRT
<213> ORGANISM: Artificial Sequence
<220> FEATURE:
<223> OTHER INFORMATION: Synthetic

<400> SEQUENCE: 758

Lys Ile Ser
1

<210> SEQ ID NO 759
<211> LENGTH: 24
<212> TYPE: DNA
<213> ORGANISM: Artificial Sequence
<220> FEATURE:
<223> OTHER INFORMATION: Synthetic

<400> SEQUENCE: 759
atgcaagcta cacaatttcc gact            24

<210> SEQ ID NO 760
<211> LENGTH: 8
<212> TYPE: PRT
<213> ORGANISM: Artificial Sequence
<220> FEATURE:
<223> OTHER INFORMATION: Synthetic

<400> SEQUENCE: 760

Met Gln Ala Thr Gln Phe Pro Thr
 1               5

<210> SEQ ID NO 761
<211> LENGTH: 357
<212> TYPE: DNA
<213> ORGANISM: Artificial Sequence
<220> FEATURE:
<223> OTHER INFORMATION: Synthetic

<400> SEQUENCE: 761
caggtgcagc tggtggagtc tgggggaggc gtggtccagc ctgggaggtc cctgagactc      60
tcctgtgtag cctctggatt caccttcagt agatatggca tgcactgggt ccgccaggct     120
ccaggcaagg gctggagtg gtggtagtt atatcatatg atggaattaa taaatactat       180
gcagactccg tgaagggccg attcaccatc tccagagaca attccaagaa cacggtgtat     240
ctgcaaatga acagcctgag agctgaggac acggctgtgt attactgtgc gaaaggggac     300
ttttggagtg gttactttga ctactggggc cagggaaccc tggtcaccgt ctcctca       357

<210> SEQ ID NO 762
<211> LENGTH: 119
<212> TYPE: PRT
<213> ORGANISM: Artificial Sequence
<220> FEATURE:
<223> OTHER INFORMATION: Synthetic

<400> SEQUENCE: 762

Gln Val Gln Leu Val Glu Ser Gly Gly Gly Val Val Gln Pro Gly Arg
 1               5                  10                  15

Ser Leu Arg Leu Ser Cys Val Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Val Val Ile Ser Tyr Asp Gly Ile Asn Lys Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Gly Asp Phe Trp Ser Gly Tyr Phe Asp Tyr Trp Gly Gln Gly
            100                 105                 110

Thr Leu Val Thr Val Ser Ser
        115

<210> SEQ ID NO 763
<211> LENGTH: 333
<212> TYPE: DNA
<213> ORGANISM: Artificial Sequence
<220> FEATURE:
<223> OTHER INFORMATION: Synthetic

<400> SEQUENCE: 763
gatattgtga tgacccagac tccactctcc tcacctgtca cccttggaca gccggcctcc      60
atctcctgca ggtctagtca aagcctcgta cacagtgatg aaacacccta cttgagttgg     120
cttcaccaga ggccaggcca gcctccaaga ctcctaattt ataagatttc taaccggttc     180
tctggggtcc agacagatt cagtggcagt ggggcaggga cagatttcac actgcaaatc      240
agcagggtgg aagctgagga tgtcgggatt tattactgca tgcaagctac acaatttccg    300
actttcggcg agggaccaa ggtggagatc aaa    333

<210> SEQ ID NO 764
<211> LENGTH: 111
<212> TYPE: PRT
<213> ORGANISM: Artificial Sequence
<220> FEATURE:
<223> OTHER INFORMATION: Synthetic

<400> SEQUENCE: 764

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu His Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Gln Ile
65                  70                  75                  80

Ser Arg Val Glu Ala Glu Asp Val Gly Ile Tyr Tyr Cys Met Gln Ala
                85                  90                  95

Thr Gln Phe Pro Thr Phe Gly Gly Gly Thr Lys Val Glu Ile Lys
            100                 105                 110

<210> SEQ ID NO 765
<211> LENGTH: 357
<212> TYPE: DNA
<213> ORGANISM: Artificial Sequence
<220> FEATURE:
<223> OTHER INFORMATION: Synthetic

<400> SEQUENCE: 765
caggtgcagc tggtggagtc tgggggaggc gtggtccagc ctggggaggtc cctgagactc    60 tcctgtgcag cctctggatt caccttcagt agatatggca tgcactgggt ccgccaggct    120
ccaggcaagg ggctggagtg ggtggcagtt atatcatatg atggaattaa taaatactat    180
gcagactccg tgaagggccg attcaccatc tccagagaca attccaagaa cacgctgtat    240
ctgcaaatga acagcctgag agctgaggac acggctgtgt attactgtgc gaagggggac    300
ttttggagtg gttactttga ctactggggc cagggaaccc tggtcaccgt ctcctca    357

<210> SEQ ID NO 766
<211> LENGTH: 119
<212> TYPE: PRT
<213> ORGANISM: Artificial Sequence
<220> FEATURE:
<223> OTHER INFORMATION: Synthetic

<400> SEQUENCE: 766

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ile Asn Lys Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Asp Phe Trp Ser Gly Tyr Phe Asp Tyr Trp Gly Gln Gly
            100                 105                 110

Thr Leu Val Thr Val Ser Ser
            115

<210> SEQ ID NO 767
<211> LENGTH: 334
<212> TYPE: DNA
<213> ORGANISM: Artificial Sequence
<220> FEATURE:
<223> OTHER INFORMATION: Synthetic

<400> SEQUENCE: 767
gatattgtga tgacccagac tccactctcc tcacctgtca cccttggaca gccggcctcc      60
atctcctgca ggtctagtca agcctcgta cacagtgatg gaaacaccta cttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tattactgca tgcaagctac acaatttccg     300
actttcggcg agggaccaa ggtggagatc aaac                                  334

<210> SEQ ID NO 768
<211> LENGTH: 111
<212> TYPE: PRT
<213> ORGANISM: Artificial Sequence
<220> FEATURE:
<223> OTHER INFORMATION: Synthetic

<400> SEQUENCE: 768

Asp Ile Val Met Thr Gln Thr Pro Leu Ser Ser Pro Val Thr Leu Gly
  1               5                  10                  15

Gln Pro Ala Ser Ile Ser Cys Arg Ser Ser Gln Ser Leu Val His Ser
             20                  25                  30

Asp Gly Asn Thr Tyr Leu Ser Trp Leu Gln Gln Arg Pro Gly Gln Pro
         35                  40                  45

Pro Arg Leu Leu Ile Tyr Lys Ile Ser Asn Arg Phe Ser Gly Val Pro
     50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Thr Gln Phe Pro Thr Phe Gly Gly Gly Thr Lys Val Glu Ile Lys
            100                 105                 110

<210> SEQ ID NO 769
<211> LENGTH: 357
<212> TYPE: DNA
<213> ORGANISM: Artificial Sequence
<220> FEATURE:
<223> OTHER INFORMATION: Synthetic

<400> SEQUENCE: 769
gaggtgcagc tggtgcagtc tgggggaggc gtggtccagc ctgggaggtc cctgagactc      60
tcctgtgtag cctctggatt caccttcagt agatatggca tgcactgggt ccgccaggct     120
```

```
ccaggcaagg ggctggagtg gctgatagtt atatcatatg atggaattaa taaatactat    180
gcagactccg tgaagggccg attcaccatc tccagagaca attccaagaa cacggtgtat    240
ctgcaaatga acagcctgag agctgaggac acggctgtgt attactgtgc gaaggggggac   300 ttttggagtg atactttga ctactggggc cagggaaccc tggtcaccgt ctcctca        357
```

<210> SEQ ID NO 770
<211> LENGTH: 119
<212> TYPE: PRT
<213> ORGANISM: Artificial Sequence
<220> FEATURE:
<223> OTHER INFORMATION: Synthetic

<400> SEQUENCE: 770

```
Glu Val Gln Leu Val Gln Ser Gly Gly Gly Val Val Gln Pro Gly Arg
 1               5                  10                  15

Ser Leu Arg Leu Ser Cys Val Ala Ser Gly Phe Thr Phe Ser Arg Tyr
            20                  25                  30

Gly Met His Trp Val Arg Gln Ala Pro Gly Lys Gly Leu Glu Trp Leu
        35                  40                  45

Ile Val Ile Ser Tyr Asp Gly Ile Asn Lys Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Gly Asp Phe Trp Ser Gly Tyr Phe Asp Tyr Trp Gly Gln Gly
            100                 105                 110

Thr Leu Val Thr Val Ser Ser
        115
```

<210> SEQ ID NO 771
<211> LENGTH: 24
<212> TYPE: DNA
<213> ORGANISM: Artificial Sequence
<220> FEATURE:
<223> OTHER INFORMATION: Synthetic

<400> SEQUENCE: 771

```
ggattcacct tcagtagata tggc                                            24
```

<210> SEQ ID NO 772
<211> LENGTH: 8
<212> TYPE: PRT
<213> ORGANISM: Artificial Sequence
<220> FEATURE:
<223> OTHER INFORMATION: Synthetic

<400> SEQUENCE: 772

```
Gly Phe Thr Phe Ser Arg Tyr Gly
 1               5
```

<210> SEQ ID NO 773
<211> LENGTH: 24
<212> TYPE: DNA
<213> ORGANISM: Artificial Sequence
<220> FEATURE:
<223> OTHER INFORMATION: Synthetic

<400> SEQUENCE: 773

```
atatcatatg atggaattaa taaa                                            24
```

<210> SEQ ID NO 774
<211> LENGTH: 8
<212> TYPE: PRT
<213> ORGANISM: Artificial Sequence
<220> FEATURE:
<223> OTHER INFORMATION: Synthetic

<400> SEQUENCE: 774

Ile Ser Tyr Asp Gly Ile Asn Lys
1               5

<210> SEQ ID NO 775
<211> LENGTH: 36
<212> TYPE: DNA
<213> ORGANISM: Artificial Sequence
<220> FEATURE:
<223> OTHER INFORMATION: Synthetic

<400> SEQUENCE: 775
gcgaaagggg actttggag tggatacttt gactac                                  36

<210> SEQ ID NO 776
<211> LENGTH: 12
<212> TYPE: PRT
<213> ORGANISM: Artificial Sequence
<220> FEATURE:
<223> OTHER INFORMATION: Synthetic

<400> SEQUENCE: 776

Ala Lys Gly Asp Phe Trp Ser Gly Tyr Phe Asp Tyr
1               5                   10

<210> SEQ ID NO 777
<211> LENGTH: 336
<212> TYPE: DNA
<213> ORGANISM: Artificial Sequence
<220> FEATURE:
<223> OTHER INFORMATION: Synthetic

<400> SEQUENCE: 777
gacatcgtga tgacccagac tccactctcc tcacctgtca cccttggaca gccggcctcc      60
atctcctgca ggtctagtca agcctcgta cacagtgatg gaaacaccta cttgagttgg     120
cttcaccaga ggccaggcca gcctccaaga ctcctaattt ataagatttc taaccggttc     180
tctggggtcc cagacagatt cagtggcagt ggggcaggga cagatttcac actgcaaatc     240
agcagggtgg aagctgagga tgtcgggatt tattactgca tgcaaggtac acaatttccg     300
actttcggcg gagggaccaa ggtggagatc aaacga                                336

<210> SEQ ID NO 778
<211> LENGTH: 112
<212> TYPE: PRT
<213> ORGANISM: Artificial Sequence
<220> FEATURE:
<223> OTHER INFORMATION: Synthetic

<400> SEQUENCE: 778

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu His Gln Arg Pro Gly Gln Pro
        35                  40                  45

```
Pro Arg Leu Leu Ile Tyr Lys Ile Ser Asn Arg Phe Ser Gly Val Pro
         50                  55                  60
Asp Arg Phe Ser Gly Ser Gly Ala Gly Thr Asp Phe Thr Leu Gln Ile
 65                  70                  75                  80
Ser Arg Val Glu Ala Glu Asp Val Gly Ile Tyr Tyr Cys Met Gln Gly
                 85                  90                  95
Thr Gln Phe Pro Thr Phe Gly Gly Gly Thr Lys Val Glu Ile Lys Arg
            100                 105                 110
```

<210> SEQ ID NO 779
<211> LENGTH: 33
<212> TYPE: DNA
<213> ORGANISM: Artificial Sequence
<220> FEATURE:
<223> OTHER INFORMATION: Synthetic

<400> SEQUENCE: 779
caaagcctcg tacacagtga tggaaacacc tac        33

<210> SEQ ID NO 780
<211> LENGTH: 11
<212> TYPE: PRT
<213> ORGANISM: Artificial Sequence
<220> FEATURE:
<223> OTHER INFORMATION: Synthetic

<400> SEQUENCE: 780

```
Gln Ser Leu Val His Ser Asp Gly Asn Thr Tyr
 1               5                  10
```

<210> SEQ ID NO 781
<211> LENGTH: 9
<212> TYPE: DNA
<213> ORGANISM: Artificial Sequence
<220> FEATURE:
<223> OTHER INFORMATION: Synthetic

<400> SEQUENCE: 781 aagatttct        9

<210> SEQ ID NO 782
<211> LENGTH: 3
<212> TYPE: PRT
<213> ORGANISM: Artificial Sequence
<220> FEATURE:
<223> OTHER INFORMATION: Synthetic

<400> SEQUENCE: 782

```
Lys Ile Ser
 1
```

<210> SEQ ID NO 783
<211> LENGTH: 24
<212> TYPE: DNA
<213> ORGANISM: Artificial Sequence
<220> FEATURE:
<223> OTHER INFORMATION: Synthetic

<400> SEQUENCE: 783
atgcaaggta cacaatttcc gact        24

<210> SEQ ID NO 784
<211> LENGTH: 8
<212> TYPE: PRT
<213> ORGANISM: Artificial Sequence
<220> FEATURE:
<223> OTHER INFORMATION: Synthetic

<400> SEQUENCE: 784

Met Gln Gly Thr Gln Phe Pro Thr
1               5

<210> SEQ ID NO 785
<211> LENGTH: 357
<212> TYPE: DNA
<213> ORGANISM: Artificial Sequence
<220> FEATURE:
<223> OTHER INFORMATION: Synthetic

<400> SEQUENCE: 785
caggtgcagc tggtggagtc tgggggaggc gtggtccagc ctgggaggtc cctgagactc      60
tcctgtgtag cctctggatt caccttcagt agatatggca tgcactgggt ccgccaggct     120
ccaggcaagg ggctggagtg gctgatagtt atatcatatg atggaattaa taaatactat     180
gcagactccg tgaagggccg attcaccatc tccagagaca attccaagaa cacggtgtat     240
ctgcaaatga acagcctgag agctgaggac acggctgtgt attactgtgc gaaggggac     300 ttttggagtg atactttga ctactggggc cagggaaccc tggtcaccgt ctcctca        357

<210> SEQ ID NO 786
<211> LENGTH: 119
<212> TYPE: PRT
<213> ORGANISM: Artificial Sequence
<220> FEATURE:
<223> OTHER INFORMATION: Synthetic

<400> SEQUENCE: 786

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Arg Tyr
            20                  25                  30

Gly Met His Trp Val Arg Gln Ala Pro Gly Lys Gly Leu Glu Trp Leu
        35                  40                  45

Ile Val Ile Ser Tyr Asp Gly Ile Asn Lys Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Gly Asp Phe Trp Ser Gly Tyr Phe Asp Tyr Trp Gly Gln Gly
            100                 105                 110

Thr Leu Val Thr Val Ser Ser
        115

<210> SEQ ID NO 787
<211> LENGTH: 333
<212> TYPE: DNA
<213> ORGANISM: Artificial Sequence
<220> FEATURE:
<223> OTHER INFORMATION: Synthetic

<400> SEQUENCE: 787
gatattgtga tgacccagac tccactctcc tcacctgtca cccttggaca gccggcctcc      60
atctcctgca ggtctagtca aagcctcgta cacagtgatg aaacaccta cttgagttgg     120 cttcaccaga ggccaggcca gcctccaaga ctcctaattt ataagatttc taaccggttc     180

```
tctggggtcc cagacagatt cagtggcagt ggggcaggga cagatttcac actgcaaatc    240
agcagggtgg aagctgagga tgtcgggatt tattactgca tgcaaggtac acaatttccg    300
actttcggcg agggaccaa ggtggagatc aaa                                  333
```

<210> SEQ ID NO 788
<211> LENGTH: 111
<212> TYPE: PRT
<213> ORGANISM: Artificial Sequence
<220> FEATURE:
<223> OTHER INFORMATION: Synthetic

<400> SEQUENCE: 788

```
Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
            20                  25                  30

Asp Gly Asn Thr Tyr Leu Ser Trp Leu His Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Gln Ile
65                  70                  75                  80

Ser Arg Val Glu Ala Glu Asp Val Gly Ile Tyr Tyr Cys Met Gln Gly
                85                  90                  95

Thr Gln Phe Pro Thr Phe Gly Gly Gly Thr Lys Val Glu Ile Lys
            100                 105                 110
```

<210> SEQ ID NO 789
<211> LENGTH: 357
<212> TYPE: DNA
<213> ORGANISM: Artificial Sequence
<220> FEATURE:
<223> OTHER INFORMATION: Synthetic

<400> SEQUENCE: 789

```
caggtgcagc tggtggagtc tgggggaggc gtggtccagc ctgggaggtc cctgagactc     60
tcctgtgcag cctctggatt caccttcagt agatatggca tgcactgggt ccgccaggct    120
ccaggcaagg ggctggagtg ggtggcagtt atatcatatg atggaattaa taaatactat    180
gcagactccg tgaagggccg attcaccatc tccagagaca attccaagaa cacgctgtat    240
ctgcaaatga acagcctgag agctgaggac acggctgtgt attactgtgc gaaggggac    300 ttttggagtg atactttga ctactggggc cagggaaccc tggtcaccgt ctcctca       357
```

<210> SEQ ID NO 790
<211> LENGTH: 119
<212> TYPE: PRT
<213> ORGANISM: Artificial Sequence
<220> FEATURE:
<223> OTHER INFORMATION: Synthetic

<400> SEQUENCE: 790

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45
```

```
Ala Val Ile Ser Tyr Asp Gly Ile Asn Lys Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Gly Asp Phe Trp Ser Gly Tyr Phe Asp Tyr Trp Gly Gln Gly
             100                 105                 110
Thr Leu Val Thr Val Ser Ser
            115
```

<210> SEQ ID NO 791
<211> LENGTH: 334
<212> TYPE: DNA
<213> ORGANISM: Artificial Sequence
<220> FEATURE:
<223> OTHER INFORMATION: Synthetic

<400> SEQUENCE: 791

```
gatattgtga tgacccagac tccactctcc tcacctgtca cccttggaca gccggcctcc     60
atctcctgca ggtctagtca aagcctcgta cacagtgatg aaacaccta cttgagttgg    120
cttcagcaga ggccaggcca gcctccaaga ctcctaattt ataagatttc taaccggttc   180
tctggggtcc cagacagatt cagtggcagt ggggcaggga cagatttcac actgaaaatc   240
agcagggtgg aagctgagga tgtcggggtt tattactgca tgcaaggtac acaatttccg   300
actttcggcg agggaccaa ggtggagatc aaac                                334
```

<210> SEQ ID NO 792
<211> LENGTH: 111
<212> TYPE: PRT
<213> ORGANISM: Artificial Sequence
<220> FEATURE:
<223> OTHER INFORMATION: Synthetic

<400> SEQUENCE: 792

```
Asp Ile Val Met Thr Gln Thr Pro Leu Ser Ser Pro Val Thr Leu Gly
 1               5                  10                  15
Gln Pro Ala Ser Ile Ser Cys Arg Ser Ser Gln Ser Leu Val His Ser
             20                  25                  30
Asp Gly Asn Thr Tyr Leu Ser Trp Leu Gln Gln Arg Pro Gly Gln Pro
         35                  40                  45
Pro Arg Leu Leu Ile Tyr Lys Ile Ser Asn Arg Phe Ser Gly Val Pro
 50                  55                  60
Asp Arg Phe Ser Gly Ser Gly Ala Gly Thr Asp Phe Thr Leu Lys Ile
 65                  70                  75                  80
Ser Arg Val Glu Ala Glu Asp Val Gly Val Tyr Tyr Cys Met Gln Gly
                 85                  90                  95
Thr Gln Phe Pro Thr Phe Gly Gly Gly Thr Lys Val Glu Ile Lys
             100                 105                 110
```

<210> SEQ ID NO 793
<211> LENGTH: 357
<212> TYPE: DNA
<213> ORGANISM: Artificial Sequence
<220> FEATURE:
<223> OTHER INFORMATION: Synthetic

<400> SEQUENCE: 793

```
caggtgcagc tgcaggagtc tgggggaggc gtggtccagc ctggaggtc cctgagactc      60
```

```
tcctgtgtag cctctggatt caccttcagt agatatggca tgcactgggt ccgccaggct    120
ccaggcaagg ggctggagtg ggtggtagtt atatcatatg atggaattaa taaatactat    180
gcagactccg tgaagggccg attcaccatc tccagagaca attccaagaa cacggtgtat    240
ctgcaaatga acagcctgag agctgaggac acggctgtgt attactgtgc gaaaggggac    300
ttttggagtg gttactttga ctactggggc cagggaaccc tggtcaccgt ctcctca       357
```

<210> SEQ ID NO 794
<211> LENGTH: 119
<212> TYPE: PRT
<213> ORGANISM: Artificial Sequence
<220> FEATURE:
<223> OTHER INFORMATION: Synthetic

<400> SEQUENCE: 794

Gln Val Gln Leu Gln Glu Ser Gly Gly Gly Val Val Gln Pro Gly Arg
 1               5                  10                  15

Ser Leu Arg Leu Ser Cys Val Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Val Val Ile Ser Tyr Asp Gly Ile Asn Lys Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Gly Asp Phe Trp Ser Gly Tyr Phe Asp Tyr Trp Gly Gln Gly
            100                 105                 110

Thr Leu Val Thr Val Ser Ser
        115

<210> SEQ ID NO 795
<211> LENGTH: 24
<212> TYPE: DNA
<213> ORGANISM: Artificial Sequence
<220> FEATURE:
<223> OTHER INFORMATION: Synthetic

<400> SEQUENCE: 795
ggattcacct tcagtagata tggc                                            24

<210> SEQ ID NO 796
<211> LENGTH: 8
<212> TYPE: PRT
<213> ORGANISM: Artificial Sequence
<220> FEATURE:
<223> OTHER INFORMATION: Synthetic

<400> SEQUENCE: 796

Gly Phe Thr Phe Ser Arg Tyr Gly
 1               5

<210> SEQ ID NO 797
<211> LENGTH: 24
<212> TYPE: DNA
<213> ORGANISM: Artificial Sequence
<220> FEATURE:
<223> OTHER INFORMATION: Synthetic

<400> SEQUENCE: 797

```
atatcatatg atggaattaa taaa                                          24
```

<210> SEQ ID NO 798
<211> LENGTH: 8
<212> TYPE: PRT
<213> ORGANISM: Artificial Sequence
<220> FEATURE:
<223> OTHER INFORMATION: Synthetic

<400> SEQUENCE: 798

Ile Ser Tyr Asp Gly Ile Asn Lys
1               5

<210> SEQ ID NO 799
<211> LENGTH: 36
<212> TYPE: DNA
<213> ORGANISM: Artificial Sequence
<220> FEATURE:
<223> OTHER INFORMATION: Synthetic

<400> SEQUENCE: 799

```
gcgaaagggg acttttggag tggttacttt gactac                             36
```

<210> SEQ ID NO 800
<211> LENGTH: 12
<212> TYPE: PRT
<213> ORGANISM: Artificial Sequence
<220> FEATURE:
<223> OTHER INFORMATION: Synthetic

<400> SEQUENCE: 800

Ala Lys Gly Asp Phe Trp Ser Gly Tyr Phe Asp Tyr
1               5                   10

<210> SEQ ID NO 801
<211> LENGTH: 321
<212> TYPE: DNA
<213> ORGANISM: Artificial Sequence
<220> FEATURE:
<223> OTHER INFORMATION: Synthetic

<400> SEQUENCE: 801

```
gacatccaga tgacccagtc tccatcctcc ctgtctgcat ctgtaggaga cagagtcacc    60
atcacttgcc gggcaagtca gggcattaga aatgatttag ctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt accctccgac gttcggccaa   300
gggaccaagg tggagatcaa a                                             321
```

<210> SEQ ID NO 802
<211> LENGTH: 107
<212> TYPE: PRT
<213> ORGANISM: Artificial Sequence
<220> FEATURE:
<223> OTHER INFORMATION: Synthetic

<400> SEQUENCE: 802

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

```
Leu Gly Trp Tyr Gln Gln Lys Pro Gly Lys Ala Pro Lys Arg Leu Ile
             35                  40                  45
Tyr Ala Ala Ser Ser Leu Gln Ser Gly Val Pro Ser Arg Phe Ser Gly
 50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Ser Tyr Pro Pro
                 85                  90                  95
Thr Phe Gly Gln Gly Thr Lys Val Glu Ile Lys
            100                 105
```

<210> SEQ ID NO 803
<211> LENGTH: 18
<212> TYPE: DNA
<213> ORGANISM: Artificial Sequence
<220> FEATURE:
<223> OTHER INFORMATION: Synthetic

<400> SEQUENCE: 803
cagggcatta gaaatgat                                             18

<210> SEQ ID NO 804
<211> LENGTH: 6
<212> TYPE: PRT
<213> ORGANISM: Artificial Sequence
<220> FEATURE:
<223> OTHER INFORMATION: Synthetic

<400> SEQUENCE: 804

Gln Gly Ile Arg Asn Asp
 1               5

<210> SEQ ID NO 805
<211> LENGTH: 9
<212> TYPE: DNA
<213> ORGANISM: Artificial Sequence
<220> FEATURE:
<223> OTHER INFORMATION: Synthetic

<400> SEQUENCE: 805 gctgcatcc                                                        9

<210> SEQ ID NO 806
<211> LENGTH: 3
<212> TYPE: PRT
<213> ORGANISM: Artificial Sequence
<220> FEATURE:
<223> OTHER INFORMATION: Synthetic

<400> SEQUENCE: 806

Ala Ala Ser
 1

<210> SEQ ID NO 807
<211> LENGTH: 27
<212> TYPE: DNA
<213> ORGANISM: Artificial Sequence
<220> FEATURE:
<223> OTHER INFORMATION: Synthetic

<400> SEQUENCE: 807
ctacagcata atagttaccc tccgacg                                   27

<210> SEQ ID NO 808

```
<211> LENGTH: 9
<212> TYPE: PRT
<213> ORGANISM: Artificial Sequence
<220> FEATURE:
<223> OTHER INFORMATION: Synthetic

<400> SEQUENCE: 808

Leu Gln His Asn Ser Tyr Pro Pro Thr
 1               5

<210> SEQ ID NO 809
<211> LENGTH: 357
<212> TYPE: DNA
<213> ORGANISM: Artificial Sequence
<220> FEATURE:
<223> OTHER INFORMATION: Synthetic

<400> SEQUENCE: 809
caggtgcagc tggtggagtc tgggggaggc gtggtccagc ctggagggtc cctgagactc      60
tcctgtgtag cctctggatt caccttcagt agatatggca tgcactgggt ccgccaggct     120
ccaggcaagg ggctggagtg ggtggtagtt atatcatatg atggaattaa taaatactat     180
gcagactccg tgaagggccg attcaccatc tccagagaca attccaagaa cacggtgtat     240
ctgcaaatga acagcctgag agctgaggac acggctgtgt attactgtgc gaaagggggac     300 ttttggagtg ttactttgac tactggggc agggaaccc tggtcaccgt ctcctca         357

<210> SEQ ID NO 810
<211> LENGTH: 119
<212> TYPE: PRT
<213> ORGANISM: Artificial Sequence
<220> FEATURE:
<223> OTHER INFORMATION: Synthetic

<400> SEQUENCE: 810

Gln Val Gln Leu Val Glu Ser Gly Gly Gly Val Val Gln Pro Gly Arg
 1               5                  10                  15

Ser Leu Arg Leu Ser Cys Val Ala Ser Gly Phe Thr Phe Ser Arg Tyr
             20                  25                  30

Gly Met His Trp Val Arg Gln Ala Pro Gly Lys Gly Leu Glu Trp Val
         35                  40                  45

Val Val Ile Ser Tyr Asp Gly Ile Asn Lys Tyr Tyr Ala Asp Ser Val
     50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Lys Gly Asp Phe Trp Ser Tyr Phe Asp Tyr Trp Gly Gln Gly
            100                 105                 110

Thr Leu Val Thr Val Ser Ser
        115

<210> SEQ ID NO 811
<211> LENGTH: 321
<212> TYPE: DNA
<213> ORGANISM: Artificial Sequence
<220> FEATURE:
<223> OTHER INFORMATION: Synthetic

<400> SEQUENCE: 811
gacatccaga tgacccagtc tccatcctcc ctgtctgcat ctgtaggaga cagagtcacc      60
```

```
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt accctccgac gttcggccaa    300
gggaccaagg tggaaatcaa a                                              321
```

<210> SEQ ID NO 812
<211> LENGTH: 107
<212> TYPE: PRT
<213> ORGANISM: Artificial Sequence
<220> FEATURE:
<223> OTHER INFORMATION: Synthetic

<400> SEQUENCE: 812

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

Thr Phe Gly Gln Gly Thr Lys Val Glu Ile Lys
            100                 105
```

<210> SEQ ID NO 813
<211> LENGTH: 357
<212> TYPE: DNA
<213> ORGANISM: Artificial Sequence
<220> FEATURE:
<223> OTHER INFORMATION: Synthetic

<400> SEQUENCE: 813

```
caggtgcagc tggtggagtc tgggggaggc gtggtccagc ctggaggtc cctgagactc     60 tcctgtgcag cctctggatt caccttcagt agatatggca tgcactgggt ccgccaggct    120
ccaggcaagg gctggagtg gtggcagtt atatcatatg atggaattaa taaatactat    180
gcagactccg tgaagggccg attcaccatc tccagagaca attccaagaa cacgctgtat    240
ctgcaaatga acagcctgag agctgaggac acggctgtgt attactgtgc gaagggggac    300
ttttggagtg gttactttga ctactggggc cagggaaccc tggtcaccgt ctcctca      357
```

<210> SEQ ID NO 814
<211> LENGTH: 119
<212> TYPE: PRT
<213> ORGANISM: Artificial Sequence
<220> FEATURE:
<223> OTHER INFORMATION: Synthetic

<400> SEQUENCE: 814

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Arg Tyr
            20                  25                  30
```

Gly Met His Trp Val Arg Gln Ala Pro Gly Lys Gly Leu Glu Trp Val
            35                  40                  45

Ala Val Ile Ser Tyr Asp Gly Ile Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gly Asp Phe Trp Ser Gly Tyr Phe Asp Tyr Trp Gly Gln Gly
            100                 105                 110

Thr Leu Val Thr Val Ser Ser
            115

<210> SEQ ID NO 815
<211> LENGTH: 322
<212> TYPE: DNA
<213> ORGANISM: Artificial Sequence
<220> FEATURE:
<223> OTHER INFORMATION: Synthetic

<400> SEQUENCE: 815
gacatccaga tgacccagtc tccatcctcc ctgtctgcat ctgtaggaga cagagtcacc    60
atcacttgcc gggcaagtca gggcattaga aatgatttag ctggtatca gcagaaacca    120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt accctccgac gttcggccaa    300
gggaccaagg tggaaatcaa ac                                             322

<210> SEQ ID NO 816
<211> LENGTH: 107
<212> TYPE: PRT
<213> ORGANISM: Artificial Sequence
<220> FEATURE:
<223> OTHER INFORMATION: Synthetic

<400> SEQUENCE: 816

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Pro
                85                  90                  95

Thr Phe Gly Gln Gly Thr Lys Val Glu Ile Lys
            100                 105

<210> SEQ ID NO 817
<211> LENGTH: 357
<212> TYPE: DNA
<213> ORGANISM: Artificial Sequence
<220> FEATURE:
<223> OTHER INFORMATION: Synthetic -continued

```
<400> SEQUENCE: 817
gaggtgcagc tggtggagtc tgggggaggc gtggtccagc ctgggaggtc cctgagactc    60
tcctgtgtag cctctggatt caccttcagt agatatggca tgcactgggt ccgccaggct   120
ccaggcaagg gctggagtg gctgatagtt atatcatatg atggaattaa taaatactat    180
gcagactccg tgaagggccg attcaccatc tccagagaca attccaagaa cacggtgtat   240
ctgcaaatga acagcctgag agttgaggac acgggagtgt attactgtgc gaaaggggac   300
ttttggagtg gttactttga ctactggggc cagggaaccc tggtcaccgt ctcctca      357
```

```
<210> SEQ ID NO 818
<211> LENGTH: 119
<212> TYPE: PRT
<213> ORGANISM: Artificial Sequence
<220> FEATURE:
<223> OTHER INFORMATION: Synthetic

<400> SEQUENCE: 818
```

Glu Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Arg Tyr
            20                  25                  30

Gly Met His Trp Val Arg Gln Ala Pro Gly Lys Gly Leu Glu Trp Leu
        35                  40                  45

Ile Val Ile Ser Tyr Asp Gly Ile Asn Lys Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Val Glu Asp Thr Gly Val Tyr Tyr Cys
            85                  90                  95

Ala Lys Gly Asp Phe Trp Ser Gly Tyr Phe Asp Tyr Trp Gly Gln Gly
            100                 105                 110

Thr Leu Val Thr Val Ser Ser
        115

```
<210> SEQ ID NO 819
<211> LENGTH: 24
<212> TYPE: DNA
<213> ORGANISM: Artificial Sequence
<220> FEATURE:
<223> OTHER INFORMATION: Synthetic

<400> SEQUENCE: 819
ggattcacct tcagtagata tggc                                           24
```

```
<210> SEQ ID NO 820
<211> LENGTH: 8
<212> TYPE: PRT
<213> ORGANISM: Artificial Sequence
<220> FEATURE:
<223> OTHER INFORMATION: Synthetic

<400> SEQUENCE: 820
```

Gly Phe Thr Phe Ser Arg Tyr Gly
1               5

```
<210> SEQ ID NO 821
<211> LENGTH: 24
<212> TYPE: DNA
<213> ORGANISM: Artificial Sequence
<220> FEATURE:
```

<223> OTHER INFORMATION: Synthetic

<400> SEQUENCE: 821
atatcatatg atggaattaa taaa                                                24

<210> SEQ ID NO 822
<211> LENGTH: 8
<212> TYPE: PRT
<213> ORGANISM: Artificial Sequence
<220> FEATURE:
<223> OTHER INFORMATION: Synthetic

<400> SEQUENCE: 822

Ile Ser Tyr Asp Gly Ile Asn Lys
1               5

<210> SEQ ID NO 823
<211> LENGTH: 36
<212> TYPE: DNA
<213> ORGANISM: Artificial Sequence
<220> FEATURE:
<223> OTHER INFORMATION: Synthetic

<400> SEQUENCE: 823
gcgaaagggg actttggag tggttacttt gactac                                    36

<210> SEQ ID NO 824
<211> LENGTH: 12
<212> TYPE: PRT
<213> ORGANISM: Artificial Sequence
<220> FEATURE:
<223> OTHER INFORMATION: Synthetic

<400> SEQUENCE: 824

Ala Lys Gly Asp Phe Trp Ser Gly Tyr Phe Asp Tyr
1               5                   10

<210> SEQ ID NO 825
<211> LENGTH: 327
<212> TYPE: DNA
<213> ORGANISM: Artificial Sequence
<220> FEATURE:
<223> OTHER INFORMATION: Synthetic

<400> SEQUENCE: 825
gaaattgtgt tgacgcagtc tccaggcacc ctgtctttgt ctccagggga aagagccacc         60
ctctcctgca gggccagtca gagtgttagc agcagctact tagcctggta ccagcagaaa        120
cctggccagg ctcccaggct cctcatctat ggtgcatcca gcagggccac tggcatccca        180
gacaggttca gtggcagtgg gtctgggaca gacttcactc tcaccatcag cagactggag        240
cctgaagatt ttgcagtgta ttactgtcag cagtatggta gctcaccgtg gacgttcggc        300
caagggacca aggtggaaat caaacga                                            327

<210> SEQ ID NO 826
<211> LENGTH: 109
<212> TYPE: PRT
<213> ORGANISM: Artificial Sequence
<220> FEATURE:
<223> OTHER INFORMATION: Synthetic

<400> SEQUENCE: 826

Glu Ile Val Leu Thr Gln Ser Pro Gly Thr Leu Ser Leu Ser Pro Gly
1               5                   10                  15

-continued

```
Glu Arg Ala Thr Leu Ser Cys Arg Ala Ser Gln Ser Val Ser Ser
         20                  25                  30
Tyr Leu Ala Trp Tyr Gln Gln Lys Pro Gly Gln Ala Pro Arg Leu Leu
     35                  40                  45
Ile Tyr Gly Ala Ser Ser Arg Ala Thr Gly Ile Pro Asp Arg Phe Ser
 50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                 85                  90                  95
Trp Thr Phe Gly Gln Gly Thr Lys Val Glu Ile Lys Arg
            100                 105
```

<210> SEQ ID NO 827
<211> LENGTH: 21
<212> TYPE: DNA
<213> ORGANISM: Artificial Sequence
<220> FEATURE:
<223> OTHER INFORMATION: Synthetic

<400> SEQUENCE: 827
cagagtgtta gcagcagcta c     21

<210> SEQ ID NO 828
<211> LENGTH: 7
<212> TYPE: PRT
<213> ORGANISM: Artificial Sequence
<220> FEATURE:
<223> OTHER INFORMATION: Synthetic

<400> SEQUENCE: 828

```
Gln Ser Val Ser Ser Ser Tyr
 1               5
```

<210> SEQ ID NO 829
<211> LENGTH: 9
<212> TYPE: DNA
<213> ORGANISM: Artificial Sequence
<220> FEATURE:
<223> OTHER INFORMATION: Synthetic

<400> SEQUENCE: 829 ggtgcatcc     9

<210> SEQ ID NO 830
<211> LENGTH: 3
<212> TYPE: PRT
<213> ORGANISM: Artificial Sequence
<220> FEATURE:
<223> OTHER INFORMATION: Synthetic

<400> SEQUENCE: 830

```
Gly Ala Ser
 1
```

<210> SEQ ID NO 831
<211> LENGTH: 27
<212> TYPE: DNA
<213> ORGANISM: Artificial Sequence
<220> FEATURE:
<223> OTHER INFORMATION: Synthetic

<400> SEQUENCE: 831
cagcagtatg gtagctcacc gtggacg     27

<210> SEQ ID NO 832
<211> LENGTH: 9
<212> TYPE: PRT
<213> ORGANISM: Artificial Sequence
<220> FEATURE:
<223> OTHER INFORMATION: Synthetic

<400> SEQUENCE: 832

Gln Gln Tyr Gly Ser Ser Pro Trp Thr
 1               5

<210> SEQ ID NO 833
<211> LENGTH: 357
<212> TYPE: DNA
<213> ORGANISM: Artificial Sequence
<220> FEATURE:
<223> OTHER INFORMATION: Synthetic

<400> SEQUENCE: 833
caggtgcagc tggtggagtc tgggggaggc gtggtccagc ctggaggtc cctgagactc      60 tcctgtgtag cctctggatt caccttcagt agatatggca tgcactgggt ccgccaggct    120
ccaggcaagg ggctggagtg gctgatagtt atatcatatg atggaattaa taatactat    180 gcagactccg tgaagggccg attcaccatc tccagagaca attccaagaa cacggtgtat    240
ctgcaaatga acagcctgag agttgaggac acggagtgt attactgtgc gaaggggac     300 ttttggagtg gttactttga ctactggggc cagggaaccc tggtcaccgt ctcctca      357

<210> SEQ ID NO 834
<211> LENGTH: 119
<212> TYPE: PRT
<213> ORGANISM: Artificial Sequence
<220> FEATURE:
<223> OTHER INFORMATION: Synthetic

<400> SEQUENCE: 834

Gln Val Gln Leu Val Glu Ser Gly Gly Gly Val Val Gln Pro Gly Arg
 1               5                  10                  15

Ser Leu Arg Leu Ser Cys Val Ala Ser Gly Phe Thr Phe Ser Arg Tyr
            20                  25                  30

Gly Met His Trp Val Arg Gln Ala Pro Gly Lys Gly Leu Glu Trp Leu
        35                  40                  45

Ile Val Ile Ser Tyr Asp Gly Ile Asn Lys Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Val Glu Asp Thr Gly Val Tyr Tyr Cys
                85                  90                  95

Ala Lys Gly Asp Phe Trp Ser Gly Tyr Phe Asp Tyr Trp Gly Gln Gly
            100                 105                 110

Thr Leu Val Thr Val Ser Ser
        115

<210> SEQ ID NO 835
<211> LENGTH: 324
<212> TYPE: DNA
<213> ORGANISM: Artificial Sequence
<220> FEATURE:
<223> OTHER INFORMATION: Synthetic

<400> SEQUENCE: 835

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccgtg gacgttcggc     300
caagggacca aggtggaaat caaa                                            324
```

<210> SEQ ID NO 836
<211> LENGTH: 108
<212> TYPE: PRT
<213> ORGANISM: Artificial Sequence
<220> FEATURE:
<223> OTHER INFORMATION: Synthetic

<400> SEQUENCE: 836

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys
            100                 105
```

<210> SEQ ID NO 837
<211> LENGTH: 357
<212> TYPE: DNA
<213> ORGANISM: Artificial Sequence
<220> FEATURE:
<223> OTHER INFORMATION: Synthetic

<400> SEQUENCE: 837

```
caggtgcagc tggtggagtc tgggggaggc gtggtccagc ctggggaggtc cctgagactc      60 tcctgtgcag cctctggatt caccttcagt agatatggca tgcactgggt ccgccaggct     120
ccaggcaagg ggctggagtg ggtggcagtt atatcatatg atggaattaa taaatactat     180
gcagactccg tgaagggccg attcaccatc tccagagaca attccaagaa cacgctgtat     240
ctgcaaatga acagcctgag agctgaggac acggctgtgt attactgtgc gaagggggac     300
ttttggagtg gttactttga ctactggggc cagggaaccc tggtcaccgt ctcctca       357
```

<210> SEQ ID NO 838
<211> LENGTH: 119
<212> TYPE: PRT
<213> ORGANISM: Artificial Sequence
<220> FEATURE:
<223> OTHER INFORMATION: Synthetic

<400> SEQUENCE: 838

```
Gln Val Gln Leu Val Glu Ser Gly Gly Gly Val Val Gln Pro Gly Arg
 1               5                  10                  15
```

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ile Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Phe Trp Ser Gly Tyr Phe Asp Tyr Trp Gly Gln Gly
            100                 105                 110

Thr Leu Val Thr Val Ser Ser
        115

<210> SEQ ID NO 839
<211> LENGTH: 325
<212> TYPE: DNA
<213> ORGANISM: Artificial Sequence
<220> FEATURE:
<223> OTHER INFORMATION: Synthetic

<400> SEQUENCE: 839
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccgtg gacgttcggc     300
caagggacca aggtggaaat caaac                                           325

<210> SEQ ID NO 840
<211> LENGTH: 108
<212> TYPE: PRT
<213> ORGANISM: Artificial Sequence
<220> FEATURE:
<223> OTHER INFORMATION: Synthetic

<400> SEQUENCE: 840

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 841
<211> LENGTH: 8
<212> TYPE: PRT
<213> ORGANISM: Artificial Sequence

```
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gly
<220> FEATURE:
<221> NAME/KEY: VARIANT
<222> LOCATION: (2)...(2)
<223> OTHER INFORMATION: Xaa = Phe
<220> FEATURE:
<221> NAME/KEY: VARIANT
<222> LOCATION: (3)...(3)
<223> OTHER INFORMATION: Xaa = Thr
<220> FEATURE:
<221> NAME/KEY: VARIANT
<222> LOCATION: (4)...(4)
<223> OTHER INFORMATION: Xaa = Phe
<220> FEATURE:
<221> NAME/KEY: VARIANT
<222> LOCATION: (5)...(5)
<223> OTHER INFORMATION: Xaa = Ser or Arg
<220> FEATURE:
<221> NAME/KEY: VARIANT
<222> LOCATION: (6)...(6)
<223> OTHER INFORMATION: Xaa = Ser or Arg
<220> FEATURE:
<221> NAME/KEY: VARIANT
<222> LOCATION: (7)...(7)
<223> OTHER INFORMATION: Xaa = Tyr
<220> FEATURE:
<221> NAME/KEY: VARIANT
<222> LOCATION: (8)...(8)
<223> OTHER INFORMATION: Xaa = Gly, Ala, or Thr

<400> SEQUENCE: 841

Xaa Xaa Xaa Xaa Xaa Xaa Xaa Xaa
 1               5

<210> SEQ ID NO 842
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ile
<220> FEATURE:
<221> NAME/KEY: VARIANT
<222> LOCATION: (2)...(2)
<223> OTHER INFORMATION: Xaa = Ser, Gly, or Thr
<220> FEATURE:
<221> NAME/KEY: VARIANT
<222> LOCATION: (3)...(3)
<223> OTHER INFORMATION: Xaa = Tyr, Gly, or Asp
<220> FEATURE:
<221> NAME/KEY: VARIANT
<222> LOCATION: (4)...(4)
<223> OTHER INFORMATION: Xaa = Asp, Gly, or Ser
<220> FEATURE:
<221> NAME/KEY: VARIANT
<222> LOCATION: (5)...(5)
<223> OTHER INFORMATION: Xaa = Gly or Arg
<220> FEATURE:
<221> NAME/KEY: VARIANT
<222> LOCATION: (6)...(6)
<223> OTHER INFORMATION: Xaa = Ile, Gly, or Ala
<220> FEATURE:
<221> NAME/KEY: VARIANT
<222> LOCATION: (7)...(7)
<223> OTHER INFORMATION: Xaa = Asn, Ser, Arg, or Gly
<220> FEATURE:
<221> NAME/KEY: VARIANT
<222> LOCATION: (8)...(8)
<223> OTHER INFORMATION: Xaa = Lys, Ala, or Thr
```

```
<400> SEQUENCE: 842

Xaa Xaa Xaa Xaa Xaa Xaa Xaa Xaa
 1               5

<210> SEQ ID NO 843
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ala or Val
<220> FEATURE:
<221> NAME/KEY: VARIANT
<222> LOCATION: (2)...(2)
<223> OTHER INFORMATION: Xaa = Lys
<220> FEATURE:
<221> NAME/KEY: VARIANT
<222> LOCATION: (3)...(3)
<223> OTHER INFORMATION: Xaa = Gly or Glu
<220> FEATURE:
<221> NAME/KEY: VARIANT
<222> LOCATION: (4)...(4)
<223> OTHER INFORMATION: Xaa = Asp or Gly
<220> FEATURE:
<221> NAME/KEY: VARIANT
<222> LOCATION: (5)...(5)
<223> OTHER INFORMATION: Xaa = Phe or Asp
<220> FEATURE:
<221> NAME/KEY: VARIANT
<222> LOCATION: (6)...(6)
<223> OTHER INFORMATION: Xaa = Trp or Ser
<220> FEATURE:
<221> NAME/KEY: VARIANT
<222> LOCATION: (7)...(7)
<223> OTHER INFORMATION: Xaa = Ser or Gly
<220> FEATURE:
<221> NAME/KEY: VARIANT
<222> LOCATION: (8)...(8)
<223> OTHER INFORMATION: Xaa = Gly or Tyr
<220> FEATURE:
<221> NAME/KEY: VARIANT
<222> LOCATION: (9)...(9)
<223> OTHER INFORMATION: Xaa = Tyr or Asp
<220> FEATURE:
<221> NAME/KEY: VARIANT
<222> LOCATION: (10)...(10)
<223> OTHER INFORMATION: Xaa = Phe or Leu
<220> FEATURE:
<221> NAME/KEY: VARIANT
<222> LOCATION: (11)...(11)
<223> OTHER INFORMATION: Xaa = Asp or Ala
<220> FEATURE:
<221> NAME/KEY: VARIANT
<222> LOCATION: (12)...(12)
<223> OTHER INFORMATION: Xaa = Tyr

<400> SEQUENCE: 843

Xaa Xaa Xaa Xaa Xaa Xaa Xaa Xaa Xaa Xaa Xaa Xaa
 1               5                  10

<210> SEQ ID NO 844
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln
<220> FEATURE:
```

```
<221> NAME/KEY: VARIANT
<222> LOCATION: (2)...(2)
<223> OTHER INFORMATION: Xaa = Ser or Gly
<220> FEATURE:
<221> NAME/KEY: VARIANT
<222> LOCATION: (3)...(3)
<223> OTHER INFORMATION: Xaa = Leu or Ile
<220> FEATURE:
<221> NAME/KEY: VARIANT
<222> LOCATION: (4)...(4)
<223> OTHER INFORMATION: Xaa = Val or Ser
<220> FEATURE:
<221> NAME/KEY: VARIANT
<222> LOCATION: (5)...(5)
<223> OTHER INFORMATION: Xaa = His, Asn, or Thr
<220> FEATURE:
<221> NAME/KEY: VARIANT
<222> LOCATION: (6)...(6)
<223> OTHER INFORMATION: Xaa = Ser, Asn, or Tyr
<220> FEATURE:
<221> NAME/KEY: VARIANT
<222> LOCATION: (7)...(7)
<223> OTHER INFORMATION: Xaa = Asp or absent
<220> FEATURE:
<221> NAME/KEY: VARIANT
<222> LOCATION: (8)...(8)
<223> OTHER INFORMATION: Xaa = Gly or absent
<220> FEATURE:
<221> NAME/KEY: VARIANT
<222> LOCATION: (9)...(9)
<223> OTHER INFORMATION: Xaa = Asn or absent
<220> FEATURE:
<221> NAME/KEY: VARIANT
<222> LOCATION: (10)...(10)
<223> OTHER INFORMATION: Xaa = Thr or absent
<220> FEATURE:
<221> NAME/KEY: VARIANT
<222> LOCATION: (11)...(11)
<223> OTHER INFORMATION: Xaa = Tyr or absent

<400> SEQUENCE: 844

Xaa Xaa Xaa Xaa Xaa Xaa Xaa Xaa Xaa Xaa Xaa
 1               5                  10

<210> SEQ ID NO 845
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Lys or Ala
<220> FEATURE:
<221> NAME/KEY: VARIANT
<222> LOCATION: (2)...(2)
<223> OTHER INFORMATION: Xaa = Ile, Ala, or Thr
<220> FEATURE:
<221> NAME/KEY: VARIANT
<222> LOCATION: (3)...(3)
<223> OTHER INFORMATION: Xaa = Ser

<400> SEQUENCE: 845

Xaa Xaa Xaa
 1

<210> SEQ ID NO 846
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
```

```
<222> LOCATION: (1)...(1)
<223> OTHER INFORMATION: Xaa = Met or Gln
<220> FEATURE:
<221> NAME/KEY: VARIANT
<222> LOCATION: (2)...(2)
<223> OTHER INFORMATION: Xaa = Gln
<220> FEATURE:
<221> NAME/KEY: VARIANT
<222> LOCATION: (3)...(3)
<223> OTHER INFORMATION: Xaa = Ala or Tyr
<220> FEATURE:
<221> NAME/KEY: VARIANT
<222> LOCATION: (4)...(4)
<223> OTHER INFORMATION: Xaa = Thr or Lys
<220> FEATURE:
<221> NAME/KEY: VARIANT
<222> LOCATION: (5)...(5)
<223> OTHER INFORMATION: Xaa = Gln, Ser, or Ile
<220> FEATURE:
<221> NAME/KEY: VARIANT
<222> LOCATION: (6)...(6)
<223> OTHER INFORMATION: Xaa = Phe or Ser
<220> FEATURE:
<221> NAME/KEY: VARIANT
<222> LOCATION: (7)...(7)
<223> OTHER INFORMATION: Xaa = Pro
<220> FEATURE:
<221> NAME/KEY: VARIANT
<222> LOCATION: (8)...(8)
<223> OTHER INFORMATION: Xaa = Thr or Leu
<220> FEATURE:
<221> NAME/KEY: VARIANT
<222> LOCATION: (9)...(9)
<223> OTHER INFORMATION: Xaa = Thr or absent

<400> SEQUENCE: 846

Xaa Xaa Xaa Xaa Xaa Xaa Xaa Xaa Xaa
 1               5

<210> SEQ ID NO 847
<211> LENGTH: 330
<212> TYPE: PRT
<213> ORGANISM: Artificial Sequence
<220> FEATURE:
<223> OTHER INFORMATION: Synthetic

<400> SEQUENCE: 847

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 848
<211> LENGTH: 327
<212> TYPE: PRT
<213> ORGANISM: Artificial Sequence
<220> FEATURE:
<223> OTHER INFORMATION: Synthetic

<400> SEQUENCE: 848

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190
```

```
Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 849
<211> LENGTH: 327
<212> TYPE: PRT
<213> ORGANISM: Artificial Sequence
<220> FEATURE:
<223> OTHER INFORMATION: Synthetic

<400> SEQUENCE: 849

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220
```

| Glu | Pro | Gln | Val | Tyr | Thr | Leu | Pro | Pro | Ser | Gln | Glu | Glu | Met | Thr | Lys |
| --- | --- | --- | --- | --- | --- | --- | --- | --- | --- | --- | --- | --- | --- | --- | --- |
| 225 | | | | 230 | | | | | 235 | | | | | 240 | |

| Asn | Gln | Val | Ser | Leu | Thr | Cys | Leu | Val | Lys | Gly | Phe | Tyr | Pro | Ser | Asp |
| --- | --- | --- | --- | --- | --- | --- | --- | --- | --- | --- | --- | --- | --- | --- | --- |
| | | | 245 | | | | | 250 | | | | | 255 | | |

| Ile | Ala | Val | Glu | Trp | Glu | Ser | Asn | Gly | Gln | Pro | Glu | Asn | Asn | Tyr | Lys |
| --- | --- | --- | --- | --- | --- | --- | --- | --- | --- | --- | --- | --- | --- | --- | --- |
| | | 260 | | | | | 265 | | | | | 270 | | | |

| Thr | Thr | Pro | Pro | Val | Leu | Asp | Ser | Asp | Gly | Ser | Phe | Phe | Leu | Tyr | Ser |
| --- | --- | --- | --- | --- | --- | --- | --- | --- | --- | --- | --- | --- | --- | --- | --- |
| | 275 | | | | | 280 | | | | | 285 | | | | |

| Arg | Leu | Thr | Val | Asp | Lys | Ser | Arg | Trp | Gln | Glu | Gly | Asn | Val | Phe | Ser |
| --- | --- | --- | --- | --- | --- | --- | --- | --- | --- | --- | --- | --- | --- | --- | --- |
| 290 | | | | | 295 | | | | | 300 | | | | | |

| Cys | Ser | Val | Met | His | Glu | Ala | Leu | His | Asn | His | Tyr | Thr | Gln | Lys | Ser |
| --- | --- | --- | --- | --- | --- | --- | --- | --- | --- | --- | --- | --- | --- | --- | --- |
| 305 | | | | 310 | | | | | 315 | | | | | 320 | |

| Leu | Ser | Leu | Ser | Leu | Gly | Lys |
| --- | --- | --- | --- | --- | --- | --- |
| | | | | 325 | | |

<210> SEQ ID NO 850
<211> LENGTH: 1194
<212> TYPE: DNA
<213> ORGANISM: Artificial Sequence
<220> FEATURE:
<223> OTHER INFORMATION: Synthetic

<400> SEQUENCE: 850

| | | | | | |
|---|---|---|---|---|---:|
| atgcggagcc | ccagcgcggc | gtggctgctg | ggggccgcca | tcctgctagc | agcctctctc | 60 |
| tcctgcagtg | gcaccatcca | aggaaccaat | agatcctcta | aggaagaag | ccttattggt | 120 |
| aaggttgatg | gcacatccca | cgtcactgga | aaaggagtta | cagttgaaac | agtcttttct | 180 |
| gtggatgagt | tttctgcatc | tgtcctcact | ggaaaactga | ccacggtctt | ccttccaatt | 240 |
| gtctacacaa | ttgtgtttgt | ggtgggtttg | ccaagtaacg | gcatggccct | gtgggtcttt | 300 |
| cttttccgaa | ctaagaagaa | gcaccctgct | gtgatttaca | tggccaatct | ggccttggct | 360 |
| gacctcctct | ctgtcatctg | gttccccttg | aagattgcct | atcacataca | tgccaacaac | 420 |
| tggatttatg | gggaagctct | ttgtaatgtg | cttattggct | ttttctatgg | caacatgtac | 480 |
| tgttccattc | tcttcatgac | ctgcctcagt | gtgcagaggt | attgggtcat | cgtgaacccc | 540 |
| atggggcact | ccaggaagaa | ggcaaacatt | gccattggca | tctccctggc | aatatggctg | 600 |
| ctgattctgc | tggtcaccat | ccctttgtat | gtcgtgaagc | agaccatctt | cattcctgcc | 660 |
| ctgaacatca | cgacctgtca | tgatgttttg | cctgagcagc | tcttggtggg | agacatgttc | 720 |
| aattacttcc | tctctctggc | cattggggtc | tttctgttcc | cagccttcct | cacagcctct | 780 |
| gcctatgtgc | tgatgatcag | aatgctgcga | tcttctgcca | tggataaaaa | ctcagagaag | 840 |
| aaaaggaaga | gggccatcaa | actcattgtc | actgtcctgg | ccatgtacct | gatctgcttc | 900 |
| actcctagta | accttctgct | tgtggtgcat | tattttctga | ttaagagcca | gggccagagc | 960 |
| catgtctatg | ccctgtacat | tgtagccctc | tgcctctcta | cccttaacag | ctgcatcgac | 1020 |
| cccttgtct | attactttgt | ttcacatgat | tcagggatc | atgcaaagaa | cgctctcctt | 1080 |
| tgccgaagtg | tccgcactgt | aaagcagatg | caagtatccc | tcacctcaaa | gaaacactcc | 1140 |
| aggaaatcca | gctcttactc | ttcaagttca | accactgtta | agacctccta | ttga | 1194 |

<210> SEQ ID NO 851
<211> LENGTH: 397
<212> TYPE: PRT
<213> ORGANISM: Artificial Sequence
<220> FEATURE:
<223> OTHER INFORMATION: Synthetic

<400> SEQUENCE: 851

```
Met Arg Ser Pro Ser Ala Ala Trp Leu Leu Gly Ala Ala Ile Leu Leu
 1               5                  10                  15

Ala Ala Ser Leu Ser Cys Ser Gly Thr Ile Gln Gly Thr Asn Arg Ser
            20                  25                  30

Ser Lys Gly Arg Ser Leu Ile Gly Lys Val Asp Gly Thr Ser His Val
        35                  40                  45

Thr Gly Lys Gly Val Thr Val Glu Thr Val Phe Ser Val Asp Glu Phe
    50                  55                  60

Ser Ala Ser Val Leu Thr Gly Lys Leu Thr Thr Val Phe Leu Pro Ile
65                  70                  75                  80

Val Tyr Thr Ile Val Phe Val Gly Leu Pro Ser Asn Gly Met Ala
                85                  90                  95

Leu Trp Val Phe Leu Phe Arg Thr Lys Lys His Pro Ala Val Ile
                100                 105                 110

Tyr Met Ala Asn Leu Ala Leu Ala Asp Leu Leu Ser Val Ile Trp Phe
                115                 120                 125

Pro Leu Lys Ile Ala Tyr His Ile His Ala Asn Asn Trp Ile Tyr Gly
        130                 135                 140

Glu Ala Leu Cys Asn Val Leu Ile Gly Phe Phe Tyr Gly Asn Met Tyr
145                 150                 155                 160

Cys Ser Ile Leu Phe Met Thr Cys Leu Ser Val Gln Arg Tyr Trp Val
                165                 170                 175

Ile Val Asn Pro Met Gly His Ser Arg Lys Lys Ala Asn Ile Ala Ile
                180                 185                 190

Gly Ile Ser Leu Ala Ile Trp Leu Leu Ile Leu Leu Val Thr Ile Pro
        195                 200                 205

Leu Tyr Val Val Lys Gln Thr Ile Phe Ile Pro Ala Leu Asn Ile Thr
    210                 215                 220

Thr Cys His Asp Val Leu Pro Glu Gln Leu Leu Val Gly Asp Met Phe
225                 230                 235                 240

Asn Tyr Phe Leu Ser Leu Ala Ile Gly Val Phe Leu Phe Pro Ala Phe
                245                 250                 255

Leu Thr Ala Ser Ala Tyr Val Leu Met Ile Arg Met Leu Arg Ser Ser
                260                 265                 270

Ala Met Asp Glu Asn Ser Glu Lys Lys Arg Lys Arg Ala Ile Lys Leu
            275                 280                 285

Ile Val Thr Val Leu Ala Met Tyr Leu Ile Cys Phe Thr Pro Ser Asn
        290                 295                 300

Leu Leu Leu Val Val His Tyr Phe Leu Ile Lys Ser Gln Gly Gln Ser
305                 310                 315                 320

His Val Tyr Ala Leu Tyr Ile Val Ala Leu Cys Leu Ser Thr Leu Asn
                325                 330                 335

Ser Cys Ile Asp Pro Phe Val Tyr Phe Val Ser Asp Phe Arg
            340                 345                 350

Asp His Ala Lys Asn Ala Leu Leu Cys Arg Ser Val Arg Thr Val Lys
            355                 360                 365

Gln Met Gln Val Ser Leu Thr Ser Lys Lys His Ser Arg Lys Ser Ser
        370                 375                 380

Ser Tyr Ser Ser Ser Ser Thr Thr Val Lys Thr Ser Tyr
385                 390                 395
```

```
<210> SEQ ID NO 852
<211> LENGTH: 18
<212> TYPE: PRT
<213> ORGANISM: Human

<400> SEQUENCE: 852

Gly Thr Asn Arg Ser Ser Lys Gly Arg Ser Leu Ile Gly Lys Val Asp
1               5                   10                  15

Gly Thr

<210> SEQ ID NO 853
<211> LENGTH: 14
<212> TYPE: PRT
<213> ORGANISM: Human

<400> SEQUENCE: 853

Ser Leu Ile Gly Lys Val Asp Gly Thr Ser His Val Thr Gly
1               5                   10

<210> SEQ ID NO 854
<211> LENGTH: 6
<212> TYPE: PRT
<213> ORGANISM: Human

<400> SEQUENCE: 854

Ser Leu Ile Gly Lys Val
1               5

<210> SEQ ID NO 855
<211> LENGTH: 276
<212> TYPE: PRT
<213> ORGANISM: Artificial Sequence
<220> FEATURE:
<223> OTHER INFORMATION: Synthetic

<400> SEQUENCE: 855

Ser Leu Ile Gly Lys Val Asp Gly Thr Ser His Val Thr Gly Lys Gly
1               5                   10                  15

Val Thr Val Glu Thr Val Phe Ser Val Asp Glu Phe Ser Ala Ser Val
                20                  25                  30

Leu Thr Gly Lys Leu Thr Thr Val Phe Leu Pro Glu Pro Arg Gly Pro
            35                  40                  45

Thr Ile Lys Pro Cys Pro Pro Cys Lys Cys Pro Ala Pro Asn Leu Leu
        50                  55                  60

Gly Gly Pro Ser Val Phe Ile Phe Pro Pro Lys Ile Lys Asp Val Leu
65                  70                  75                  80

Met Ile Ser Leu Ser Pro Ile Val Thr Cys Val Val Asp Val Ser
                85                  90                  95

Glu Asp Asp Pro Asp Val Gln Ile Ser Trp Phe Val Asn Asn Val Glu
                100                 105                 110

Val His Thr Ala Gln Thr Gln Thr His Arg Glu Asp Tyr Asn Ser Thr
            115                 120                 125

Leu Arg Val Val Ser Ala Leu Pro Ile Gln His Gln Asp Trp Met Ser
        130                 135                 140

Gly Lys Glu Phe Lys Cys Lys Val Asn Asn Lys Asp Leu Pro Ala Pro
145                 150                 155                 160

Ile Glu Arg Thr Ile Ser Lys Pro Lys Gly Ser Val Arg Ala Pro Gln
                165                 170                 175

Val Tyr Val Leu Pro Pro Pro Glu Glu Glu Met Thr Lys Lys Gln Val
                180                 185                 190
```

```
Thr Leu Thr Cys Met Val Thr Asp Phe Met Pro Glu Asp Ile Tyr Val
        195                 200                 205

Glu Trp Thr Asn Asn Gly Lys Thr Glu Leu Asn Tyr Lys Asn Thr Glu
    210                 215                 220

Pro Val Leu Asp Ser Asp Gly Ser Tyr Phe Met Tyr Ser Lys Leu Arg
225                 230                 235                 240

Val Glu Lys Lys Asn Trp Val Glu Arg Asn Ser Tyr Ser Cys Ser Val
                245                 250                 255

Val His Glu Gly Leu His Asn His His Thr Thr Lys Ser Phe Ser Arg
            260                 265                 270

Thr Pro Gly Lys
        275

<210> SEQ ID NO 856
<211> LENGTH: 20
<212> TYPE: PRT
<213> ORGANISM: Mouse

<400> SEQUENCE: 856

Leu Ala Pro Gly Arg Asn Asn Ser Lys Gly Arg Ser Leu Ile Gly Arg
1               5                   10                  15

Leu Glu Thr Gln
        20

<210> SEQ ID NO 857
<211> LENGTH: 18
<212> TYPE: PRT
<213> ORGANISM: Monkey

<400> SEQUENCE: 857

Gly Thr Asn Arg Ser Ser Lys Gly Arg Ser Leu Ile Gly Arg Val Asp
1               5                   10                  15

Gly Thr

<210> SEQ ID NO 858
<211> LENGTH: 16
<212> TYPE: PRT
<213> ORGANISM: Rat

<400> SEQUENCE: 858

Gly Pro Asn Ser Lys Gly Arg Ser Leu Ile Gly Arg Leu Asp Thr Pro
1               5                   10                  15

<210> SEQ ID NO 859
<211> LENGTH: 18
<212> TYPE: PRT
<213> ORGANISM: Rabbit

<400> SEQUENCE: 859

Gly Thr Asn Lys Thr Ser Lys Gly Arg Ser Leu Ile Gly Arg Asn Thr
1               5                   10                  15

Gly Ser

<210> SEQ ID NO 860
<211> LENGTH: 18
<212> TYPE: PRT
<213> ORGANISM: Dog

<400> SEQUENCE: 860

Gly Thr Asn Arg Thr Ser Lys Gly Arg Ser Leu Ile Gly Lys Thr Asp
```

```
                1               5                  10                 15
Ser Ser

<210> SEQ ID NO 861
<211> LENGTH: 18
<212> TYPE: PRT
<213> ORGANISM: Pig

<400> SEQUENCE: 861

Gly Thr Ser Arg Pro Ser Lys Gly Arg Ser Leu Ile Gly Lys Ala Asp
 1               5                  10                  15

Asn Thr

<210> SEQ ID NO 862
<211> LENGTH: 18
<212> TYPE: PRT
<213> ORGANISM: Human

<400> SEQUENCE: 862

Ala Thr Asn Ala Thr Leu Asp Pro Arg Ser Phe Leu Leu Arg Asn Pro
 1               5                  10                  15

Asn Asp

<210> SEQ ID NO 863
<211> LENGTH: 18
<212> TYPE: PRT
<213> ORGANISM: Human

<400> SEQUENCE: 863

Asp Thr Asn Asn Leu Ala Lys Pro Thr Leu Pro Ile Lys Thr Phe Arg
 1               5                  10                  15

Gly Ala

<210> SEQ ID NO 864
<211> LENGTH: 19
<212> TYPE: PRT
<213> ORGANISM: Human

<400> SEQUENCE: 864

Glu Ser Gly Ser Thr Gly Gly Gly Asp Asp Ser Thr Pro Ser Ile Leu
 1               5                  10                  15

Pro Ala Pro

<210> SEQ ID NO 865
<211> LENGTH: 2772
<212> TYPE: DNA
<213> ORGANISM: Mouse

<400> SEQUENCE: 865
gtccgcccac gcgtccgggg aagggaccct gtgctcagag tagggctccg agtttcgaac      60
cactggtggc ggattgcccg cccgccccac gtccggggat gcgaagtctc agcctggcgt     120
ggctgctggg aggtatcacc cttctggcgg cctcggtctc ctgcagccgg accgagaacc     180
ttgcaccggg acgcaacaac agtaaaggaa gaagtcttat tggcagattg gaaacccagc     240
ctccaatcac tgggaaaggg gttccggtag aaccaggctt ttccatcgat gagttctctg     300
cgtccatcct caccgggaag ctgaccactg tctttcttcc ggtcgtctac attattgtgt     360
tgtgattgg tttgcccagt aatgcatgg ccctctggat cttcctttc cgaacgaaga     420
agaaacaccc cgccgtgatt tacatggcca acctggcctt ggctgacctc ctctctgtca     480
```

```
tctggttccc cctggccatt gcctaccacc tacatggcaa caactgggtc tatggggagg    540
ccctgtgcaa ggtgctcatt ggcttttct atggcaacat gtattgctcc atcctcttca    600
tgacctgcct cagcgtgcag aggtactggg tgatcgtgaa ccccatgggg cacccagga    660 agaaggcaaa catcgccgtt ggcgtctcct tggcaatctg gctcctgatt tttctggtca    720 ccatccctt gtatgtcatg aagcagacca tctacattcc agccttgaac atcaccacct    780
gccacgatgt gctgcctgag gaggtattgg tgggggacat gttcaattac ttcctctcac    840
tggccattgg agtcttcctg ttcccggcca tccttactgc atctgcctac gtgctcatga    900
tcaagacgct ccgctcttct gctatggatg aacactcaga aagaaaagg cagagggcta    960 tccgactcat catcaccgtg ctggccatgt acttcatctg ctttgctcct agcaaccttc   1020
tgctcgtagt gcattatttc ctaatcaaaa cccagaggca gagccacgtc tacgccctct   1080
acctcgtcgc cctctgcctg tcgactctca acagctgcat agaccccttt gtctattact   1140
ttgtctcaaa agatttcagg gatcacgcca ggaacgcgct cctctgccga agtgtccgca   1200
ctgtgaatcg catgcaaatc tccctcagct ccaacaagtt ctccaggaag tccggctcct   1260
actcttcaag ctcaaccagt gttaaaacct cctactgagc tgtacctgag gatgtcaagc   1320
ctgcttgatg atgatgatga tgatgatgat gatgtgtgtg tgtgtgtgtg tgtgtgtgtg   1380
tgtgcacccg tgtgtgagag cgtagtagga atgcaccaac atgcatgagg ctgtcatttc   1440
ctatccaagc tgctggtctc tgcaccaatc acaagcatgc agctctcccc aagatcgcca   1500
gaagcctcct cctttgcatg agaacagtct tccactctga tgaaaagcat cagtatcaga   1560
aactgaaaca aactgagagg agcatgtttt gtggaagtga agagaggatg gagggtcagt   1620
gacttgcaaa aaaacccaa ccaaacaaaa acgacacctg gcaagaaggc taagactctc   1680
tgaaatgctt cctttccat ctggagttcg tcacggcttt gttcaggacc tgaggccctg   1740
gtagagcttc agtccagttg attgacttta cagacttgag agaggaatga atgaggagtg   1800
aatgcggctc ctggcggcat cctaaccggc taacagtggc cttgctggac aataggattc   1860
agatggctgg agttacattc tcacaccatt tcatcagaac tattgggat cttgatcaat   1920 gtgcaggtcc cttagcgtca gtaaccctgg gagctcagac acgatggggg tgagggtggg   1980
ggtgggggtg ggggtgaggc tctacaaacc ttagtgatga ctgcagacac agaaccatgg   2040
agctgagcct gcttctgctt gccagggcac cactgtaatg ttggcaaaga aaaccaaca   2100 gcagtgtttt gagcctcttt ttttggtcag tttatgatga atttgcctat tggtttattg   2160
ggattttcag ttcctttatt actttgttgt aattttgtgt gttattagt caagaaaaag   2220 aagatgaggc tcttaaaaat gtaaataaaa tttttggttt tttggttttt taacttgggc   2280
caactacaaa tactgcttag gtttttttct aacttaattt ttaactacat catgtgaact   2340
taagacattt tcatgataaa gcattactgt agtgtcagtt ttccctcatc ctcgatcata   2400
gtccttccca tgaagcaggg cccttcccct ccccccctt tgccgtttcc ctccccacca   2460
gatagtcccc tgtctgcttt aacctaccag ttagtatttt ataaaaactg atcattggaa   2520
tatttattat cagttttgtt cactgttatc agttttgttc actaatttgt ccaataatgg   2580
aattaacgtc ttctcatctg tttgagaaag atctgaaaca aggggccatt gcaggagtac   2640
atggctccag gcttacttta tatactgcct gtatttgtgg cttttaaaaaa atgacctttg   2700 ttatatgaat gctttataaa taaataatgc atgaactttt ttaaaaaaaa aaaaaaaaaa   2760
aaaaaaaaaa aa                                                       2772
```

```
<210> SEQ ID NO 866
<211> LENGTH: 399
<212> TYPE: PRT
<213> ORGANISM: Mouse

<400> SEQUENCE: 866

Met Arg Ser Leu Ser Leu Ala Trp Leu Leu Gly Gly Ile Thr Leu Leu
 1               5                  10                  15

Ala Ala Ser Val Ser Cys Ser Arg Thr Glu Asn Leu Ala Pro Gly Arg
            20                  25                  30

Asn Asn Ser Lys Gly Arg Ser Leu Ile Gly Arg Leu Glu Thr Gln Pro
        35                  40                  45

Pro Ile Thr Gly Lys Gly Val Pro Val Glu Pro Gly Phe Ser Ile Asp
    50                  55                  60

Glu Phe Ser Ala Ser Ile Leu Thr Gly Lys Leu Thr Thr Val Phe Leu
65                  70                  75                  80

Pro Val Val Tyr Ile Ile Val Phe Val Ile Gly Leu Pro Ser Asn Gly
                85                  90                  95

Met Ala Leu Trp Ile Phe Leu Phe Arg Thr Lys Lys His Pro Ala
            100                 105                 110

Val Ile Tyr Met Ala Asn Leu Ala Leu Ala Asp Leu Leu Ser Val Ile
        115                 120                 125

Trp Phe Pro Leu Ala Ile Ala Tyr His Leu His Gly Asn Asn Trp Val
130                 135                 140

Tyr Gly Glu Ala Leu Cys Lys Val Leu Ile Gly Phe Phe Tyr Gly Asn
145                 150                 155                 160

Met Tyr Cys Ser Ile Leu Phe Met Thr Cys Leu Ser Val Gln Arg Tyr
                165                 170                 175

Trp Val Ile Val Asn Pro Met Gly His Pro Arg Lys Lys Ala Asn Ile
            180                 185                 190

Ala Val Gly Val Ser Leu Ala Ile Trp Leu Leu Ile Phe Leu Val Thr
        195                 200                 205

Ile Pro Leu Tyr Val Met Lys Gln Thr Ile Tyr Ile Pro Ala Leu Asn
    210                 215                 220

Ile Thr Thr Cys His Asp Val Leu Pro Glu Glu Val Leu Val Gly Asp
225                 230                 235                 240

Met Phe Asn Tyr Phe Leu Ser Leu Ala Ile Gly Val Phe Leu Phe Pro
                245                 250                 255

Ala Ile Leu Thr Ala Ser Ala Tyr Val Leu Met Ile Lys Thr Leu Arg
            260                 265                 270

Ser Ser Ala Met Asp Glu His Ser Glu Lys Lys Arg Gln Arg Ala Ile
        275                 280                 285

Arg Leu Ile Ile Thr Val Leu Ala Met Tyr Phe Ile Cys Phe Ala Pro
    290                 295                 300

Ser Asn Leu Leu Leu Val Val His Tyr Phe Leu Ile Lys Thr Gln Arg
305                 310                 315                 320

Gln Ser His Val Tyr Ala Leu Tyr Leu Val Ala Leu Cys Leu Ser Thr
                325                 330                 335

Leu Asn Ser Cys Ile Asp Pro Phe Val Tyr Tyr Phe Ser Lys Asp
            340                 345                 350

Phe Arg Asp His Ala Arg Asn Ala Leu Leu Cys Arg Ser Val Arg Thr
        355                 360                 365

Val Asn Arg Met Gln Ile Ser Leu Ser Ser Asn Lys Phe Ser Arg Lys
    370                 375                 380
```

Ser Gly Ser Tyr Ser Ser Ser Thr Ser Val Lys Thr Ser Tyr
385             390             395

<210> SEQ ID NO 867
<211> LENGTH: 3011
<212> TYPE: DNA
<213> ORGANISM: Rat

<400> SEQUENCE: 867

| | | | | | |
|---|---|---|---|---|---|
| gttaaaggaa | ggggacccgg | tactccgagt | ggggctcgga | gtttcgaacc | actggtggcg | 60 |
| gattgcccgc | ccgtcccacg | tccggggatg | cgaagtctca | gcctggcgtg | gctgctggga | 120 |
| ggtatcaccc | ttctggcggc | ctcggcctcc | tgcaaccgga | ccgtgaatgc | accgggaccc | 180 |
| aacagtaaag | ggagaagtct | gattggcaga | ttggacacgc | cgcctcccat | cactgggaaa | 240 |
| ggggctccag | ttgaaccagg | cttttccgtt | gatgaattct | ctgcatccgt | cctcaccggg | 300 |
| aagctgacca | ccgtctttct | cccggtcatc | tacatcattg | tctttgtaat | tggtttgccc | 360 |
| agtaatggta | tggccctctg | ggtcttcttc | ttccgaacga | agaagaagca | ccctgctgtg | 420 |
| atttacatgg | ccaacctggc | cttggcagac | ctcctctctg | tcatctggtt | cccccctgaag | 480 |
| atctcctacc | acctccatgg | caacgactgg | acctatgggg | atgcgctctg | caaggtgctc | 540 |
| attggctttt | tctacggcaa | tatgtactgc | tccatccttt | tcatgacctg | cctcagcgtg | 600 |
| cagaggtact | gggtgatcgt | gaaccccatg | ggacactcca | ggaagagggc | caacatcgct | 660 |
| gttggcgtct | ccctggccat | ctggctcctg | attttctgg | tcaccatccc | tctgtacgtc | 720 |
| atgaggcaga | ccatctacat | tccagccttg | aacatcacca | cctgtcacga | cgtgctgccc | 780 |
| gaggaggtcc | tggtggggga | catgttcagt | tacttcctct | ccctggccat | tggagtctttt | 840 |
| ctgttcccag | ccctccttac | tgcgtctgcc | tacgtgctca | tgatcaaaac | gctccgttcc | 900 |
| tccgccatgg | acgagcactc | ggagaagaaa | aggcggaggg | ctatccgcct | catcatcacg | 960 |
| gtgctgtcca | tgtacttcat | ctgcttcgct | cccagcaacg | tgctgctcgt | cgtgcattat | 1020 |
| ttcctcatca | aaagccagag | gcagagccac | gtctacgccc | tctacctcgt | cgccctctgc | 1080 |
| ctgtccaccc | tcaacagctg | catagacccc | tttgtctact | actttgtttc | gaaagatttc | 1140 |
| agggaccagg | ccagaaacgc | gctcctctgc | cgaagcgtcc | gcaccgtgaa | acgcatgcag | 1200 |
| atatcgctca | cctccaacaa | gttctccagg | aaatccagct | cttactcctc | cagctcaacc | 1260 |
| agtgttaaaa | cctcctactg | agctgggtct | gaggatatgg | agccagcttg | atgatgatgc | 1320 |
| tggtgatgat | gatgatgatg | atgatggtga | tgatgctgat | gatgctgatg | atgctgatga | 1380 |
| tgctgatgat | gatgatgtat | gtgtgtgcat | atgtgcgtgc | atgcgtgtgt | gtgtgtgtgt | 1440 |
| gtgtgtgtgt | gtgtgtgtgt | tagggatgca | ccacaacgca | cggggctgtc | atttcctatc | 1500 |
| caagttgcta | gtctctgtac | cagtcacaag | aatgatggac | gtcagcgtcc | gaaactgaag | 1560 |
| gaaccgagag | gaacatgctt | tgcagaagtg | aggaaggaaa | ttcgttgacc | tgcagagaac | 1620 |
| tacacctggc | aagaaagtta | agacccccccc | gaaatgcttt | cttgttcatc | tggagtccgt | 1680 |
| catggctttg | tcaggatctg | agatccttgt | agagcttcag | tccagctgat | aatgactcta | 1740 |
| tagacttgga | agatgtgtct | gcgaatgagg | ctcctggccg | gcattccaac | tggttaacac | 1800 |
| tgagcttgct | ggacgacagg | attcaaatgg | ccacagtggt | tccgttctcg | catggtttca | 1860 |
| tcagaactac | tggggatctt | gttcaatgtg | caggtccctc | agcctcagtg | cccagggagc | 1920 |
| tcggatacga | gggggccgct | ctacaaactt | cagtgatgtc | tgcatacaca | gaaccgcaga | 1980 |
| ggcgagcccc | gttccgcttg | ccagggcacc | gtagtgacgt | tggcaaagaa | aaaccaacag | 2040 |

```
cagtgtttga gcctcctttt ggtcaattta tgatgaattt ccctatgggt taactgggat    2100
ttctggttcc tttattaccc ctttgtagtt ttatatgtct gtaagtcaac aaaatgaggc    2160
tcctaaacat gtaaataaaa attttgttta ttttttttaa ttttacataa gtcagtgtgg    2220
gtaatagagt attaggccga ctgcaaatac tgcttagttt ttttctaagt taattttta   2280 atacatcatg caaacttaag acattttcat gataaagcac tattacagtg tcagttccct    2340
tctccctcag tcatatgcct tcccgggatg ctggcccttc cctcctctc cttccccct    2400 tgccttcccc ctcccccag atagccagtg tgccttcatg taccatttag tattttataa    2460
aaaccgtcgt tgaaatattt attatcagtt ttgttcacct tttaccgtcc attgaatgaa    2520
cgtcttctcg tctgtttggg caagagcagg aacaagaggc tacggccatt gcagggtac     2580 gtggttccag acttacttta tataccgcct ggatctgcgg cttgagaaat taccttgtac    2640
gaaggctttc taaataatgt ataacccttg acctttttt ttttaaacaa cttctttcca    2700
gctgtgtgtt cttttgtaga aggaggagga gaagggaatc ccctgttgt agatacagtg    2760 atctgatcac cctatcctgt tctgttcttt cttcctttct tctttaacac agtgcgatgc    2820
ccaccccacc actttccagt ccttccttct tccttcttc cttcctttct tctctttcca    2880
caacactagg gatctaaacc tagccttgtg aatttacact ttttccccca cactagtttt    2940
tctaataaac aaaatgtagt tcacgttgct ccacaaaaaa aaaaaaaaaa aaaaaaaaa    3000 aaaaaaaaaa a                                                        3011
```

<210> SEQ ID NO 868
<211> LENGTH: 397
<212> TYPE: PRT
<213> ORGANISM: Rat

<400> SEQUENCE: 868

```
Met Arg Ser Leu Ser Leu Ala Trp Leu Leu Gly Gly Ile Thr Leu Leu
 1               5                  10                  15

Ala Ala Ser Ala Ser Cys Asn Arg Thr Val Asn Ala Pro Gly Pro Asn
            20                  25                  30

Ser Lys Gly Arg Ser Leu Ile Gly Arg Leu Asp Thr Pro Pro Ile
        35                  40                  45

Thr Gly Lys Gly Ala Pro Val Glu Pro Gly Phe Ser Val Asp Glu Phe
    50                  55                  60

Ser Ala Ser Val Leu Thr Gly Lys Leu Thr Thr Val Phe Leu Pro Val
65                  70                  75                  80

Ile Tyr Ile Ile Val Phe Val Ile Gly Leu Pro Ser Asn Gly Met Ala
                85                  90                  95

Leu Trp Val Phe Phe Arg Thr Lys Lys Lys His Pro Ala Val Ile
            100                 105                 110

Tyr Met Ala Asn Leu Ala Leu Ala Asp Leu Leu Ser Val Ile Trp Phe
        115                 120                 125

Pro Leu Lys Ile Ser Tyr His Leu His Gly Asn Asp Trp Thr Tyr Gly
    130                 135                 140

Asp Ala Leu Cys Lys Val Leu Ile Gly Phe Phe Tyr Gly Asn Met Tyr
145                 150                 155                 160

Cys Ser Ile Leu Phe Met Thr Cys Leu Ser Val Gln Arg Tyr Trp Val
                165                 170                 175

Ile Val Asn Pro Met Gly His Ser Arg Lys Arg Ala Asn Ile Ala Val
            180                 185                 190
```

```
Gly Val Ser Leu Ala Ile Trp Leu Leu Ile Phe Leu Val Thr Ile Pro
        195                 200                 205

Leu Tyr Val Met Arg Gln Thr Ile Tyr Ile Pro Ala Leu Asn Ile Thr
    210                 215                 220

Thr Cys His Asp Val Leu Pro Glu Glu Val Val Gly Asp Met Phe
225                 230                 235                 240

Ser Tyr Phe Leu Ser Leu Ala Ile Gly Val Phe Leu Phe Pro Ala Leu
                245                 250                 255

Leu Thr Ala Ser Ala Tyr Val Leu Met Ile Lys Thr Leu Arg Ser Ser
            260                 265                 270

Ala Met Asp Glu His Ser Glu Lys Lys Arg Arg Arg Ala Ile Arg Leu
        275                 280                 285

Ile Ile Thr Val Leu Ser Met Tyr Phe Ile Cys Phe Ala Pro Ser Asn
290                 295                 300

Val Leu Leu Val Val His Tyr Phe Leu Ile Lys Ser Gln Arg Gln Ser
305                 310                 315                 320

His Val Tyr Ala Leu Tyr Leu Val Ala Leu Cys Leu Ser Thr Leu Asn
                325                 330                 335

Ser Cys Ile Asp Pro Phe Val Tyr Tyr Phe Val Ser Lys Asp Phe Arg
                340                 345                 350

Asp Gln Ala Arg Asn Ala Leu Leu Cys Arg Ser Val Arg Thr Val Lys
            355                 360                 365

Arg Met Gln Ile Ser Leu Thr Ser Asn Lys Phe Ser Arg Lys Ser Ser
        370                 375                 380

Ser Tyr Ser Ser Ser Ser Thr Ser Val Lys Thr Ser Tyr
385                 390                 395

<210> SEQ ID NO 869
<211> LENGTH: 22
<212> TYPE: PRT
<213> ORGANISM: Artificial Sequence
<220> FEATURE:
<223> OTHER INFORMATION: Synthetic

<400> SEQUENCE: 869

Gly Pro Asn Ser Lys Gly Arg Ser Leu Ile Gly Arg Leu Asp Thr Pro
1               5                   10                  15

Gly Gly Gly Gly Ser Lys
            20

<210> SEQ ID NO 870
<211> LENGTH: 23
<212> TYPE: PRT
<213> ORGANISM: Artificial Sequence
<220> FEATURE:
<223> OTHER INFORMATION: Synthetic

<400> SEQUENCE: 870

Gly Arg Asn Asn Ser Lys Gly Arg Ser Leu Ile Gly Arg Leu Glu Thr
1               5                   10                  15

Gln Gly Gly Gly Gly Ser Lys
            20

<210> SEQ ID NO 871
<211> LENGTH: 24
<212> TYPE: PRT
<213> ORGANISM: Artificial Sequence
<220> FEATURE:
<223> OTHER INFORMATION: Synthetic
```

```
<400> SEQUENCE: 871

Gly Thr Asn Arg Ser Ser Lys Gly Arg Ser Leu Ile Gly Lys Val Asp
1               5                   10                  15

Gly Thr Gly Gly Gly Gly Ser Lys
            20

<210> SEQ ID NO 872
<211> LENGTH: 24
<212> TYPE: PRT
<213> ORGANISM: Artificial Sequence
<220> FEATURE:
<223> OTHER INFORMATION: Synthetic

<400> SEQUENCE: 872

Gly Thr Asn Arg Ser Ser Lys Ala Arg Ser Leu Ile Gly Lys Val Asp
1               5                   10                  15

Gly Thr Gly Gly Gly Gly Ser Lys
            20

<210> SEQ ID NO 873
<211> LENGTH: 24
<212> TYPE: PRT
<213> ORGANISM: Artificial Sequence
<220> FEATURE:
<223> OTHER INFORMATION: Synthetic

<400> SEQUENCE: 873

Gly Thr Asn Arg Ser Ser Lys Gly Ala Ser Leu Ile Gly Lys Val Asp
1               5                   10                  15

Gly Thr Gly Gly Gly Gly Ser Lys
            20

<210> SEQ ID NO 874
<211> LENGTH: 24
<212> TYPE: PRT
<213> ORGANISM: Artificial Sequence
<220> FEATURE:
<223> OTHER INFORMATION: Synthetic

<400> SEQUENCE: 874

Gly Thr Asn Arg Ser Ser Lys Gly Arg Ala Leu Ile Gly Lys Val Asp
1               5                   10                  15

Gly Thr Gly Gly Gly Gly Ser Lys
            20

<210> SEQ ID NO 875
<211> LENGTH: 24
<212> TYPE: PRT
<213> ORGANISM: Artificial Sequence
<220> FEATURE:
<223> OTHER INFORMATION: Synthetic

<400> SEQUENCE: 875

Gly Thr Asn Arg Ser Ser Lys Gly Arg Ser Ala Ile Gly Lys Val Asp
1               5                   10                  15

Gly Thr Gly Gly Gly Gly Ser Lys
            20

<210> SEQ ID NO 876
<211> LENGTH: 24
<212> TYPE: PRT
<213> ORGANISM: Artificial Sequence
<220> FEATURE:
<223> OTHER INFORMATION: Synthetic
```

<400> SEQUENCE: 876

Gly Thr Asn Arg Ser Ser Lys Gly Arg Ser Leu Ala Gly Lys Val Asp
1               5                   10                  15

Gly Thr Gly Gly Gly Gly Ser Lys
            20

<210> SEQ ID NO 877
<211> LENGTH: 24
<212> TYPE: PRT
<213> ORGANISM: Artificial Sequence
<220> FEATURE:
<223> OTHER INFORMATION: Synthetic

<400> SEQUENCE: 877

Gly Thr Asn Arg Ser Ser Lys Gly Arg Ser Leu Ile Ala Lys Val Asp
1               5                   10                  15

Gly Thr Gly Gly Gly Gly Ser Lys
            20

<210> SEQ ID NO 878
<211> LENGTH: 24
<212> TYPE: PRT
<213> ORGANISM: Artificial Sequence
<220> FEATURE:
<223> OTHER INFORMATION: Synthetic

<400> SEQUENCE: 878

Gly Thr Asn Arg Ser Ser Lys Gly Arg Ser Leu Ile Gly Ala Val Asp
1               5                   10                  15

Gly Thr Gly Gly Gly Gly Ser Lys
            20

<210> SEQ ID NO 879
<211> LENGTH: 24
<212> TYPE: PRT
<213> ORGANISM: Artificial Sequence
<220> FEATURE:
<223> OTHER INFORMATION: Synthetic

<400> SEQUENCE: 879

Gly Thr Asn Arg Ser Ser Lys Gly Arg Ser Leu Ile Gly Lys Ala Asp
1               5                   10                  15

Gly Thr Gly Gly Gly Gly Ser Lys
            20

<210> SEQ ID NO 880
<211> LENGTH: 24
<212> TYPE: PRT
<213> ORGANISM: Artificial Sequence
<220> FEATURE:
<223> OTHER INFORMATION: Synthetic

<400> SEQUENCE: 880

Gly Thr Asn Arg Ser Ser Lys Gly Arg Ser Leu Ile Gly Lys Val Ala
1               5                   10                  15

Gly Thr Gly Gly Gly Gly Ser Lys
            20

<210> SEQ ID NO 881
<211> LENGTH: 24
<212> TYPE: PRT
<213> ORGANISM: Artificial Sequence
<220> FEATURE:

<223> OTHER INFORMATION: Synthetic

<400> SEQUENCE: 881

Gly Thr Asn Arg Ser Ser Lys Gly Arg Ser Leu Ile Gly Lys Val Asp
1               5                   10                  15

Ala Thr Gly Gly Gly Gly Ser Lys
            20

<210> SEQ ID NO 882
<211> LENGTH: 24
<212> TYPE: PRT
<213> ORGANISM: Artificial Sequence
<220> FEATURE:
<223> OTHER INFORMATION: Synthetic

<400> SEQUENCE: 882

Gly Thr Asn Arg Ser Ser Lys Gly Arg Ser Leu Ile Gly Lys Val Asp
1               5                   10                  15

Gly Ala Gly Gly Gly Gly Ser Lys
            20

<210> SEQ ID NO 883
<211> LENGTH: 20
<212> TYPE: PRT
<213> ORGANISM: Artificial Sequence
<220> FEATURE:
<223> OTHER INFORMATION: Synthetic

<400> SEQUENCE: 883

Gly Arg Asn Asn Ser Lys Gly Arg Ser Leu Ile Gly Arg Leu Glu Thr
1               5                   10                  15

Gln Pro Pro Ile
            20

<210> SEQ ID NO 884
<211> LENGTH: 20
<212> TYPE: PRT
<213> ORGANISM: Artificial Sequence
<220> FEATURE:
<223> OTHER INFORMATION: Synthetic

<400> SEQUENCE: 884

Ser Leu Ile Gly Lys Val Asp Gly Thr Ser His Val Thr Gly Gly Gly
1               5                   10                  15

Gly Gly Ser Lys
            20

<210> SEQ ID NO 885
<211> LENGTH: 20
<212> TYPE: PRT
<213> ORGANISM: Artificial Sequence
<220> FEATURE:
<223> OTHER INFORMATION: Synthetic

<400> SEQUENCE: 885

Ser Leu Ile Gly Lys Ala Asp Gly Thr Ser His Val Thr Gly Gly Gly
1               5                   10                  15

Gly Gly Ser Lys
            20

<210> SEQ ID NO 886
<211> LENGTH: 20
<212> TYPE: PRT
<213> ORGANISM: Artificial Sequence

```
<220> FEATURE:
<223> OTHER INFORMATION: Synthetic

<400> SEQUENCE: 886

Ser Leu Ile Gly Lys Val Ala Gly Thr Ser His Val Thr Gly Gly Gly
 1               5                  10                  15

Gly Gly Ser Lys
         20

<210> SEQ ID NO 887
<211> LENGTH: 20
<212> TYPE: PRT
<213> ORGANISM: Artificial Sequence
<220> FEATURE:
<223> OTHER INFORMATION: Synthetic

<400> SEQUENCE: 887

Ser Leu Ile Gly Lys Ala Ala Gly Thr Ser His Val Thr Gly Gly Gly
 1               5                  10                  15

Gly Gly Ser Lys
         20
```

METHODS OF ALLEVIATING ITCH BY ADMINISTERING HUMAN ANTIBODIES TO HUMAN PROTEASE-ACTIVATED RECEPTOR 2

CROSS-REFERENCE TO RELATED APPLICATIONS

This application is a continuation of U.S. application Ser. No. 13/325,098, filed on Dec. 14, 2011, now U.S. Pat. No. 8,425,907, which is a divisional of U.S. application Ser. No. 12/877,133, filed on Sep. 8, 2010, now issued as U.S. Pat. No. 8,101,724, which claims to benefit under 35 U.S.C. §119(e) of U.S. provisional application No. 61/240,783, filed on Sep. 9, 2009, 61/242,821, filed on Sep. 16, 2009, and 61/317,839, filed on Mar. 26, 2010, the disclosures of which are herein incorporated by reference in their entireties.

FIELD OF THE INVENTION

The present invention relates to antibodies, and antigen-binding fragments thereof, which are specific for protease-activated receptor-2 (PAR-2).

BACKGROUND

Protease-activated receptors ("PARs") are a family of seven-transmembrane G-protein-coupled receptors. Among seven-transmembrane G-protein-coupled receptors PARs have a unique mode of activation; that is, PARs are activated by proteolytic cleavage at the amino terminus to generate a new N-terminal domain which serves as a "tethered ligand." The tethered ligand interacts with the extracellular loop-2 of the receptor thereby resulting in receptor activation. Currently, there are four known members of the PAR family, designated PAR-1, PAR-2, PAR-3 and PAR-4.

PAR-2 has also been referred to as "C140." (see U.S. Pat. No. 5,874,400). Both human and murine PAR-2 share the protease cleavage domain SKGRSLIG (residues 6-13 of SEQ ID NO:852, and residues 8-15 of SEQ ID NO:856). This sequence is cleaved between the R and S residues by a variety of proteases such as trypsin, as well as by mast cell tryptase, tissue factor/factor VIIa complex and factor Xa, neutrophil proteinase 3 (PR-3), human leukocyte elastase, and proteases originating from pathogenic organisms.

PAR-2 activity has been implicated in or associated with several diseases and conditions including inflammatory diseases, pain, gastrointestinal conditions, neurological diseases, and cardiovascular disorders (see, e.g., Linder et al., 2000, J. Immunol. 165:6504-6510; Vergnolle et al., 2001, Nature Medicine 7:821-826; Cenac et al., 2007, J. Clin. Investigation 117:636-647; Vergnolle, 2004, British J. Pharmacol. 141:1264-1274; Knight et al., 2001, J. Allergy Clin. Immunol. 108:797-803; Schmidlin et al., 2002, J. Immunol. 169: 5315-5321). Antibodies that bind to PAR-2 have the potential to antagonize the activity of PAR-2 in vivo. Anti-PAR-2 antibodies are therefore potentially useful for treating and/or ameliorating a variety of disease conditions.

Antibodies that bind to PAR-2, and certain therapeutic uses thereof, are mentioned in U.S. Pat. No. 5,874,400, US 2007/0237759, WO 2009/005726, and US 2010/0119506. Nonetheless, there remains a need in the art for novel PAR-2 modulating agents, including anti-PAR-2 antibodies, that can be used to treat PAR-2-mediated diseases and conditions.

BRIEF SUMMARY OF THE INVENTION

The present invention provides human antibodies that bind to human PAR-2. The antibodies of the invention are useful, inter alia, for inhibiting PAR-2-mediated signaling and for treating diseases and disorders caused by or related to PAR-2 activation.

The present invention includes antibodies which interact with the N-terminal region of PAR-2 and block proteolytic cleavage at the activating PAR-2 protease cleavage site (as defined herein) but do not block proteolytic cleavage at one or more non-activating protease cleavage sites. According to certain embodiments, anti-PAR-2 antibodies which exhibit such proteolytic cleavage blocking properties interact with specific amino acids in the vicinity of the activating PAR-2 protease cleavage site. For example, the present invention provides anti-PAR-2 antibodies with protease cleavage blocking activity and which interact with Val-42 and Asp-43 of human PAR-2 (SEQ ID NO:851), and may further interact with one or more human PAR-2 residues selected from the group consisting of Ser-37, Leu-38, Ile-39, Gly-40, and Gly-44.

According to other embodiments, the anti-PAR-2 antibodies of the present invention specifically bind to human PAR-2 and monkey PAR-2 but do not bind to at least one member selected from the group consisting of mouse, rat, rabbit, dog and pig PAR-2. The present invention also includes antibodies that are capable of inhibiting or attenuating proteolytic activation of PAR-2 but do not block proteolytic cleavage of PAR-2. Exemplary methods for measuring/assessing an antibody's ability to block PAR-2 cleavage or proteolytic activation are described herein.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, J. Immunol. 164:1925-1933).

The present invention provides an antibody or antigen-binding fragment of an antibody comprising a heavy chain variable region (HCVR) having an amino acid sequence selected from the group consisting of SEQ ID NO: 2, 18, 22, 26, 42, 46, 50, 66, 70, 74, 90, 94, 98, 114, 118, 122, 138, 142, 146, 162, 166, 170, 186, 190, 194, 210, 214, 218, 234, 238, 242, 258, 262, 266, 282, 286, 290, 306, 310, 314, 330, 334, 338, 354, 358, 362, 378, 382, 386, 402, 406, 410, 426, 430, 434, 450, 454, 458, 474, 478, 482, 498, 502, 506, 522, 526, 530, 546, 550, 554, 570, 574, 578, 594, 598, 602, 618, 622, 626, 642, 646, 650, 666, 670, 674, 690, 694, 698, 714, 718, 722, 738, 742, 746, 762, 766, 770, 786, 790, 794, 810, 814, 818, 834, and 838, or a substantially similar sequence thereof having at least 90%, at least 95%, at least 98% or at least 99% sequence identity. According to certain embodiments, the antibody or antigen-binding portion of an antibody comprises a HCVR having an amino acid sequence selected from the group consisting of SEQ ID NO: 98, 146, 338, and 714.

The present invention also provides an antibody or antigen-binding fragment of an antibody comprising a light chain variable region (LCVR) having an amino acid sequence selected from the group consisting of SEQ ID NO: 10, 20, 24, 34, 44, 48, 58, 68, 72, 82, 92, 96, 106, 116, 120, 130, 140, 144, 154, 164, 168, 178, 188, 192, 202, 212, 216, 226, 236, 240, 250, 260, 264, 274, 284, 288, 298, 308, 312, 322, 332, 336, 346, 356, 360, 370, 380, 384, 394, 404, 408, 418, 428, 432, 442, 452, 456, 466, 476, 480, 490, 500, 504, 514, 524, 528, 538, 548, 552, 562, 572, 576, 586, 596, 600, 610, 620, 624, 634, 644, 648, 658, 668, 672, 682, 692, 696, 706, 716, 720, 730, 740, 744, 754, 764, 768, 778, 788, 792, 802, 812, 816, 826, 836, and 840, or a substantially similar sequence thereof having at least 90%, at least 95%, at least 98% or at least 99% sequence identity. According to certain embodiments, the antibody or antigen-binding portion of an antibody comprises a LCVR having an amino acid sequence selected from the group consisting of SEQ ID NO: 106, 154, 346, and 692.

The present invention also provides an antibody or antigen-binding fragment thereof comprising a HCVR and LCVR (HCVR/LCVR) sequence pair selected from the group consisting of SEQ ID NO: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260, 262/264, 266/274, 282/284, 286/288, 290/298, 306/308, 310/312, 314/322, 330/332, 334/336, 338/346, 354/356, 358/360, 362/370, 378/380, 382/384, 386/394, 402/404, 406/408, 410/418, 426/428, 430/432, 434/442, 450/452, 454/456, 458/466, 474/476, 478/480, 482/490, 498/500, 502/504, 506/514, 522/524, 526/528, 530/538, 546/548, 550/552, 554/562, 570/572, 574/576, 578/586, 594/596, 598/600, 602/610, 618/620, 622/624, 626/634, 642/644, 646/648, 650/658, 666/668, 670/672, 674/682, 690/692, 694/696, 698/706, 714/716, 714/692, 718/720, 722/730, 738/740, 742/744, 746/754, 762/764, 766/768, 770/778, 786/788, 790/792, 794/802, 810/812, 814/816, 818/826, 834/836, and 838/840. According to certain embodiments, the antibody or fragment thereof comprises a HCVR and LCVR selected from the amino acid sequence pairs of SEQ ID NO: 98/106, 146/154, 338/346, and 714/692.

The present invention also provides an antibody or antigen-binding fragment of an antibody comprising a heavy chain CDR3 (HCDR3) domain having an amino acid sequence selected from the group consisting of SEQ ID NO: 8, 32, 56, 80, 104, 128, 152, 176, 200, 224, 248, 272, 296, 320, 344, 368, 392, 416, 440, 464, 488, 512, 536, 560, 584, 608, 632, 656, 680, 704, 728, 752, 776, 800, and 824, or a substantially similar sequence thereof having at least 90%, at least 95%, at least 98% or at least 99% sequence identity; and a light chain CDR3 (LCDR3) domain having an amino acid sequence selected from the group consisting of SEQ ID NO: 16, 40, 64, 88, 112, 136, 160, 184, 208, 232, 256, 280, 304, 328, 352, 376, 400, 424, 448, 472, 496, 520, 544, 568, 592, 616, 640, 664, 688, 712, 736, 760, 784, 808, and 832, or a substantially similar sequence thereof having at least 90%, at least 95%, at least 98% or at least 99% sequence identity.

In certain embodiments, the antibody or antigen-binding portion of an antibody comprises a HCDR3/LCDR3 amino acid sequence pair selected from the group consisting of SEQ ID NO: 8/16, 32/40, 56/64, 80/88, 104/112, 128/136, 152/160, 176/184, 200/208, 224/232, 248/256, 272/280, 296/304, 320/328, 344/352, 368/376, 392/400, 416/424, 440/448, 464/472, 488/496, 512/520, 536/544, 560/568, 584/592, 608/616, 632/640, 656/664, 680/688, 704/712, 728/736, 752/760, 776/784, 800/808, and 824/832. According to certain embodiments, the antibody or antigen-binding portion of an antibody comprises a HCDR3/LCDR3 amino acid sequence pair selected from the group consisting of SEQ ID NO: 104/112, 152/160, 344/352 and 704/712. Non-limiting examples of anti-PAR-2 antibodies having these HCDR3/LCDR3 pairs are the antibodies designated H4H588N, H4H591N, H4H618N, and H4H581P, respectively.

The present invention also provides an antibody or fragment thereof further comprising a heavy chain CDR1 (HCDR1) domain having an amino acid sequence selected from the group consisting of SEQ ID NO: 4, 28, 52, 76, 100, 124, 148, 172, 196, 220, 244, 268, 292, 316, 340, 364, 388, 412, 436, 460, 484, 508, 532, 556, 580, 604, 628, 652, 676, 700, 724, 748, 772, 796, and 820, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 6, 30, 54, 78, 102, 126, 150, 174, 198, 222, 246, 270, 294, 318, 342, 366, 390, 414, 438, 462, 486, 510, 534, 558, 582, 606, 630, 654, 678, 702, 726, 750, 774, 798, and 822, or a substantially similar sequence thereof having at least 90%, at least 95%, at least 98% or at least 99% sequence identity; a light chain CDR1 (LCDR1) domain having an amino acid sequence selected from the group consisting of SEQ ID NO: 12, 36, 60, 84, 108, 132, 156, 180, 204, 228, 252, 276, 300, 324, 348, 372, 396, 420, 444, 468, 492, 516, 540, 564, 588, 612, 636, 660, 684, 708, 732, 756, 780, 804, and 828, or a substantially similar sequence thereof having at least 90%, at least 95%, at least 98% or at least 99% sequence identity; and a light chain CDR2 (LCDR2) domain having an amino acid sequence selected from the group consisting of SEQ ID NO: 14, 38, 62, 86, 110, 134, 158, 182, 206, 230, 254, 278, 302, 326, 350, 374, 398, 422, 446, 470, 494, 518, 542, 566, 590, 614, 638, 662, 686, 710, 734, 758, 782, 806, and 830, or a substantially similar sequence thereof having at least 90%, at least 95%, at least 98% or at least 99% sequence identity.

Certain non-limiting, exemplary antibodies and antigen-binding fragments of the invention comprise HCDR1, HCDR2, HCDR3, LCDR1, LCDR2 and LCDR3 domains, respectively, selected from the group consisting of: (i) SEQ ID NO: 100, 102, 104, 108, 110 and 112 (e.g., H4H588N); (ii) SEQ ID NO: 148, 150, 152, 156, 158 and 160 (e.g., H4H591N); (iii) SEQ ID NO: 340, 342, 344, 348, 350 and 352 (e.g., H4H618N); and (iv) SEQ ID NO: 700, 702, 704, 708, 710 and 712 (e.g., H4H581P). The amino acid sequences of these exemplary CDRs are depicted in FIGS. 2 and 3.

In a related embodiment, the invention comprises an antibody or antigen-binding fragment of an antibody which specifically binds PAR-2, wherein the antibody or fragment comprises the heavy and light chain CDR domains contained within heavy and light chain sequences selected from the group consisting of SEQ ID NO: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260, 262/264, 266/274, 282/284, 286/288, 290/298, 306/308, 310/312, 314/322, 330/332, 334/336, 338/346, 354/356, 358/360, 362/370, 378/380, 382/384, 386/394, 402/404, 406/408, 410/418, 426/428, 430/432, 434/442, 450/452, 454/456, 458/466, 474/476, 478/480, 482/490, 498/500, 502/504, 506/514, 522/524, 526/528, 530/538, 546/548, 550/552, 554/562, 570/572, 574/576, 578/586, 594/596, 598/600, 602/610, 618/620, 622/624, 626/634, 642/644, 646/648, 650/658, 666/668, 670/672, 674/682, 690/692, 694/696, 698/706, 714/716, 714/692, 718/720, 722/730, 738/740, 742/744, 746/754, 762/764, 766/768, 770/778, 786/788, 790/792, 794/802, 810/812, 814/816, 818/826, 834/836, and 838/840. According to certain embodiments, the antibody or fragment thereof comprises the CDR sequences contained within HCVRs and LCVRs selected from the amino acid sequence pairs of SEQ ID NO: 98/106, 146/154, 338/346, and 714/692. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273: 927-948 (1997); and Martin et al., *Proc. Natl. Acad. Sci.* USA 86:9268-9272 (1989). Public databases are also available for identifying CDR sequences within an antibody.

In another aspect, the invention provides nucleic acid molecules encoding anti-PAR-2 antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 21, 25, 41, 45, 49, 65, 69, 73, 89, 93, 97, 113, 117, 121, 137, 141, 145, 161, 165, 169, 185, 189, 193, 209, 213, 217, 233, 237, 241, 257, 261, 265, 281, 285, 289, 305, 309, 313, 329, 333, 337, 353, 357, 361, 377, 381, 385, 401, 405, 409, 425, 429, 433, 449, 453, 457, 473, 477, 481, 497, 501, 505, 521, 525, 529, 545, 549, 553, 569, 573, 577, 593, 597, 601, 617, 621, 625, 641, 645, 649, 665, 669, 673, 689, 693, 697, 713, 717, 721, 737, 741, 745, 761, 765, 769, 785, 789, 793, 809, 813, 817, 833, and 837, or a substantially identical sequence having at least 90%, at least 95%, at least 98%, or at least 99% homology thereof. According to certain embodiments, the antibody or fragment thereof comprises a HCVR encoded by a nucleic acid sequence selected from the group consisting of SEQ ID NO: 97, 145, 337, and 713.

The present invention also provides an antibody or fragment thereof comprising a LCVR encoded by a nucleic acid sequence selected from the group consisting of SEQ ID NO: 9, 19, 23, 33, 43, 47, 57, 67, 71, 81, 91, 95, 105, 115, 119, 129, 139, 143, 153, 163, 167, 177, 187, 191, 201, 211, 215, 225, 235, 239, 249, 259, 263, 273, 283, 287, 297, 307, 311, 321, 331, 335, 345, 355, 359, 369, 379, 383, 393, 403, 407, 417, 427, 431, 441, 451, 455, 465, 475, 479, 489, 499, 503, 513, 523, 527, 537, 547, 551, 561, 571, 575, 585, 595, 599, 609, 619, 623, 633, 643, 647, 657, 667, 671, 681, 691, 695, 705, 715, 719, 729, 739, 743, 753, 763, 767, 777, 787, 791, 801, 811, 815, 825, 835, and 839, or a substantially identical sequence having at least 90%, at least 95%, at least 98%, or at least 99% homology thereof. According to certain embodiments, the antibody or fragment thereof comprises a LCVR encoded by a nucleic acid sequence selected from the group consisting of SEQ ID NO: 105, 153, 345, and 715.

The present invention also provides an antibody or antigen-binding fragment of an antibody comprising a HCDR3 domain encoded by a nucleotide sequence selected from the group consisting of SEQ ID NO: 7, 31, 55, 79, 103, 127, 151, 175, 199, 223, 247, 271, 295, 319, 343, 367, 391, 415, 439, 463, 487, 511, 535, 559, 583, 607, 631, 655, 679, 703, 727, 751, 775, 799, and 823, or a substantially identical sequence having at least 90%, at least 95%, at least 98%, or at least 99% homology thereof; and a LCDR3 domain encoded by a nucleotide sequence selected from the group consisting of SEQ ID NO: 15, 39, 63, 87, 111, 135, 159, 183, 207, 231, 255, 279, 303, 327, 351, 375, 399, 423, 447, 471, 495, 519, 543, 567, 591, 615, 639, 663, 687, 711, 735, 759, 783, 807, and 831, or a substantially identical sequence having at least 90%, at least 95%, at least 98%, or at least 99% homology thereof. According to certain embodiments, the antibody or fragment thereof comprises HCDR3 and LCDR3 sequences encoded by the nucleic acid sequence pairs selected from the group consisting of SEQ ID NO: 103/111, 151/159, 343/351, and 703/711.

The present invention also provides an antibody or fragment thereof which further comprises a HCDR1 domain encoded by a nucleotide sequence selected from the group consisting of SEQ ID NO: 3, 27, 51, 75, 99, 123, 147, 171, 195, 219, 243, 267, 291, 315, 339, 363, 387, 411, 435, 459, 483, 507, 531, 555, 579, 603, 627, 651, 675, 699, 723, 747, 771, 795, and 819, or a substantially identical sequence having at least 90%, at least 95%, at least 98%, or at least 99% homology thereof; a HCDR2 domain encoded by a nucleotide sequence selected from the group consisting of SEQ ID NO: 5, 29, 53, 77, 101, 125, 149, 173, 197, 221, 245, 269, 293, 317, 341, 365, 389, 413, 437, 461, 485, 509, 533, 557, 581, 605, 629, 653, 677, 701, 725, 749, 773, 797, and 821, or a substantially identical sequence having at least 90%, at least 95%, at least 98%, or at least 99% homology thereof; a LCDR1 domain encoded by a nucleotide sequence selected from the group consisting of SEQ ID NO: 11, 35, 59, 83, 107, 131, 155, 179, 203, 227, 251, 275, 299, 323, 347, 371, 395, 419, 443, 467, 491, 515, 539, 563, 587, 611, 635, 659, 683, 707, 731, 755, 779, 803, and 827, or a substantially identical sequence having at least 90%, at least 95%, at least 98%, or at least 99% homology thereof; and a LCDR2 domain encoded by a nucleotide sequence selected from the group consisting of SEQ ID NO: 13, 37, 61, 85, 109, 133, 157, 181, 205, 229, 253, 277, 301, 325, 349, 373, 397, 421, 445, 469, 493, 517, 541, 565, 589, 613, 637, 661, 685, 709, 733, 757, 781, 805, 829, or a substantially identical sequence having at least 90%, at least 95%, at least 98%, or at least 99% homology thereof.

According to certain embodiments, the antibody or fragment thereof comprises the heavy and light chain CDR sequences encoded by the nucleic acid sequences of SEQ ID NO: 97 and 105; SEQ ID NO: 145 and 153; SEQ ID NO: 337 and 345; or SEQ ID NO: 713 and 715.

The present invention also provides an isolated antibody or antigen-binding fragment of an antibody that specifically binds PAR-2, comprising a HCDR3 and a LCDR3, wherein the HCDR3 comprises an amino acid sequence of the formula $X^1$-$X^2$-$X^3$-$X^4$-$X^5$-$X^6$-$X^7$-$X^8$-$X^9$-$X^{10}$-$X^{11}$-$X^{12}$ (SEQ ID NO:843) wherein $X^1$ is Ala or Val, $X^2$ is Lys, $X^3$ is Gly or Glu, $X^4$ is Asp or Gly, $X^5$ is Phe or Asp, $X^6$ is Trp or Ser, $X^7$ is Ser or Gly, $X^8$ is Gly or Tyr, $X^9$ is Tyr or Asp, $X^{10}$ is Phe or Leu, $X^{11}$ is Asp or Ala, and $X^{12}$ is Tyr; and the LCDR3 comprises an amino acid sequence of the formula $X^1$-$X^2$-$X^3$-$X^4$-$X^5$-$X^6$-$X^7$-$X^8$-$X^9$ (SEQ ID NO:846) wherein $X^1$ is Met or Gln, $X^2$ is Gln, $X^3$ is Ala or Tyr, $X^4$ is Thr or Lys, $X^5$ is Gln, Ser or Ile, $X^6$ is Phe or Ser, $X^7$ is Pro, $X^8$ is Thr or Leu, and $X^9$ is Thr or absent.

In a more specific embodiment, the invention features an isolated antibody or fragment thereof that specifically binds PAR-2, comprising a HCDR1 sequence of the formula $X^1$-$X^2$-$X^3$-$X^4$-$X^5$-$X^6$-$X^7$-$X^8$ (SEQ ID NO:841), wherein $X^1$ is Gly, $X^2$ is Phe, $X^3$ is Thr, $X^4$ is Phe, $X^5$ is Ser or Arg, $X^6$ is Ser or Arg, $X^7$ is Tyr, and $X^8$ is Gly, Ala or Thr; a HCDR2 sequence of the formula $X^1$-$X^2$-$X^3$-$X^4$-$X^5$-$X^6$-$X^7$-$X^8$ (SEQ ID NO:842), wherein $X^1$ is Ile, $X^2$ is Ser, Gly or Thr, $X^3$ is Tyr, Gly or Asp, $X^4$ is Asp, Gly or Ser, $X^5$ is Gly or Arg, $X^6$ is Ile, Gly or Ala, $X^7$ is Asn, Ser, Arg or Gly, and $X^8$ is Lys, Ala or Thr; a HCDR3 sequence of the formula $X^1$-$X^2$-$X^3$-$X^4$-$X^5$-$X^6$-$X^7$-$X^8$-$X^9$-$X^{10}$-$X^{11}$-$X^{12}$ (SEQ ID NO:843) wherein $X^1$ is Ala or Val, $X^2$ is Lys, $X^3$ is Gly or Glu, $X^4$ is Asp or Gly, $X^5$ is Phe or Asp, $X^6$ is Trp or Ser, $X^7$ is Ser or Gly, $X^8$ is Gly or Tyr, $X^9$ is Tyr or Asp, $X^1$ is Phe or Leu, $X^{11}$ is Asp or Ala, and $X^{12}$ is Tyr; a LCDR1 sequence of the formula $X^1$-$X^2$-$X^3$-$X^4$-$X^5$-$X^6$-$X^7$-$X^8$-$X^9$-$X^{10}$-$X^{11}$ (SEQ ID NO:844) wherein $X^1$ is Gln, $X^2$ is Ser or Gly, $X^3$ is Leu or Ile, $X^4$ is Val or Ser, $X^5$ is His, Asn or Thr, $X^6$ is Ser, Asn or Tyr, $X^7$ is Asp or absent; $X^8$ is Gly or absent, $X^9$ is Asn or absent, $X^{10}$ is Thr or absent, and $X^{11}$ is Tyr or absent; a LCDR2 sequence of the formula $X^1$-$X^2$-$X^3$ (SEQ ID NO:845) wherein $X^1$ is Lys or Ala, $X^2$ is Ile, Ala or Thr, and $X^3$ is Ser; and a LCDR3 comprises an amino acid sequence of the formula $X^1$-$X^2$-$X^3$-$X^4$-$X^5$-$X^6$-$X^7$-$X^8$-$X^9$ (SEQ ID NO:846) wherein $X^1$ is Met or Gln, $X^2$ is Gln, $X^3$ is Ala or Tyr, $X^4$ is Thr or Lys, $X^5$ is Gln, Ser or Ile, $X^6$ is Phe or Ser, $X^7$ is Pro, $X^8$ is Thr or Leu, and $X^9$ is Thr or absent.

The invention encompasses anti-PAR-2 antibodies having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the invention provides a pharmaceutical composition comprising a recombinant human antibody or fragment thereof which specifically binds PAR-2 and a pharmaceutically acceptable carrier. In a related aspect, the invention features a composition which is a combination of a PAR-2 inhibitor and a second therapeutic agent. In one embodiment, the PAR-2 inhibitor is an antibody or fragment thereof. In one embodiment, the second therapeutic agent is any agent that is advantageously combined with a PAR-2 inhibitor. Exemplary agents that may be advantageously combined with a PAR-2 inhibitor include, without limitation, other agents that inhibit PAR-2 activity (including other antibodies or antigen-binding fragments thereof, peptide inhibitors, small molecule antagonists, etc) and/or agents which interfere with PAR-2 upstream or downstream signaling.

In yet another aspect, the invention provides methods for inhibiting PAR-2 activity using the anti-PAR-2 antibody or antigen-binding portion of an antibody of the invention, wherein the therapeutic methods comprise administering a therapeutically effective amount of a pharmaceutical composition comprising an antibody or antigen-binding fragment of an antibody of the invention. The disorder treated is any disease or condition which is improved, ameliorated, inhibited or prevented by removal, inhibition or reduction of PAR-2 activity. The anti-PAR-2 antibody or antibody fragment of the invention may function to block the interaction between PAR-2 and a protease (e.g., trypsin or trypsin-like serine proteases) or otherwise inhibit protease-mediated activation of PAR-2. Alternatively, or additionally, the anti-PAR-2 antibodies of the invention may interfere with the interaction between the PAR-2 tethered ligand and one or more of the PAR-2 extracellular loops (see, e.g., MacFarlane et al., 2001, Pharmacological Reviews 53:245-282 for a general discussion of PAR-2 proteolytic cleavage and activation). The antibody or antibody fragment may be used alone or in combination with one or more additional therapeutic agents.

The present invention also includes the use of an anti-PAR-2 antibody or antigen binding portion of an antibody of the invention in the manufacture of a medicament for the treatment of a disease or disorder related to or caused by PAR-2 activity in a patient.

Other embodiments will become apparent from a review of the ensuing detailed description.

BRIEF DESCRIPTION OF THE FIGURES

FIG. 2. Sequence comparison table of light chain variable regions and CDRs of antibodies H1H581P LCVR (SEQ ID NO:692, H2M588N LCVR (SEQ ID NO:106), H2M591N LCVR (SEQ ID NO:154) and H2M618N LCVR (SEQ ID NO:346).

FIGS. 3A and 3B. The top panel (A) shows C- and N-terminal biotin labeled peptides corresponding to the sequence surrounding the activating PAR-2 protease cleavage site (GTNRSSKGRSLIGKVDGT; SEQ ID NO:852). The protease cleavage sites are designated by number 1 (an upstream, non-activating protease cleavage site) and number 2 (the activating PAR-2 protease cleavage site). The expected sizes of the uncleaved and cleaved fragments are indicated in the top table. The bottom panel (B) shows the fragment sizes that were observed following 0, 5, and 15 minutes of trypsin treatment in the presence of anti-PAR-2 antibodies or negative control.

DETAILED DESCRIPTION

Figure 1:
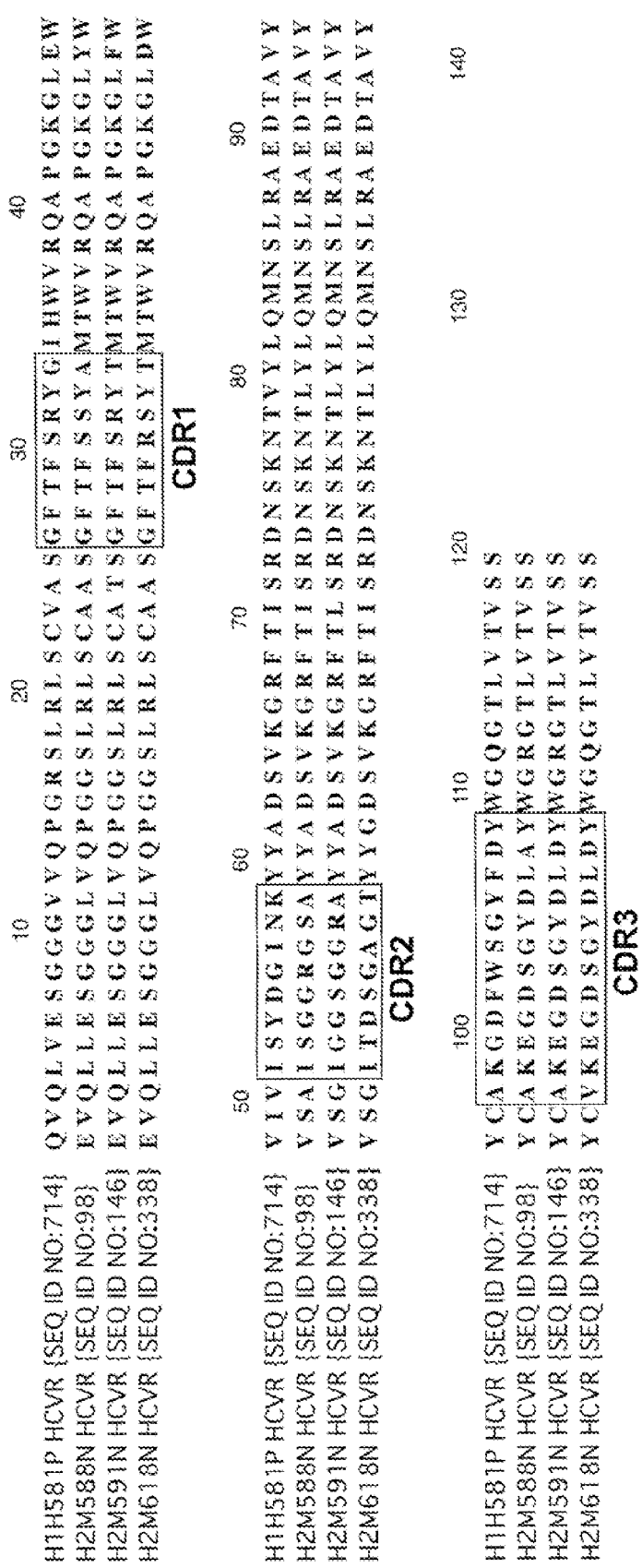
FIG. 1. Sequence comparison table of heavy chain variable regions and CDRs of antibodies H1H581P HCVR (SEQ ID NO:714, H2M588N HCVR (SEQ ID NO:98), H2M591N HCVR (SEQ ID NO:146) and H2M618N HCVR (SEQ ID NO:338).

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

As used herein, the terms "proteinase-activated receptor-2," "protease-activated receptor-2," and "PAR-2", refer to full-length PAR-2 protein. Human PAR-2 is encoded by the nucleic acid sequence shown in SEQ ID NO:850 and has the amino acid sequence of SEQ ID NO:851. Amino acid sequences of PAR-2 molecules from non-human species (e.g., mouse, monkey, rabbit, dog, pig, etc.) are available from public sources.

The term "PAR-2 fragment," as used herein, means a peptide or polypeptide comprising 4, 5, 6, 7, 8, 9, 10 or more contiguous amino acids located upstream from (i.e., N-terminal to) the activating PAR-2 protease cleavage site (as defined herein below) and/or 4, 5, 6, 7, 8, 9, 10 or more contiguous amino acids located downstream from (i.e., C-terminal to) the activating PAR-2 protease cleavage site. Exemplary PAR-2 fragments are illustrated in Example 2, Table 2 (designated Peptides "A" through "J"; i.e., SEQ ID NOs:852 through 861, respectively).

The expressions "PAR-2" and "PAR-2 fragment," as used herein refer to the human PAR-2 protein or fragment unless specified as being from a non-human species (e.g., "mouse PAR-2," mouse PAR-2 fragment," "monkey PAR-2," "monkey PAR-2 fragment," etc.).

As used in the context of the present disclosure, the expression "activating PAR-2 protease cleavage site" means the junction of residues Arg-36 and Ser-37 of human PAR-2 (SEQ ID NO:851). The activating PAR-2 protease cleavage site is the site which, when cleaved, results in the formation of the PAR-2 tethered ligand in the naturally occurring protein.

The term "PAR-2 protease," as used herein, means an enzyme which is capable of cleaving a PAR-2 or PAR-2 fragment at the activating PAR-2 protease cleavage site. Exemplary PAR-2 proteases include trypsin, cathepsin G, acrosin, tissue factor VIIa, tissue factor Xa, human airway trypsin-like protease, tryptase, membrane-type serine protease-1 (MT-SP1), TMPRSS2, protease-3, elastase, kallikrein-5, kallikrein-6, kallikrein-14, activated protein C, duodenase, gingipains-R, Der p1, Der p3, Der p9, thermolysin, serralysin, and *T. denticla* protease.

The term "antibody", as used herein, is intended to refer to immunoglobulin molecules comprising four polypeptide chains, two heavy (H) chains and two light (L) chains interconnected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-Ang-2 antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies and minibodies, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H1$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, tissue or cell in which the antibody naturally exists or is naturally produced is an "isolated antibody" for purposes of the present invention. An isolated antibody also includes an antibody in situ within a recombinant cell, as well as an antibody that has been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Specific binding can be characterized by a dissociation constant of $1 \times 10^{-6}$ M or less. Methods for determining whether two molecules specifically bind are well known in the art and include, for example, equilibrium dialysis, surface plasmon resonance, and the like. For example, an antibody that "specifically binds" human PAR-2, as used in the context of the present invention, includes antibodies that bind human PAR-2 or portion thereof (e.g., a PAR-2 fragment comprising the activating protease cleavage site) with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. (See, e.g., Example 4, herein). An isolated antibody that specifically binds human PAR-2 may, however, have cross-reactivity to other antigens, such as PAR-2 molecules from other species.

A "neutralizing" or "blocking" antibody, as used herein, is intended to refer to an antibody whose binding to PAR-2: (i) interferes with the interaction between PAR-2 or a PAR-2 fragment and one or more proteases, (ii) prevents cleavage of PAR-2 or a PAR-2 fragment by a PAR-2 protease, (iii) inhibits the interaction between the PAR-2 tethered ligand and a PAR-2 extracellular loop, and/or (iv) results in inhibition of at least one biological function of PAR-2. The inhibition caused by a PAR-2 neutralizing or blocking antibody need not be complete so long as it is detectable using an appropriate assay. Exemplary assays for detecting PAR-2 inhibition are described herein.

The fully-human anti-PAR-2 antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are back-mutated to the corresponding germline residue(s) or to a conservative amino acid substitution (natural or non-natural) of the corresponding germline residue(s) (such sequence changes are referred to herein as "germline back-mutations"). A person of ordinary skill in the art, starting with the heavy and light chain variable region sequences disclosed herein, can easily produce numerous antibodies and antigen-binding fragments which comprise one or more individual germline back-mutations or combinations thereof. In certain embodiments, all of the framework and/or CDR residues within the $V_H$ and/or $V_L$ domains are mutated back to the germline sequence. In other embodiments, only certain residues are mutated back to the germline sequence, e.g., only the mutated residues found within the first 8 amino acids of FR1 or within the last 8 amino acids of FR4, or only the mutated residues found within CDR1, CDR2 or CDR3. Furthermore, the antibodies of the present invention may contain any combination of two or more germline back-mutations within the framework and/or CDR regions, i.e., wherein certain individual residues are mutated back to the germline sequence while certain other residues that differ from the germline sequence are maintained. Once obtained, antibodies and antigen-binding fragments that contain one or more germline back-mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-PAR-2 antibodies comprising variants of any of the HCVR, LCVR, and/or CDR amino acid sequences disclosed herein having one or more conservative substitutions. For example, the present invention includes anti-PAR-2 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein. In one embodiment, the antibody comprises an HCVR having the amino acid sequence of SEQ ID NO:698 with 8 or fewer conservative amino acid substitutions. In another embodiment, the antibody comprises an HCVR having the amino acid sequence of SEQ ID NO:698 with 6 or fewer conservative amino acid substitutions. In another embodiment, the antibody comprises an HCVR having the amino acid sequence of SEQ ID NO:698 with 4 or fewer conservative amino acid substitutions. In another embodiment, the antibody comprises an HCVR having the amino acid sequence of SEQ ID NO:698 with 2 or fewer conservative amino acid substitutions. In one embodiment, the antibody comprises an LCVR having the amino acid sequence of SEQ ID NO:706 with 8 or fewer conservative amino acid substitutions. In another embodiment, the antibody comprises an LCVR having the amino acid sequence of SEQ ID NO:706 with 6 or fewer conservative amino acid substitutions. In another embodiment, the antibody comprises an LCVR having the amino acid sequence of SEQ ID NO:706 with 4 or fewer conservative amino acid substitutions. In another embodiment, the antibody comprises an LCVR having the amino acid sequence of SEQ ID NO:706 with 2 or fewer conservative amino acid substitutions.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Preparation of Human Antibodies

Methods for generating monoclonal antibodies, including fully human monoclonal antibodies are known in the art. Any such known methods can be used in the context of the present invention to make human antibodies that specifically bind to human PAR-2.

Using VELOCIMMUNE™ technology or any other known method for generating monoclonal antibodies, high affinity chimeric antibodies to PAR-2 are initially isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Bioequivalents

The anti-PAR-2 antibodies and antibody fragments of the present invention encompass proteins having amino acid sequences that vary from those of the described antibodies, but that retain the ability to bind human PAR-2. Such variant antibodies and antibody fragments comprise one or more additions, deletions, or substitutions of amino acids when compared to parent sequence, but exhibit biological activity that is essentially equivalent to that of the described antibodies. Likewise, the anti-PAR-2 antibody-encoding DNA sequences of the present invention encompass sequences that comprise one or more additions, deletions, or substitutions of nucleotides when compared to the disclosed sequence, but that encode an anti-PAR-2 antibody or antibody fragment that is essentially bioequivalent to an anti-PAR-2 antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-PAR-2 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-PAR-2 antibody variants comprising amino acid changes which modify the glycosylation characteristics of the antibodies, e.g., mutations which eliminate or remove glycosylation.

Biological Characteristics of the Antibodies

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656).

Alternatively, or additionally, the antibodies of the invention may be therapeutically useful in blocking a PAR-2 interaction or inhibiting receptor component interaction. In the case of the PAR-2 antibodies of the present invention, the antibodies may function by, inter alia, blocking or obscuring the activating PAR-2 protease cleavage site. Alternatively, the antibodies of the invention may function by interfering with the interaction between the tethered ligand and one or more extracellular loops (e.g., loop-1, loop-2 and/or loop-3).

More specifically, the anti-PAR-2 antibodies of the invention may exhibit one or more of the following characteristics: (1) ability to bind to a human PAR-2 or human PAR-2 fragment and to a non-human (e.g., mouse, monkey, rat, rabbit, dog, pig, etc.) PAR-2 or PAR-2 fragment; (2) ability to bind to a human PAR-2 or human PAR-2 fragment but not to a non-human (e.g., mouse, monkey, rat, rabbit, dog, pig, etc.) PAR-2 or PAR-2 fragment; (3) ability to bind to a human PAR-2 or human PAR-2 fragment and to a monkey PAR-2 or monkey PAR-2 fragment, but not to a mouse, rat, rabbit, dog or pig PAR-2 or PAR-2 fragment; (4) ability to bind to a human PAR-2 or human PAR-2 fragment and to a human PAR-1, PAR-3 or PAR-4 or fragment thereof; (5) ability to bind to a human PAR-2 or human PAR-2 fragment but not to a human PAR-1, PAR-3, or PAR-4 or fragment thereof; (6) ability to bind to a human PAR-2 or human PAR-2 fragment and to a non-human (e.g., mouse, monkey, rat, rabbit, dog, pig, etc.) PAR-1, PAR-3 or PAR-4 or fragment thereof; (7) ability to bind to a human PAR-2 or human PAR-2 fragment but not to a non-human (e.g., mouse, monkey, rat, rabbit, dog, pig, etc.) PAR-1, PAR-3 or PAR-4 or fragment thereof; (8) ability to block proteolytic cleavage of a PAR-2 or a PAR-2 fragment; (9) ability to block proteolytic cleavage of a human PAR-2 or human PAR-2 fragment and a non-human (e.g., mouse, monkey, rat, rabbit, dog, pig, etc.) PAR-2 or PAR-2 fragment; (10) ability to block proteolytic cleavage of a human PAR-2 or human PAR-2 fragment but not a non-human (e.g., mouse, monkey, rat, rabbit, dog, pig, etc.) PAR-2 or PAR-2 fragment; (11) ability to block proteolytic cleavage of a human PAR-2 or human PAR-2 fragment and a human PAR-1, PAR-3 or PAR-4 or fragment thereof; (12) ability to block proteolytic cleavage of a human PAR-2 or human PAR-2 fragment but not a human PAR-1, PAR-3 or PAR-4 or fragment thereof; (13) ability to block proteolytic cleavage of a human PAR-2 or human PAR-2 fragment and a non-human (e.g., mouse, monkey, rat, rabbit, dog, pig, etc.) PAR-1, PAR-3 or PAR-4 or fragment thereof; and/or (14) ability to block proteolytic cleavage of a human PAR-2 or human PAR-2 fragment but not a non-human (e.g., mouse, monkey, rat, rabbit, dog, pig, etc.) PAR-1, PAR-3 or PAR-4 or fragment thereof.

As used in items (8)-(14) above, the term "proteolytic cleavage" means cleavage of a PAR molecule (PAR-1, PAR-2, PAR-3 or PAR-4) or fragment thereof by a PAR-2 protease or other enzyme that is capable of cleaving PAR-2 at the activating PAR-2 protease cleavage site.

The N-terminal region of human PAR-2 has at least two "non-activating" protease cleavage sites, i.e., sites that are capable of being cleaved by trypsin but do not result in activation of the receptor. The N-terminal non-activating protease cleavage sites are located: (a) at the junction of residues Arg-31 and Ser-32 of human PAR-2 (SEQ ID NO:851); and (b) at the junction of residues Lys-34 and Gly-35 of human PAR-2 (SEQ ID NO:851). The activating and non-activating cleavage sites at the N-terminus of PAR-2 are illustrated in FIG. 5 (white triangles indicate the non-activating protease cleavage sites and the black triangle indicates the activating PAR-2 protease cleavage site); see also FIG. 4. The present invention includes anti-PAR-2 antibodies that block the activating PAR-2 protease cleavage site but do not block one or both of the non-activating protease cleavage sites. Whether a candidate antibody blocks or does not block a particular protease cleavage site can be determined by a person of ordinary skill in the art using any suitable assay such as the exemplary in vitro blocking assays set forth in Example 8 herein. As illustrated in Example 8, the exemplary antibody H4H581P was shown to block trypsin cleavage at the activating PAR-2 protease cleavage site and at the non-activating protease cleavage site located at the junction of residues Lys-34 and Gly-35 of human PAR-2 (SEQ ID NO:851), but did not block cleavage at the non-activating protease cleavage site located at the junction of residues Arg-31 and Ser-32 of human PAR-2 (SEQ ID NO:851). By contrast, the comparator antibody used in Example 8 blocked cleavage at the activating PAR-2 protease cleavage site and at both non-activating sites. The differential blocking capabilities of these exemplary anti-PAR-2 antibodies most likely reflects differences in the particular regions of the PAR-2 molecule with which these antibodies bind (see, e.g., Example 9 herein).

As used herein, an antibody "does not bind" to a specified target molecule (e.g., mouse PAR-2, rat PAR-2, rabbit PAR-2, dog PAR-2, pig PAR-2, or fragment thereof) if the antibody, when tested for binding to the target molecule at 25° C. in a surface plasmon resonance assay, exhibits a $K_D$ of greater than 500 nM, or if tested for binding to the target molecule at 25° C. in an enzyme-linked immunosorbent assay (ELISA) exhibits an $EC_{50}$ of greater than 50 nM, or fails to exhibit any binding in either type of assay or equivalent thereof.

Certain anti-PAR-2 antibodies of the present invention are able to inhibit or attenuate PAR-2 activation in an in vitro cellular assay. A non-limiting, exemplary in vitro cellular assay for PAR-2 activation is illustrated in Example 6, herein. In this Example, cells are used which express PAR-2 and harbor a construct comprising NF-κB fused to a reporter molecule (e.g., luciferase). Briefly, such cells are combined with an anti-PAR-2 antibody, followed by treatment with a PAR-2 protease. Cells that are treated with the protease in the presence of an inhibitory anti-PAR-2 antibody will exhibit significantly less or no reporter signal as compared to cells treated with the protease in the absence of an inhibitory anti-PAR-2 antibody. The concentration of antibody necessary to achieve half-maximal inhibition of reporter signal ($IC_{50}$) can be calculated using such an assay. The present invention includes inhibitory anti-PAR-2 antibodies that exhibit an $IC_{50}$ of less than 300 nM when tested in an in vitro cellular assay for PAR-2 activation as described above. For example, the invention includes anti-PAR-2 antibodies with an $IC_{50}$ of less than 300, 290, 280, 270, 260, 250, 240, 230, 220, 210, 200, 190, 180, 170, 160, 150, 140, 130, 120, 110, 100, 90, 80, 70, 60, 50, 40, 30, 20, 10, 18, 16, 14, 12, 10, 9, 8, 7, 6, 5, 4, 3, 2, or 1 nM when tested in an in vitro cellular assay for PAR-2 activation as described above in which the cells are incubated with the antibody for 1 h at 37° C. followed by treatment with 20 nM trypsin (or other PAR-2 protease) for 5 h at 37° C.

The present invention includes anti-PAR-2 antibodies and antigen binding fragments thereof which bind to one or more of the following peptides: Peptide A (GTNRSSKGRSLIGKVDGT, SEQ ID NO:852); Peptide B (SLIGKVDGTSHVTG, SEQ ID NO:853); Peptide C (SLIGKV, SEQ ID NO:854); Peptide D (N-terminal domain of human PAR-2-mouse IgG, SEQ ID NO:855); Peptide E (LAPGRNNSKGRSLIGRLETQ, SEQ ID NO:856); Peptide F (GTNRSSKGRSLIGRVDGT, SEQ ID NO:857); Peptide G (GPNSKGRSLIGRLDTP, SEQ ID NO:858); Peptide H (GTNKTSKGRSLIGRNTGS, SEQ ID NO:859); Peptide I (GTNRTSKGRSLIGKTDSS, SEQ ID NO:860); Peptide J (GTSRPSKGRSLIGKADNT, SEQ ID NO:861); Peptide K (ATNATLDPRSFLLRNPND, SEQ ID NO:862); Peptide L (DTNNLAKPTLPIKTFRGA, SEQ ID NO:863); or Peptide M (ESGSTGGGDDSTPSILPAP, SEQ ID NO:864). Additional information regarding these peptides can be found in Example 3 herein. These peptides may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

With regard to the aforementioned Peptides, the present invention includes anti-PAR-2 antibodies with one or more of the following binding profiles: (1) binding to Peptides A and B, but not binding to Peptide C; (2) binding to Peptides A, B and D, but not binding to Peptide C; (3) binding to Peptides A, B, D and F, but not binding to Peptide C; (4) binding to Peptides A, B, D and F, but not binding to either of Peptides C or E; (5) binding to Peptides A, B and D, but not binding to any of Peptides K, L or M; (6) binding to Peptides A, B and F, but not binding to any of Peptides K, L or M; (7) binding to Peptides A, B, D and F, but not binding to any of Peptides K, L or M; and/or (8) binding to at least three of Peptides A, B, C, D, E, F, G, I and J, but not binding to Peptide H. Other binding profiles of the antibodies of the invention will be evident from the examples herein.

Epitope Mapping and Related Technologies

To screen for antibodies that bind to a particular epitope (e.g., those which block binding of IgE to its high affinity receptor), a routine cross-blocking assay such as that described Antibodies, Harlow and Lane (Cold Spring Harbor Press, Cold Spring Harb., NY) can be performed. Other methods include alanine scanning mutants, peptide blots (Reineke, 2004, Methods Mol Biol 248:443-463, herein specifically incorporated by reference in its entirety), or peptide cleavage analysis. In addition, methods such as epitope excision, epitope extraction and chemical modification of antigens can be employed (Tomer, 2000, Protein Science 9:487-496, herein specifically incorporated by reference in its entirety).

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the anti-PAR-2 antibodies of the invention into groups of antibodies binding different epitopes.

The present invention includes anti-PAR-2 antibodies which bind to an epitope at or near (e.g., within 5, 10, 15 or 20 amino acids of) the activating PAR-2 protease cleavage site.

In certain embodiments, the anti-PAR-2 antibodies bind to an epitope located upstream from (i.e., N-terminal to) the activating PAR-2 protease cleavage site. In certain other embodiments of the invention, the anti-PAR-2 antibodies bind to an epitope located downstream from (i.e., C-terminal to) the activating PAR-2 protease cleavage site. In yet other embodiments, the anti-PAR-2 antibodies of the invention may bind an epitope that includes both amino acid sequences located upstream from the activating PAR-2 protease cleavage site and amino acid sequences located downstream from the activating PAR-2 protease cleavage site.

Alternatively, the anti-PAR-2 antibodies of the invention may, in certain embodiments, bind to an epitope located on one or more extracellular loops of the PAR-2 protein (e.g., extracellular loop 1, extracellular loop 2 and/or extracellular loop 3).

The present invention includes isolated human antibodies or antigen-binding fragments thereof that interact with certain amino acid residues located downstream from the activating PAR-2 protease cleavage site. For example, the present invention includes isolated human antibodies or antigen-binding fragments thereof that interact with Val-42 and Asp-43 of human PAR-2 (SEQ ID NO:851). In addition to these two residues, the isolated human antibodies or antigen-binding fragments thereof may also interact with one or more of the following residues located downstream from the activating PAR-2 protease cleavage site: Ser-37, Leu-38, Ile-39, Gly-40 or Gly-44 of human PAR-2 (SEQ ID NO:851). In certain embodiments, the isolated human antibody or antigen binding fragment thereof does not interact with Lys-41 of human PAR-2 (SEQ ID NO:851). For example, the present invention includes isolated human antibodies or antigen-binding fragments thereof that interact with Ser-37, Leu-38, Ile-39, Gly-40, Val-42 and Asp-43 of human PAR-2 (SEQ ID NO:851), and do not interact with Lys-41 of human PAR-2 (SEQ ID NO:851). The experimental procedures illustrated in Example 9 can be used to determine if a candidate anti-PAR-2 antibody "interacts with" or "does not interact with" a particular amino acid residue of PAR-2. For example, if a candidate antibody is tested for binding to a peptide having SEQ ID NO:879 (corresponding to the N-terminal region of PAR-2 wherein Val-42 of PAR-2 is mutated to alanine, see, e.g., Tables 24-28) using the procedure of Example 9, and the $T_{1/2}$ of the antibody is less than 30% the $T_{1/2}$ observed when the candidate antibody is tested for binding to the wild-type peptide (SEQ ID NO:871), then for purposes of the present disclosure, the candidate antibody is deemed to "interact with" the amino acid that was mutated to alanine (in this case, Val-42); that is, binding of the candidate antibody is substantially reduced when the amino acid corresponding to Val-42 is mutated to alanine (such residues are depicted by black circles in FIG. 5). On the other hand, if a candidate antibody is tested for binding to a peptide having SEQ ID NO:878 (corresponding to the N-terminal region of PAR-2 wherein Lys-41 of PAR-2 is mutated to alanine, see, e.g., Tables 24-28) using the procedure of Example 9, and the $T_{1/2}$ of the antibody is greater than or equal to 30% the $T_{1/2}$ observed when the candidate antibody is tested for binding to the wild-type peptide (SEQ ID NO:871), then for purposes of the present disclosure, the candidate antibody is deemed to "not interact with" the amino acid that was mutated to alanine (in this case, Lys-41); that is, binding of the candidate antibody is not substantially reduced when the amino acid corresponding to Lys-41 is mutated to alanine (such residues are depicted by white circles in FIG. 5).

The present invention includes anti-PAR-2 antibodies that bind to the same epitope as any of the specific exemplary antibodies described herein (e.g., H4H581P, H4H588N, H4H591N or H4H618N). Likewise, the present invention also includes anti-PAR-2 antibodies that cross-compete for binding to PAR-2 or a PAR-2 fragment with any of the specific exemplary antibodies described herein (e.g., H4H581P, H4H588N, H4H591N or H4H618N).

One can easily determine whether an antibody binds to the same epitope as, or competes for binding with, a reference anti-PAR-2 antibody by using routine methods known in the art. For example, to determine if a test antibody binds to the same epitope as a reference anti-PAR-2 antibody of the invention, the reference antibody is allowed to bind to a PAR-2 protein or peptide under saturating conditions. Next, the ability of a test antibody to bind to the PAR-2 molecule is assessed. If the test antibody is able to bind to PAR-2 following saturation binding with the reference anti-PAR-2 antibody, it can be concluded that the test antibody binds to a different epitope than the reference anti-PAR-2 antibody. On the other hand, if the test antibody is not able to bind to the PAR-2 molecule following saturation binding with the reference anti-PAR-2 antibody, then the test antibody may bind to the same epitope as the epitope bound by the reference anti-PAR-2 antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding with a reference anti-PAR-2 antibody, the above-described binding methodology is performed in two orientations: In a first orientation, the reference antibody is allowed to bind to a PAR-2 molecule under saturating conditions followed by assessment of binding of the test antibody to the PAR-2 molecule. In a second orientation, the test antibody is allowed to bind to a PAR-2 molecule under saturating conditions followed by assessment of binding of the reference antibody to the PAR-2 molecule. If, in both orientations, only the first (saturating) antibody is capable of binding to the PAR-2 molecule, then it is concluded that the test antibody and the reference antibody compete for binding to PAR-2. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Species Selectivity and Species Cross-Reactivity

According to certain embodiments of the invention, the anti-PAR-2 antibodies bind to human PAR-2 but not to PAR-2 from other species. Alternatively, the anti-PAR-2 antibodies of the invention, in certain embodiments, bind to human PAR-2 and to PAR-2 from one or more non-human species. For example, the anti-PAR-2 antibodies of the invention may bind to human PAR-2 and may bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee PAR-2.

Immunoconjugates

The invention encompasses anti-PAR-2 monoclonal antibodies conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, see for example, WO 05/103081, herein specifically incorporated by reference).

Multispecific Antibodies

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-PAR-2 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present invention includes bi-specific antibodies wherein one arm of an immunoglobulin is specific for human PAR-2 or a fragment thereof, and the other arm of the immunoglobulin is specific for a second therapeutic target or is conjugated to a therapeutic moiety such as a trypsin inhibitor.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82lI (by IMGT; Q355R, N384S, K392N, V397M, R409K, E419Q, and V422I by EU) in the case of IgG4 antibodies. Variations on the bi-specific antibody format described above are contemplated within the scope of the present invention.

Therapeutic Formulation and Administration

The invention provides therapeutic compositions comprising the anti-PAR-2 antibodies or antigen-binding fragments thereof of the present invention. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. The preferred dose is typically calculated according to body weight or body surface area. When an antibody of the present invention is used for treating a condition or disease associated with PAR-2 activity in an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering PAR-2 antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN™ JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The antibodies of the invention are useful, inter alia, for the treatment, prevention and/or amelioration of any disease or disorder associated with PAR-2 activity, including diseases or disorders associated with the proteolytic activation of PAR-2. Exemplary diseases and disorders that can be treated with the anti-PAR-2 antibodies of the present invention include pain conditions such as nociceptive pain and visceral pain, as well as pain associated with conditions such as inflammation, post-operative incision, neuropathy, bone fracture, burn, osteoporotic fracture, bone cancer, gout, migraine headache, fibromyalgia, etc. The antibodies of the invention may also be used to treat, prevent and/or ameliorate inflammatory conditions such as joint inflammation, airway inflammation (e.g., asthma), skin inflammation, dermatitis (e.g., atopic dermatitis, allergic contact dermatitis, etc.), inflammatory bowel disease (IBD), glomerulonephritis, interstitial cystitis, bladder inflammation, hyperalgesia, rheumatoid arthritis, osteoarthritis, inflammatory arthritis, multiple sclerosis, anti-phospholipid syndrome, alpha-1-antitrypsin deficiency, etc. The antibodies of the present invention may be used to treat fibrotic conditions, including, e.g., scleroderma, biliary cirrhosis, post-transplant fibrosis, renal fibrosis, lung fibrosis, liver fibrosis, pancreatic fibrosis, testicular fibrosis, hypertrophic scarring and cutaneous keloids. In certain embodiments, the antibodies of the invention are useful for the treatment of gastrointestinal conditions (e.g., celiac disease, Crohn's disease, ulcerative colitis, idiopathic gastroparesis, pancreatitis, irritable bowel syndrome (IBS) and ulcers (including gastric and duodenal ulcers)); acute lung injury; acute renal injury; and sepsis. The anti-PAR-2 antibodies of the present invention are also useful for the treatment of pruritus; e.g., dermal/pruritoceptive, neuropathic, neurogenic, and psychogenic itch, as well as pruritus associated with atopic dermatitis, psoriasis, burn scarring (burn-related itch), hypertrophic scarring, keloids, renal failure and hepatic failure. Other therapeutic uses of the anti-PAR-2 antibodies of the present invention include the treatment, prevention and/or amelioration of Alzheimer's disease, Netherton's disease, pathological angiogenesis, chronic urticaria, angioedema, mastocytosis, endometriosis, infertility (e.g., male infertility associated with testicular fibrosis), mast cell-mediated diseases, *Clostridium difficile* Toxin-A induced enteritis, and cancer (e.g., blood cell cancer, brain cancer, breast cancer, colon cancer, head and neck cancer, liver cancer, lung cancer, ovarian cancer, pancreatic cancer, prostate cancer, skin cancer, stomach cancer, etc.).

Combination Therapies

The present invention includes therapeutic administration regimens which comprise administering an anti-PAR-2 antibody of the present invention in combination with at least one additional therapeutically active component. Non-limiting examples of such additional therapeutically active components include other PAR-2 antagonists (e.g., anti-PAR-2 antibody or small molecule inhibitor of PAR-2 (e.g., N1-3-methylbutyryl-N4-6-aminohexanoyl-piperazine; ENMD-1068)), cytokine inhibitors (e.g., an interleukin-1 (IL-1) inhibitor (such as rilonacept or anakinra, a small molecule IL-1 antagonist, or an anti-IL-1 antibody); IL-18 inhibitor (such as a small molecule IL-18 antagonist or an anti-IL-18 antibody); IL-4 inhibitor (such as a small molecule IL-4 antagonist, an anti-IL-4 antibody or an anti-IL-4 receptor antibody); IL-6 inhibitor (such as a small molecule IL-6 antagonist, an anti-IL-6 antibody or an anti-IL-6 receptor antibody); antiepileptic drugs (e.g., gabapentain); nerve growth factor (NGF) inhibitors (e.g., a small molecule NGF antagonist or an anti-NGF antibody); low dose cochicine; aspirin; NSAIDs; steroids (e.g., prednisone, methotrexate, etc.); low dose cyclosporine A; tumor necrosis factor (TNF) or TNF receptor inhibitors (e.g., a small molecule TNF or TNFR antagonist or an anti-TNF or TNFR antibody); uric acid synthesis inhibitors (e.g., allopurinol); uric acid excretion promoters (e.g., probenecid, sulfinpyrazone, benzbromarone, etc.); other inflammatory inhibitors (e.g., inhibitors of caspase-1, p38, IKK1/2, CTLA-4Ig, etc.); and/or corticosteroids. The additional therapeutically active component(s) may be administered prior to, concurrent with, or after the administration of the anti-PAR-2 antibody of the present invention.

Diagnostic Uses of the Antibodies

The anti-PAR-2 antibodies of the present invention may also be used to detect and/or measure PAR-2 in a sample, e.g., for diagnostic purposes. For example, an anti-PAR-2 antibody, or fragment thereof, may be used to diagnose a condition or disease characterized by aberrant expression (e.g., over-expression, under-expression, lack of expression, etc.) of PAR-2. Exemplary diagnostic assays for PAR-2 may comprise, e.g., contacting a sample, obtained from a patient, with an anti-PAR-2 antibody of the invention, wherein the anti-PAR-2 antibody is labeled with a detectable label or reporter molecule. Alternatively, an unlabeled anti-PAR-2 antibody can be used in diagnostic applications in combination with a secondary antibody which is itself detectably labeled. The detectable label or reporter molecule can be a radioisotope, such as $^3$H, $^{14}$C, $^{32}$P, $^{35}$S or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure PAR-2 in a sample include enzyme-linked immunosorbent assay (ELISA), radioimmunoassay (RIA), and fluorescence-activated cell sorting (FACS).

Samples that can be used in PAR-2 diagnostic assays according to the present invention include any tissue or fluid sample obtainable from a patient which contains detectable quantities of PAR-2 protein, or fragments thereof, under normal or pathological conditions. Generally, levels of PAR-2 in a particular sample obtained from a healthy patient (e.g., a patient not afflicted with a disease or condition associated with abnormal PAR-2 levels or activity) will be measured to initially establish a baseline, or standard, level of PAR-2. This baseline level of PAR-2 can then be compared against the levels of PAR-2 measured in samples obtained from individuals suspected of having a PAR-2 related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to Human PAR-2

An immunogen comprising human PAR-2 peptide having the amino acid sequence GTNRSSKGRSLIGKVDGT (SEQ ID NO:852) was administered directly, with an adjuvant to stimulate the immune response, to a VELOCIMMUNE® mouse comprising DNA encoding human Immunoglobulin heavy and kappa light chain variable regions. The antibody immune response was monitored by a PAR-2-specific immunoassay. When a desired immune response was achieved splenocytes were harvested and fused with mouse myeloma cells to preserve their viability and form hybridoma cell lines. The hybridoma cell lines were screened and selected to identify cell lines that produce PAR-2-specific antibodies. Using this technique several anti-PAR-2 chimeric antibodies (i.e., antibodies possessing human variable domains and mouse constant domains) were obtained; exemplary antibodies generated in this manner were designated as follows: H2M588, H2M589, H1M590, H2M591, H1M592, H1M595, H2M609, H2M610, H2M611, H1M612, H1M613, H2M614, H1M615, H1M616, H3M617, H2M618, H1M619, and H3M620.

Anti-PAR-2 antibodies were also isolated directly from antigen-positive B cells without fusion to myeloma cells, as described in U.S. 2007/0280945A1, herein specifically incorporated by reference in its entirety. Using this method, several fully human anti-PAR-2 antibodies (i.e., antibodies possessing human variable domains and human constant domains) were obtained; exemplary antibodies generated in this manner were designated as follows: H1H571, H1H572, H1H573, H1H574, H1H575, H1H576, H1H577, H1H578, H1H579, H1H580, H1H581, H1H583, H1H584, H1H585, H1H586, and H1H587.

The biological properties of the exemplary anti-PAR-2 antibodies generated in accordance with the methods of this Example are described in detail in the Examples set forth below.

Example 2

Heavy and Light Chain Variable Region Amino Acid Sequences

Table 1 sets forth the heavy and light chain variable region amino acid sequence pairs of selected anti-PAR-2 antibodies and their corresponding antibody identifiers. The N, P and G designations refer to antibodies having heavy and light chains with identical CDR sequences but with sequence variations in regions that fall outside of the CDR sequences (i.e., in the framework regions). Thus, N, P and G variants of a particular antibody have identical CDR sequences within their heavy and light chain variable regions but differ from one another within their framework regions.

TABLE 1

| Name | HCVR/LCVR SEQ ID NOs | Name | HCVR/LCVR SEQ ID NOs | Name | HCVR/LCVR SEQ ID NOs |
|---|---|---|---|---|---|
| H1H571N | 458/466 | H1H571P | 474/476 | H1H571G | 478/480 |
| H1H572N | 482/490 | H1H572P | 498/500 | H1H572G | 502/504 |
| H1H573N | 506/514 | H1H573P | 522/524 | H1H573G | 526/528 |
| H1H574N | 530/538 | H1H574P | 546/548 | H1H574G | 550/552 |
| H1H575N | 554/562 | H1H575P | 570/572 | H1H575G | 574/576 |
| H1H576N | 578/586 | H1H576P | 594/596 | H1H576G | 598/600 |
| H1H577N | 602/610 | H1H577P | 618/620 | H1H577G | 622/624 |
| H1H578N | 626/634 | H1H578P | 642/644 | H1H578G | 646/648 |
| H1H579N | 650/658 | H1H579P | 666/668 | H1H579G | 670/672 |
| H1H580N | 674/682 | H1H580P | 690/692 | H1H580G | 694/696 |
| H1H581N | 698/706 | H1H581P | 714/692 | H1H581G | 718/720 |
| H1H583N | 722/730 | H1H583P | 738/740 | H1H583G | 742/744 |
| H1H584N | 746/754 | H1H584P | 762/764 | H1H584G | 766/768 |
| H1H585N | 770/778 | H1H585P | 786/788 | H1H585G | 790/792 |
| H1H586N | 794/802 | H1H586P | 810/812 | H1H586G | 814/816 |
| H1H587N | 818/826 | H1H587P | 834/836 | H1H587G | 838/840 |
| H2M588N | 98/106 | H2M588P | 114/116 | H2M588G | 118/120 |
| H2M589N | 122/130 | H2M589P | 138/140 | H2M589G | 142/144 |
| H1M590N | 218/226 | H1M590P | 234/236 | H1M590G | 238/240 |
| H2M591N | 146/154 | H2M591P | 162/164 | H2M591G | 166/168 |
| H1M592N | 242/250 | H1M592P | 258/260 | H1M592G | 262/264 |
| H1M595N | 266/274 | H1M595P | 282/284 | H1M595G | 286/288 |
| H2M609N | 170/178 | H2M609P | 186/188 | H2M609G | 190/192 |
| H2M610N | 194/202 | H2M610P | 210/212 | H2M610G | 214/216 |
| H2M611N | 290/298 | H2M611P | 306/308 | H2M611G | 310/312 |
| H1M612N | 2/10 | H1M612P | 18/20 | H1M612G | 22/24 |
| H1M613N | 410/418 | H1M613P | 426/428 | H1M613G | 430/432 |
| H2M614N | 314/322 | H2M614P | 330/332 | H2M614G | 334/336 |
| H1M615N | 26/34 | H1M615P | 42/44 | H1M615G | 46/48 |
| H1M616N | 50/58 | H1M616P | 66/68 | H1M616G | 70/72 |
| H3M617N | 362/370 | H3M617P | 378/380 | H3M617G | 382/384 |
| H2M618N | 338/346 | H2M618P | 354/356 | H2M618G | 358/360 |
| H1M619N | 74/82 | H1M619P | 90/92 | H1M619G | 94/96 |
| H3M620N | 386/394 | H3M620P | 402/404 | H3M620G | 406/408 |
| FP3B12F6N | 434/442 | FP3B12F6P | 450/452 | FP3B12F6G | 454/456 |

Example 3

Antibody Binding to PAR-2 Peptides

Synthetic peptides (Celtek Bioscience, Nashville, Tenn.) of PAR-2 and PAR-2 related sequences were generated to characterize the binding profiles of anti-PAR-2 antibodies. Both biotinylated and unbiotinylated forms for the various peptides were generated for the examples set forth below. For biotinylated forms, biotin moieties were covalently attached to the peptide at either the C-terminus or the N-terminus via a $G_4S$ linker. Table 2 sets forth the sequence and derivation of these peptides.

TABLE 2

| Designation | Species | Gene | Sequence | SEQ ID NO: |
|---|---|---|---|---|
| Peptide A | Human | PAR-2 | GTNRSSKGRSLIGKVDGT | 852 |
| Peptide B | Human | PAR-2 | SLIGKVDGTSHVTG | 853 |
| Peptide C | Human | PAR-2 | SLIGKV | 854 |
| Peptide D | Human | PAR-2 | SLIGKVDGTSHVTGKGVTVE TVFSVDEFSASVLTGKLTTVF LP-mouse IgG2a | 855 |
| Peptide E | Mouse (Mus musculus) | PAR-2 | LAPGRNNSKGRSLIGRLETQ | 856 |
| Peptide F | Monkey (Macaca mulatta) | PAR-2 | GTNRSSKGRSLIGRVDGT | 857 |
| Peptide G | Rat (Rattus norvegicus) | PAR-2 | GPNSKGRSLIGRLDTP | 858 |
| Peptide H | Rabbit (Oryctolagus cuniculus) | PAR-2 | GTNKTSKGRSLIGRNTGS | 859 |
| Peptide I | Dog (Canis familiaris) | PAR-2 | GTNRTSKGRSLIGKTDSS | 860 |
| Peptide J | Pig (Sus scrofa) | PAR-2 | GTSRPSKGRSLIGKADNT | 861 |
| Peptide K | Human | PAR-1 | ATNATLDPRSFLLRNPND | 862 |
| Peptide L | Human | PAR-3 | DTNNLAKPTLPIKTFRGA | 863 |
| Peptide M | Human | PAR-4 | ESGSTGGGDDSTPSILPAP | 864 |

Anti-PAR-2 antibodies were tested for their ability to bind to the PAR-2 peptides. Various PAR-2 Peptides (Table 3) were coated onto 96-well plates at a concentration of 2 µg/ml and incubated overnight followed by blocking in a suitable blocking agent for one hour. In a similar fashion, for biotinylated peptides (N-Term: N-terminal biotinylated; C-Term: C-terminal biotinylated), avidin was coated on plates at 2 µg/ml followed by incubation with biotinylated PAR-2 peptides at a concentration of 0.2 µg/ml and incubated for one hour. Purified anti-PAR-2 antibodies were added to the plate coated with PAR-2 peptides to a final concentration ranging from 0.2 to 2.0 µg/ml and incubated for one hour at room temperature. Detection of bound antibodies was determined with Horse-Radish Peroxidase (HRP) conjugated anti-mouse or human IgG (Jackson Immuno Research Lab, West Grove, Pa.) and developed by standard colorimetric response using tetramethylbenzidine (TMB) substrate. Absorbance was read at $OD_{450}$ for 0.1 second.

Relative binding (+++, ++, +) to unbiotinylated (No Biotin) or biotinylated Peptides A, B and C as compared to no binding (−) for each anti-PAR-2 antibody tested according to the observed $OD_{450}$ value (1.0–4.0, 0.50–0.99, 0.1–0.49, 0.0–0.09, respectively) is shown in Table 3. Control: "Sam11," a commercially available mouse monoclonal antibody that binds human PAR-2 (Santa Cruz Biotechnology, Santa Cruz, Calif.).

TABLE 3

| | Peptide A | | | Peptide B | | | Peptide C | |
|---|---|---|---|---|---|---|---|---|
| Antibody | No Biotin | N-Term | C-Term | No Biotin | N-Term | C-Term | N-Term | C-Term |
| H2M588N | +++ | +++ | +++ | +++ | +++ | +++ | − | − |
| H2M589N | +++ | +++ | +++ | +++ | +++ | +++ | − | − |
| H1M590N | +++ | +++ | +++ | − | − | − | − | − |
| H2M591N | +++ | +++ | +++ | +++ | +++ | +++ | − | − |
| H1M592N | +++ | +++ | +++ | − | ++ | +++ | +++ | +++ |
| H1M595N | +++ | +++ | +++ | − | − | − | ++ | − |

TABLE 3-continued

| | Peptide A | | | Peptide B | | | Peptide C | |
|---|---|---|---|---|---|---|---|---|
| Antibody | No Biotin | N-Term | C-Term | No Biotin | N-Term | C-Term | N-Term | C-Term |
| H2M609N | +++ | +++ | +++ | − | − | − | − | − |
| H2M610N | +++ | +++ | +++ | − | − | − | − | − |
| H2M611N | +++ | +++ | +++ | +++ | +++ | +++ | − | − |
| H1M612N | +++ | +++ | +++ | − | − | − | − | − |
| H1M613N | +++ | +++ | +++ | − | ++ | +++ | +++ | +++ |
| H2M614N | ++ | +++ | +++ | − | − | − | − | − |
| H1M615N | +++ | +++ | +++ | − | − | − | − | − |
| H1M616N | +++ | +++ | +++ | − | − | − | − | − |
| H2M618N | +++ | +++ | +++ | +++ | +++ | +++ | − | − |
| H1M619N | +++ | +++ | +++ | − | − | − | − | − |
| H3M620N | +++ | ++ | +++ | − | − | − | − | − |
| Control | − | − | − | +++ | +++ | +++ | − | − |

In a similar experiment, selected anti-PAR-2 antibodies cloned onto a mutant human IgG4 (SEQ ID NO:849) were tested for their ability to bind unbiotinylated and biotinylated forms of human PAR-2 peptides (as described above). Results are shown in Table 4.

TABLE 4

| | Peptide A | | | Peptide B | | | Peptide C | |
|---|---|---|---|---|---|---|---|---|
| Antibody | No Biotin | N-Term | C-Term | No Biotin | N-Term | C-Term | N-Term | C-Term |
| H4H572P | − | − | − | − | − | − | − | − |
| H4H573P | +++ | +++ | +++ | − | − | − | − | − |
| H4H576P | + | − | − | − | − | − | − | − |
| H4H578P | +++ | +++ | +++ | − | − | − | − | − |
| H4H579P | +++ | +++ | +++ | +++ | +++ | +++ | − | − |
| H4H580P | +++ | +++ | +++ | +++ | +++ | +++ | − | − |
| H4H581P | +++ | +++ | +++ | +++ | +++ | +++ | ++ | + |
| H4H583P | +++ | +++ | +++ | − | − | − | − | − |
| H4H584P | +++ | +++ | +++ | +++ | +++ | +++ | − | − |
| H4H585P | +++ | +++ | +++ | +++ | +++ | +++ | + | + |
| H4H587P | − | − | − | − | − | − | − | + |

TABLE 4-continued

| | Peptide A | | | Peptide B | | | Peptide C | |
|---|---|---|---|---|---|---|---|---|
| Antibody | No Biotin | N-Term | C-Term | No Biotin | N-Term | C-Term | N-Term | C-Term |
| H4H588N | +++ | +++ | +++ | +++ | +++ | +++ | – | – |
| H4H591N | +++ | +++ | +++ | +++ | +++ | +++ | – | – |
| H4H618N | +++ | +++ | +++ | +++ | +++ | +++ | – | – |
| Control | – | – | – | +++ | +++ | +++ | – | – |

In another experiment, selected anti-PAR-2 antibodies were tested for binding to unbiotinylated Peptides D, K, L and M (as described above). Results for chimeric antibodies (e.g. H2M588N) and fully human antibodies (e.g. H4H572P) are shown in Tables 5 and 6, respectively. For Peptide D, detection of bound antibodies was determined with Horse-Radish Peroxidase (HRP) conjugated anti-mouse κ (Southern Biotech, Birmingham, Ala.).

TABLE 5

| Antibody | Peptide D | Peptide K | Peptide L | Peptide M |
|---|---|---|---|---|
| H2M588N | +++ | – | – | – |
| H2M589N | +++ | – | – | – |
| H1M590N | – | – | – | – |
| H2M591N | +++ | – | – | – |
| H1M592N | + | – | – | – |
| H1M595N | – | – | – | – |
| H2M609N | + | – | – | – |
| H2M610N | – | – | – | – |
| H2M611N | + | – | – | – |
| H1M612N | – | – | – | – |
| H1M613N | + | – | – | – |
| H2M614N | – | – | – | – |
| H1M615N | – | – | – | – |
| H1M616N | – | – | – | – |
| H2M618N | +++ | – | – | – |
| H1M619N | – | – | – | – |
| H3M620N | – | – | – | – |
| Control | +++ | – | – | – |

TABLE 6

| Antibody | Peptide D | Peptide K | Peptide L | Peptide M |
|---|---|---|---|---|
| H4H572P | + | – | – | – |
| H4H573P | + | – | – | – |
| H4H576P | + | – | – | – |

TABLE 6-continued

| Antibody | Peptide D | Peptide K | Peptide L | Peptide M |
|---|---|---|---|---|
| H4H578P | + | – | – | – |
| H4H579P | +++ | – | – | – |
| H4H580P | +++ | – | – | – |
| H4H581P | +++ | + | + | + |
| H4H583P | ++ | – | – | – |
| H4H584P | +++ | – | – | – |
| H4H585P | +++ | + | + | + |
| H4H587P | + | – | – | – |
| H4H588N | +++ | – | – | – |
| H4H591N | +++ | + | + | + |
| H4H618N | +++ | – | – | – |
| Control | +++ | – | – | – |

In another experiment, selected anti-PAR-2 antibodies were tested for binding to N-terminal biotinylated mouse (Peptide E N-Term) and monkey (Peptide F N-Term) PAR-2 peptides (as described above).

TABLE 7

| Antibody | Peptide E N-Term | Peptide F N-Term |
|---|---|---|
| H2M588N | – | +++ |
| H2M589N | – | +++ |
| H1M590N | +++ | +++ |
| H2M591N | – | +++ |
| H1M592N | – | – |
| H1M595N | +++ | +++ |
| H2M609N | +++ | +++ |
| H2M610N | +++ | +++ |
| H2M611N | – | +++ |
| H1M612N | +++ | +++ |
| H1M613N | – | – |
| H2M614N | +++ | +++ |
| H1M615N | +++ | +++ |
| H1M616N | +++ | +++ |
| H2M618N | – | +++ |
| H1M619N | +++ | +++ |
| H3M620N | +++ | ++ |
| Control | – | – |

In another experiment, selected anti-PAR-2 antibodies cloned onto human IgG4 were tested for binding to unbiotinylated and biotinylated forms of Peptides E through J (as described above). Results are shown in Table 8.

TABLE 8

| | Peptide E | | | Peptide G | | | | | |
|---|---|---|---|---|---|---|---|---|---|
| Antibody | No Biotin | N-Term | Peptide F N-Term | No Biotin | N-Term | C-Term | Peptide H | Peptide I | Peptide J |
| H4H572P | + | – | – | – | – | + | – | – | – |
| H4H573P | +++ | +++ | +++ | +++ | +++ | ++ | +++ | +++ | +++ |
| H4H576P | + | – | – | – | – | + | – | – | – |
| H4H578P | +++ | +++ | +++ | +++ | +++ | + | +++ | +++ | +++ |
| H4H579P | +++ | +++ | +++ | +++ | +++ | +++ | + | +++ | + |
| H4H580P | +++ | +++ | +++ | +++ | +++ | +++ | – | +++ | + |
| H4H581P | +++ | +++ | +++ | +++ | +++ | +++ | – | +++ | +++ |
| H4H583P | +++ | +++ | +++ | +++ | +++ | +++ | +++ | +++ | +++ |
| H4H584P | +++ | +++ | +++ | +++ | +++ | +++ | – | +++ | ++ |
| H4H585P | +++ | +++ | +++ | +++ | +++ | +++ | + | +++ | +++ |
| H4H587P | – | – | – | – | + | – | – | – | + |
| H4H588N | – | – | +++ | – | + | – | – | – | – |
| H4H591N | + | + | +++ | + | + | + | + | – | + |
| H4H618N | – | – | +++ | – | – | – | – | – | – |
| Control | – | – | – | – | – | – | – | – | – |

In another experiment, selected anti-PAR-2 antibodies cloned onto human IgG4 were tested for binding to unbiotinylated and biotinylated forms of PAR-2 peptides (Peptides A, E, F and G; as described above). In this experiment, anti-PAR-2 antibodies, serially diluted three-fold from 13.3 nM to 0.22 pM, were incubated on the peptide-coated plates for one hour at room temperature. Absorbance values at 450 nm were analyzed using a sigmoidal dose-response model in GraphPad Prism (GraphPad Software, Inc., La Jolla, Calif.) and $EC_{50}$ values were reported (Table 9). $EC_{50}$ values are defined as the antibody concentration required to achieve 50% maximal binding to PAR-2 peptide.

and half-life of antigen/antibody complex dissociation (Table 10). For those antibodies where no $T_{1/2}$ value is shown, steady state analysis was used to calculate the $K_D$ value. NB: no binding observed under current experimental conditions. ND: not determined.

TABLE 10

| Antibody | Peptide A | | Peptide B | |
|---|---|---|---|---|
| | $K_D$ (nM) | $T_{1/2}$ (min) | $K_D$ (nM) | $T_{1/2}$ (min) |
| H4H572P | NB | — | ND | — |
| H4H573P | 749 | — | ND | — |

TABLE 9

| | $EC_{50}$ (nM) | | | | | | | | |
|---|---|---|---|---|---|---|---|---|---|
| | Peptide A | | | Peptide E | | | Peptide G | | |
| Antibody | No Biotin | C-Term | N-Term | No Biotin | N-Term | Peptide F N-Term | No Biotin | C-Term | N-Term |
| H4H572P | >50 | >50 | >50 | >50 | >50 | >50 | >50 | >50 | >50 |
| H4H573P | 0.093 | 0.022 | 0.093 | 0.355 | 0.016 | 0.018 | 0.014 | 10.130 | 0.017 |
| H4H576P | >50 | >50 | >50 | >50 | >50 | >50 | >50 | >50 | >50 |
| H4H578P | 0.034 | 0.040 | 0.062 | 2.778 | 0.090 | 0.036 | 0.046 | >50 | 0.081 |
| H4H579P | 0.038 | 0.076 | 0.077 | 0.713 | 0.540 | 0.061 | 0.055 | 0.044 | 0.059 |
| H4H580P | 0.090 | 0.202 | 0.160 | 2.533 | 0.932 | 0.148 | 0.139 | 0.100 | 0.142 |
| H4H581P | 0.012 | 0.028 | 0.020 | 0.029 | 0.032 | 0.020 | 0.020 | 0.013 | 0.019 |
| H4H583P | 0.008 | 0.018 | 0.015 | 0.019 | 0.014 | 0.013 | 0.012 | 0.630 | 0.015 |
| H4H584P | 0.012 | 0.015 | 0.019 | 2.152 | 0.511 | 0.012 | 0.013 | 0.015 | 0.012 |
| H4H585P | 0.017 | 0.021 | 0.026 | 0.308 | 0.189 | 0.017 | 0.018 | 0.021 | 0.017 |
| H4H587P | >50 | >50 | >50 | >50 | >50 | >50 | >50 | >50 | >50 |
| H4H588N | 0.010 | 0.016 | 0.019 | >50 | >50 | 0.012 | >50 | >50 | >50 |
| H4H591N | 0.010 | 0.016 | 0.022 | >50 | >50 | 0.011 | >50 | >50 | >50 |
| H4H618N | 0.009 | 0.016 | 0.021 | >50 | >50 | 0.011 | >50 | >50 | >50 |
| Control | >50 | >50 | >50 | >50 | >50 | >50 | >50 | >50 | >50 |

As indicated by the foregoing experiments, antibodies H4H581P, H4H588N, H4H591N or H4H618N all show substantial binding to human Peptides A, B and D, which comprise the sequence SLIGKVDGT (amino acids 10-18 of SEQ ID NO:852), as well as to monkey Peptide F, which comprises the sequence SLIGRVDGT (amino acids 10-18 of SEQ ID NO:857). For antibodies H4H588N, H4H591N and H4H618N, the sequence VDGT, located downstream from the activating PAR-2 protease cleavage site, appears to be particularly important for binding since changes to this sequence resulted in substantially reduced or no binding by these antibodies (see, e.g., binding data for Peptides E (mouse), G (rat), H (rabbit), I (dog) and J (pig)).

Example 4

Antigen Binding Affinity Determination

Equilibrium dissociation constants ($K_D$ values) for antigen binding to selected purified PAR-2 antibodies were determined by surface kinetics using a real-time surface plasmon resonance biosensor assay. Antibody was captured on either a rabbit anti-mouse IgG polyclonal antibody (GE Healthcare, Piscataway, N.J.) surface or a goat anti-human IgG polyclonal antibody (Jackson Immuno Research Lab, West Grove, Pa.) surface created through direct amine chemical coupling to a BIACORE™ CM5 sensor chip to form a captured antibody surface. Various concentrations (ranging from 15.6 to 250 nM) of monomeric human PAR-2 peptides (Peptides A and B) were injected at a rate of 100 µl/min over the captured antibody surface for 90 seconds. Antigen-antibody binding and dissociation were monitored in real time at room temperature. Kinetic analysis was performed to calculate $K_D$ TABLE 10-continued

| Antibody | Peptide A | | Peptide B | |
|---|---|---|---|---|
| | $K_D$ (nM) | $T_{1/2}$ (min) | $K_D$ (nM) | $T_{1/2}$ (min) |
| H4H576P | NB | — | ND | — |
| H4H578P | 245 | 0.17 | ND | — |
| H4H579P | 15 | 4 | >500 | — |
| H4H580P | 103 | 0.88 | ND | — |
| H4H581P | 9.44 | 1.4 | >500 | — |
| H4H583P | 37.1 | 0.37 | NB | — |
| H4H584P | 22 | 0.73 | >500 | — |
| H4H585P | 8.78 | 3.7 | >500 | — |
| H4H587P | NB | — | ND | — |
| H1M590N | 173 | — | ND | — |
| H1M592N | 2100 | — | ND | — |
| H1M595N | 510 | — | ND | — |
| H1M612N | 180 | — | ND | — |
| H1M613N | 2100 | — | ND | — |
| H1M615N | 162 | — | ND | — |
| H1M616N | 144 | — | ND | — |
| H1M619N | 164 | — | ND | — |
| H2M588N | 4.47 | 60.8 | 61.7 | 7.7 |
| H2M589N | 3.75 | 51.3 | 128 | 7.3 |
| H2M591N | 4.22 | 42.7 | 151 | 8.1 |
| H2M610N | 71.3 | — | 360 | 0.8 |
| H2M611N | 72.8 | 4.1 | 1090 | 1.2 |
| H2M614N | 470 | — | ND | — |
| H2M618N | 9.62 | 6.7 | 126 | 3.5 |
| Control | NB | — | 149 | 0.1 |

In a similar experiment, $K_D$ values for binding to unbiotinylated monomeric mouse (Peptide E) and N-terminal biotinylated monkey (Peptide F N-Term) PAR-2 peptides of selected antibodies cloned onto human IgG4 were determined (as described above) (Table 11). Antibodies H4H588N, H4H591N, and H4H618N did not bind Peptide E, while the Control antibody did not bind to either Peptide E or F.

TABLE 11

| Antibody | Peptide F N-Term | |
|---|---|---|
| | $K_D$ (nM) | $T_{1/2}$ (min) |
| H4H588N | 7.10 | 24 |
| H4H591N | 8.54 | 21 |
| H4H618N | 13.8 | 5 |

In another series of experiments, equilibrium dissociation constants ($K_D$ values) for purified antibody binding to selected biotinylated and unbiotinylated forms of PAR-2 peptides were determined by surface kinetics using a real-time surface plasmon resonance biosensor assay. Neutravidin (Pierce, Rockford, Ill.) was covalently coupled to the surface of a Biacore™ C1 chip or CM5 chip using amine coupling chemistry. Biotinylated (N-Term or C-Term) PAR-2 peptides (Peptides A and B) were immobilized on the surface via the high affinity binding interaction between biotin and the amine coupled Neutravidin.

In a first experiment using this format, varying concentrations (ranging from 5 to 100 µg/ml) of purified antibody were injected at a rate of 50 µl/min over a surface coated with immobilized peptide at low-density (<1 RU) for 300 seconds. Antibody-peptide binding and dissociation was monitored in real time 25° C. (Table 12).

TABLE 12

| Antibody | Peptide A C-Term | | Peptide B C-Term | |
|---|---|---|---|---|
| | $K_D$ (nM) | $T_{1/2}$ (min) | $K_D$ (nM) | $T_{1/2}$ (min) |
| H2M588N | 0.826 | 169 | 1.49 | 140 |
| H1M590N | 1.27 | 13 | NB | — |
| H2M591N | 0.545 | 209 | 1.82 | 94 |
| H2M618N | 1.8 | 79 | 2.32 | 60 |
| Control | NB | — | 0.99 | 19 |

In another similar experiment, $K_D$ values for binding to a low-density surface (<1 RU) of biotinylated forms of Peptides A, B, C, E, F and G of selected antibodies cloned onto human IgG4 were determined (as described above). Results for binding to C-terminal and N-terminal biotinylated PAR-2 peptides are shown in Tables 13-14, respectively. In this experiment, only antibody H4H581P demonstrated affinity for N-terminal biotinylated Peptide C ($K_D$ of >100 nM), while all other antibodies tested, including the control, showed no binding to this peptide.

TABLE 13

| Antibody | Peptide A C-Term | | Peptide B C-Term | |
|---|---|---|---|---|
| | $K_D$ (nM) | $T_{1/2}$ (min) | $K_D$ (nM) | $T_{1/2}$ (min) |
| H4H579P | 0.143 | 479 | 0.453 | 96 |
| H4H581P | 0.237 | 134 | 0.346 | 49 |
| H4H583P | 0.898 | 34 | NB | — |
| H4H584P | 0.688 | 55 | 1.66 | 15 |
| H4H585P | 0.151 | 493 | 0.376 | 123 |
| H4H588N | 0.517 | 141 | 1.03 | 70 |
| H4H590N | 3.56 | 3 | NB | — |
| Control | NB | — | 0.935 | 14 |

TABLE 14

| Antibody | Peptide A N-Term | | Peptide B N-Term | | Peptide E N-Term | | Peptide F N-Term | | Peptide G N-Term | |
|---|---|---|---|---|---|---|---|---|---|---|
| | $K_D$ (nM) | $T_{1/2}$ (min) | $K_D$ (nM) | $T_{1/2}$ (min) | $K_D$ (nM) | $T_{1/2}$ (min) | $K_D$ (nM) | $T_{1/2}$ (min) | $K_D$ (nM) | $T_{1/2}$ (min) |
| H4H579P | 1.61 | 46 | 5.44 | 55 | 3.40 | 20 | 0.796 | 70 | 1.16 | 38 |
| H4H581P | 0.498 | 41 | 2.72 | 38 | 1.13 | 21 | 0.272 | 78 | 0.354 | 62 |
| H4H583P | 0.412 | 46 | NB | — | 1.68 | 11 | 0.291 | 73 | 1.49 | 13 |
| H4H584P | 0.525 | 43 | 3.20 | 30 | >100 | — | 0.565 | 40 | 1.39 | 15 |
| H4H585P | 1.69 | 48 | 5.41 | 63 | >100 | — | 0.899 | 66 | 1.36 | 35 |
| H4H588N | 1.05 | 189 | 0.0272 | >1155 | NB | — | 1.81 | 94 | NB | — |
| H4H590N | 1.52 | 3 | NB | — | 1.28 | 7 | 1.84 | 2 | 2.94 | 2 |
| Control | NB | — | 0.279 | 32 | NB | — | NB | — | NB | — |

In a similar experiment, $K_D$ values for binding to monomeric biotinylated and unbiotinylated forms of PAR-2 peptides (Peptides A, B, E-M) for selected antibodies cloned onto human IgG4 were determined (as described above for the captured antibody surface). Results are shown in Tables 15-16. None of the antibodies tested showed binding to Peptides K, L or M.

TABLE 15

| Antibody | Peptide A | | Peptide B | | Peptide E | |
|---|---|---|---|---|---|---|
| | $K_D$ (nM) | $T_{1/2}$ (min) | $K_D$ (nM) | $T_{1/2}$ (min) | $K_D$ (nM) | $T_{1/2}$ (min) |
| H4H579P | 15 | 4.1 | >500 | — | >500 | — |
| H4H581P | 9.44 | 1.4 | >500 | — | >500 | — |
| H4H583P | 37.1 | 0.37 | NB | — | >500 | — |
| H4H584P | 22 | 0.73 | NB | — | NB | — |
| H4H585P | 8.78 | 3.7 | >500 | — | >500 | — |
| H4H588N | 4.95 | 25.1 | 84 | 9 | NB | — |
| H4H590N | >500 | — | NB | — | >500 | — |
| Control | ND | — | 149 | 0.1 | ND | — |

TABLE 16

| Antibody | Peptide F N-Term K$_D$ (nM) | Peptide F N-Term T$_{1/2}$ (min) | Peptide G K$_D$ (nM) | Peptide G T$_{1/2}$ (min) | Peptide H K$_D$ (nM) | Peptide H T$_{1/2}$ (min) | Peptide I K$_D$ (nM) | Peptide I T$_{1/2}$ (min) | Peptide J K$_D$ (nM) | Peptide J T$_{1/2}$ (min) |
|---|---|---|---|---|---|---|---|---|---|---|
| H4H579P | 49.4 | 2 | 134 | 0.45 | NB | — | 311 | 0.26 | NB | — |
| H4H581P | 36.6 | 0.53 | 40.2 | 0.63 | NB | — | 143 | 0.07 | NB | — |
| H4H583P | 112 | 0.47 | 530 | 0.07 | 189 | 0.17 | 320 | 0.16 | 190 | 0.16 |
| H4H584P | 93.3 | 0.23 | 246 | 0.13 | NB | — | >500 | — | NB | — |
| H4H585P | 46.2 | 2 | 162 | 0.33 | NB | — | 372 | 0.19 | NB | — |
| H4H588N | 10.8 | 20 | NB | — | NB | — | NB | — | NB | — |
| H4H590N | >500 | — | >500 | — | >500 | — | >500 | — | >500 | — |

Example 5

Antibody Binding to Cells Engineered to Express PAR-2

To further characterize anti-PAR-2 antibodies, cells of the human embryonic kidney 293 cell line (HEK293) were genetically engineered to overexpress either full length human (SEQ ID NO:851) or mouse (SEQ ID NO:866) PAR-2.

HEK293 cells were transfected with an NF-κB-luciferase-IRES-eGFP reporter plasmid. Stability of transfected cells was demonstrated by response to IL-1β as detected by eGFP expression through flow cytometry and luciferase activity. A clonal cell line, named D9, having low background levels of luciferase activity and high levels of eGFP when induced with IL-1β was made by a series of successive sorts of cell populations using flow cytometry. The 293/D9 cell line was then separately transfected with human PAR-2 or mouse PAR-2 to create the stable cell lines 293/D9/h PAR-2rec and 293/D9/m PAR-2rec, respectively.

Binding of anti-PAR-2 antibodies to 293/D9/hPAR-2rec cells was determined by ELISA. 293/D9 and 293/D9/hPAR-2rec cells were plated at a density of 5×10$^4$ cells/well in media and incubated overnight at 37° C. and 5% CO$_2$. Purified antibody was added to the cells to a final concentration of 10 µg/ml and incubated at room temperature for one hour. Cells were then fixed and washed before detection of bound antibodies with HRP conjugated anti-mouse IgG and developed by standard colorimetric response using TMB substrate. Absorbance was read at OD$_{450}$ for 0.1 second. The A$_{450}$ ratio of antibody binding to 293/D9/hPAR-2rec cells compared to 293/D9 cells is shown in Table 17.

TABLE 17

| Antibody | A$_{450}$ ratio |
|---|---|
| H2M588N | 2.50 |
| H2M589N | 2.03 |
| H1M590N | 1.81 |
| H2M591N | 2.25 |
| H1M592N | 1.25 |
| H1M595N | 1.80 |
| H2M609N | 1.54 |
| H2M610N | 1.66 |
| H2M611N | 1.76 |
| H1M612N | 1.90 |
| H1M613N | 1.27 |
| H2M614N | 1.17 |
| H1M615N | 2.18 |
| H1M616N | 2.78 |
| H2M618N | 2.44 |
| H1M619N | 1.51 |

TABLE 17-continued

| Antibody | A$_{450}$ ratio |
|---|---|
| H3M620N | 1.24 |
| Control | 1.49 |

In a similar experiment, anti-PAR-2 antibodies were tested for binding to 293/D9, 293/D9/hPAR-2rec and 293/D9/mPAR-2rec cells using electro-chemiluminescence technology (Meso Scale Discovery, MSD, Gaithersburg, Md.). Cells were plated on MSD high-bind 96 well plates at a density of 4×10$^4$ cells/well in PBS and incubated for one hour at room temperature. Cells were then blocked in PBS with 2% BSA and incubated at room temperature for one hour. Anti-PAR-2 antibodies (ranging from 100 nM to 0.098 nM) were serially diluted two-fold in PBS with 0.5% BSA and incubated with the cells for one hour at room temperature followed by washing in PBS with 0.5% BSA. Sulfo-tagged anti-human IgG antibody (MSD) at a concentration of 0.1 µg/ml was then added to the cell/antibody mixture and incubated at room temperature for an additional hour. After another wash, a 1× non-surfactant containing read buffer was added and electro-chemiluminescent signal was read on the MSD Sector Imager. Signal of antibody binding to 293/D9 cells was subtracted from signal to 293/D9/hPAR-2rec or 293/D9/mPAR-2rec cells. Subtracted data were analyzed using a sigmoidal dose-response model in GraphPad Prism and EC$_{50}$ and B$_{max}$ values were reported (Table 18). EC$_{50}$ values are defined as the antibody concentration required to achieve 50% maximal binding (B$_{max}$) to cells.

TABLE 18

| Antibody | 293/D9/hPAR-2rec EC$_{50}$ (nM) | 293/D9/hPAR-2rec B$_{max}$ (MSD Unit) | 293/D9/mPAR-2rec EC$_{50}$ (nM) | 293/D9/mPAR-2rec B$_{max}$ (MSD Unit) |
|---|---|---|---|---|
| H4H579P | 1.86 | 25049 | NB | — |
| H4H580P | 8.69 | 30177 | NB | — |
| H4H581P | 0.652 | 28224 | NB | — |
| H4H583P | 2.12 | 13252 | 9.28 | 7219 |
| H4H584P | 1.45 | 26044 | NB | — |
| H4H585P | 1.95 | 22540 | NB | — |
| H4H588N | 5.95 | 27549 | NB | — |
| H4H590N | 9.72 | 6554 | 5.76 | 13255 |

Example 6

In Vitro Blocking of Human PAR-2 Activation by Anti-PAR-2 Antibodies

Blocking of PAR-2 activation (signaling) was determined by binding of selected purified anti-PAR-2 antibodies to 293/D9/hPAR-2rec cells (see Example 5) by a luciferase assay.

293/D9/hPAR-2rec cells were plated at a concentration ranging from $5 \times 10^4$ to $10^5$ cells/well in a 96 well plate in low serum media and incubated overnight at 37° C. with 5% $CO_2$. The media was removed and purified anti-PAR-2 antibodies were added to the cells at various concentrations (ranging from 51 pM to 1 μM) and incubated for one hour at 37° C. with 5% $CO_2$. Various concentrations of different serine proteases (Trypsin, Human Trypsin 1, Factor Xa and Lung Tryptase) were then added separately to the cell/antibody mixture and incubated for five hours at 37° C. with 5% $CO_2$. Proteolytic cleavage of PAR-2 in this assay leads to expression of the NF-κB-luciferase reporter construct, whereas a reduced or attenuated level of luciferase signal indicates inhibition of PAR-2 cleavage. $IC_{50}$ values are shown in Table 19. ND: not determined.

TABLE 19

| | $IC_{50}$ (nM) | | | | | | | |
|---|---|---|---|---|---|---|---|---|
| | Trypsin | | | | | 10 nM Human Trypsin 1 | 200 nM Factor Xa | 750 nM Lung Tryptase |
| Antibody | 250 nM | 75 nM | 30 nM | 20 nM | 10 nM | | | |
| H2M588N | 2.3 | 5.7 | 33.0 | 26.8 | 10.4 | 164.9 | 45.3 | 1.0 |
| H2M589N | 6.3 | 3.7 | ND | ND | ND | ND | ND | ND |
| H1M591N | 4.5 | ND | ND | 121.8 | 24.2 | 149.6 | 51.5 | 88.1 |
| H2M618N | 6.6 | 7.8 | ND | 70 | 12.4 | 153.5 | 54.2 | 7.0 |

As shown in Table 20, antibodies H4H581P, H4H588N, H4H591N and H4H618N were able to significantly block protease activation of PAR-2 in reporter cells. By contrast, anti-PAR-2 antibodies H4H592N, H4H595N, H4H611N, H4H613N, H4H614N, H4H615N, H4H616N, H4H617N and H4H619N did not demonstrate any measurable blocking of PAR-2 cleavage/activation in this assay (data not shown).

TABLE 20

| Antibody | 20 nM Trypsin $IC_{50}$ (nM) |
|---|---|
| H4H579P | 4.1 |
| H4H580P | 3.5 |
| H4H581P | 1.1 |
| H4H583P | 14 |
| H4H584P | 5.6 |
| H4H585P | 8.9 |
| H4H588N | 16.9 |
| H4H591N | 204.1 |
| H4H618N | 50.2 |

Under the experimental conditions used in this Example, no blocking of PAR-2 signaling was observed for antibodies H4H572P, H4H573P, H4H576P, H4H578P or H4H587P, whereas significant blockage (to varying degrees) was observed with antibodies H4H579P, H4H580P, H4H581P, H4H583P, H4H584P, H4H585P, H4H588N, H4H591N and H4H618N.

In another similar experiment, antibody blocking of PAR-2 signaling mediated by human Trypsin 1, Factor Xa and Lung Tryptase was determined for selected purified anti-PAR-2 antibodies cloned onto human IgG4 (as described above). Results are shown in Table 21.

TABLE 21

| | $IC_{50}$ (nM) | | |
|---|---|---|---|
| Antibody | 10 nM Human Trypsin 1 | 200 nM Factor Xa | 750 nM Lung Tryptase |
| H4H581P | 7.4 | 5.3 | 1.1 |
| H4H588N | 42.7 | 17.1 | 1.6 |
| H4H591N | 104.7 | 74.6 | 62.9 |
| H4H618N | 92.2 | 47.2 | 8.5 |

HEK293/NFκB-luciferase cells expressing human, monkey, mouse or rat PAR-2 were treated with various proteases after preincubation with increasing amounts of anti-PAR-2 antibody H4H581P, and the $IC_{50}$ was determined. Results are summarized in Table 22.

TABLE 22

| Activator (6 h) | PAR-2 Species | $EC_{50}$ (nM) | H4H581P $IC_{50}$ (nm) |
|---|---|---|---|
| Human Pancreatic Trypsin | Human | 0.8 | 1.9 |
| | mouse | 1.4 | 491.0 |
| | monkey | 2.4 | 5.4 |
| | rat | 6.0 | 700.0 |
| Human Kallikrein 5 | Human | 28.0 | 0.9 |
| | mouse | ND | ND |
| | monkey | 16.8 | 11 |
| Human Kallikrein 14 | Human | 5.0 | 1.2 |
| | mouse | 8.0 | 256.0 |
| | monkey | 6.3 | 11.6 |
| Bovine Factor Xa | Human | 27.2 | 2.5 |
| | mouse | 46.3 | 340.4 |
| | monkey | 58.2 | 0.9 |
| Human Factor Xa | Human | 46.3 | 1.1 |
| | mouse | 78.7 | 109 |
| | monkey | ND | ND |
| Tryptase | Human | 61.1 | 3.5 |
| | mouse | ND | ND |
| | monkey | ND | ND |

Under the particular experimental conditions used, the H4H581P antibody effectively inhibited protease-activation of human and monkey PAR-2, but not mouse or rat PAR-2.

Example 7

In Vitro Antibody Blocking of Human PAR-2 Dependent Calcium Mobilization

Blocking of trypsin-stimulated PAR-2 activation (signaling) was determined by treating HEK293 cells with selected purified anti-PAR-2 antibodies cloned onto human IgG4 in a calcium mobilization FLIPR assay (Molecular Devices, Sunnyvale, Calif.). Also tested in this assay was a non-PAR-2 specific control antibody.

Briefly, $8\times10^4$ HEK293 cells were plated on Poly-D-Lysine plates (BD Biosciences, San Jose, Calif.) in low serum media (DME with 0.5% FBS) and incubated overnight at 37° C. with 5% $CO_2$. The following day cells were incubated with various concentrations (ranging from 0 to 1 µM) of selected anti-PAR-2 antibodies, or a control antibody, followed by the addition of trypsin. Trypsin-mediated activation of PAR-2 is indicated by calcium mobilization. In-cell measurement of calcium signaling was measured using a Fluo-4 NW Calcium Assay Kit (Invitrogen, Carlsbad, Calif.) on a FlexStation 3 (Molecular Devices, Sunnyvale, Calif.). The antibody concentration necessary to cause half-maximal inhibition of trypsin-mediated calcium signaling ($IC_{50}$) was measured for each experimental and control antibody. Results are shown in Table 23 as $IC_{50}$ (nM).

TABLE 23

| Antibody | 100 nM Trypsin |
| --- | --- |
| H4H581P | 54.96 |
| H4H588N | 29.47 |
| Non-Specific Control | >1000 |

As shown in this Example, antibodies H4H581P and H4H588N each inhibited trypsin-stimulated calcium signaling to a significant extent as compared to the control antibody.

Example 8

In Vitro Blocking of Trypsin-Mediated Cleavage of PAR-2 Peptides

A Matrix Assisted Laser Desorption Ionization—Time of Flight (MALDI-TOF) assay was developed to determine the ability of selected purified anti-PAR-2 antibodies to block Trypsin-mediated cleavage of human PAR-2 peptide (Peptide A, SEQ ID NO:852). Biotinylated versions of Peptide A (containing C-terminal or N-terminal biotin) were mixed with anti-PAR-2 antibody to achieve a 3:1 molar ratio of antibody to peptide, and then trypsin was added to the peptide-antibody mixture. Biotinlyated peptides were recovered by immuno-precipitation (IP) via mono-avidin and analyzed by MALDI-TOF.

In a typical experiment, selected purified anti-PAR-2 antibodies cloned onto human IgG4 (H4H581P and H4H588N) were tested for their ability to block Trypsin-mediated cleavage of the biotinylated PAR-2 peptides. A non-PAR-2-specific antibody of the same isotype was used as a negative control ("Neg Ctrl" in FIG. 3). For H4H581P and the negative control antibody, biotinylated peptides were used at a final concentration of 4.75 µM and antibodies were used at 14.25 µM. For H4H588N, biotinylated peptides were used at a final concentration of 2.45 µM and the antibody at 7.35 µM. Peptide and antibody were mixed in PBS and allowed to come to equilibrium for 1 hr at room temperature. Trypsin (96 ng) was then added and the mixture incubated at 37° C. for 0, 5, 10 and 15 minutes. At each time point an aliquot equaling 100 ng of biotinylated peptide was removed and mixed with 10 µl of monomeric avidin resin (Pierce) for 1 minute. The bound peptides were rinsed 3x with 200 µl of PBS and then eluted with 20 µl of 100 mM glycine pH 2.5. Salt was removed from the eluted peptide mixture using ZipTips (Millipore). The molecular weights of the major biotinylated PAR-2 peptides produced after trypsin cleavage, as revealed by MALDI-TOF analysis, are summarized in FIG. 3.

The PAR-2 peptides used in these experiments contain two R/S protease cleavage sites. The first site (designated site "(1)" in FIG. 3) is an "upstream" cleavage site located N-terminal to the activating PAR-2 protease cleavage site. The activating PAR-2 protease cleavage site (designated site "(2)" in FIG. 3) is the site which, when cleaved, results in the formation of the PAR-2 tethered ligand in the naturally occurring protein. The sizes of the peptides detected following cleavage at the different sites are shown in the top portion of FIG. 3 (panel A).

As indicated in FIG. 3 (panel B), the C-terminal biotin PAR-2 peptide, when treated with the isotype-matched control antibody, followed by trypsin incubation, produced a cleavage fragment of 1558 Da (containing residues 10-18 of SEQ ID NO:852). The 1558 Da fragment is the result of cleavage at the activating PAR-2 protease cleavage site (2). This cleavage pattern was also observed in the experiment using the H4H588N anti-PAR-2 antibody. Thus, according to this assay, neither the control antibody nor the H4H588N antibody inhibit trypsin cleavage at the activating PAR-2 protease cleavage site (2).

By contrast, the C-terminal biotin PAR-2 peptide, when treated with the H4H581P antibody, followed by trypsin incubation, produced a cleavage fragment of 2073 Da (containing residues 5-18 of SEQ ID NO:852). The 2073 Da fragment is the fragment produced by cleavage at the upstream cleavage site (1) only. Thus, cleavage at the activating PAR-2 protease cleavage site (2) was apparently blocked by the H4H581P antibody.

Experiments with the N-terminal biotin PAR-2 peptide showed trypsin cleavage at the upstream cleavage site (1) and thus produced a 988 Da N-biotinylated fragment (containing residues 1-4 of SEQ ID NO:852) in the presence of all antibodies tested. Therefore, none of the antibodies tested blocked cleavage at the upstream cleavage site (1) under these experimental conditions.

As shown in Examples 6 and 7 above, both H4H581P and H4H588N blocked PAR-2 activation by trypsin in cell-based assays. In the present Example, however, only H4H581P blocked trypsin cleavage at the activating PAR-2 protease cleavage site. Without being bound by any mechanistic theory, it therefore appears that H4H588N may exert its inhibitory effect(s) by interfering with the interaction between the tethered ligand and one or more extracellular loops (e.g., loop 1, loop 2 and/or loop 3) of PAR-2. On the other hand, H4H581P may inhibit PAR-2 activity primarily by blocking protease cleavage but may also interfere with tethered ligand interactions as well.

To further investigate the protease cleavage-blocking properties of anti-PAR-2 antibodies, additional MALDI-TOF experiments were conducted using C-terminal biotinylated mouse, rat and human PAR-2 peptides. (See FIG. 4). The antibodies tested in these experiments were H4H581P, H4H588N, a comparator antibody having the heavy and light chain variable regions of the antibody referred to as "1A1" in WO 2009/005726 (referred to in FIG. 4 as "Comp. Ab"), and a negative control antibody (referred to in FIG. 4 as "Neg Ctrl"). The same experimental procedures that were used in the previous MALD-TOF experiment (described above) were used in this experiment as well.

The peptides used in these experiments each possess multiple sites capable of being cleaved by trypsin (designated "(1)," "(2)," and "(3)" in FIG. 5.) Site (3) for each peptide is the activating protease cleavage site. The sizes of the peptides produced following cleavage at the different sites are shown in the top portion (panel A) of FIG. 4.

Figure 4:
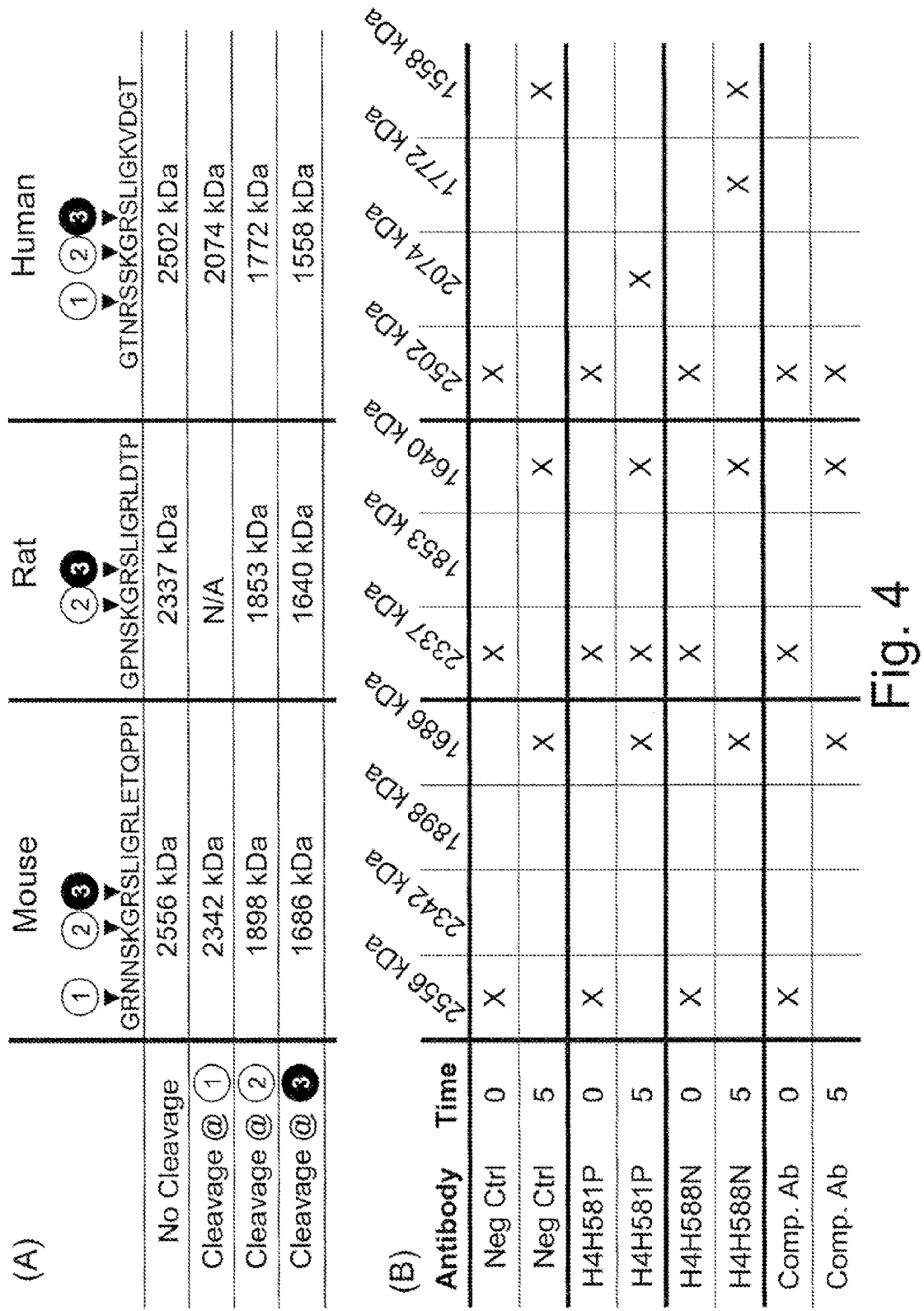
FIGS. 4A and 4B. The top panel (A) shows the mouse, rat and human peptides corresponding to the sequence surrounding the activating PAR-2 protease cleavage sites (SEQ ID NOs:883, 858 and 852, respectively). The protease cleavage sites are designated by numbers 1 and 2 (upstream, non-activating protease cleavage sites) and number 3 (the activating PAR-2 protease cleavage site). The expected sizes of the uncleaved and cleaved fragments are indicated in the top table. The bottom panel (B) shows the fragment sizes that were observed following 0 and 5 minutes of trypsin treatment in the presence of anti-PAR-2 antibodies or negative control.
Figure 5:
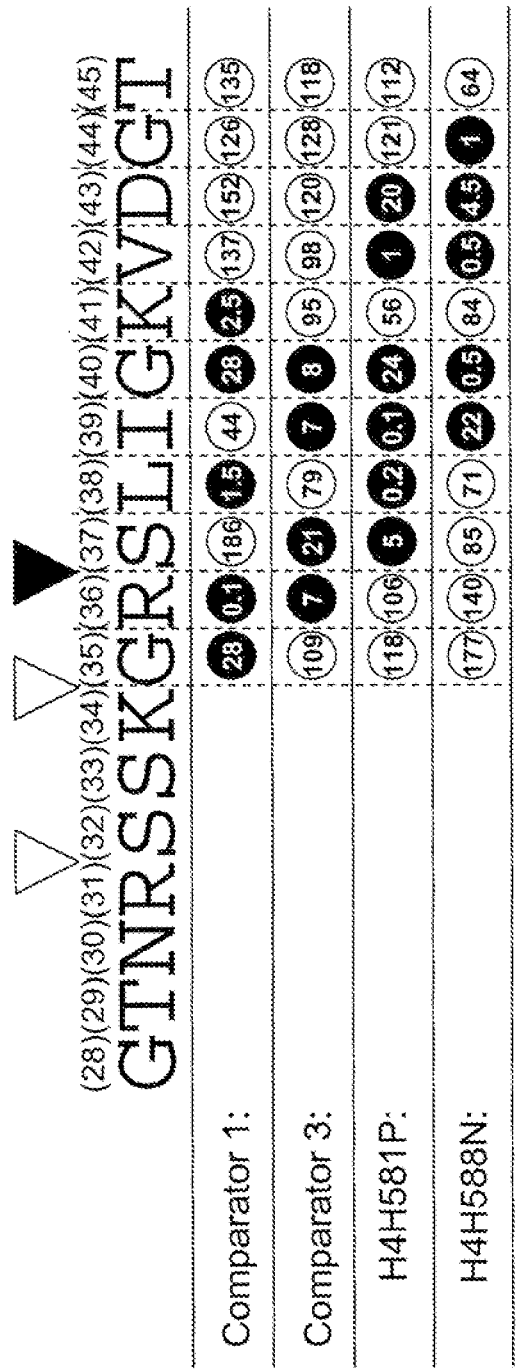
FIG. 5. Depiction of alanine scanning epitope mapping results for antibody binding to the sequence surrounding the PAR-2 activating protease cleavage site (SEQ ID NO:852). Open triangles represent protease cleavage sites located upstream from the activating PAR-2 protease cleavage site. The activating PAR-2 protease cleavage site is designated by a closed triangle. The numbers in parentheses indicate the amino acid numbering in the full-length human PAR-2 sequence (SEQ ID NO:851). Numbers in circles under the amino acid residues indicate the percent of T½ of antibody binding to alanine-scan mutant peptide relative to the T½ of antibody binding to wild-type peptide, as shown in Tables 24-26 and 28. If duplicate experiments were conducted, the average T½ percentage is shown in the circle. Black circles with white numbers indicate amino acids that, when changed to alanine, reduce the T½ of antibody binding to 30% or less of the T½ of antibody binding to wild-type peptide. Such amino acids are defined herein as residues with which the antibody interacts.

As summarized in FIG. 4, the biotinylated human PAR-2 peptide, after being treated with H4H581P, and following trypsin incubation, produced a 2074 kDa peptide which corresponds to cleavage at site (1) only. Thus, H4H581P blocks cleavage at both site (2) and at site (3). By contrast, the human PAR-2 peptide, after being treated with the comparator antibody, and following trypsin incubation, remained at 2502 kDa which signifies no cleavage. Thus, the comparator antibody blocks all three protease cleavage sites in this assay, including the N-terminal-most site (1). When pre-treated with antibody H4H588N, the human PAR-2 peptide produces both a 1772 kDa and a 1558 kDa fragment following trypsin cleavage. This cleavage pattern suggests that H4H588N partially blocks cleavage at the activating site (3) but completely blocks the middle site (2).

This experiment was also conducted using a comparator antibody having the heavy and light chain variable regions of the antibody referred to as Sam-11 (Molino et al., Arterioscler. Thromb. Vasc. Biol. 18:825-832 (1998)). As expected, this particular comparator antibody did not block cleavage at any of the protease cleavage sites (data not shown).

Example 9

Epitope Mapping by Alanine Scanning Mutagenesis of PAR-2 Peptide

In order to more particularly identify the amino acids of PAR-2 with which the PAR-2 antibodies interact, an alanine scanning study was carried out using peptides comprising the activating PAR-2 protease cleavage site. For these experiments, 11 separate C-terminal biotinylated peptides were synthesized in which each amino acid from position 35 through 45 of human PAR-2 (SEQ ID NO:851) was individually replaced with an alanine (SEQ ID NOs: 871-882). An additional set of C-terminal biotinylated peptides was also used which comprise the 14 amino acids located immediately C-terminal to the activating PAR-2 protease cleavage site, with Val-42 and/or Asp-43 changed to alanine (SEQ ID NOs: 884-887).

The ability of each peptide mutant to bind to PAR-2 antibodies was measured using biolayer interferometry (Octet Red; ForteBio). Each peptide (2.5 μg/ml) was captured on streptavidin coated biosensor tips (Octet SA sensor) for 10 seconds. To measure binding and dissociation between each peptide and PAR-2 antibody, the peptide-coated biosensors were contacted with 200 nM solutions of PAR-2 antibodies for 5 minutes (binding) followed by transfer to buffer with no antibody for 10 min (dissociation). The binding of PAR-2 antibody to each peptide was expressed as percent native signal after dividing individual antibody binding signals by the original peptide loading signal observed for that peptide, to correct for slight variations in peptide loading on the individual biosensors. Dissociation half-lives ($T_{1/2}$) were calculated from the dissociation curves using the Scrubber version 2.0a curve-fitting software, and relative half-lives were calculated by dividing observed half-lives for an individual peptide by the half-life of the native peptide. The results are expressed as percent binding and percent $T_{1/2}$ relative to WT peptide (Tables 24-28). [Comparator 1=an antibody having the heavy and light chain variable regions of the antibody referred to as "1A1" in WO 2009/005726; Comparator 2=an antibody having the heavy and light chain variable regions of the antibody referred to as Sam-11 (Molino et al., Arterioscler. Thromb. Vasc. Biol. 18:825-832 (1998)); and Comparator 3=an antibody having the heavy and light chain variable regions of the antibody referred to as "PAR-B" in US 2010/0119506]. In certain cases, the binding experiments were repeated (indicated under the column headings Exp1 and Exp2). NB=no binding observed.

TABLE 24

| | | % Rel Binding | | % Rel $T_{1/2}$ | |
|---|---|---|---|---|---|
| SEQ ID NO: | SEQUENCE | Exp1 | Exp2 | Exp1 | Exp2 |
| 871 | GTNRSSKGRSLIGKVDGT------GGGGSK-B | 100 | 100 | 100 | 100 |
| 872 | GTNRSSKARSLIGKVDGT------GGGGSK-B | 78 | 97 | 118 | 117 |
| 873 | GTNRSSKGASLIGKVDGT------GGGGSK-B | 87 | 105 | 122 | 90 |
| 874 | GTNRSSKGRALIGKVDGT------GGGGSK-B | 45 | 56 | 7 | 3 |
| 875 | GTNRSSKGRSAIGKVDGT------GGGGSK-B | 9 | 19 | 0.4 | 0 |
| 876 | GTNRSSKGRSLAGKVDGT------GGGGSK-B | 8 | 14 | 0.2 | 0 |
| 877 | GTNRSSKGRSLIAKVDGT------GGGGSK-B | 101 | 92 | 33 | 15 |
| 878 | GTNRSSKGRSLIGAVDGT------GGGGSK-B | 113 | 109 | 63 | 49 |
| 879 | GTNRSSKGRSLIGKADGT------GGGGSK-B | 36 | 46 | 1 | 1 |
| 880 | GTNRSSKGRSLIGKVAGT------GGGGSK-B | 18 | 5 | 36 | 4 |
| 881 | GTNRSSKGRSLIGKVDAT------GGGGSK-B | 67 | 102 | 117 | 124 |
| 882 | GTNRSSKGRSLIGKVDGA------GGGGSK-B | 65 | 91 | 129 | 94 |
| 884 | SLIGKVDGTSHVTG-GGGGSK-B | — | 100 | — | 100 |
| 885 | SLIGKADGTSHVTG-GGGGSK-B | — | 19 | — | 0 |

TABLE 24 -continued

H4H581P

| SEQ ID NO: | SEQUENCE | % Rel Binding | | % Rel T$_{1/2}$ | |
|---|---|---|---|---|---|
| | | Exp1 | Exp2 | Exp1 | Exp2 |
| 886 | SLIGKVAGTSHVTG------GGGGSK-B | — | NB | — | NB |
| 887 | SLIGKAAGTSHVTG------GGGGSK-B | — | NB | — | NB |

TABLE 25

H4H588N

| SEQ ID NO: | SEQUENCE | % Rel Binding | | % Rel T$_{1/2}$ | |
|---|---|---|---|---|---|
| | | Exp1 | Exp2 | Exp1 | Exp2 |
| 871 | GTNRSSKGRSLIGKVDGT------GGGGSK-B | 100 | 100 | 100 | 100 |
| 872 | GTNRSSKARSLIGKVDGT------GGGGSK-B | 122 | 99 | 100 | 253 |
| 873 | GTNRSSKGASLIGKVDGT------GGGGSK-B | 208 | 115 | 100 | 180 |
| 874 | GTNRSSKGRALIGKVDGT------GGGGSK-B | 119 | 93 | 100 | 70 |
| 875 | GTNRSSKGRSAIGKVDGT------GGGGSK-B | 127 | 105 | 100 | 42 |
| 876 | GTNRSSKGRSLAGKVDGT------GGGGSK-B | 92 | 85 | 36 | 8 |
| 877 | GTNRSSKGRSLIAKVDGT------GGGGSK-B | 30 | 30 | 1 | 0 |
| 878 | GTNRSSKGRSLIGAVDGT------GGGGSK-B | 217 | 121 | 108 | 60 |
| 879 | GTNRSSKGRSLIGKADGT------GGGGSK-B | 74 | 52 | 1 | 0 |
| 880 | GTNRSSKGRSLIGKVAGT------GGGGSK-B | 35 | 8 | 4 | 5 |
| 881 | GTNRSSKGRSLIGKVDAT------GGGGSK-B | 81 | 67 | 1 | 1 |
| 882 | GTNRSSKGRSLIGKVDGA------GGGGSK-B | 125 | 121 | 94 | 33 |
| 884 | SLIGKVDGTSHVTG------GGGGSK-B | — | 100 | — | 100 |
| 885 | SLIGKADGTSHVTG------GGGGSK-B | — | 83 | — | 0 |
| 886 | SLIGKVAGTSHVTG------GGGGSK-B | — | NB | — | NB |
| 887 | SLIGKAAGTSHVTG------GGGGSK-B | — | NB | — | NB |

TABLE 26

Comparator 1

| SEQ ID NO: | SEQUENCE | % Rel Binding | | % Rel T$_{1/2}$ | |
|---|---|---|---|---|---|
| | | Exp1 | Exp2 | Exp1 | Exp2 |
| 871 | GTNRSSKGRSLIGKVDGT------GGGGSK-B | 100 | 100 | 100 | 100 |
| 872 | GTNRSSKARSLIGKVDGT------GGGGSK-B | 111 | 111 | 29 | 27 |
| 873 | GTNRSSKGASLIGKVDGT------GGGGSK-B | 135 | 87 | 0.2 | 0 |
| 874 | GTNRSSKGRALIGKVDGT------GGGGSK-B | 126 | 102 | 223 | 148 |
| 875 | GTNRSSKGRSAIGKVDGT------GGGGSK-B | 147 | 105 | 2 | 1 |
| 876 | GTNRSSKGRSLAGKVDGT------GGGGSK-B | 156 | 108 | 47 | 41 |
| 877 | GTNRSSKGRSLIAKVDGT------GGGGSK-B | 139 | 108 | 31 | 24 |
| 878 | GTNRSSKGRSLIGAVDGT------GGGGSK-B | 118 | 84 | 3 | 2 |
| 879 | GTNRSSKGRSLIGKADGT------GGGGSK-B | 148 | 104 | 173 | 100 |

TABLE 26 -continued

| | Comparator 1 | | | | |
|---|---|---|---|---|---|
| SEQ ID | | % Rel Binding | | % Rel T$_{1/2}$ | |
| NO: | SEQUENCE | Exp1 | Exp2 | Exp1 | Exp2 |
| 880 | GTNRSSKGRSLIGKVAGT------GGGGSK-B | 124 | 102 | 192 | 111 |
| 881 | GTNRSSKGRSLIGKVDAT------GGGGSK-B | 119 | 97 | 130 | 121 |
| 882 | GTNRSSKGRSLIGKVDGA------GGGGSK-B | 132 | 119 | 154 | 116 |
| 884 | SLIGKVDGTSHVTG-GGGGSK-B | — | NB | — | NB |
| 885 | SLIGKADGTSHVTG-GGGGSK-B | — | NB | — | NB |
| 886 | SLIGKVAGTSHVTG-GGGGSK-B | — | NB | — | NB |
| 887 | SLIGKAAGTSHVTG-GGGGSK-B | — | NB | — | NB |

TABLE 27

| | Comparator 2 | | | | |
|---|---|---|---|---|---|
| SEQ ID | | % Rel Binding | | % Rel T$_{1/2}$ | |
| NO: | SEQUENCE | Exp1 | Exp2 | Exp1 | Exp2 |
| 871 | GTNRSSKGRSLIGKVDGT------GGGGSK-B | — | NB | — | NB |
| 872 | GTNRSSKARSLIGKVDGT------GGGGSK-B | — | NB | — | NB |
| 873 | GTNRSSKGASLIGKVDGT------GGGGSK-B | — | NB | — | NB |
| 874 | GTNRSSKGRALIGKVDGT------GGGGSK-B | — | NB | — | NB |
| 875 | GTNRSSKGRSAIGKVDGT------GGGGSK-B | — | NB | — | NB |
| 876 | GTNRSSKGRSLAGKVDGT------GGGGSK-B | — | NB | — | NB |
| 877 | GTNRSSKGRSLIAKVDGT------GGGGSK-B | — | NB | — | NB |
| 878 | GTNRSSKGRSLIGAVDGT------GGGGSK-B | — | NB | — | NB |
| 879 | GTNRSSKGRSLIGKADGT------GGGGSK-B | — | NB | — | NB |
| 880 | GTNRSSKGRSLIGKVAGT------GGGGSK-B | — | NB | — | NB |
| 881 | GTNRSSKGRSLIGKVDAT------GGGGSK-B | — | NB | — | NB |
| 882 | GTNRSSKGRSLIGKVDGA------GGGGSK-B | — | NB | — | NB |
| 884 | SLIGKVDGTSHVTG-GGGGSK-B | — | 100 | — | 100 |
| 885 | SLIGKADGTSHVTG-GGGGSK-B | — | 120 | — | 159 |
| 886 | SLIGKVAGTSHVTG-GGGGSK-B | — | 88 | — | 27 |
| 887 | SLIGKAAGTSHVTG-GGGGSK-B | — | 87 | — | 27 |

TABLE 28

Comparator 3

| SEQ ID NO: | SEQUENCE | % Rel Binding Exp1 | % Rel Binding Exp2 | % Rel T$_{1/2}$ Exp1 | % Rel T$_{1/2}$ Exp2 |
|---|---|---|---|---|---|
| 871 | GTNRSSKGRSLIGKVDGT------GGGGSK-B | — | 100 | — | 100 |
| 872 | GTNRSSKARSLIGKVDGT------GGGGSK-B | — | 101 | — | 109 |
| 873 | GTNRSSKGASLIGKVDGT------GGGGSK-B | — | 98 | — | 7 |
| 874 | GTNRSSKGRALIGKVDGT------GGGGSK-B | — | 106 | — | 21 |
| 875 | GTNRSSKGRSAIGKVDGT------GGGGSK-B | — | 115 | — | 79 |
| 876 | GTNRSSKGRSLAGKVDGT------GGGGSK-B | — | 92 | — | 7 |
| 877 | GTNRSSKGRSLIAKVDGT------GGGGSK-B | — | 101 | — | 8 |
| 878 | GTNRSSKGRSLIGAVDGT------GGGGSK-B | — | 109 | — | 95 |
| 879 | GTNRSSKGRSLIGKADGT------GGGGSK-B | — | 96 | — | 98 |
| 880 | GTNRSSKGRSLIGKVAGT------GGGGSK-B | — | 99 | — | 120 |
| 881 | GTNRSSKGRSLIGKVDAT------GGGGSK-B | — | 93 | — | 128 |
| 882 | GTNRSSKGRSLIGKVDGA------GGGGSK-B | — | 117 | — | 118 |
| 884 | SLIGKVDGTSHVTG-GGGGSK-B | — | NB | — | NB |
| 885 | SLIGKADGTSHVTG-GGGGSK-B | — | NB | — | NB |
| 886 | SLIGKVAGTSHVTG-GGGGSK-B | — | NB | — | NB |
| 887 | SLIGKAAGTSHVTG-GGGGSK-B | — | NB | — | NB |

The results from the alanine scanning experiments are summarized in FIG. 5, where the black circles indicate amino acids of PAR-2 which, when changed to alanine, substantially reduce binding by the corresponding antibody (i.e., the T½ of antibody binding to the mutated peptide is less

TABLE 29

| Dose of mAb H4H581P | Percent Change in Scratching Bouts Relative to Control | |
|---|---|---|
| (mg/kg) | Trypsin | Tryptase |
| 10 | 9.9 ± 23.1 | −40.7 ± 23.4 |
| 25 | −26.6 ± 11.3 | −38.5 ± 11.1 |
| 50 | −31.3 ± 13.5 | −47.7 ± 8.0* |
| 75 | −34.9 ± 4.7* | ND |
| 100 | −55.2 ± 8.0* | −39.6 ± 6.9* |
| 150 | −42.9 ± 9.7* | ND |

As shown in this Example, mAb H4H581P was able to block protease-induced pruritus behaviors in a dose dependent manner using two different protease-induced itch models.

Example 11

Reduction of Pruritus Behaviors by Administration of an Anti-PAR-2 Antibody in a Hapten-Induced Chronic Dermatitis Model To further assess the ability of the anti-PAR-2 antibody H4H581P to reduce pruritus behaviors in a physiologically relevant disease state, a mouse model of chronic dermatitis was used. In this model, mice received repeated cutaneous applications of the haptenizing agent, oxazolone. This chronic oxazolone-induced dermatitis model has been shown to recapitulate many of the clinical, histological, and immunological hallmarks of atopic dermatitis in humans (Man et al., 2008, *J. Invest. Dermatol.* 128(1):79-86).

Mice were sensitized with a single cutaneous application of 1% oxazolone on the left ear or vehicle (100 mg/kg, s.c.). The mice then received nine total cutaneous applications (challenges) of 0.6% oxazolone between the scapulae beginning seven days after the sensitization application. Weekly dosing (3 total) of the H4H581P anti-PAR2 antibody was initiated 24 hours prior to the first oxazolone challenge (100 mg/kg, s.c.). This dosing paradigm significantly reduced pruritus behaviors as measured by reduced numbers of scratching bouts elicited by the final oxazolone challenge. All data are represented as mean number of scratching bouts ±SEM for n=6 mice/group; *=p<0.05 by Tukey post-hoc test as compared to the Oxazolone+IgG control group; #=p<0.05 by Tukey post-hoc test compared to the Vehicle+IgG control group).

Histological analysis showed a significant increase in epidermal hyperplasia and immune cell infiltrate in the oxazolone-challenged animals. (Data not shown). No significant differences were observed in any of these parameters between the H4H581P anti-PAR2 antibody and the isotype control.

Example 12

Comparison of Pruritus Inhibiting Activities of mAb H4H581P

In this Example, the ability of mAb H4H581P to attenuate itching bouts in a mouse pruritus model was compared to that of a comparator anti-PAR-2 mAb (Comparator "1A1" described in WO 2009/005726).

Transgenic mice expressing human PAR-2 (hPAR2$^{+/+}$) were divided into 3 cohorts. Cohort A received 50 mg/kg (s.c.) of an isotype control mAb, cohort B received 50 mg/kg (s.c.) of H4H581P, and Cohort C received 50 mg/kg (s.c.) of the comparator anti-PAR-2 antibody. Twenty-four hours after antibody dosing all cohorts received 150 μg of trypsin (s.c., interscapular), which produced bouts of scratching behavior for 30 minutes. The percent change in the number of scratching bouts observed for the treated mice as compared to control-treated mice is shown in Table 29 (all data are represented as mean±SEM).

TABLE 31

| Antibody Treatment (50 mg/kg) | (% change in scratching bouts from control) |
|---|---|
| mAb H4H581P | −41.1 ± 13.5 |
| Comparator mAb | −13.9 ± 9.9 |

As shown in this Example, mAb H4H581P was substantially more effective than the comparator mAb in reducing pruritus behaviors in the trypsin-induced itch model used herein.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

TABLE 30

| Treatment | Time (minutes) | | | | | | |
|---|---|---|---|---|---|---|---|
| | 0-10 | 10-20 | 20-30 | 30-40 | 40-50 | 50-60 | Total |
| Vehicle + IgG control | 0.0 ± 0.0 | 0.8 ± 0.6 | 2.2 ± 1.4 | 3.4 ± 1.3 | 4.8 ± 2.0 | 2.4 ± 1.0 | 13.6 ± 4.2 |
| Oxazolone + IgG control | 0.5 ± 0.5 | 11.3 ± 3.9 | 24.8 ± 9.7 | 28.0 ± 7.3 | 21.0 ± 7.9 | 21.3 ± 7.3 | #106.8 ± 33.2 |
| Oxazolone + H4H581P | 0.2 ± 0.2 | 1.6 ± 1.2 | *6.0 ± 2.4 | 16.6 ± 5.1 | 18.2 ± 4.8 | 18.0 ± 5.5 | 60.6 ± 11.6 |

What is claimed is:

1. A method of alleviating itch in a patient, the method comprising:
administering to the patient an effective amount of a pharmaceutical composition comprising a human antibody or an antigen-binding fragment thereof, wherein the antibody or antigen-binding fragment specifically binds to human protease-activated receptor-2 (PAR-2) (SEQ ID NO:851) and interacts with Val-42 and Asp-43 of human PAR-2.

2. The method of claim 1, wherein the antibody or antigen-binding fragment also interacts with one or more residues selected from the group consisting of Ser-37, Leu-38, Ile-39, Gly-40, and Gly-44 of human PAR-2.

3. The method of claim 2, wherein the antibody or antigen-binding fragment does not interact with Lys-41 of human PAR-2.

4. The method of claim 3, wherein the antibody or antigen-binding fragment comprises the complementary determining regions (CDRs) of a heavy chain variable region (HCVR) having the amino acid sequence of SEQ ID NO:714, and the CDRs of a light chain variable region (LCVR) having the amino acid sequence of SEQ ID NO:692.

5. The method of claim 4, wherein the antibody or antigen-binding fragment comprises HCDR1-HCDR2-HCDR3 having the amino acid sequences of SEQ ID NOs:700-702-704, and LCDR1-LCDR2-LCDR3 having the amino acid sequences of SEQ ID NOs:708-710-712.

6. The method of claim 3, wherein the antibody or antigen-binding fragment blocks trypsin cleavage of human PAR-2 at the activating cleavage site located at the junction of residues Arg-36 and Ser-37 of human PAR-2.

7. The method of claim 6, wherein the antibody or antigen-binding fragment does not block trypsin cleavage of human PAR-2 at one or more non-activating cleavage sites selected from the non-activating cleavage site located at the junction of residues Arg-31 and Ser-32 of human PAR-2 and the non-activating cleavage site located at the junction of residues Lys-34 and Gly-35 of human PAR-2.

8. The method of claim 7, wherein the antibody or antigen-binding fragment interacts with Ser-37, Leu-38, Ile-39, Gly-40, Val-42 and Asp-43 of human PAR-2.

9. The method of claim 8, wherein the antibody or antigen-binding fragment comprises the complementarity determining regions (CDRs) of a heavy chain variable region (HCVR) having the amino acid sequence of SEQ ID NO:714, and the CDRs of a light chain variable region (LCVR) having the amino acid sequence of SEQ ID NO:692.

10. The method of claim 9, wherein the antibody or antigen-binding fragment comprises a HCVR and a LCVR, wherein the HCVR comprises heavy chain CDRs (HCDR1-HCDR2-HCDR3) having the amino acid sequences of SEQ ID NOs:700-702-704, and wherein the LCVR comprises light chain CDRs (LCDR1-LCDR2-LCDR3) having the amino acid sequences of SEQ ID NOs:708-710-712.

11. The method of claim 10, wherein the antibody or antigen-binding fragment comprises a HCVR having the amino acid sequence of SEQ ID NO:714 and a LCVR having the amino acid sequence of SEQ ID NO:692.

12. A therapeutic method comprising administering an effective amount of a pharmaceutical composition to a patient, wherein the patient exhibits itch due to a disease or disorder caused by protease-activated receptor-2 (PAR-2) activity, and wherein the pharmaceutical composition comprises a human antibody or antigen-binding fragment thereof, wherein the antibody or antigen-binding fragment interacts with Val-42 and Asp-43 of human PAR-2 (SEQ ID NO:851).

13. The therapeutic method of claim 12, wherein the antibody or antigen-binding fragment also interacts with one or more residues selected from the group consisting of Ser-37, Leu-38, Ile-39, Gly-40, and Gly-44 of human PAR-2.

14. The therapeutic method of claim 13, wherein the antibody or antigen-binding fragment does not interact with Lys-41 of human PAR-2.

15. The therapeutic method of claim 14, wherein the antibody or antigen-binding fragment comprises the complementary determining regions (CDRs) of a heavy chain variable region (HCVR) having the amino acid sequence of SEQ ID NO:714, and the CDRs of a light chain variable region (LCVR) having the amino acid sequence of SEQ ID NO:692.

16. The therapeutic method of claim 15, wherein the antibody or antigen-binding fragment comprises HCDR1-HCDR2-HCDR3 having the amino acid sequences of SEQ ID NOs:700-702-704, and LCDR1-LCDR2-LCDR3 having the amino acid sequences of SEQ ID NOs:708-710-712.

17. The therapeutic method of claim 14, wherein the antibody or antigen-binding fragment blocks trypsin cleavage of human PAR-2 at the activating cleavage site located at the junction of residues Arg-36 and Ser-37 of human PAR-2.

18. The therapeutic method of claim 17, wherein the antibody or antigen-binding fragment does not block trypsin cleavage of human PAR-2 at one or more non-activating cleavage sites selected from the non-activating cleavage site located at the junction of residues Arg-31 and Ser-32 of human PAR-2 and the non-activating cleavage site located at the junction of residues Lys-34 and Gly-35 of human PAR-2.

19. The therapeutic method of claim 18, wherein the antibody or antigen-binding fragment interacts with Ser-37, Leu-38, Ile-39, Gly-40, Val-42 and Asp-43 of human PAR-2.

20. The therapeutic method of claim 19, wherein the antibody or antigen-binding fragment comprises the complementarity determining regions (CDRs) of a heavy chain variable region (HCVR) having the amino acid sequence of SEQ ID NO:714, and the CDRs of a light chain variable region (LCVR) having the amino acid sequence of SEQ ID NO:692.

21. The therapeutic method of claim 20, wherein the antibody or antigen-binding fragment comprises a heavy chain variable region (HCVR) and a light chain variable region (LCVR), wherein the HCVR comprises heavy chain CDRs (HCDR1-HCDR2-HCDR3) having the amino acid sequences of SEQ ID NOs:700-702-704, and wherein the LCVR comprises light chain CDRs (LCDR1-LCDR2-LCDR3) having the amino acid sequences of SEQ ID NOs: 708-710-712.

22. The therapeutic method of claim 21, wherein the antibody or antigen-binding fragment comprises a HCVR having the amino acid sequence of SEQ ID NO:714 and a LCVR having the amino acid sequence of SEQ ID NO:692.

23. The therapeutic method of claim 12, wherein the disease or disorder caused by PAR-2 activity is a disease or disorder selected from the group consisting of asthma, rheumatoid arthritis, fibrosis, atopic dermatitis, inflammatory bowel disease, ulcerative colitis, pancreatitis, ulcer, Crohn's disease, skin cancer, and Netherton's disease.

24. The therapeutic method of claim 23, further comprising administering to the patient one or more additional therapeutic agent(s) selected from the group consisting of an IL-1 inhibitor, an IL-18 inhibitor, an IL-4 inhibitor, an IL-4 receptor inhibitor, an IL-6 inhibitor, an IL-6 receptor inhibitor, a nerve growth factor (NGF) inhibitor, a tumor necrosis factor (TNF) inhibitor, a TNF receptor inhibitor, a uric acid synthesis inhibitor and a corticosteroid.

25. A method of alleviating itch in a patient, comprising;
administering to a patient an isolated human antibody or antigen-binding fragment thereof that specifically binds to human protease-activated receptor-2 (PAR-2) (SEQ ID NO:851), wherein the antibody or antigen-binding fragment thereof comprises:
(a) heavy chain complimentary determining regions (HCDR1-HCDR2-HCDR3) having the amino acid sequences of SEQ ID NOs:700-702-704; and
(b) light chain CDRs (LCDR1-LCDR2-LCDR3) having the amino acid sequences of SEQ ID NOs:708-710-712.

26. A method of alleviating itch in a patient, comprising;
administering to a patient an isolated human antibody or antigen-binding fragment thereof that specifically binds to human protease-activated receptor-2 (PAR-2) (SEQ ID NO:851), wherein the antibody or antigen-binding fragment thereof:
(a) interacts with Ser-37, Leu-38, Ile-39, Gly-40, Val-42 and Asp-43 of human PAR-2;
(b) does not interact with Lys-41 of human PAR-2;
(c) blocks trypsin cleavage of human PAR-2 at the activating cleavage site located at the junction of residues Arg-36 and Ser-37 of human PAR-2;
(d) does not block trypsin cleavage of human PAR-2 at the non-activating cleavage site located at the junction of residues Arg-31 and Ser-32; and
(e) competes for binding to human PAR-2 with a reference antibody comprising heavy chain complimentary determining regions (HCDR1-HCDR2-HCDR3) having the amino acid sequences of SEQ ID NOs:700-702-704; and the light chain CDRs (LCDR1-LCDR2-LCDR3) having the amino acid sequences of SEQ ID NOs:708-710-712.

* * * * *